US012753218B2

(12) United States Patent
Riley et al.

(10) Patent No.: US 12,753,218 B2
(45) Date of Patent: Oct. 6, 2026

(54) DUAL CAR EXPRESSING T CELLS INDIVIDUALLY LINKED TO CD28 AND 4-1BB

(71) Applicant: THE TRUSTEES OF THE UNIVERSITY OF PENNSYLVANIA, Philadelphia, PA (US)

(72) Inventors: James L. Riley, Downingtown, PA (US); Colby Maldini, Newington, NH (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 549 days.

(21) Appl. No.: 16/894,558

(22) Filed: Jun. 5, 2020

(65) Prior Publication Data

US 2020/0384029 A1 Dec. 10, 2020

Related U.S. Application Data

(60) Provisional application No. 62/858,506, filed on Jun. 7, 2019.

(51) Int. Cl.
*C12N 15/62* (2006.01)
*A61K 40/11* (2025.01)
(Continued)

(52) U.S. Cl.
CPC .......... *C07K 14/7051* (2013.01); *A61K 40/11* (2025.01); *A61K 40/22* (2025.01);
(Continued)

(58) Field of Classification Search
None
See application file for complete search history.

(56) References Cited

U.S. PATENT DOCUMENTS 10,117,896 B2 11/2018 Powell, Jr.
10,253,086 B2 * 4/2019 Bitter ................ C07K 16/2866
(Continued)

FOREIGN PATENT DOCUMENTS

WO 2012079000 A1 6/2012
WO 2015157384 10/2015
(Continued)

OTHER PUBLICATIONS

Prinz et al., Preclinical targeting of human T-cell malignancies using CD4-specific chimeric antigen receptor (CAR)-engineered T cells, Leukemia, 30:701-707, 2016.*
(Continued)

*Primary Examiner* — Claire Kaufman
(74) *Attorney, Agent, or Firm* — Saul Ewing LLP; Alireza Behrooz; Kathryn Doyle

(57) ABSTRACT

The present invention relates to modified immune cells or precursors thereof, comprising dual (a first and a second) chimeric receptors (e.g. CARs). One aspect includes a first CAR comprising a 4-1BB intracellular domain and a second CAR comprising a CD28 intracellular domain. Another aspect includes a method for treating of an HIV infected mammal using a modified T cell comprising a first CD4 CAR comprising a 4-1BB intracellular domain and a second CD4 CAR comprising a CD28 intracellular domain.

26 Claims, 101 Drawing Sheets

Specification includes a Sequence Listing.

(51) Int. Cl.

| | |
|---|---|
| ***A61K 40/22*** | (2025.01) |
| ***A61K 40/31*** | (2025.01) |
| ***A61K 40/42*** | (2025.01) |
| ***A61K 40/46*** | (2025.01) |
| ***C07K 14/705*** | (2006.01) |
| ***C12N 15/86*** | (2006.01) |

(52) U.S. Cl.

CPC .......... *A61K 40/31* (2025.01); *A61K 40/4211* (2025.01); *A61K 40/4212* (2025.01); *A61K 40/46* (2025.01); *C07K 14/70514* (2013.01); *C07K 14/70517* (2013.01); *C07K 14/70521* (2013.01); *C07K 14/70578* (2013.01); *C12N 15/86* (2013.01); *A61K 2239/29* (2023.05); *A61K 2239/48* (2023.05); *C07K 2317/53* (2013.01); *C07K 2319/03* (2013.01)

(56) References Cited

U.S. PATENT DOCUMENTS

| | | | | |
|---|---|---|---|---|
| 10,689,431 | B2 * | 6/2020 | Orentas | C07K 16/2827 |
| 10,711,282 | B2 | 7/2020 | Slepushkin | |
| 11,149,073 | B2 * | 10/2021 | Hudecek | C07K 14/70517 |
| 11,980,640 | B2 * | 5/2024 | Qin | C07K 14/395 |
| 2018/0105573 | A1 | 4/2018 | Pulé | |
| 2018/0265565 | A1 | 9/2018 | Riley | |
| 2019/0083596 | A1 | 3/2019 | Orentas | |

FOREIGN PATENT DOCUMENTS

| | | | | |
|---|---|---|---|---|
| WO | WO-2015164594 | A1 * | 10/2015 | C07K 16/2809 |
| WO | 2016055551 | A1 | 4/2016 | |
| WO | 2016102965 | | 6/2016 | |
| WO | 2016160618 | | 10/2016 | |
| WO | 2016174405 | | 11/2016 | |
| WO | 2016210293 | A1 | 12/2016 | |
| WO | 2017027291 | A1 | 2/2017 | |
| WO | 2017091786 | A1 | 6/2017 | |
| WO | 2017222593 | A1 | 12/2017 | |

OTHER PUBLICATIONS

Merten, Production of lentiviral vectors, Mol. Therapy—Meth. Clin. Devel. 3:10617, 14 pages, 2016; doi:10.1038/mtm.2016.17.*

Cappell et al., A comparison of chimeric antigen receptors containing CD28 versus 4-1BB costimulatory domains, Nat. Rev. Clin. Oncol. 18:715-727, 2021.*

Golubovskaya et al, GITR domain inside CAR co-stimulates activity of CAR-T cells against cancer, Front. Biosci. (Landmark Ed), 23 (12), 2245-2254, Jun. 1, 2018.*

Song et al., CD27 costimulation augments the survival and antitumor activity of redirected human T cells in vivo. Blood; 119(3):696-706, 2012.*

Guedan et al., Enhancing CAR T cell persistence through ICOS and 4-1BB costimulation, JCI Insight. 3(1):e96976, 17 pages, Jan. 11, 2018.*

Zhao et al., Structural design of engineered constimulation determines tumor rejection kinetics and persistence of CAR T cells, Canc. Cell, 28:415-428, 2015.*

Petrov et al. Compound CAR T-cells as a double-pronged approach for treating acute myeloid leukemia, Leukemia. 32(6): 1317-1326, 2018.*

Weinkove et al., Selecting costimulatory domains for chimeric antigen receptors: functional and clinical considerations, Clin. Transl. Immunol. 8:e1049, 14 pages, May 11, 2019.*

Fox et al., Thumor necrosis factor-related apoptosis-inducing ligand (TRAIL) receptor-1 and receptor-2 agonists for cancer therapy, Expert. Opin. Biol. Ther. 10(1):1-18, 2010.*

Dostert et al., The TNF Family of Ligands and Receptors_ Communication Modules in the Immune System and Beyond, Pysiol. Rev. 99:115-160, published Oct. 24, 2018, 2019.*

Ruella et al., Dual CD19 and CD123 targeting prevents antigen-loss relapses after CD19-directed immunotherapies, J. Clin. Invest. 126(10):3814-3826, 2016.*

Casucci et al., Extracellular NGFR Spacers Allow Efficient Tracking and Enrichment of Fully Functional CAR-T Cells Co-Expressing a Suicide Gene, Front. Immunol. 9:507, 13 pages, Mar. 2018.*

Dever et al., CRISPR/Cas9 β-globin gene targeting in human haematopoietic stem cells, Nature, 539(7629):384-389, 19 pages, Nov. 17, 2016.*

Wang et al., Atransgene-encoded cell surface polypeptide for selection, in vivo tracking, and ablation of engineered cells, Blood, 118(5):1255-1263, 2011.*

Miltenyi Biotech, MACS® Cell Separation, Retrieved online from: <URL:https://static.miltenyibiotec.com/asset/150655405641/document_tpt3ah2lit3ch30k01jtvtmh6h?content-disposition=inline> [retrieved on Jul. 7, 2025], 12 pages, 2017.*

BioAlta, Educational Appendix, Antibody Structure, Retrieved onine from: <URL:https://www.bioatla.com/appendix/antibody-structure/> [retrieveed on Oct. 31, 2025], 5 pages, 2025.*

Leibman, et al., "Supraphysiologic control over HIV-1 replication mediated by CD8 T cells expressing a re-engineered CD4-based chimeric antigen receptor.", PLOS Pathogens 13(10:e1006613, Oct. 12, 2017.

Van Der Stegen, et al., The pharmacology of second-generation chimeric antigen receptors., Nat Rev Drug Discov. Jul. 2015;14(7):499-509. (Abstract).

Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.

Buggert et al., "T-bet and eomes are differentially linked to the exhausted phenotype of CD8+ T Cells in HIV infection", (2014) PLoS Pathog 10, e1004251, 15 pages.

Brelot et al. "Identification of residues of CXCR4 critical for human immunodeficiency virus coreceptor and chemokine receptor activities", (2000) J Biol Chem 275, 23736-23744.

Wang & Riviere, "Clinical manufacturing of CAR T cells: foundation of a promising therapy", (2016), Mol Ther Oncolytics 3, 16015, 7 pages.

Fesnak et al. "Engineered T cells: The promise and challenges of cancer immunotherapy", (2016) Nat Rev Cancer 16, 566-581.

Anthony-Gonda, K., et al., "Multispecific anti-HIV duoCAR-T cells display broad antiviral activity and potent in vivo elimination of HIV-infected cells in vivo", Sci Transl Med 11(2019), 40 pages.

Song, D.G., et al., "In vivo persistence, tumor localization, and antitumor activity of CAR-engineered T cells is enhanced by costimulatory signaling through CD137 (4-1BB)", Cancer Res 71, 4617-4627 (2011).

Zhao, Z., et al., "Structural Design of Engineered Costimulation Determines Tumor Rejection Kinetics and Persistence of CAR T Cells", Cancer Cell 28, 415-428 (2015).

Guedan, S., et al., "Enhancing CAR T cell persistence through ICOS and 4-1BB costimulation", JCI Insight 3(2018), 17 pages.

Pule, M.A., et al., "A chimeric T cell antigen receptor that augments cytokine release and supports clonal expansion of primary human T cells", Mol Ther 12, 933-941 (2005).

Hombach, A.A., Heiders, J., Foppe, M., Chmielewski, M. & Abken, H., "OX40 costimulation by a chimeric antigen receptor abrogates CD28 and IL-2 induced IL-10 secretion by redirected CD4(+) T cells", Oncoimmunology 1, 458-466 (2012).

International Search Report and Written Opinion issued Oct. 13, 2020—PCT/US2020/036447.

Leibman, R., "Engineering Chimeric Antigen Receptors For Durable Control Over Hiv-1 Replication", University of Pennsylvania Scholarly Commons, Part of the Allergy and Immunology Commons, 190 pages, 2017.

Extended European Search Report issued Jun. 6, 2023 in European Patent Application No. 20818563.7.

(56) References Cited

OTHER PUBLICATIONS

Leibman, R., "Engineering Chimeric Antigen Receptors For Durable Control Over Hiv-1 Replication", University of Pennsylvania Scholarly Commons, Part of the Allergy and Immunology Commons Doctoral Disseratation, 190 pages, 2017.

* cited by examiner

CD4 CAR(BBζ)
CD4 CAR(28ζ)
Dual CD4 CAR T cell
Extracellular
Intracellular
CD4
4-1BB
CD3ζ
CD28

%HIV GAG+ target cells
Days post coculture
CAR(BBζ)
CAR(28ζ)
UTD

Dual transduced CD4 CAR T cells
iRFP670-CAR(BBζ)
GFP-CAR(28ζ)

BLT mouse
Weeks
HIVJRCSF or HIVMJ4 challenge
Dual transduced CAR T cell infusion
d2
Blood analysis CAR.BBζ
CAR.BBΔζ
CAR⁻ CD45RA⁻ CD4⁺ T cells (%)
Weeks post-ART discontinuation CAR.BBζ (G1)
CAR.BBΔζ (G2)
ART
CAR T cells μl⁻¹ blood
Weeks post-CAR T cell infusion CAR.BBζ (G3)
CAR.BBΔζ (G4)
ART
CAR T cells μl⁻¹ blood
Weeks post-CAR T cell infusion CAR.BBζ (G1/3)
CAR.BBΔζ (G2/4)
CAR T cells of CD3⁺ cells (%)
Bone Marrow
Liver
Genital Tract
Lung
Mes.
Cerv.
Lymph Node
Spleen FIG. 26C
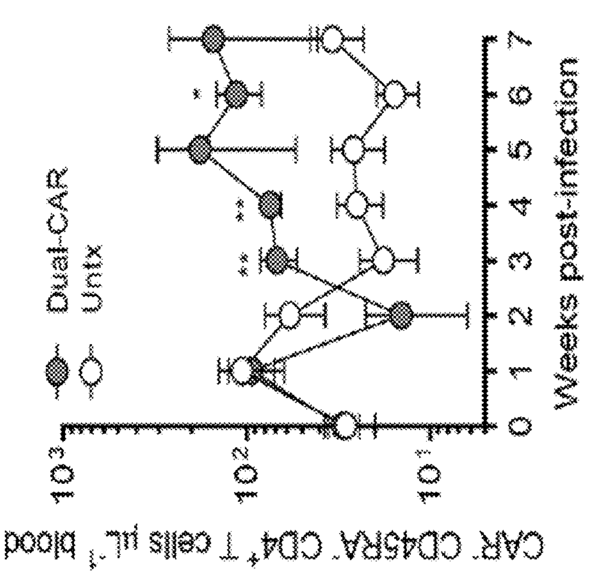
FIG. 26D
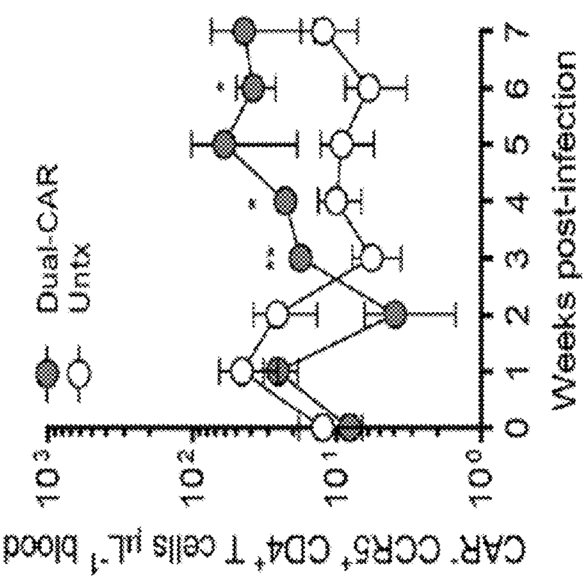
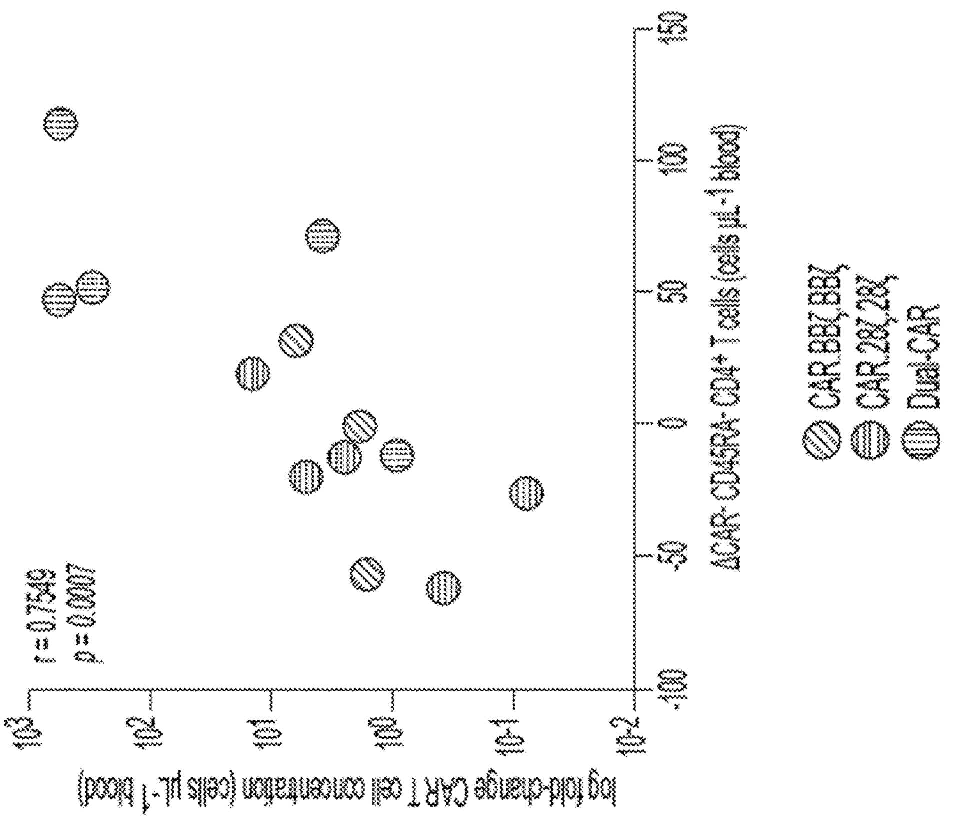
FIG. 26E

| CARs condition | Nalm6-CBG-GFP | No. of mice |
|---|---|---|
| 1. CD19.BBz.EGFRt and CD19.28z.NGFR | $1x10^6$ | 5 |
| 2. CD19.BBz.EGFRt and CD22.28z.NGFR | $1x10^6$ | 5 |
| 3. CD19.28z.NGFR and CD22.BBz.EGFRt | $1x10^6$ | 5 |
| 4. CD22.BBz.EGFRt and CD22.28z.NGFR | $1x10^6$ | 5 |
| 5. CD19.BBz.EGFRt and CD19.BBz.NGFR | $1x10^6$ | 5 |
| 6. UTD | $1x10^6$ | 5 |

FIG. 42
UTD
CD19.BBz.EGFRt
CD22.BBz.T2A.CD19.BBz
CD22.BBz.T2A.CD19.28z
CD22.28z.T2A.CD19.BBz
CD22.28z.T2A.CD19.28z
CD22.28z.T2A.CD22.BBz
CD19.BBz.T2A.CD19.28z
Unstimulated
PMA & Ion
WT K562
NALM6
IL-2
IFNγ
TNFα

SEQUENCE LISTING

```
<160> NUMBER OF SEQ ID NOS: 45

<210> SEQ ID NO 1
<211> LENGTH: 621
<212> TYPE: PRT
<213> ORGANISM: Artificial Sequence
<220> FEATURE:
<223> OTHER INFORMATION: CD4 4-1BB CD3-zeta

<400> SEQUENCE: 1

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160
```

```
Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Ser Gly Thr Thr
385                 390                 395                 400

Thr Pro Ala Pro Arg Pro Pro Thr Pro Ala Pro Thr Ile Ala Ser Gln
                405                 410                 415

Pro Leu Ser Leu Arg Pro Glu Ala Cys Arg Pro Ala Ala Gly Gly Ala
            420                 425                 430

Val His Thr Arg Gly Leu Asp Phe Ala Cys Asp Ile Tyr Ile Trp Ala
        435                 440                 445

Pro Leu Ala Gly Thr Cys Gly Val Leu Leu Leu Ser Leu Val Ile Thr
    450                 455                 460

Leu Tyr Cys Lys Arg Gly Arg Lys Lys Leu Leu Tyr Ile Phe Lys Gln
465                 470                 475                 480

Pro Phe Met Arg Pro Val Gln Thr Thr Gln Glu Glu Asp Gly Cys Ser
                485                 490                 495

Cys Arg Phe Pro Glu Glu Glu Glu Gly Gly Cys Glu Leu Arg Val Lys
            500                 505                 510

Phe Ser Arg Ser Ala Asp Ala Pro Ala Tyr Gln Gln Gly Gln Asn Gln
        515                 520                 525

Leu Tyr Asn Glu Leu Asn Leu Gly Arg Arg Glu Glu Tyr Asp Val Leu
    530                 535                 540

Asp Lys Arg Arg Gly Arg Asp Pro Glu Met Gly Gly Lys Pro Arg Arg
545                 550                 555                 560

Lys Asn Pro Gln Glu Gly Leu Tyr Asn Glu Leu Gln Lys Asp Lys Met
                565                 570                 575
```

```
Ala Glu Ala Tyr Ser Glu Ile Gly Met Lys Gly Glu Arg Arg Arg Gly
            580                 585                 590

Lys Gly His Asp Gly Leu Tyr Gln Gly Leu Ser Thr Ala Thr Lys Asp
        595                 600                 605

Thr Tyr Asp Ala Leu His Met Gln Ala Leu Pro Pro Arg
    610                 615                 620


<210> SEQ ID NO 2
<211> LENGTH: 396
<212> TYPE: PRT
<213> ORGANISM: Artificial Sequence
<220> FEATURE:
<223> OTHER INFORMATION: CD4 EC domain

<400> SEQUENCE: 2

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320
```

```
Gln Leu Gln Lys Asn Leu Thr Cys Glu Val Trp Gly Pro Thr Ser Pro
            325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro
385                 390                 395


<210> SEQ ID NO 3
<211> LENGTH: 45
<212> TYPE: PRT
<213> ORGANISM: Artificial Sequence
<220> FEATURE:
<223> OTHER INFORMATION: CD8a hinge

<400> SEQUENCE: 3

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 4
<211> LENGTH: 24
<212> TYPE: PRT
<213> ORGANISM: Artificial Sequence
<220> FEATURE:
<223> OTHER INFORMATION: CD8a TM

<400> SEQUENCE: 4

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 5
<211> LENGTH: 42
<212> TYPE: PRT
<213> ORGANISM: Artificial Sequence
<220> FEATURE:
<223> OTHER INFORMATION: 4-1BB ICD

<400> SEQUENCE: 5

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 6
<211> LENGTH: 112
<212> TYPE: PRT
<213> ORGANISM: Artificial Sequence
<220> FEATURE:
<223> OTHER INFORMATION: CD3 zeta

<400> SEQUENCE: 6
```

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 7
<211> LENGTH: 625
<212> TYPE: PRT
<213> ORGANISM: Artificial Sequence
<220> FEATURE:
<223> OTHER INFORMATION: CD4 CD28 CD3-zeta

<400> SEQUENCE: 7

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255
```

```
Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Ser Gly Thr Thr
385                 390                 395                 400

Thr Pro Ala Pro Arg Pro Pro Thr Pro Ala Pro Thr Ile Ala Ser Gln
                405                 410                 415

Pro Leu Ser Leu Arg Pro Glu Ala Cys Arg Pro Ala Ala Gly Gly Ala
            420                 425                 430

Val His Thr Arg Gly Leu Asp Phe Ala Cys Asp Phe Trp Val Leu Val
        435                 440                 445

Val Val Gly Gly Val Leu Ala Cys Tyr Ser Leu Leu Val Thr Val Ala
    450                 455                 460

Phe Ile Ile Phe Trp Val Arg Ser Lys Arg Ser Arg Leu Leu His Ser
465                 470                 475                 480

Asp Tyr Met Asn Met Thr Pro Arg Arg Pro Gly Pro Thr Arg Lys His
                485                 490                 495

Tyr Gln Pro Tyr Ala Pro Pro Arg Asp Phe Ala Ala Tyr Arg Ser Ile
            500                 505                 510

Asp Arg Val Lys Phe Ser Arg Ser Ala Asp Ala Pro Ala Tyr Gln Gln
        515                 520                 525

Gly Gln Asn Gln Leu Tyr Asn Glu Leu Asn Leu Gly Arg Arg Glu Glu
    530                 535                 540

Tyr Asp Val Leu Asp Lys Arg Arg Gly Arg Asp Pro Glu Met Gly Gly
545                 550                 555                 560

Lys Pro Arg Arg Lys Asn Pro Gln Glu Gly Leu Tyr Asn Glu Leu Gln
                565                 570                 575

Lys Asp Lys Met Ala Glu Ala Tyr Ser Glu Ile Gly Met Lys Gly Glu
            580                 585                 590

Arg Arg Arg Gly Lys Gly His Asp Gly Leu Tyr Gln Gly Leu Ser Thr
        595                 600                 605

Ala Thr Lys Asp Thr Tyr Asp Ala Leu His Met Gln Ala Leu Pro Pro
    610                 615                 620

Arg
625
```

<210> SEQ ID NO 8
<211> LENGTH: 68
<212> TYPE: PRT
<213> ORGANISM: Artificial Sequence
<220> FEATURE:
<223> OTHER INFORMATION: CD28 TM and ICD

```
<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65


<210> SEQ ID NO 9
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: repeat n times, where n is an integer of at
      least one

<400> SEQUENCE: 9

Gly Ser Gly Gly Ser
1               5


<210> SEQ ID NO 10
<211> LENGTH: 4
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(4)
<223> OTHER INFORMATION: repeat n times, where n is an integer of at
      least one

<400> SEQUENCE: 10

Gly Gly Gly Ser
1


<210> SEQ ID NO 11
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: repeat n times, where n is an integer of at
      least one

<400> SEQUENCE: 11

Gly Gly Gly Gly Ser
1               5


<210> SEQ ID NO 12
<211> LENGTH: 4
<212> TYPE: PRT
<213> ORGANISM: Artificial Sequence
<220> FEATURE:
<223> OTHER INFORMATION: Linker
```

<400> SEQUENCE: 12

Gly Gly Ser Gly
1

<210> SEQ ID NO 13
<211> LENGTH: 5
<212> TYPE: PRT
<213> ORGANISM: Artificial Sequence
<220> FEATURE:
<223> OTHER INFORMATION: Linker

<400> SEQUENCE: 13

Gly Gly Ser Gly Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Linker

<400> SEQUENCE: 14

Gly Ser Gly Ser Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Linker

<400> SEQUENCE: 15

Gly Ser Gly Gly Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Linker

<400> SEQUENCE: 16

Gly Gly Gly Ser Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Linker

<400> SEQUENCE: 17

Gly Ser Ser Ser Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Linker

<400> SEQUENCE: 18

Gly Gly Gly Gly Ser
1 5

<210> SEQ ID NO 19
<211> LENGTH: 15
<212> TYPE: PRT
<213> ORGANISM: Artificial Sequence
<220> FEATURE:
<223> OTHER INFORMATION: Linker

<400> SEQUENCE: 19

Gly Gly Gly Gly Ser Gly Gly Gly Gly Ser Gly Gly Gly Gly Ser
1 5 10 15

<210> SEQ ID NO 20
<211> LENGTH: 45
<212> TYPE: PRT
<213> ORGANISM: Artificial Sequence
<220> FEATURE:
<223> OTHER INFORMATION: Linker

<400> SEQUENCE: 20

Gly Gly Thr Gly Gly Cys Gly Gly Thr Gly Gly Cys Thr Cys Gly Gly
1 5 10 15

Gly Cys Gly Gly Thr Gly Gly Thr Gly Gly Gly Thr Cys Gly Gly Gly
20 25 30

Thr Gly Gly Cys Gly Gly Cys Gly Gly Ala Thr Cys Thr
35 40 45

<210> SEQ ID NO 21
<211> LENGTH: 5
<212> TYPE: PRT
<213> ORGANISM: Artificial Sequence
<220> FEATURE:
<223> OTHER INFORMATION: Hinge

<400> SEQUENCE: 21

Asp Lys Thr His Thr
1 5

<210> SEQ ID NO 22
<211> LENGTH: 4
<212> TYPE: PRT
<213> ORGANISM: Artificial Sequence
<220> FEATURE:
<223> OTHER INFORMATION: Hinge

<400> SEQUENCE: 22

Cys Pro Pro Cys
1

<210> SEQ ID NO 23
<211> LENGTH: 15
<212> TYPE: PRT
<213> ORGANISM: Artificial Sequence
<220> FEATURE:
<223> OTHER INFORMATION: Hinge

<400> SEQUENCE: 23

Cys Pro Glu Pro Lys Ser Cys Asp Thr Pro Pro Pro Cys Pro Arg
1 5 10 15

<210> SEQ ID NO 24
<211> LENGTH: 12

<212> TYPE: PRT
<213> ORGANISM: Artificial Sequence
<220> FEATURE:
<223> OTHER INFORMATION: Hinge

<400> SEQUENCE: 24

Glu Leu Lys Thr Pro Leu Gly Asp Thr Thr His Thr
1 5 10

<210> SEQ ID NO 25
<211> LENGTH: 10
<212> TYPE: PRT
<213> ORGANISM: Artificial Sequence
<220> FEATURE:
<223> OTHER INFORMATION: Hinge

<400> SEQUENCE: 25

Lys Ser Cys Asp Lys Thr His Thr Cys Pro
1 5 10

<210> SEQ ID NO 26
<211> LENGTH: 7
<212> TYPE: PRT
<213> ORGANISM: Artificial Sequence
<220> FEATURE:
<223> OTHER INFORMATION: Hinge

<400> SEQUENCE: 26

Lys Cys Cys Val Asp Cys Pro
1 5

<210> SEQ ID NO 27
<211> LENGTH: 7
<212> TYPE: PRT
<213> ORGANISM: Artificial Sequence
<220> FEATURE:
<223> OTHER INFORMATION: Hinge

<400> SEQUENCE: 27

Lys Tyr Gly Pro Pro Cys Pro
1 5

<210> SEQ ID NO 28
<211> LENGTH: 15
<212> TYPE: PRT
<213> ORGANISM: Artificial Sequence
<220> FEATURE:
<223> OTHER INFORMATION: Hinge

<400> SEQUENCE: 28

Glu Pro Lys Ser Cys Asp Lys Thr His Thr Cys Pro Pro Cys Pro
1 5 10 15

<210> SEQ ID NO 29
<211> LENGTH: 12
<212> TYPE: PRT
<213> ORGANISM: Artificial Sequence
<220> FEATURE:
<223> OTHER INFORMATION: Hinge

<400> SEQUENCE: 29

Glu Arg Lys Cys Cys Val Glu Cys Pro Pro Cys Pro
1 5 10

<210> SEQ ID NO 30
<211> LENGTH: 17
<212> TYPE: PRT

<213> ORGANISM: Artificial Sequence
<220> FEATURE:
<223> OTHER INFORMATION: Hinge

<400> SEQUENCE: 30

Glu Leu Lys Thr Pro Leu Gly Asp Thr Thr His Thr Cys Pro Arg Cys
1 5 10 15

Pro

<210> SEQ ID NO 31
<211> LENGTH: 12
<212> TYPE: PRT
<213> ORGANISM: Artificial Sequence
<220> FEATURE:
<223> OTHER INFORMATION: Hinge

<400> SEQUENCE: 31

Ser Pro Asn Met Val Pro His Ala His His Ala Gln
1 5 10

<210> SEQ ID NO 32
<211> LENGTH: 15
<212> TYPE: PRT
<213> ORGANISM: Artificial Sequence
<220> FEATURE:
<223> OTHER INFORMATION: Hinge

<400> SEQUENCE: 32

Glu Pro Lys Ser Cys Asp Lys Thr Tyr Thr Cys Pro Pro Cys Pro
1 5 10 15

<210> SEQ ID NO 33
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 33

Arg Xaa Lys Arg
1

<210> SEQ ID NO 34
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 34

Arg Xaa Arg Arg
1

<210> SEQ ID NO 35
<211> LENGTH: 5
<212> TYPE: PRT
<213> ORGANISM: Artificial Sequence
<220> FEATURE:
<223> OTHER INFORMATION: Furin cleavage site
<220> FEATURE:

<221> NAME/KEY: misc_feature
<222> LOCATION: (1)..(1)
<223> OTHER INFORMATION: Xaa is Lys or Arg
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is Lys or Arg

<400> SEQUENCE: 35

Xaa Arg Xaa Xaa Arg
1               5

<210> SEQ ID NO 36
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: misc_feature
<222> LOCATION: (2)..(3)
<223> OTHER INFORMATION: Xaa can be any naturally occurring amino acid

<400> SEQUENCE: 36

Arg Xaa Xaa Arg
1

<210> SEQ ID NO 37
<211> LENGTH: 4
<212> TYPE: PRT
<213> ORGANISM: Artificial Sequence
<220> FEATURE:
<223> OTHER INFORMATION: Furin cleavage site

<400> SEQUENCE: 37

Arg Gln Lys Arg
1

<210> SEQ ID NO 38
<211> LENGTH: 26
<212> TYPE: DNA
<213> ORGANISM: Artificial Sequence
<220> FEATURE:
<223> OTHER INFORMATION: Primer

<400> SEQUENCE: 38
cacgtcctag gatggcctta ccagtg 26

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
gtggtcgact tatgcgctcc tgctgaac 28

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
agtgggggga catcaagcag ccatgcaaat 30

<210> SEQ ID NO 41
<211> LENGTH: 27
<212> TYPE: DNA
<213> ORGANISM: Artificial Sequence
<220> FEATURE:
<223> OTHER INFORMATION: Primer

<400> SEQUENCE: 41
tgctatgtca gttccccttg gttctct 27

<210> SEQ ID NO 42
<211> LENGTH: 28
<212> TYPE: DNA
<213> ORGANISM: Artificial Sequence
<220> FEATURE:
<223> OTHER INFORMATION: Primer

<400> SEQUENCE: 42
ccatcaatga ggaagctgca gaatggga 28

<210> SEQ ID NO 43
<211> LENGTH: 18
<212> TYPE: DNA
<213> ORGANISM: Artificial Sequence
<220> FEATURE:
<223> OTHER INFORMATION: Primer

<400> SEQUENCE: 43
gatttggacc tgcgagcg 18

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
gcggctgtct ccacaagt 18

<210> SEQ ID NO 45
<211> LENGTH: 16
<212> TYPE: DNA
<213> ORGANISM: Artificial Sequence
<220> FEATURE:
<223> OTHER INFORMATION: Probe

<400> SEQUENCE: 45
ctgacctgaa ggctct 16

DUAL CAR EXPRESSING T CELLS INDIVIDUALLY LINKED TO CD28 AND 4-1BB

CROSS-REFERENCE TO RELATED APPLICATION

The present application is entitled to priority under 35 U.S.C. § 119(e) to U.S. Provisional Patent Application No. 62/858,506, filed Jun. 7, 2019, which is hereby incorporated by reference in its entirety herein.

STATEMENT REGARDING FEDERALLY SPONSORED RESEARCH OR DEVELOPMENT

This invention was made with government support under AI117950 and AI126620 awarded by the National Institutes of Health. The government has certain rights in the invention.

REFERENCE TO SEQUENCE LISTING

The Sequence Listing concurrently submitted herewith as a text file named "046483_7261US1_Sequence_Listing.txt." created on Jun. 5, 2020 and having a size of 24,700 bytes is herein incorporated by reference pursuant to 37 C.F.R. § 1.52 (e) (5).

BACKGROUND OF THE INVENTION

Chimeric Antigen Receptor ($CAR^-$) T cell immunotherapies have induced durable remissions for treatment-refractory malignancies by infusing engineered, cancer-specific effector T cells. In contrast, less progress has been made developing a successful CAR T cell therapy for HIV infection, despite the fact that next-generation CAR T cells may be uniquely equipped to overcome many of the mechanisms by which HIV undermines host immunity, including epitope escape through rapid evolution, T cell exhaustion, and waning $CD4^+$ T cell-help. Indeed, a potent and sustained T cell response of the kind that CAR T cells can afford is likely to be essential for the development of an effective HIV cure.

CARs endow novel immune specificity to patient T cells through expression of an extracellular antigen recognition domain linked to an intracellular T cell costimulatory domain and the CD3-ζ chain. The archetypal costimulatory domains for second-generation CARs are CD28 and 4-1BB, both of which are incorporated into licensed CD19-targeting CAR T cell therapies. Preclinical cancer models demonstrate that CD28-costimulated CAR T cells exhibit profound effector function resulting in rapid tumor clearance, but have limited persistence in vivo. In contrast, 4-1BB-costimulated CAR T cells have slower antitumor response kinetics, but sustained cellular division and greater long-term survival. Importantly, the distinct signaling pathways used by CD28 and 4-1BB prompt unique metabolic, phenotypic and functional T cell profiles that appear to engender optimal CAR T cell activity for specific diseases. Hence, great emphasis has been placed on discovering costimulatory signals that fully potentiate CAR T cell function.

The earliest clinical trials of CAR T cell therapy utilized first-generation, HIV-specific CD4-based CAR T cells expressing the CD3-ζ endodomain, and were ineffective at treating either chronically-infected or antiretroviral therapy (ART)-suppressed individuals. However, the cancer immunotherapy field has since driven significant developments in CAR technology, which has renewed interest in applying these advances to treatment of HIV. In fact, several recent studies have evaluated the utility of CAR T cells in this disease setting. However, critical knowledge gaps remain in our understanding of the mechanistic underpinnings of successful and failed CAR T cell therapy, particularly in a model system that recapitulates HIV pathogenesis, which would serve to accelerate the development of this strategy for cure initiatives.

There is a need in the art for improved CAR T cell design. The present invention addresses this need.

SUMMARY OF THE INVENTION

As described herein, the present invention relates to compositions and methods for T cells that express dual CARs individually linked to distinct costimulatory domains.

In one aspect, a nucleic acid comprising a first polynucleotide sequence encoding a first chimeric receptor comprising a first binding domain, a first transmembrane domain, a first costimulatory domain that confers enhanced pro-survival function, and a CD3z intracellular signaling domain; and a second polynucleotide sequence encoding a second chimeric receptor comprising a second binding domain, a second transmembrane domain, a second costimulatory domain that confers enhanced effector function, and a CD3z intracellular signaling domain, is provided.

In another aspect, a nucleic acid comprising a first polynucleotide sequence encoding a first chimeric receptor comprising the extracellular domains of a CD4 molecule, a CD8α transmembrane domain, a 4-1BB costimulatory domain, and a CD3z intracellular signaling domain; and a second polynucleotide sequence encoding a second chimeric receptor comprising the extracellular domains of a CD4 molecule, a CD28 transmembrane domain, a CD28 costimulatory domain, and a CD3z intracellular signaling domain, is provided.

In another aspect, a modified immune cell or precursor cell thereof, comprising a first chimeric receptor comprising a first binding domain, a first transmembrane domain, a first costimulatory domain that confers enhanced pro-survival function, and a CD3z intracellular signaling domain; and a second chimeric receptor comprising a second binding domain, a second transmembrane domain, a second costimulatory domain that confers enhanced effector function, and a CD3z intracellular signaling domain, is provided.

In certain embodiments, the first costimulatory domain is a 4-1BB costimulatory domain. In certain embodiments, the second costimulatory domain is a CD28 costimulatory domain.

In certain embodiments, the first transmembrane domain and/or the second transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In certain embodiments, the first transmembrane domain is a 4-1BB transmembrane domain. In certain embodiments, the first transmembrane domain is a CD8α transmembrane domain. In certain embodiments, the second transmembrane domain is a CD28 transmembrane domain.

In certain embodiments, the first chimeric receptor and/or the second chimeric receptor further comprises a hinge domain. In certain embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof.

In certain embodiments, the first binding domain binds to a first target, and the second binding domain binds to a second target. In certain embodiments, the first target and the second target are the same. In certain embodiments, the first target and the second target are distinct epitopes of the same molecule. In certain embodiments, the first target and the second target are different.

In certain embodiments, the first target and/or the second target is human immunodeficiency virus type 1 (HIV-1). In certain embodiments, the first target and the second target is human immunodeficiency virus type 1 (HIV-1). In certain embodiments, the first target and/or the second target is envelope glycoprotein gp120. In certain embodiments, the first target and the second target is envelope glycoprotein gp120.

In certain embodiments, the first binding domain and/or the second binding domain comprises the extracellular domains of a CD4 molecule. In certain embodiments, the first binding domain and the second binding domain comprises the extracellular domains of a CD4 molecule.

In certain embodiments, the first target and/or the second target is a tumor associated antigen. In certain embodiments, the tumor associated antigen is a liquid tumor antigen. In certain embodiments, the liquid tumor antigen is CD19 or CD22. In certain embodiments, the tumor associated antigen is a solid tumor antigen.

In certain embodiments, the first polynucleotide sequence and the second polynucleotide sequence is separated by a linker. In certain embodiments, the linker comprises an internal ribosome entry site (IRES), a furin cleavage site, a self-cleaving peptide, or any combination thereof. In certain embodiments, the linker comprises a furin cleavage site and a self-cleaving peptide. In certain embodiments, the self-cleaving peptide is a 2A peptide. In certain embodiments, the 2A peptide is selected from the group consisting of porcine teschovirus-1 2A (P2A), *Thosea asigna* virus 2A (T2A), equine rhinitis A virus 2A (E2A), and foot-and-mouth disease virus 2A (F2A).

In certain embodiments, the nucleic acid comprises from 5' to 3': the first polynucleotide sequence, the linker, and the second polynucleotide sequence. In certain embodiments, the nucleic acid comprises from 5' to 3': the second polynucleotide sequence, the linker, and the first polynucleotide sequence.

In certain embodiments, the nucleic acid further comprises a polynucleotide sequence encoding an HIV fusion inhibitor. Examples of fusion inhibitors include but are not limited to Enfuvirtide, Maraviroc, BMS-488043, PRO-542, Leronlimab, Aplaviroc, Ibalizumab, Temsavir, and the like. In certain embodiments, the nucleic acid further comprises a polynucleotide sequence encoding an HIV fusion inhibitor, wherein the HIV fusion inhibitor is a cell-surface-expressed HIV fusion inhibitor. In certain embodiments, the nucleic acid further comprises a polynucleotide sequence encoding an HIV fusion inhibitor, wherein the HIV fusion inhibitor is C34-CXCR4.

In certain embodiments, the cell expressing the HIV fusion inhibitor exhibits increased resistance to infection by HIV, as compared to a control cell not expressing the HIV fusion inhibitor.

In another aspect, an expression construct comprising any one of the nucleic acids disclosed herein, is provided.

In certain embodiments, the expression construct further comprises an EF-1α promoter.

In certain embodiments, the expression construct further comprises a rev response element (RRE). In certain embodiments, the expression construct further comprises a woodchuck hepatitis virus posttranscriptional regulatory element (WPRE). In certain embodiments, the expression construct further comprises a cPPT sequence.

In certain embodiments, the expression construct is a viral vector selected from the group consisting of a retroviral vector, a lentiviral vector, an adenoviral vector, and an adeno-associated viral vector.

In certain embodiments, the expression construct is a lentiviral vector. In certain embodiments, the lentiviral vector is a self-inactivating lentiviral vector.

In another aspect, a modified immune cell or precursor cell thereof, comprising a first chimeric receptor comprising the extracellular domains of a CD4 molecule, a CD8α transmembrane domain, a 4-1BB costimulatory domain, and a CD3z intracellular signaling domain; and a second chimeric receptor comprising the extracellular domains of a CD4 molecule, a CD28 transmembrane domain, a CD28 costimulatory domain, and a CD3z intracellular signaling domain, is provided.

In certain embodiments, the modified cell is a modified immune cell. In certain embodiments, the modified cell is a modified T cell. In certain embodiments, the modified cell is an autologous cell. In certain embodiments, the modified cell is an autologous cell obtained from a human subject.

In another aspect, a pharmaceutical composition comprising a therapeutically effective amount of a modified immune cell or precursor cell thereof, wherein the modified cell comprises a first chimeric receptor comprising a first binding domain, a first transmembrane domain, a first costimulatory domain that confers enhanced pro-survival function, and a CD3z intracellular signaling domain; and a second chimeric receptor comprising a second binding domain, a second transmembrane domain, a second costimulatory domain that confers enhanced effector function, and a CD3z intracellular signaling domain, is provided.

In another aspect, a pharmaceutical composition comprising a therapeutically effective amount of a modified immune cell or precursor cell thereof, wherein the modified cell comprises a first chimeric receptor comprising the extracellular domains of a CD4 molecule, a CD8α transmembrane domain, a 4-1BB costimulatory domain, and a CD3z intracellular signaling domain; and a second chimeric receptor comprising the extracellular domains of a CD4 molecule, a CD28 transmembrane domain, a CD28 costimulatory domain, and a CD3z intracellular signaling domain, is provided.

In another aspect, a method of treating a disease or disorder in a subject in need thereof, is provided. The method comprises administering any one of the modified cells disclosed herein, or any one of the pharmaceutical compositions disclosed herein, to the subject.

In another aspect, a method of treating a disease or disorder in a subject in need thereof, comprising administering a modified immune cell or precursor cell thereof comprising: a first chimeric receptor comprising a first binding domain, a first transmembrane domain, a first costimulatory domain that confers enhanced pro-survival function, and a CD3z intracellular signaling domain; and a second chimeric receptor comprising a second binding domain, a second transmembrane domain, a second costimulatory domain that confers enhanced effector function, and a CD3z intracellular signaling domain, is provided.

In certain embodiments, the disease or disorder is a viral disease. In certain embodiments, the viral disease is HIV-1 infection.

In certain embodiments, the disease or disorder is a cancer. In certain embodiments, the cancer is a liquid tumor. In certain embodiments, the cancer is a hematological malignancy. In certain embodiments, the cancer is a solid tumor.

In another aspect, a method of treating an HIV-1 infection in a subject in need thereof, comprising administering a modified immune cell or precursor cell thereof comprising: a first chimeric receptor comprising the extracellular domains of a CD4 molecule, a CD8α transmembrane domain, a 4-1BB costimulatory domain, and a CD3z intracellular signaling domain; and a second chimeric receptor comprising the extracellular domains of a CD4 molecule, a CD28 transmembrane domain, a CD28 costimulatory domain, and a CD3z intracellular signaling domain, is provided.

In another aspect, a method of treating a cancer in a subject in need thereof, comprising administering a modified T cell comprising: a first chimeric receptor comprising a first binding domain, a first transmembrane domain, a first costimulatory domain that confers enhanced pro-survival function, and a CD3z intracellular signaling domain; and a second chimeric receptor comprising a second binding domain, a second transmembrane domain, a second costimulatory domain that confers enhanced effector function, and a CD3z intracellular signaling domain, is provided.

In another aspect, a method of treating an HIV-1 infection in a subject in need thereof, comprising administering a modified T cell comprising: a first chimeric receptor comprising the extracellular domains of a CD4 molecule, a CD8α transmembrane domain, a 4-1BB costimulatory domain, and a CD3z intracellular signaling domain; and a second chimeric receptor comprising the extracellular domains of a CD4 molecule, a CD28 transmembrane domain, a CD28 costimulatory domain, and a CD3z intracellular signaling domain, is provided.

In certain embodiments, the modified cell is a modified immune cell. In certain embodiments, the modified cell is a modified T cell. In certain embodiments, the modified cell is an autologous cell. In certain embodiments, the modified cell is an autologous cell obtained from a human subject.

In certain embodiments, the subject is human.

In certain embodiments, administration of the modified cell decreases HIV-induced loss of one or more of the following cells: $CD4^+$ T cells, $CD4^-$ T cells, $CD8^+$ T cell, $CD8^-$ T cells, memory $CD4^+$ T cells, and $CD14^+$ macrophages as compared to a subject not having been administered the modified cell. In certain embodiments the decrease is at least 5%, at least 10%, at least 20%, at least 30%, at least 40%, at least 50%, at least 60%, at least 70%, at least 80%, or at least 90%.

In certain embodiments, administration of the modified cell decreases incidence of HIV-infected cells in one or more of the following cells: $CD4^+$ T cells, $CD4^-$ T cells, $CD8^+$ T cell, $CD8^-$ T cells, central memory $CD4^+$ T cells, and $CD14^+$ macrophages as compared to a subject not having been administered the modified cell. In certain embodiments administration decreases the incidence of HIV-infected cells by at least 5%, at least 10%, at least 20%, at least 30%, at least 40%, at least 50%, at least 60%, at least 70%, at least 80%, or at least 90%. In certain embodiments administration decreases the incidence of HIV-infected $CD4^+$ cells by at least 5%, at least 10%, at least 20%, at least 30%, at least 40%, at least 50%.

In certain embodiments, the subject's blood comprises at least about 100 modified cells/L of blood by at least week three after a single administration of the modified T cell.

In certain embodiments, the modified cell binds to the first and second targets of a cell expressing the first and second targets, and kills the cell via granule-mediated cytolysis.

In certain embodiments, the method further comprises administering one or more anti-retroviral therapeutic agents.

In another aspect, a method for generating a modified immune cell comprising introducing into an immune cell any of the nucleic acids disclosed herein, is provided.

In certain embodiments, the immune cell is obtained from the group consisting of T cells, dendritic cells, and stem cells. In certain embodiments, the immune cell is a T cell selected from the group consisting of a $CD8^+$ T cell, a $CD4^+$ T cell, a naïve T cell, a central memory T cell, a stem cell memory T cell, an effector memory T cell, a natural killer T cell, and a regulatory T cell.

In certain embodiments, the method further comprises expanding the T cell. In certain embodiments, the method further comprises expanding the T cell, wherein the T cell is expanded in the range of about 150 fold to about 500 fold. In certain embodiments, the method further comprises expanding the T cell, wherein the T cell is expanded by at least about 150 fold. In certain embodiments, the method further comprises expanding the T cell, wherein the T cell is expanded by at least about 300 fold. In certain embodiments, the method further comprises expanding the T cell, wherein the T cell expansion is in vivo.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments, which are presently preferred. It should be understood, however, that the invention is not limited to the precise arrangements and instrumentalities of the embodiments shown in the drawings.

CAR T cell populations are capable of suppressing HIV replication compared to untransduced T cells (UTD), but CD28 CAR T cells exert greater control over HIV at the indicated time points than 4-1BBζ CAR T cells. This demonstrates that CD28 CAR T cells exert greater effector function than 4-1BB CAR T cells.

FIG. 4A is a schematic for the manufacturing of BLT mouse-derived CAR T cells. FIG. 4B shows representative growth kinetics of BLT mouse-derived and adult human PBMC-derived CAR.ζ T cells following activation with anti-CD3/CD28 Dynabeads. FIG. 4C is a series of FACS plots of $CD4^+$ CAR. ζ T cells expressing MIP-1β, TNF, IL-2 and GM-CSF after in vitro stimulation with $HIV_{yu2}$ $GP160^+$ K562 cells (K.Env). FIG. 4D shows quantification of intracellular expression of the indicated effector molecules by $CD8^+$ CAR.ζ T cells. FIG. 4E shows quantification of intracellular expression of the indicated effector molecules Data shows expression of each molecule from 3 distinct donors per source. FIG. 4F shows a schematic of a gating strategy used to identify active caspase-$3^+$ $HIV_{GAG}^+$ target cells for analysis of HIV elimination assay. FIG. 4G shows FACS plots and FIG. 4H shows cumulative data demonstrating the coordinated upregulation of granzyme B and perforin in BLT mouse-derived and human donor-derived CAR.ζ T cells following in vitro stimulation with K.Env (stim) or K.WT (unstim) cells. Data shows expression from 3 distinct donors per source. For data in FIG. 4C, line and error bars indicate mean SEM.

FIG. 5A is a set of FACS plots identifying CAR.ζ T cells from each T cell source as GFP+ and $CD4^+$. FIG. 5B shows after 10 days of culture, $CD8^+$ CAR.ζ T cells were mixed with $HIV_{YU2}$ $GP160^+$ K562 cells (K.Env) and upregulation of human cytokines was measured. FIG. 5C shows polyfunctionality profiles of combinatorial subsets for $CD4^+$ and $CD8^+$ CAR.ζ T cells producing 0 to 5 of the human cytokines GM-CSF, IFN-γ, IL-2, MIP-1β, and TNF. Average of 3 unique donors per T cell source. FIGS. 5D-5F show results from HIV suppression assays as described in Materials and Methods. FIG. 5D shows FACS plots indicating the frequency of HIV-infected T cells 6 days after co-culturing with BLT mouse- or human-derived CAR.ζ T cells at indicated effector-to-target (E:T) ratios. FIGS. 5E-5F show a summary of the frequency of HIV-infected target cells (live CAR $CD8^-$ T cells) at 2, 4 and 6 days after co-culture with BLT mouse-derived (FIG. 5E), or human-derived CAR.ζ and untransduced (UTD) T cells (FIG. 5F) at indicated E:T ratios. FIGS. 5G-5H show results from HIV elimination assays as described in Materials and Methods. FIG. 5G is a series of FACS plots and FIG. 5H is a summary of the data for frequency of active caspase-3 within live target cells ($CTV^+$ $HIVgag^+$ T cells) after 24-hour co-culture with BLT mouse- or human-derived CAR.ζ and UTD T cells at 1:1 E:T ratio. Each symbol represents the average of duplicates per donor (n=3). For FIGS. 5E-5F each donor was performed in triplicate. Symbols and lines indicate mean and error bars show ±SEM.

FIGS. 6A-6E show BLT mouse-derived T cells were transduced with either mCherry.T2A.CAR.ζ, iRFP670.T2A.CAR.BBζ, or GFP.T2A.CAR.28ζ. $5\times10^6$ CAR-transduced T cells of each type were mixed prior to infusion into syngeneic mice (n=8). FIG. 6A shows the frequency of each CAR T cell type within the pre-infusion T cell product. FIG. 6B shows the frequency of peripheral CAR T cells within the same mouse 5 weeks post-infusion. FIG. 6C shows peripheral concentration and FIG. 6D shows cumulative persistence of each CAR T cell type over 5 weeks. FIG. 6E shows relative tissue frequency of each CAR T cell type 7 weeks post-infusion. FIG. 6F shows in a separate study, 2 weeks after infusion of the CAR T cell mixture described in FIG. 6A, BLT mice received $10^7$ irradiated wild-type K562 (K.WT; n=8) or $HIV_{YU2}$ $GP160^+$ K562 (K.Env; n=8) cells. Peripheral concentration of each CAR T cell type following K.WT or K.Env stimulation. FIG. 6G is a series of FACS plots indicating frequency of MIP-$1\beta^+$ and $TNF^+$ CAR.BBζ and CAR.28ζ T cells within the same mouse after ex vivo stimulation. CAR.ζ cells were too infrequency for analysis. FIG. 6H shows frequency of granzyme B and perforin in $CD8^+$ CAR T cells within the same mice ex vivo. FIGS. 6I-6K show results from experiments wherein mice were infused with 5×10[6] CD19-specific CAR.BBζ (n=4) or control CD4-based CAR.BBζ T cells (n=3). FIG. 6I shows concentrations of peripheral $CD19^+$ cells following infusion. FIG. 6J is a series of FACS plots showing frequency of $CD19^+$ cells out of total $huCD45^+$ cells. FIG. 6K shows the number of $CD19^+$ cells in tissues 7 weeks post-infusion. FIGS. 6C, 6F, and 6I symbols indicate mean and error bars show ±SEM, and FIGS. 6D and 6K symbols represent individual mice, bars indicate mean and error bars show ±SEM. FIG. 6D Friedman's test with Dunn's multiple corrections test, and FIGS. 6F and 6H, Wilcoxon matched-pairs signed rank test performed to calculate significance (*P<0.05, **P<0.01).

FIG. 8A shows mean log plasma viral RNA (copies $mL^{-1}$) in $HIV_{JRCSF}$-infected mice treated with ART from week 3 to 5 (G1 and G2 mice; gray box) or from week 3 to 8 (G3 and G4 mice). At 5 weeks post-infection, mice in G1 (n=6) and G3 (n=10) received 107 CAR.BBζ T cells, and mice in G2 (n=6) and G4 (n=9) received 107 inactive control CAR.BBΔζ T cells. Thin dotted line denotes limit of quantification. FIG. 8B shows FACS plots and FIG. 8C depicts summary data showing the frequency of total memory CD4+ T cells (CAR−) following ART cessation in CAR.BBζ and control CAR.BBΔζ T cell-treated mice. FIGS. 8D-8E shows concentrations of peripheral CAR T cells for G1/G2 and G3/G4. FIG. 8F shows frequency of CAR T cells in tissues 12 weeks post-CAR T cell infusion for G1/G3 and G2/G4. FIG. 8G shows PD-1 and TIGIT expression on peripheral CAR.BBζ or CAR.BBΔζ T cells from G1/G2 after ART discontinuation. FIGS. 8H-8L show FACS analysis of splenic tissue of BLT mice 12 weeks after ART cessation. FIG. 8H shows co-expression of TOX and 2B4, PD-1 or TIGIT on peripheral CAR.BBζ or CAR.BBΔζ T cells. FIG. 8I shows frequency of TOX− and TOX+ CAR.BBΔζ T cells positive for indicated inhibitory receptors. FIG. 8J shows requency of T-bet and Eomes expressing CAR.BBζ and CAR.BBΔζ T cells. FIG. 8K shows frequency of TOX expression within T-bet+ and Eomes+ CAR.BBζ and CAR.BBΔζ T cells. FIG. 8L shows memory distribution of $2B4^+PD\text{-}1^+$ $TIGIT^+$ and $Eomes^{hi}T\text{-}bet^{dim}$ CAR.BBζ T cells. FIGS. 8F, 8I, 8J, and 8K: Wilcoxon rank sum test used to calculate significance (P<0.01, *P<0.001, **P<0.0001). Bars and symbols indicate mean and error bars show ±SEM. FIGS. 8I, 8J, and 8**K: Symbols represent individual mice.

FIG. 9A is a schematic of a gating strategy used to identify total memory CD4+ T cells (CAR−). FIG. 9B shows percentages of $CD4^+$ T cells (CAR−) out of total CD3+ cells from the indicated tissues in BLT mice treated with CAR.BBζ T cells (G1) or control CAR.BBΔζ (G2) T cells, 12 weeks after the discontinuation of ART. FIG. 9C shows results from 9 weeks after the discontinuation of ART for G3/4. Symbols represent individual mice. Bars indicate mean and error bars show ±SEM. N/A denotes tissue samples where viable human cells were too infrequent for analysis.

FIG. 10A shows mean plasma viral RNA (copies $mL^{-1}$) for mice in G1 (thick line; right axis) and frequency of post-challenge peripheral memory ($CD45RA^-$) $CD4^+$ T cells in $HIV^-$ mice (white circles) and $HIV^+$ mice (G1; black circles) (left y-axis). Thin dotted line denotes limit of viral load quantification. Shaded box indicates window of ART. Symbols indicate mean and error bars show ±SEM. FIG. 10B shows frequency of CCR5 expression on the indicated populations of CD4+ T cells from the peripheral blood of BLT mice.

FIG. 11A shows frequency of CD4+ and FIG. 11B shows frequency of CD8+ CAR.BBζT cells (G1) and control CAR.BBΔζ T cells (G2) co-expressing TIGIT and PD-1 after infusion. Shaded box indicates the window of ART. Symbols indicate mean and error bars show ±SEM. FIG. 11C shows frequency of CD4+ and FIG. 11B shows frequency of CD8+ CAR.BBζ T cells (G1) and control CAR.BBΔζ T cells (G2) co-expressing TIGIT, PD-1 and 2B4 in tissues 12 weeks post-infusion. FIG. 11W shows cumulative data indicating the frequency of 2B4+, PD-1+ and TIGIT+CD4+ CAR.BBζ T cells (G1) compared to CAR-$CD4^+$ T cells (G1) within the spleens of the same mice, and (FIG. 11F) CD8+ CAR.BBζ T cells (G1) compared to CAR-$CD8^+$ T cells (G1) within the spleens of the same mice. FIGS. 11C-11F: Bars indicate mean, error bars show ±SEM and symbols represent individual mice. Significance was calculated using Wilcoxon rank sum test (*P<0.05al**P<0.01).

FIG. 12A is a series of FACS plots showing the change in Eomes and T-bet expression within the different CAR T cell types over time. FIG. 12B shows summary data indicating the longitudinal frequency of $Eomes^{hi}T\text{-}bet^{dim}$ CD8+(left panel) and CD4+ (right panel) CAR T cells (left y-axis), and mean log plasma viral RNA (copies $mL^{-1}$) (right y-axis). Thin dotted line denotes limit of viral load quantification. Symbols indicate mean and error bars show ±SEM. FIG. 12C shows Spearman correlation analysis of frequency of $Eomes^{hi}T\text{-}bet^{dim}$ CD8+ CAR.BBζ T cells compared with viral burden measured as the frequency of $HIV_{GAG}{}^+$ $CD8^-$ T cells in various tissues 10 weeks post-infection.

FIG. 13A shows FACS plots and FIG. 13B shows cumulative data for the expression of MIP-10, CD107a and granzyme B in $CD8^+$ CAR.BBζ or CAR.BBΔζ T cells. The dotted line indicates the frequency of $CD8^+$ CAR.BBζ T cells from the pre-infusion TCP expressing the indicated protein. The bars indicate mean and the error bars show ±SEM. Significance was calculated using Wilcoxon rank sum test (*P<0.05 and ***P<0.001).

FIGS. 14A-14N illustrate the finding that dual-CAR T cell product mitigates $CD4^+$ T cell loss and exhibits superior proliferative capacity. FIGS. 14A-14J show results from experiments wherein mice were challenged with $HIV_{JRCSF}$ (n=12) or $HIV_{MJ4}$ (n=12) and 48 hours later 6 mice from each group were infused with Dual-CAR T cell product (TCP) or were untreated (Untx). FIG. 14A illustrates dual-CAR TCP comprises CAR.BBζ, CAR.28ζ and Dual-CAR T cells. FIGS. 14B and 14D show concentrations of total peripheral CAR T cells in individual mice (dotted lines; left y-axis) and mean log plasma viral RNA (copies $mL^{-1}$) (solid lines; right y-axis) in $HIV_{JRCSF}$- and $HIV_{MJ4}$-infected mice, respectively. Thin black dotted line denotes limit of quantification. FIGS. 14C and 14E show frequency of peripheral memory $CD4^+$ T cells ($CAR^-$). FIG. 14F shows frequency of $CD4^+$ T cell ($CAR^-$) memory subsets in tissue from $HIV_{MJ4}$- and (FIG. 14G) $HIV_{JRCSF}$-infected mice 8 weeks post-CAR T cell infusion. FIG. 14H shows longitudinal frequency of each CAR T cell type present in the Dual-CAR TCP. FIG. 14I shows peak peripheral frequency and FIG. 14J shows cumulative persistence of CAR T cells. FIGS. 14K-14N show dual-CAR TCP and $3^{rd}$-generation (3G) CD4-based CAR T cells were combined, equalizing the frequency of Dual-CAR and 3G-CAR T cells (FIG. 19C) prior to infusion into $HIVw_4$-infected mice (n=6). FIG. 14K show overlaid FACS plots showing frequency of peripheral Dual-CAR ($iRFP670^+NGFR^+$) and 3G-CAR ($GFP^+$) T cells within the same mouse. FIG. 14L shows concentration of peripheral CAR T cells. FIG. 14M shows total number of splenic CAR T cells and FIG. 14N shows cumulative CAR T cell persistence 5 weeks post-infection. For all data, bars and symbols indicate mean and error bars show ±SEM, except FIGS. 14M-14N where symbols represent individual mice. Significance was calculated using Wilcoxon rank sum test (*P<0.05, P<0.01, **P<0.0001).

FIG. 16A shows concentration of peripheral total memory $CD4^+$ T cells (CAR−). FIG. 16B shows concentration of peripheral central memory ($CD45RA^-CD27^+CCR7^+$; left panel), transitional memory ($CD45RA^-CD27^+CCR7$; middle panel), and effector memory ($CD45RA^-CD27^+CCR7^-$; right panel) CD4+ T cells ($CAR^-$). Significance was calculated using Wilcoxon rank sum test (*P<0.05, **P<0.01). FIG. 16C shows frequency of memory $CD4^+$ T cell ($CAR^-$) subsets in tissues 8 weeks post-infection. Symbols and bars indicate mean, while error bars show ±SEM.

FIG. 17A shows results from an in vitro replication assay comparing the replication kinetics of $HIV_{JRCSF}$ and $HIV_{MJ4}$ in human PBMCs stimulated with PHA and infected at a matched multiplicity of infection of 0.002. Virus replication was assessed by measuring p24 antigen in culture supernatants. FIG. 17B shows mean log plasma viral RNA (copies $mL^{-1}$) in BLT mice challenged with $HIV_{JRCSF}$ (n=3) or $HIV_{MJ4}$ (n=4). Thin dotted line denotes limit of quantification. Symbols indicate mean values and error bars show ±SEM. Significance was calculated using Wilcoxon rank sum test (*P<0.05).

FIG. 18A shows concentration of peripheral total memory $CD4^+$ T cells ($CAR^-$). FIG. 18B shows concentration of peripheral central memory ($CD45RA^-CD27^+CCR7^+$; right panel), transitional memory ($CD45RA^-CD27^+CCR7^-$; middle panel), and effector memory ($CD45RA^-CD27^-CCR7^-$; left panel) $CD4^+$ T cells ($CAR^-$). Significance was calculated using Wilcoxon rank sum test (**P<0.07). FIG. 18C shows frequency of memory $CD4^+$ T cell ($CAR^-$) subsets in tissues 8 weeks post-infection. Symbols and bars indicate mean, while error bars show ±SEM.

FIG. 19A shows results from experiments wherein BLT mice were challenged with either $HIV_{JCSF}$ (n=6) or $HIV_{MJ4}$ (n=6) and infused with $2\times10^7$ Dual-CAR T cell product (TCP). Fold-change in CAR T cell concentration from baseline to peak levels in peripheral blood. Data is the aggregate of both infection cohorts. FIG. 19B is a schematic showing the components of the 3rd-generation (3G) CD4-based CAR construct. FIGS. 19C-19E show results wherein Dual-CAR T cell product and 3G-CAR T cells were combined, equalizing the frequency of Dual-CAR and 3G-CAR T cells prior to infusion into uninfected mice (n=9). FIG. 19C shows FACS plots indicating the frequency of Dual-CAR and 3G-CAR T cells present within the pre-infusion T cell product. FIG. 19D shows longitudinal concentration of peripheral CAR T cells following adoptive transfer into HIV-negative mice. Symbols indicate mean and error bars show ±SEM. FIG. 19E shows at 2 weeks post-infusion, mice received either $10^7$ irradiated K.Env cells (n=6) or $10^7$ irradiated K.WT cells (n=3). Fold change in the concentration of peripheral CAR T cells 1-week post-K562 boost from baseline concentration prior to K562 infusion. Bar indicates mean, error bars show±SEM and symbols represent individual mice. FIGS. 19A, 19D, and 19E: Wilcoxon rank sum test was used to calculate significance (*P<0.05, **P<0.01).

FIG. 20A shows FACS plots and FIG. 20B shows cumulative data of the frequency of $HIV_{GAG}^+$ T cell populations sampled within the same mice (n=5) 10 weeks post-$HIV_{JRCSF}$ infection. Data in FIG. 20B is the aggregate of tissues: bone marrow, liver, lung, lymph node, terminal blood, and spleen from 5 mice. FIG. 20C shows FACS plots and FIG. 20D shows cumulative data showing the expression of granzyme B and perforin within $HIV_{GAG}^+$ and $HIV_{GAG}^-$ CAR T cell populations from $HIV_{JRCSF}$-infected mice after ex vivo stimulation with K.Env (stim) or K.WT (unstim) cells. Data in FIG. 20D is represented as the average of 3 distinct CAR T cell populations. Significance was calculated using paired t test (*P<0.05). Symbols and bars indicate mean and error bars show ±SEM.

FIG. 21A is a schematic of HIV-resistant (C34-$CXCR4^+$) Dual-CAR T cells. FIG. 21C shows longitudinal peripheral concentration and FIG. 21D shows peak peripheral CAR T cell concentration. FIGS. 21E-21N illustrate experiments wherein $HIV_{MJ4}$-infected mice were infused 48 hours post-challenge with $10^6$ C34-$CXCR4^+$, purified CAR.BBζBBζ (n=5), CAR.28ζ.28ζ (n=5) or Dual-CAR (n=5) T cells, or were untreated (n=4). Purification strategy is described in FIGS. 25A-25D. FIG. 21E shows frequency of CAR T cell populations out of total human $CD45^+$ cells 2 and 3 weeks post-infection. FIG. 21F shows longitudinal concentration and FIG. 21G shows cumulative peripheral CAR T cell persistence. FIG. 21H is a series of FACS plots showing CCR5 expression within peripheral memory $CD4^+$ T cells ($CAR^-$). FIG. 21I shows concentration of total memory and FIG. 21J shows CCR5+ CD4+ T cells ($CAR^-$) at 6 weeks post-infection. FIG. 21K is a series of FACS plots and FIG. 21L shows frequency of MIP-$1\beta^+$ and $CD107a^+$ $CD8^+$CAR T cells from tissue at 8 weeks post-infection after ex vivo stimulation. FIG. 21M shows distribution and FIG. 21N shows frequency of granzyme $BB^+$ $perforin^+$ cells with $CD107a^+$ CAR T cells from tissues after ex vivo stimulation. FIG. 21B: Wilcoxon matched pairs signed rank test used to calculate significance. For remaining analyses, Wilcoxon rank sum test used to calculate significance (*P<0.05, P<0.01, *P<0.001). Bars indicate mean, error bars show ±SEM, and symbols represent individual mice except for FIG. 21C symbols indicate mean.

FIG. 22A shows Dual-CAR T cell product (TCP) was co-transduced with C34-CXCR4 linked to mCherry by an intervening T2A sequence. FACS plots indicate the frequency of C34-$CXCR4^+$ cells within each cell population comprising the Dual-CAR TCP prior to infusion. FIG. 22B shows Log plasma viral RNA (copies $mL^1$) in individual BLT mice challenged with $HIV_{JRCSF}$ and 48 hours later mice were infused with HIV-resistant (C34-CXCR4+) Dual-CAR TCP (n=7) or were untreated (Untx; n=7). Thin dotted line denotes limit of quantification.

FIG. 23A shows mice were infected with $HIV_{JRCSF}$ and 48 hours later infused with $10^7$C34-$CXCR4^+$ Dual-CAR T cell product (TCP). FACS plots indicate the frequency of C34-$CXCR4^+$ throughout infection. FIG. 23B shows mice were infected with $HIV_{MJ4}$ and 48 hours later were infused with $10^6$ C34-$CXCR4^+$ CAR.BBζ (n=5), CAR.28ζ (n=5), or purified Dual-CAR (n=4) T cells. Frequency of C34-$CXCR4^+$ CAR T cells in tissue 8 weeks post-infection. Thin dotted line indicates the frequency of C34-$CXCR4^+$ CAR T cells in the pre-infusion TCP for the indicated CAR T cell type. FIGS. 23C-23D show mice were infected with $HIV_{MJ4}$ and 48 hours later received $10^6$ C34-$CXCR4^+$, purified CAR.BBζ.BBζ (n=3), CAR.28ζ.28ζ (n=4), or Dual-CAR (n=3) T cells, FIG. 23C shows FACS plots and FIG. 23D shows cumulative data of the frequency of each $CD8^+$ CAR T cell population expressing MIP-1β and CD107a, and the frequency of CAR T cells with cytotoxic potential (granzyme $B^+$ $perforin^+$ $CD107a^+$). CART cells were isolated from the spleen and bone marrow of mice 8 weeks post-infection and ex vivo stimulated. Significance was calculated using Wilcoxon matched-pairs signed rank test (**P<0.01). For all data, symbols represent individual mice.

FIG. 25A is a schematic of lentivirus constructs used to generate dual CD4-based CAR-transduced T cells. The CD4-based CARs with the 4-1BB/CD3-ζ or CD28/CD3-ζ endodomains were linked with NGFR or truncated EGFR (EGFRt) to enable two-step positive magnetic selection during the T cell manufacturing process. FIG. 25B illustrates a time line for CAR T cell manufacturing. One day after T cell activation with αCD3/CD28 Dynabeads, the cells were transduced with an equivalent MOI of lentivirus depicted in FIG. 25A. On days 4 and 7 after activation, the CAR T cells were positively selected using anti-EGFR and anti-NGFR coated magnetic beads, respectively, as described in Materials and Methods. FIG. 25C shows representative FACS plots illustrating the purity of dual CAR-transduced T cells after EGFR and NGFR selection. FIG. 25D shows FACS plots indicating the frequency of CAR.BBζ.BBζ, CAR.28ζ.28ζ, and Dual-CAR T cells post-selection in their respective pre-infusion T cell products, prior to adoptive transfer into mice described in FIGS. 21E-21N.

FIGS. 26A-26E illustrate Dual-CAR T cells mediate superior expansion and protection of $CD4^+$ T cells during HIV infection in vivo. BLT mice were infected with $HIV_{MJ4}$ and 48 hours later received $10^6$ C34-$CXCR4^+$, purified CAR.BBζ.BBζ (n=5), CAR.28ζ.28ζ (n=5), Dual-CAR (n=5) T cells, or were untreated (Untx; n=4). FIG. 26A shows fold-change in the concentration of CAR T cells in peripheral blood between weeks 2 and 3 post-infection. The numbers above the bars indicate mean fold-change. Symbols represent individual mice. FIG. 26B shows absolute count of each CAR T cell population in tissues 8 weeks post-infection. FIG. 26C shows concentration of peripheral total memory ($CD45RA^-$) and FIG. 26D shows concentration of $CD45RA^-$ $CCR5^+$ $CD4^+$ T cells ($CAR^-$). Symbols represent mean. FIG. 26E depicts association between fold-change in the concentration of CAR T cells and change in total memory ($CD45RA^-$) CD4+ T cells ($CAR^-$) in peripheral blood between weeks 2 and 3 post-infection. Symbols represent individual mice. Spearman correlation test was used to calculate significance. FIGS. 26B-26D: Error bars show ±SEM and Wilcoxon rank sum test was used to calculate significance (*P<0.05 and **P<0.01).

FIG. 27A shows representative FACS plots and FIG. 27B shows cumulative data demonstrating the induction of active caspase-3 within target cells. Symbols indicate mean and error bars show ±SEM.

FIG. 28A shows frequency of CD8+ and FIG. 28B shows CD4+ CAR T cell populations from tissue at necropsy (8-weeks post-infection) within the same mice expressing CD107a, MIP-1β, IL-2 and TNF after ex vivo stimulation. Bars indicate mean, error bars show ±SEM and symbols represent individual mice. Significance was calculated using Wilcoxon rank sum test (**P<0.07). FIG. 28C shows Principle Components Analysis (PCA) of IL-2, TNF, MIP-1β, and CD107a expression in ex vivo stimulated $CD8^+$ and $CD4^+$ CAR T cells from PBMCs of $HIV_{JRCSF}$-infected mice (n=5).

FIG. 29A shows mean log plasma viral RNA (copies $mL^{-1}$) of active, unprotected CAR T cell-treated mice (n=38), and untreated/inactive CAR T cell-treated mice (n=36). Data are aggregated across 6 independent studies. Thin dotted line denotes limit of quantification. FIG. 29B shows mean log plasma viral RNA (copies $mL^{-1}$) in mice infused 48 hours post-$HIV_{MJ4}$ challenge with $10^7$ fully-protected (>98% C34-$CXCR4^+$) Dual-CAR TCP (n=12) or untreated mice (n=12). FIG. 29C shows frequency of splenic $HIV_{GAG}{}^+CD8^-$ T cells ($CAR^-$) and FIG. 29D shows cell-associated HIV DNA load in lymph nodes 6-8 weeks post-infection. FIGS. 29E-29K show results from experiments wherein $HIV_{JRCSF}$-infected mice were ART-treated and simultaneously infused with $10^7$ HIV-resistant Dual CAR TCP (n=12), inactive Dual-ΔCAR TCP (n=5), or were untreated (n=7). FIG. 29E shows mean log plasma HIV RNA (copies $mL^{-1}$). Shaded box indicates ART and arrow indicates TCP infusion. FIG. 29F shows percent log reduction in plasma HIV RNA from pre-ART (week 3) to 1 and 1.5 weeks post-ART. FIG. 29G-29H show data aggregated from $HIV_{JRCSF}$- and $HIV_{BA}$L-infected cohorts. FIG. 29G shows correlation between percent viral load reduction at first post-ART time-point and contemporaneous peripheral CAR T cell concentration. FIG. 29H shows a Kaplan-Meier curve of time to viral suppression after treatment initiation for Dual-CAR TCP versus control mice. FIG. 29I shows frequency of $HIV_{GAG}{}^+CD8^-$ T cells ($CAR^-$) and FIG. 29J shows $HIV_{GAG}{}^+CD14^+$ macrophages aggregated from various tissues of plasma viremia suppressed mice. FIG. 29K shows cell-associated HIV DNA load in sorted central memory ($CAR^-CD45RA^-CCR7^+$) $CD4^+$ T cells. Statistical significance calculated for FIGS. 29A-29E and FIGS. 29I-29K by Wilcoxon rank sum test, FIG. 29G Spearman correlation, and FIG. 29H Log-rank test. For all data, *P<0.05, P<0.01, and *P<0.001. Bars indicate mean and error bars show ±SEM. Symbols represent individual mice.

FIG. 30A shows frequency of $HIV_{GAG}{}^+$ $CD8^-$ T cells ($CAR^-$) within the bone marrow and spleen of $HIV_{JRCSF}$-infected mice and FIG. 30B shows $HIV_{MJ4}$-infected mice that were treated 48 hours post-challenge with the Dual-CAR T cell product (TCP) or were untreated (Untx). FIG. 30C shows mean log plasma $HIV_{MJ4}$ RNA (copies $mL^{-1}$) after ART discontinuation of mice infused at ART initiation with $10^7$ fully-protected >98% C34-CXCR4+(n=5) or partially-protected <20% C34-CXCR4+(n=7) Dual-CAR TCP, or were untreated (n=9). FIGS. 30D-30E show results from experiments wherein $HIV_{BAL}$-infected mice were ART-treated and simultaneously infused with $10^7$ HIV-resistant Dual-CAR TCP (n=6) or were untreated (n=6). FIG. 30D shows mean log plasma HIV RNA (copies $mL^{-1}$). Shaded box indicates ART and arrow indicates TCP infusion, FIG. 30E shows percent log reduction in plasma viral RNA from pre-ART (week 3) and 0.5 and 1 week post-ART. For all data, bars indicate mean, error bars show ±SEM and symbols represent individual mice. Significance was calculated using Wilcoxon rank sum test (*P<0.05, P<0.01, **P<0.0001).

FIG. 31A: For the study described in FIG. 21B, C34-$CXCR4^+$ and C34-$CXCR4^-$ CAR T cells were bulk sorted by FACS following the depicted gating strategy. FIG. 31B: For the study described in FIG. 29E, endogenous central memory CD4+ T cells (CAR−) were sorted from splenocytes harvested at necropsy (7 weeks post infection) following the depicted gating strategy. For all data, cell-associated HIV DNA load was quantified on sorted cell populations by droplet-digital PCR.

DETAILED DESCRIPTION

A. Definitions

Figures 1A, 1B, 1C, 1D:
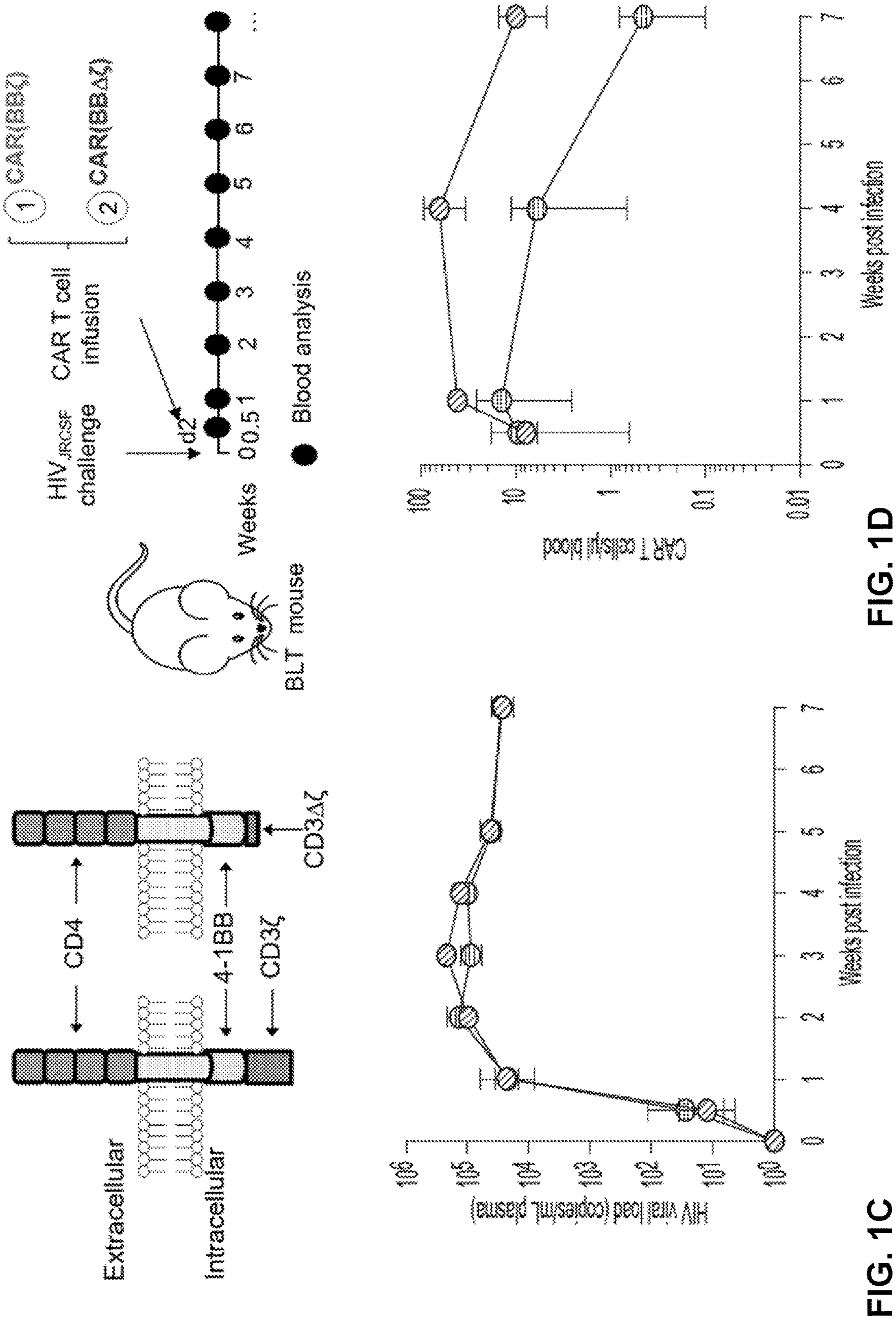
FIG. 1A is a schematic depicting a CD4 CART cell infusion product comprising T cells that express an intracellular 4-1BB costimulatory domain and an active signaling (left) or inactive signaling (right) CD3ζ domain. The inactive signaling CAR T cells (right) do not induce T cell activation following recognition of an HIV-infected cell.
FIG. 1B is a schematic of an experimental design used herein wherein CAR T cells were infused into humanized BLT mice 48 hours after HIV challenge. Mice were bled at the indicated time points to measure 1) the level of virus and 2) the number of CAR T cells in peripheral blood.
FIG. 1C depicts quantification of HIV in peripheral blood demonstrating that active CAR T cells (circle with diagonal lines) were incapable of preventing early virus replication relative to inactive CAR T cells (circle with horizontal lines).
FIG. 1D depicts expansion of active CAR T cells (circle with diagonal lines) in peripheral blood relative to inactive CAR T cells (circle with horizontal lines). These data demonstrate that signaling competent CAR T cells that express a 4-1BB signaling domain are capable of robust cellular proliferation and survival after encountering HIV-infected cells.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, the term "adaptor molecule" refers to a polypeptide with a sequence that permits interaction with two or more molecules, and in certain embodiments, promotes activation or inactivation of a cytotoxic cell.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. $\alpha$ and $\beta$ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), epididymitis, glomerulonephritis, Graves' disease, Guillain-Barre syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "broadly neutralizing antibody (bnAb)" refers to an antibody that defends a cell from multiple strains of a particular virus by neutralizing its effect. In some embodiments, broadly neutralizing HIV-1 Antibodies (bnAbs) are neutralizing antibody which neutralize multiple HIV-1 viral strain.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

By the term "CD4" as used herein is meant any amino acid sequence specifying CD4 from any source, including an amino acid sequence of CD4 that has been generated through codon optimization of the nucleic acid sequence encoding CD4. Codon optimization may be accomplished using any available technology and algorithms designed to optimize codons in an amino acid sequence.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs have been expressed with specificity to a tumor associated antigen, for example. CARs may also comprise an intracellular activation domain, a transmembrane domain and an extracellular domain comprising a tumor associated antigen binding region. In some aspects, CARs comprise fusions of single-chain variable fragments (scFv) derived monoclonal antibodies, fused to transmembrane and intracellular domain. The specificity of CAR designs may be derived from ligands of receptors (e.g., peptides). In some embodiments, a CAR can target HIV infected cells by redirecting the specificity of a T cell expressing the CAR specific for HIV associated antigens.

The term "chimeric intracellular signaling molecule" refers to recombinant receptor comprising one or more intracellular domains of one or more co-stimulatory molecules. The chimeric intracellular signaling molecule substantially lacks an extracellular domain. In some embodiments, the chimeric intracellular signaling molecule comprises additional domains, such as a transmembrane domain, a detectable tag, and a spacer domain.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to TCR, CD3 zeta, CD3 gamma, CD3 delta, CD3 epsilon, CD86, common FcR gamma, FcR beta (Fc Epsilon Rb), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CDIId, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

A "co-stimulatory signal", as used herein, refers to a signal, which in combination with a primary signal, such as TCR/CD3 ligation, leads to T cell proliferation and/or upregulation or downregulation of key molecules.

The term "cytotoxic" or "cytotoxicity" refers to killing or damaging cells. In one embodiment, cytotoxicity of the modified cells is improved, e.g. increased cytolytic activity of T cells.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein "envelope glycoprotein gp120" or "gp120" refers to a 120 kDa glycoprotein on the surface of the HIV envelope. gp120 binds to a CD4 receptor on a host cell, such as a CD4 T lymphocyte. This starts the process by which HIV fuses its viral membrane with the host cell membrane and enters the host cell.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

By the terms "Human Immunodeficiency Virus" or HIV" as used herein is meant any HIV strain or variant that is known in the art or that is heretofore unknown, including without limitation, HIV-1 and HIV-2.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. As applied to the nucleic acid or protein, "homologous" as used herein refers to a sequence that has about 50% sequence identity. More preferably, the homologous sequence has about 75% sequence identity, even more preferably, has at least about 80%, 85%, 90%, 91%, 92%, 93%, 94%, 95%, 96%, 97%, 98%, 99% sequence identity.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

The guide nucleic acid sequence may be complementary to one strand (nucleotide sequence) of a double stranded DNA target site. The percentage of complementation between the guide nucleic acid sequence and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The guide nucleic acid sequence can be at least 10, 11, 12, 13, 14, 15, 16, 17, 18, 19, 20, 21, 22, 23, 24, 25, 26, 27, 28, 29, 30, 31, 32, 33, 34, 35 or more nucleotides in length. In some embodiments, the guide nucleic acid sequence comprises a contiguous stretch of 10 to 40 nucleotides. The variable targeting domain can be composed of a DNA sequence, a RNA sequence, a modified DNA sequence, a modified RNA sequence (see for example modifications described herein), or any combination thereof.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "resistance to immunosuppression" refers to lack of suppression or reduced suppression of an immune system activity or activation.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, the term "substantially lacks an extracellular domain" refers to a molecule that is essentially free of a domain that extrudes extracellularly. In one embodiment, the chimeric intracellular signaling molecule lacks any function performed by an extracellular domain, such as antigen binding. In another embodiment, the chimeric intracellular signaling molecule includes a transmembrane domain but lacks a functional extracellular domain.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen.

The TCR is responsible for recognizing antigens bound to major histocompatibility complex molecules. TCR is composed of a heterodimer of an alpha (a) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The term "tumor" as used herein, refers to an abnormal growth of tissue that may be benign, pre-cancerous, malignant, or metastatic.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Modified Immune Cells

The present invention provides modified immune cells or precursors thereof (e.g., a T cell) comprising dual (a first and a second) chimeric receptors (e.g. chimeric antigen receptors (CARs)). Also provided are modified immune cells or precursor cell thereof comprising a nucleic acid encoding a first and an second chimeric receptor. Each chimeric receptor (e.g. CAR) comprises affinity for an antigen on a target cell. Accordingly, such modified cells possess the specificity directed by the chimeric receptor that is expressed therein. For example, a modified cell of the present disclosure comprising an HIV-1 chimeric receptor possesses specificity for HIV-1 on a target cell.

In certain embodiments, the modified immune cells or precursors thereof comprise a first chimeric receptor comprising a first binding domain, a first transmembrane domain, a first costimulatory domain that confers enhanced pro-survival function, and a CD3z intracellular signaling domain. The cells also comprise a second chimeric receptor comprising a second binding domain, a second transmembrane domain, a second costimulatory domain that confers enhanced effector function, and a CD3z intracellular signaling domain.

As such, in certain embodiments, the first costimulatory domain and the second costimulatory domain are different costimulatory domains. Accordingly, in certain embodiments, the invention provides a modified immune cell or precursor cell thereof, comprising a first and second chimeric receptor, each comprising a distinct costimulatory domain. In certain embodiments, the first costimulatory domain is a 4-1BB costimulatory domain and/or the second costimulatory domain is a CD28 costimulatory domain.

In certain embodiments, the first transmembrane domain and/or the second transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154.

In certain embodiments, the first transmembrane domain is a 4-1BB or a CD8α transmembrane domain and/or the second transmembrane domain is a CD28 transmembrane domain.

In certain embodiments, the first chimeric receptor and/or the second chimeric receptor further comprises a hinge domain. In certain embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof.

In certain embodiments, the first binding domain binds to a first target (e.g. antigen), and the second binding domain binds to a second target. The first target and the second target may be the same or different. The first target and the second target may be distinct epitopes of the same molecule.

In certain embodiments, the first target and the second target is human immunodeficiency virus type 1 (HIV-1). In certain embodiments, the first target and the second target is envelope glycoprotein gp120. In certain embodiments, the first binding domain and/or the second binding domain comprises the extracellular domains of a CD4 molecule.

In certain embodiments, the first target and/or the second target is a tumor associated antigen. Tumor associated antigens are discussed in detail elsewhere herein. The tumor associated antigen may be a liquid tumor antigen (e.g. CD19 or CD22) or a solid tumor antigen.

In certain embodiments, the first target is a tumor associated antigen, and the second target is human immunodeficiency virus type 1 (HIV-1).

In certain aspects, the invention provides a modified immune cell or precursor cell thereof, comprising a first chimeric receptor comprising the extracellular domains of a CD4 molecule, a CD8α transmembrane domain, a 4-1BB costimulatory domain, and a CD3z intracellular signaling domain; and a second chimeric receptor comprising the extracellular domains of a CD4 molecule, a CD28 transmembrane domain, a CD28 costimulatory domain, and a CD3z intracellular signaling domain. In certain embodiments, the invention provides a modified immune cell or precursor cell thereof, comprising a first chimeric receptor comprising a first binding domain, a CD8α hinge domain, a CD8α transmembrane domain, a 4-1BB costimulatory domain, and a CD3z intracellular signaling domain; and a second chimeric receptor comprising a second binding domain, CD8α hinge domain, a CD28 transmembrane domain, a CD28 costimulatory domain, and a CD3z intracellular signaling domain.

In certain embodiments, the invention provides a modified immune cell or precursor cell thereof, comprising a first chimeric receptor comprising the amino acid sequence set forth in SEQ ID NO: 1 and/or a second chimeric receptor comprising the amino acid sequence set forth in SEQ ID NO: 7.

In certain embodiments, the modified immune cell is a modified T cell. In certain embodiments, the modified immune cell is an autologous cell. In certain embodiments, the modified immune cell is an autologous cell obtained from a human subject.

In certain embodiments, the cell further comprises an HIV fusion inhibitor. In certain embodiments, the cell further comprises a polynucleotide sequence encoding an HIV fusion inhibitor. In certain embodiments, the HIV fusion inhibitor is a cell-surface-expressed HIV fusion inhibitor. In certain embodiments, the HIV fusion inhibitor is C34-CXCR4.

In certain embodiments, the cell expressing the HIV fusion inhibitor exhibits increased resistance to infection by HIV, as compared to a control cell not expressing the HIV fusion inhibitor.

One aspect of the invention includes a modified immune cell or precursor cell thereof: (a) comprising any of the nucleic acids disclosed herein, or any of the expression constructs disclosed herein; or (b) comprising: (i) a first chimeric receptor comprising a first binding domain, a first transmembrane domain, a first costimulatory domain that confers enhanced pro-survival function, and a CD3z intracellular signaling domain; and (ii) a second chimeric receptor comprising a second binding domain, a second transmembrane domain, a second costimulatory domain that confers enhanced effector function, and a CD3z intracellular signaling domain.

In certain embodiments of the modified cell:

(a) the first costimulatory domain is a 4-1BB costimulatory domain; and/or
(b) the second costimulatory domain is a CD28 costimulatory domain; and/or
(c) the first transmembrane domain and/or the second transmembrane domain is selected from the group consisting of an artificial hydrophobic sequence, a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154; and/or
(d) the first transmembrane domain is a 4-1BB or a CD8α transmembrane domain; and/or (e) the second transmembrane domain is a CD28 transmembrane domain; and/or
(f) the first chimeric receptor and/or the second chimeric receptor further comprises a hinge domain; and/or
(g) the first chimeric receptor and/or the second chimeric receptor further comprises a hinge domain, and wherein the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof, and/or
(h) the first binding domain binds to a first target, and the second binding domain binds to a second target; and/or (i) the first binding domain binds to a first target, and the second binding domain binds to a second target, and wherein the first target and the second target are the same; and/or
(j) the first binding domain binds to a first target, and the second binding domain binds to a second target, wherein the first target and the second target are distinct epitopes of the same molecule; and/or
(k) the first binding domain binds to a first target, and the second binding domain binds to a second target, wherein the first target and the second target are different; and/or
(l) the first binding domain binds to a first target, and the second binding domain binds to a second target, wherein the first target and/or the second target is human immunodeficiency virus type 1 (HIV-1); and/or
(m) the first binding domain binds to a first target, and the second binding domain binds to a second target, wherein the first target and the second target is human immunodeficiency virus type 1 (HIV-1); and/or
(n) the first binding domain binds to a first target, and the second binding domain binds to a second target, wherein the first target and/or the second target is envelope glycoprotein gp 120 of human immunodeficiency virus type 1 (HIV-1); and/or
(o) the first binding domain binds to a first target, and the second binding domain binds to a second target, wherein the first target and the second target is envelope glycoprotein gp120 of human immunodeficiency virus type 1 (HIV-1); and/or
(p) the first binding domain and/or the second binding domain comprises the extracellular domains of a CD4 molecule; and/or
(q) the first binding domain and the second binding domain comprises the extracellular domains of a CD4 molecule; and/or
(r) the first binding domain binds to a first target, and the second binding domain binds to a second target, wherein the first target and/or the second target is a tumor associated antigen; and/or
(s) the first binding domain binds to a first target, and the second binding domain binds to a second target, wherein the first target and/or the second target is a tumor associated antigen, and wherein the tumor associated antigen is a liquid tumor antigen, and optionally wherein the liquid tumor antigen is CD19 or CD22; and/or
(t) the first binding domain binds to a first target, and the second binding domain binds to a second target, wherein the first target and/or the second target is a tumor associated antigen, and wherein the tumor associated antigen is a solid tumor antigen; and/or
(u) the cell expressing the HIV fusion inhibitor exhibits increased resistance to infection by HIV, as compared to a control cell not expressing the HIV fusion inhibitor.

Another aspect of the invention includes a modified immune cell or precursor cell thereof, comprising: (a) a first chimeric receptor comprising the extracellular domains of a CD4 molecule, a CD8α transmembrane domain, a 4-1BB costimulatory domain, and a CD3z intracellular signaling domain; and (b) a second chimeric receptor comprising the extracellular domains of a CD4 molecule, a CD28 transmembrane domain, a CD28 costimulatory domain, and a CD3z intracellular signaling domain.

In certain embodiments of the modified cell: (a) the modified cell is a modified immune cell; and/or (b) the modified cell is a modified T cell; and/or (c) the modified cell is an autologous cell; and/or (d) the modified cell is an autologous cell obtained from a human subject.

C. Chimeric Receptors

The present invention provides compositions and methods for modified immune cells or precursors thereof, e.g., modified T cells, comprising dual (a first and a second) chimeric receptors (e.g. chimeric antigen receptors (CARs)). Thus, in some embodiments, the immune cell has been genetically modified to express the first and second chimeric receptor. Chimeric receptors of the present invention comprise a binding domain, a transmembrane domain, a costimulatory domain, and an intracellular signaling domain.

Binding Domain

The binding domain of a chimeric receptor is an extracellular region of the chimeric receptor for binding to a specific target antigen including proteins, carbohydrates, and glycolipids. In some embodiments, the chimeric receptor comprises affinity to a target antigen on a target cell. The target antigen may include any type of protein, or epitope thereof, associated with the target cell. For example, the chimeric receptor may comprise affinity to a target antigen on a target cell that indicates a particular disease state of the target cell.

In certain embodiments, the binding domain of the chimeric receptor comprises a CD4 domain, particularly a CD4 extracellular domain that specifically binds to HIV virions or HIV infected cells. CD4 is a member of the immunoglobulin superfamily and includes four extracellular immunoglobulin domains (D1 to D4). D1 and D3 are similar to immunoglobulin variable domains, and D2 and D4 are similar to immunoglobulin constant domains. D1 includes the region of CD4 that interacts with beta2-microglobulin of major histocompatibility complex class II molecules. In one embodiment, the chimeric receptor comprises an extracellular domain of CD4 or a fragment thereof. In another embodiment, the membrane-bound chimeric receptor comprises at least one immunoglobulin domain of CD4. In another embodiment, the CD4 extracellular domain comprises SEQ ID NO: 2.

In certain embodiments, the binding domain of the chimeric receptor comprises an antigen binding domain. The antigen binding domain binds a specific target antigen e.g. a target antigen on a target cell that indicates a particular disease state of the target cell.

In one embodiment, the target cell antigen is a tumor associated antigen (TAA). Examples of tumor associated antigens (TAAs), include but are not limited to, differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS. In a preferred embodiment, the antigen binding domain of the chimeric receptor targets an antigen that includes but is not limited to CD19, CD20, CD22, ROR1, Mesothelin, CD33/IL3Ra, c-Met, PSMA, PSCA, Glycolipid F77, EGFRvIII, GD-2, MY-ESO-1 TCR, MAGE A3 TCR, and the like.

Depending on the desired antigen to be targeted, the chimeric receptor of the invention can be engineered to include the appropriate antigen binding domain that is specific to the desired antigen target. For example, if CD19 is the desired antigen that is to be targeted, an antibody for CD19 can be used as the antigen bind moiety for incorporation into the chimeric receptor of the invention.

In one embodiment, the target cell antigen is CD19. As such, in one embodiment, a chimeric receptor of the present disclosure has affinity for CD19 on a target cell. This should not be construed as limiting in any way, as a chimeric receptor having affinity for any target antigen is suitable for use in a composition or method of the present invention.

As described herein, a chimeric receptor of the present disclosure having affinity for a specific target antigen on a target cell may comprise a target-specific binding domain. In some embodiments, the target-specific binding domain is a murine target-specific binding domain, e.g., the target-specific binding domain is of murine origin. In some embodiments, the target-specific binding domain is a human target-specific binding domain, e.g., the target-specific binding domain is of human origin. In one embodiment, a chimeric receptor of the present disclosure having affinity for CD19 on a target cell may comprise a CD19 binding domain.

In some embodiments, a chimeric receptor of the present disclosure may have affinity for one or more target antigens on one or more target cells. In some embodiments, a chimeric receptor may have affinity for one or more target antigens on a target cell. In such embodiments, the chimeric receptor is a bispecific chimeric receptor or a multispecific chimeric receptor. In some embodiments, the chimeric receptor comprises one or more target-specific binding domains that confer affinity for one or more target antigens. In some embodiments, the chimeric receptor comprises one or more target-specific binding domains that confer affinity for the same target antigen. For example, a chimeric receptor comprising one or more target-specific binding domains having affinity for the same target antigen could bind distinct epitopes of the target antigen. When a plurality of target-specific binding domains is present in a chimeric receptor, the binding domains may be arranged in tandem and may be separated by linker peptides. For example, in a chimeric receptor comprising two target-specific binding domains, the binding domains are connected to each other covalently on a single polypeptide chain, through an oligo- or polypeptide linker, an Fc hinge region, or a membrane hinge region.

In some embodiments, the antigen binding domain is selected from the group consisting of an antibody, an antigen binding fragment (Fab), and a single-chain variable fragment (scFv).

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. In some embodiments, the antigen binding domain portion comprises a mammalian antibody or a fragment thereof. The choice of antigen binding domain may depend upon the type and number of antigens that are present on the surface of a target cell.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., CD19 binding domain) comprises an scFv having the configuration from N-terminus to C-terminus, VH-linker-VL. In some embodiments, the antigen binding domain comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as $(GS)_n$, $(GSGGS)_n$ (SEQ ID NO:9), $(GGGS)_n$ (SEQ ID NO:10), and $(GGGGS)_n$ (SEQ ID NO:11), where n represents an integer of at least 1. Exemplary linker sequences can comprise amino acid sequences including, without limitation, GGSG (SEQ ID NO:12), GGSGG (SEQ ID NO:13), GSGSG (SEQ ID NO:14), GSGGG (SEQ ID NO:15), GGGSG (SEQ ID NO:16), GSSSG (SEQ ID NO:17), GGGGS (SEQ ID NO:18), GGGGSGGGGSGGGGS (SEQ ID NO:19) and the like. Those of skill in the art would be able to select the appropriate linker sequence for use in the present invention. In one embodiment, an antigen binding domain of the present invention comprises a heavy chain variable region (VH) and a light chain variable region (VL), wherein the VH and VL is separated by the linker sequence having the amino acid sequence GGGGSGGGGSGGGGS (SEQ ID NO: 19), which may be encoded by the nucleic acid sequence GGTGGCGGTGGCTCGGGCGGTGGTGGGTCGGGTG GCGGCGGATCT (SEQ ID NO: 20).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some embodiments, the antigen binding domain may be derived from the same species in which the chimeric receptor will ultimately be used. For example, for use in humans, the antigen binding domain of the chimeric receptor may comprise a human antibody or a fragment thereof. In some embodiments, the antigen binding domain may be derived from a different species in which the chimeric receptor will ultimately be used. For example, for use in humans, the antigen binding domain of the chimeric receptor may comprise a murine antibody or a fragment thereof.

The binding domains described herein can be combined with any of the transmembrane domains described herein, any of the costimulatory domains described herein, any of the intracellular signaling domains, or any of the other domains described herein that may be included in a chimeric receptor of the present invention. A subject chimeric receptor of the present invention may also include a hinge domain as described herein. A subject chimeric receptor of the present invention may also include a spacer domain as described herein. In some embodiments, each of the binding domain, transmembrane domain, costimulatory domain, and intracellular signaling domain is separated by a linker.

Transmembrane Domain

Chimeric receptors of the present invention may comprise a transmembrane domain that connects the binding domain of the chimeric receptor to the intracellular domain (e.g. costimulatory domain) of the chimeric receptor. The transmembrane domain of a subject chimeric receptor is a region that is capable of spanning the plasma membrane of a cell (e.g., an immune cell or precursor thereof). The transmembrane domain is for insertion into a cell membrane, e.g., a eukaryotic cell membrane. In some embodiments, the transmembrane domain is interposed between the antigen binding domain and the intracellular domain of a chimeric receptor.

In some embodiments, the transmembrane domain is naturally associated with one or more of the domains in the chimeric receptor. In some embodiments, the transmembrane domain can be selected or modified by one or more amino acid substitutions to avoid binding of such domains to the transmembrane domains of the same or different surface membrane proteins, to minimize interactions with other members of the receptor complex.

The transmembrane domain may be derived either from a natural or a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the chimeric receptor into a cell membrane, e.g., an artificial hydrophobic sequence. Examples of the transmembrane domain of particular use in this invention include, without limitation, transmembrane domains derived from (i.e. comprise at least the transmembrane region(s) of) the alpha, beta or zeta chain of the T cell receptor, CD28, CD3 epsilon, CD45, CD4, CD5, CD7, CD8, CD9, CD16, CD22, CD33, CD37, CD64, CD80, CD86, CD134 (OX-40), CD137 (4-1B), CD154 (CD40L), Toll-like receptor 1 (TLR1), TLR2, TLR3, TLR4, TLR5, TLR6, TLR7, TLR8, and TLR9. In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

In certain embodiments, the transmembrane domain (of a first and/or second chimeric receptor) is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154.

In certain embodiments, the transmembrane domain is a 4-1BB transmembrane domain. In certain embodiments, the transmembrane domain is a CD8α transmembrane domain. In certain embodiments, the transmembrane domain comprises SEQ ID NO: 4. In certain embodiments, the transmembrane domain is a CD28 transmembrane domain.

The transmembrane domains described herein can be combined with any of the antigen binding domains described herein, any of the intracellular domains described herein, or any of the other domains described herein that may be included in a subject chimeric receptor.

In some embodiments, the transmembrane domain further comprises a hinge region. A subject chimeric receptor of the present invention may also include a hinge region. The hinge region of the chimeric receptor is a hydrophilic region which is located between the antigen binding domain and the transmembrane domain. In some embodiments, this domain facilitates proper protein folding for the chimeric receptor. The hinge region is an optional component for the chimeric receptor. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject chimeric receptor of the present disclosure includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., *Cancer Immunol. Res.* (2015) 3(2): 125-135). In some embodiments, the hinge region is a flexible domain, thus allowing the antigen binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa. In some embodiments, the hinge region can have a length of greater than 5 aa, greater than 10 aa, greater than 15 aa, greater than 20 aa, greater than 25 aa, greater than 30 aa, greater than 35 aa, greater than 40 aa, greater than 45 aa, greater than 50 aa, greater than 55 aa, or more.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. Suitable hinge regions can have a length of greater than 20 amino acids (e.g., 30, 40, 50, 60 or more amino acids).

For example, hinge regions include glycine polymers $(G)_n$, glycine-serine polymers (including, for example, $(GS)_n$, $(GSGGS)_n$ (SEQ ID NO:9) and $(GGGS)_n$ (SEQ ID NO:10), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2: 73-142). Exemplary hinge regions can comprise amino acid sequences including, but not limited to, GGSG (SEQ ID NO:12), GGSGG (SEQ ID NO:13), GSGSG (SEQ ID NO:14), GSGGG (SEQ ID NO:15), GGGSG (SEQ ID NO:16), GSSSG (SEQ ID NO:17), and the like.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1):162-166; and Huck et al., Nucleic Acids Res. (1986) 14(4): 1779-1789. As non-limiting examples, an immunoglobulin hinge region can include one of the following amino acid sequences: DKTHT (SEQ ID NO:21); CPPC (SEQ ID NO:22); CPEPKSCDTPPPCPR (SEQ ID NO:23) (see, e.g., Glaser et al., *J. Biol. Chem.* (2005) 280:41494-41503); ELKTPLGDTTHT (SEQ ID NO:24); KSCDKTHTCP (SEQ ID NO:25); KCCVDCP (SEQ ID NO:26); KYGPPCP (SEQ ID NO:27); EPKSCDKTHTCPPCP (SEQ ID NO:28) (human IgG1 hinge); ERKCCVECPPCP (SEQ ID NO:29) (human IgG2 hinge); ELKTPLGDTTHTCPRCP (SEQ ID NO:30) (human IgG3 hinge); SPNMVPHAHHAQ (SEQ ID NO:31) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:32); see, e.g., Yan et al., *J. Biol. Chem.* (2012) 287: 5891-5897. In one embodiment, the hinge region can comprise an amino acid sequence derived from human CD8, or a variant thereof.

Intracellular Domain

A subject chimeric receptor of the present invention also includes an intracellular domain. In certain embodiments, the intracellular domain comprises a costimulatory domain and an intracellular signaling domain. The intracellular domain of the chimeric receptor is responsible for activation of at least one of the effector functions of the cell in which the chimeric receptor is expressed (e.g., immune cell). The intracellular domain transduces the effector function signal and directs the cell (e.g., immune cell) to perform its specialized function, e.g., harming and/or destroying a target cell.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular domain include, without limitation, the ζ chain of the T cell receptor complex or any of its homologs, e.g., η chain, FcsRIγ and β chains, MB 1 (Iga) chain, B29 (Ig) chain, etc., human CD3 zeta chain, CD3 polypeptides (A, 6 and F), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcsRI, cytoplasmic tails of Fc receptors, an immunoreceptor tyrosine-based activation motif (ITAM) bearing cytoplasmic receptors, and combinations thereof.

In one embodiment, the intracellular domain of the chimeric receptor includes any portion of one or more co-stimulatory molecules, such as at least one signaling domain from CD2, CD3, CD8, CD27, CD28, ICOS, 4-1BB, PD-1, any derivative or variant thereof, any synthetic sequence thereof that has the same functional capability, and any combination thereof.

In certain embodiments, the chimeric receptor comprises a costimulatory domain that confers enhanced pro-survival function. For example, members of the TNF family of receptors (4-1BB, OX40, CD27, GITR etc.) are thought to contribute more to cell survival. In certain embodiments, the costimulatory domain is a 4-1BB costimulatory domain. In certain embodiments, the costimulatory domain comprises SEQ ID NO: 5.

In certain embodiments, the chimeric receptor comprises a costimulatory domain that confers enhanced effector function. For example, members of the CD28 family of receptors (CD28 and ICOS) are thought to contribute more to cell effector function. In certain embodiments, the costimulatory domain is a CD28 costimulatory domain.

In certain embodiments, the chimeric receptor comprises CD28 transmembrane and costimulatory domains. In certain embodiments, the CD28 transmembrane and costimulatory domains comprise SEQ ID NO: 8.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon RIb), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CDlib, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular signaling domains suitable for use in a subject chimeric receptor of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the chimeric receptor (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound chimeric receptor, but is instead diffused in the cytoplasm.

Intracellular signaling domains suitable for use in a subject chimeric receptor of the present invention include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of a subject chimeric receptor comprises 3 ITAM motifs.

In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCER1G (also known as FCRG; Fc epsilon receptor I gamma chain; Fc receptor gamma-chain; fc-epsilon RI-gamma; fcRgamma; fceRl gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in an FN3 chimeric receptor of the present disclosure includes a DAP10/CD28 type signaling chain. In one embodiment, an intracellular signaling domain suitable for use in an FN3 chimeric receptor of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the chimeric receptor includes a cytoplasmic signaling domain of human CD3 zeta. In certain embodiments, the intracellular signaling domain comprises SEQ ID NO: 6.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular signaling domains described herein can be combined with any of the binding domains described herein, any of the transmembrane domains described herein, or any of the other domains described herein that may be included in the chimeric receptor.

In certain embodiments, the chimeric receptor comprises a CD4 binding domain, a CD8α hinge domain, a CD8α transmembrane domain, a 4-1BB domain and a CD3 zeta domain. In certain embodiments, the chimeric receptor comprises the amino acid sequence set forth in SEQ ID NO: 1. In certain embodiments, the chimeric receptor comprises a CD4 binding domain, a CD8α hinge domain, a CD28 transmembrane domain, a CD28 intracellular domain and a CD3 zeta domain. In certain embodiments, the chimeric receptor comprises the amino acid sequence set forth in SEQ ID NO: 7.

Tolerable variations of the chimeric receptor sequences will be known to those of skill in the art. For example, in some embodiments the chimeric receptor comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence set forth in SEQ ID NO: 1 or 7.

CD4 4-1BB CD3-zeta sequence:

(SEQ ID NO: 1)

MNRGVPFRHLLLVLQLALLPAATQGKKVVLGKKGDTVELTCTASQKKSIQFHWKNSNQIKILGNQGS

FLTKGPSKLNDRADSRRSLWDQGNFPLIIKNLKIEDSDTYICEVEDQKEEVQLLVFGLTANSDTHLL

QSQSLTLTLESPPGSSPSVQCRSPRGKNIQGGKTLSVSQLELQDSGTWTCTVLQNQKKVEFKIDIVV

LAFQKASSIVYKKEGEQVEFSFPLAFTVEKLTGSGELWWQAERASSSKSWITFDLKNKEVSVKRVTQ

DPKLQMGKKLPLHLTLPQALPQYAGSGNLTLALEAKTGKLHQEVNLVVMRATQLQKNLTCEVWGPTS

PKLMLSLKLENKEAKVSKREKAVWVLNPEAGMWQCLLSDSGQVLLESNIKVLPTWSTPVQPSG*TTTP*

*APRPPTPAPTIASQPLSLRPEACRPAAGGAVHTRGLDFACD*IYIWAPLAGTCGVLLLSLVITYLCKR

PFMRPVQTTQEEDGCSCRFPEEEEGGCEL*RVKFSRSADAPAYQQGQNQLY*

*NELNLGRREEYDVLDKRRGRDPEMGGKPRRKNPQEGLYNELQKDKMEAYSEIGMKG*

*ERRRGKGHDGLYQGLSTATKDTYDALHMQALPPR*

Underlined (SEQ ID NO: 2)

CD4 EC domain

Italicized (SEQ ID NO: 3)

CD8α hinge

Bold (SEQ ID NO: 4)

CD8α TM

Double underlined (SEQ ID NO: 5)

4-1BB ICD

Bold italics (SEQ ID NO: 6)

CD3 zeta

CD4 CD28 CD3-zeta sequence:

(SEQ ID NO: 7)

MNRGVPFRHLLLVLQLALLPAATQGKKVVLGKKGDTVELTCTASQKKSIQFHWKNSNQIKILGNQGS

FLTKGPSKLNDRADSRRSLWDQGNFPLIIKNLKIEDSDTYICEVEDQKEEVQLLVFGLTANSDTHLL

QGQSLTLTLESPPGSSPSCQCRSPRGKNIQGGKTLSVSQLELQDSGTWTCTVLQNQKKVEFKIDIVV

LAFQKASSIVYKKEGEQVEFSFPLAFTVEKLTGSGELWWQAERASSSKSWITFDLKNKEVSVKRVTQ

DPKLQMGKKLPLHLTLPQALPQYAGSGNLTLALEAKTGKLHQEVNLVVMRATQLKNLTCEVWGPTSP

KLMLSLKLENKEAKVSKREKAVWVLNPEAGMWQCLLSDSGQVLLESNIKVLPTWSTPVQPSG*TTTPA*

*PRPPTPAPTIASQPLSLRPEACRPAAGGAVHTRGLDFACD*FWVLVVVGGVLACYSLLVTVAFIIWVR

-continued

SKRSRLLHSDYMNMTPRRPGPTRKHYQPYAPPRDFAAYRSID*RVKFSRSADAPAYQQGQ*

*NQLYNELNLGRREEYDVLDKRRGRDPEMGGKPRRKNPQEGLYNELQKDKMAEAYSEI*

*GMKGERRRGKGHDGLYQGLSTATKDTYDALHMQALPPR*

Underlined

CD4 EC domain (SEQ ID NO: 2)

Italicized

CD8α hinge (SEQ ID NO: 3)

Double underlined

CD28 TM and ICD (SEQ ID NO: 8)

Bold italics

CD3 zeta (SEQ ID NO: 6)

D. Nucleic Acids and Expression Vectors

The present disclosure provides a nucleic acid comprising a first polynucleotide sequence encoding a first chimeric receptor and a second polynucleotide sequence encoding a second chimeric receptor. The first chimeric receptor comprises a first binding domain, a first transmembrane domain, a first costimulatory domain that confers enhanced pro-survival function, and a CD3z intracellular signaling domain. The second chimeric receptor comprises a second binding domain, a second transmembrane domain, a second costimulatory domain that confers enhanced effector function, and a CD3z intracellular signaling domain.

In one aspect, the invention provides a nucleic acid comprising a first polynucleotide sequence encoding a first chimeric receptor comprising the extracellular domains of a CD4 molecule, a CD8α transmembrane domain, a 4-1BB costimulatory domain, and a CD3z intracellular signaling domain; and a second polynucleotide sequence encoding a second chimeric receptor comprising the extracellular domains of a CD4 molecule, a CD28 transmembrane domain, a CD28 costimulatory domain, and a CD3z intracellular signaling domain. In certain embodiments, the invention provides a nucleic acid comprising a first polynucleotide sequence encoding a first chimeric receptor comprising a first binding domain, a CD8α transmembrane domain, a 4-1BB costimulatory domain, and a CD3z intracellular signaling domain; and a second polynucleotide sequence encoding a second chimeric receptor comprising a second binding domain, a CD28 transmembrane domain, a CD28 costimulatory domain, and a CD3z intracellular signaling domain.

In certain embodiments, the first and second binding domain bind the same target. In certain embodiments, the first and second binding domains bind distinct targets. In some embodiments, the first binding domain binds a tumor associated antigen, and the second binding domain binds HIV-1. In some embodiments, the first and second binding domains bind HIV-1. In some embodiments, the first and second binding domains bind a tumor associated antigen. In some embodiments, the first and second binding domains bind the same tumor associated antigen. In some embodiments, the first and second binding domains bind distinct tumor associated antigens.

In certain embodiments, the nucleic acid further comprises a polynucleotide sequence encoding an HIV fusion inhibitor. In certain embodiments, the HIV fusion inhibitor is a cell-surface-expressed HIV fusion inhibitor. In certain embodiments, the HIV fusion inhibitor is C34-CXCR4. In certain embodiments, the cell expressing the HIV fusion inhibitor exhibits increased resistance to infection by HIV, as compared to a control cell not expressing the HIV fusion inhibitor.

In certain embodiments, the first polynucleotide sequence and the second polynucleotide sequence are separated by a linker.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunoglobulin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAVO, *Thosea asigna* virus (TaV), and porcine tescho virus-1 (PTV-1); and carioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a linker further comprises a nucleic acid sequence that encodes a furin cleavage site.

Furin is a ubiquitously expressed protease that resides in the trans-golgi and processes protein precursors before their secretion. Furin cleaves at the COOH— terminus of its consensus recognition sequence. Various furin consensus recognition sequences (or "furin cleavage sites") are known to those of skill in the art, including, without limitation, Arg-X1-Lys-Arg (SEQ ID NO:33) or Arg-X1-Arg-Arg (SEQ ID NO:34), X2-Arg-X1-X3-Arg (SEQ ID NO:35) and Arg-X1-X1-Arg (SEQ ID NO:36), such as an Arg-Gln-Lys-Arg (SEQ ID NO:37), where X1 is any naturally occurring amino acid, X2 is Lys or Arg, and X3 is Lys or Arg. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding Furin and F2A, a linker comprising a nucleic acid sequence encoding Furin and E2A, a linker comprising a nucleic acid sequence encoding Furin and P2A, a linker comprising a nucleic acid sequence encoding Furin and T2A. Those of skill in the art would be able to select the appropriate combination for use in the present invention. In such embodiments, the linker may further comprise a spacer sequence between the Furin and 2A peptide. Various spacer sequences are known in the art, including, without limitation, glycine serine (GS) spacers such as (GS)n, (GSGGS)n (SEQ ID NO:9) and (GGGS)n (SEQ ID NO:10), where n represents an integer of at least 1. Exemplary spacer sequences can comprise amino acid sequences including, without limitation, GGSG (SEQ ID NO:12), GGSGG (SEQ ID NO:13), GSGSG (SEQ ID NO:14), GSGGG (SEQ ID NO:15), GGGSG (SEQ ID NO:16), GSSSG (SEQ ID NO:17), and the like. Those of skill in the art would be able to select the appropriate spacer sequence for use in the present invention.

In some embodiments, a nucleic acid of the present disclosure is provided for the production of a chimeric receptor as described herein, e.g., in a mammalian cell. In some embodiments, a nucleic acid of the present disclosure provides for amplification of the chimeric receptor-encoding nucleic acid.

In some embodiments, a nucleic acid of the present disclosure may comprise a leader sequence. Suitable leader sequences are known to those of skill in the art.

In some embodiments, a nucleic acid of the present disclosure may be operably linked to a transcriptional control element, e.g., a promoter, and enhancer, etc. Suitable promoter and enhancer elements are known to those of skill in the art.

In certain embodiments, the nucleic acid is in operable linkage with a promoter. In certain embodiments, the promoter is a phosphoglycerate kinase-1 (PGK) promoter.

For expression in a bacterial cell, suitable promoters include, but are not limited to, lac, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art.

Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (A1cR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHOS promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996).

22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the Lad repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters.

Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a chimeric receptor inducible expression cassette. In one embodiment, the chimeric receptor inducible expression cassette is for the production of a transgenic polypeptide product that is released upon chimeric receptor signaling. See, e.g., Chmielewski and Abken, Expert Opin. Biol. Ther. (2015) 15(8): 1145-1154; and Abken, Immunotherapy (2015) 7(5): 535-544. In some embodiments, a nucleic acid of the present disclosure further comprises a nucleic acid sequence encoding a cytokine operably linked to a T-cell activation responsive promoter. In some embodiments, the cytokine operably linked to a T-cell activation responsive promoter is present on a separate nucleic acid sequence. In one embodiment, the cytokine is IL-12.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the chimeric receptor into an immune cell or precursor thereof (e.g., a T cell). Accordingly, an expression vector (e.g., a lentiviral vector) of the present invention may comprise a nucleic acid encoding for a chimeric receptor. In some embodiments, the expression vector (e.g., lentiviral vector) will comprise additional elements that will aid in the functional expression of the chimeric receptor encoded therein. In some embodiments, an expression vector comprising a nucleic acid encoding for a chimeric receptor further comprises a mammalian promoter. In one embodiment, the vector further comprises an elongation-factor-1-alpha promoter (EF-la promoter). Use of an EF-la promoter may increase the efficiency in expression of downstream transgenes (e.g., a chimeric receptor encoding nucleic acid sequence). Physiologic promoters (e.g., an EF-la promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention.

In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a chimeric receptor.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a chimeric receptor of the present disclosure. Methods for introducing RNA into a host cell are known in the art. See, e.g., Zhao et al. Cancer Res. (2010) 15: 9053. Introducing RNA comprising a nucleotide sequence encoding a chimeric receptor of the present disclosure into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a chimeric receptor of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

One aspect of the invention includes a nucleic acid comprising: (a) a first polynucleotide sequence encoding a first chimeric receptor comprising a first binding domain, a first transmembrane domain, a first costimulatory domain that confers enhanced pro-survival function, and a CD3z intracellular signaling domain; and (b) a second polynucleotide sequence encoding a second chimeric receptor comprising a second binding domain, a second transmembrane domain, a second costimulatory domain that confers enhanced effector function, and a CD3z intracellular signaling domain.

In certain embodiments of the nucleic acid:

(a) the first costimulatory domain is a 4-1BB costimulatory domain; and/or (b) the second costimulatory domain is a CD28 costimulatory domain; and/or (c) the first transmembrane domain and/or the second transmembrane domain is selected from the group consisting of an artificial hydrophobic sequence, a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154; and/or (d) the first transmembrane domain is a 4-1BB or a CD8α transmembrane domain; and/or (e) the second transmembrane domain is a CD28 transmembrane domain; and/or (f) the first chimeric receptor and/or the second chimeric receptor further comprises a hinge domain; and/or (g) the first chimeric receptor and/or the second chimeric receptor further comprises a hinge domain, wherein the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of CD8, and any combination thereof, and/or (h) the first binding domain binds to a first target, and the second binding domain binds to a second target; and/or (i) the first binding domain binds to a first target, and the second binding domain binds to a second target, wherein the first target and the second target are the same; and/or (j) the first binding domain binds to a first target, and the second binding domain binds to a second target, wherein the first target and the second target are distinct epitopes of the same molecule; and/or (k) the first binding domain binds to a first target, and the second binding domain binds to a second target, and wherein the first target and the second target are different; and/or (l) the first binding domain binds to a first target, and the second binding domain binds to a second target, wherein the first target and/or the second target is human immunodeficiency virus type 1 (HIV-1); and/or (m) the first binding domain binds to a first target, and the second binding domain binds to a second target, wherein the first target and the second target is human immunodeficiency virus type 1 (HIV-1); and/or (n) the first binding domain binds to a first target, and the second binding domain binds to a second target, wherein the first target and/or the second target is envelope glycoprotein gp 120 of human immunodeficiency virus type 1 (HIV-1); and/or (o) the first binding domain binds to a first target, and the second binding domain binds to a second target, wherein the first target and the second target is envelope glycoprotein gp120 of human immunodeficiency virus type 1 (HIV-1); and/or (p) the first binding domain binds to a first target, and the second binding domain binds to a second target, wherein the first binding domain and/or the second binding domain comprises the extracellular domains of a CD4 molecule; and/or (q) the first binding domain binds to a first target, and the second binding domain binds to a second target, wherein the first binding domain and the second binding domain comprises the extracellular domains of a CD4 molecule; and/or (r) the first binding domain binds to a first target, and the second binding domain binds to a second target, wherein the first target and/or the second target is a tumor associated antigen; and/or (s) the first binding domain binds to a first target, and the second binding domain binds to a second target, wherein the first target and/or the second target is a tumor associated antigen, wherein the tumor associated antigen is a liquid tumor antigen, and optionally wherein the liquid tumor antigen is CD 19 or CD22; and/or (t) the first binding domain binds to a first target, and the second binding domain binds to a second target, wherein the first target and/or the second target is a tumor associated antigen, wherein the tumor associated antigen is a solid tumor antigen.

Another aspect of the invention includes a nucleic acid comprising: (a) a first polynucleotide sequence encoding a first chimeric receptor comprising the extracellular domains of a CD4 molecule, a CD8α transmembrane domain, a 4-1BB costimulatory domain, and a CD3z intracellular signaling domain; and (b) a second polynucleotide sequence encoding a second chimeric receptor comprising the extracellular domains of a CD4 molecule, a CD28 transmembrane domain, a CD28 costimulatory domain, and a CD3z intracellular signaling domain.

In certain embodiments of the nucleic acid:

(a) the first polynucleotide sequence and the second polynucleotide sequence is separated by a linker; and/or (b) the first polynucleotide sequence and the second polynucleotide sequence is separated by a linker, and wherein the linker comprises an internal ribosome entry site (RES), a furin cleavage site, a self-cleaving peptide, or any combination thereof; and/or (c) the first polynucleotide sequence and the second polynucleotide sequence is separated by a linker, wherein the linker comprises a furin cleavage site and a self-cleaving peptide; and/or (d) the first polynucleotide sequence and the second polynucleotide sequence is separated by a linker, wherein the linker comprises a furin cleavage site and a self-cleaving peptide, wherein the self-cleaving peptide is a 2A peptide, and optionally wherein the 2A peptide is selected from the group consisting of porcine teschovirus-1 2A (P2A), *Thosea asigna* virus 2A (T2A), equine rhinitis A virus 2A (E2A), and foot-and-mouth disease virus 2A (F2A); and/or (e) the nucleic acid comprises from 5' to 3': the first polynucleotide sequence, the linker, and the second polynucleotide sequence; and/or (f) the nucleic acid comprises from 5' to 3': the second polynucleotide sequence, the linker, and the first polynucleotide sequence; and/or (g) the nucleic acid further comprises a polynucleotide sequence encoding an HIV fusion inhibitor; and/or (h) the nucleic acid further comprises a polynucleotide sequence encoding an HIV fusion inhibitor, wherein the HIV fusion inhibitor is a cell-surface-expressed HIV fusion inhibitor; and/or (i) the nucleic acid further comprises a polynucleotide sequence encoding an HIV fusion inhibitor, wherein the HIV fusion inhibitor is C34-CXCR4.

Another aspect of the invention includes an expression construct comprising:

(a) any of the nucleic acids disclosed herein; and/or (b) any of the nucleic acids disclosed herein, and further comprising an EF-la promoter; and/or (c) any of the nucleic acids disclosed herein, and further comprising a rev response element (RRE); and/or (d) any of the nucleic acids disclosed herein, and further comprising a woodchuck hepatitis virus posttranscriptional regulatory element (WPRE); and/or (e) any of the nucleic acids disclosed herein, and further comprising a cPPT sequence; and/or (f) any of the nucleic acids disclosed herein, wherein the expression construct is a viral vector selected from the group consisting of a retroviral vector, a lentiviral vector, an adenoviral vector, and an adeno-associated viral vector; and/or (g) any of the nucleic acids disclosed herein, wherein the expression construct is a lentiviral vector; and/or (h) any of the nucleic acids disclosed herein, wherein the expression construct is a lentiviral vector, and wherein the lentiviral vector is a self-inactivating lentiviral vector.

E. Methods of Treatment

The modified cells (e.g., T cells comprising dual chimeric cell receptors) described herein may be included in a composition for use in treating a disease or disorder. The composition may include a pharmaceutical composition and further include a pharmaceutically acceptable carrier. A therapeutically effective amount of the pharmaceutical composition comprising the modified T cells may be administered.

In one aspect, the invention includes a method of treating a disease or disorder (e.g. cancer or HIV) in a subject comprising administering to a subject in need thereof a population of modified T cells of the present invention. In another aspect, the invention includes a method for adoptive cell transfer therapy comprising administering to a subject in need thereof a modified T cell of the present invention.

In one aspect, the invention includes a method of treating a disease or disorder in a subject in need thereof, comprising administering a modified immune cell or precursor cell thereof comprising: a first chimeric receptor comprising a first binding domain, a first transmembrane domain, a first costimulatory domain that confers enhanced pro-survival function, and a CD3z intracellular signaling domain; and a second chimeric receptor comprising a second binding domain, a second transmembrane domain, a second costimulatory domain that confers enhanced effector function, and a CD3z intracellular signaling domain.

Diseases or disorders that may be treated include, but are not limited to, cancer, infectious diseases, autoimmunity and transplant. In certain embodiments, the disease or disorder is a viral disease. In certain embodiments, the viral disease is HIV-1 infection. In certain embodiments, the disease or disorder is a cancer.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g. the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

The modified immune cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

In certain exemplary embodiments, the modified immune cells of the invention are used to treat a myeloma, or a condition related to myeloma. Examples of myeloma or conditions related thereto include, without limitation, light chain myeloma, non-secretory myeloma, monoclonal gamopathy of undetermined significance (MGUS), plasmacytoma (e.g., solitary, multiple solitary, extramedullary plasmacytoma), amyloidosis, and multiple myeloma. In one embodiment, a method of the present disclosure is used to treat multiple myeloma. In one embodiment, a method of the present disclosure is used to treat refractory myeloma. In one embodiment, a method of the present disclosure is used to treat relapsed myeloma.

In certain exemplary embodiments, the modified immune cells of the invention are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In one embodiment, a method of the present disclosure is used to treat cutaneous melanoma. In one embodiment, a method of the present disclosure is used to treat refractory melanoma. In one embodiment, a method of the present disclosure is used to treat relapsed melanoma.

In yet other exemplary embodiments, the modified immune cells of the invention are used to treat a sarcoma, or a condition related to sarcoma. Examples of sarcoma or conditions related thereto include, without limitation, angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, and synovial sarcoma. In one embodiment, a method of the present disclosure is used to treat synovial sarcoma. In one embodiment, a method of the present disclosure is used to treat liposarcoma such as myxoid/round cell liposarcoma, differentiated/dedifferentiated liposarcoma, and pleomorphic liposarcoma. In one embodiment, a method of the present disclosure is used to treat myxoid/round cell liposarcoma. In one embodiment, a method of the present disclosure is used to treat a refractory sarcoma. In one embodiment, a method of the present disclosure is used to treat a relapsed sarcoma.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1\times10^5$ cells/kg to about 1×10 cells/kg $10^4$ and at or about $10^{11}$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In other exemplary embodiments, a suitable dosage range of modified cells for use in a method of the present disclosure includes, without limitation, from about $1\times10^5$ cells/kg to about $1\times10^6$ cells/kg, from about $1\times10^6$ cells/kg to about $1\times10^7$ cells/kg, from about $1\times10^7$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg. In an exemplary embodiment, a suitable dosage for use in a method of the present disclosure is about $1\times10^8$ cells/kg. In an exemplary embodiment, a suitable dosage for use in a method of the present disclosure is about $1\times10^7$ cells/kg. In other embodiments, a suitable dosage is from about $1\times10^7$ total cells to about $5\times10^7$ total cells. In some embodiments, a suitable dosage is from about $1\times10^8$ total cells to about $5\times10^9$ total cells. In some embodiments, a suitable dosage is from about $1.4\times10^7$ total cells to about $1.1\times10^9$ total cells. In an exemplary embodiment, a suitable dosage for use in a method of the present disclosure is about $7\times10^9$ total cells.

In some embodiments, the cells are administered at or within a certain range of error of between at or about $10^4$ and at or about $10^9$ $CD4^+$ and/or $CD8^+$ cells/kilograms (kg) body weight, such as between $10^5$ and $10^6$ $CD4^+$ and/or $CD8^+$ cells/kg body weight, for example, at or about $1\times10^5$ $CD4^+$ and/or $CD8^+$ cells/kg, $1.5\times10^5$ $CD4^+$ and/or $CD8^+$ cells/kg, $2\times10^5$ $CD4^+$ and/or $CD8^+$ cells/kg, or $1\times10^6$ $CD4^+$ and/or $CD8^+$ cells/kg body weight. In some embodiments, the cells are administered at or within a certain range of error of, greater than, and/or at least about $1\times10^6$, about $2.5\times10^6$, about $5\times10^6$, about $7.5\times10^6$, or about $9\times10^6$ CD4+ cells, and/or at least about $1\times10^6$, about $2.5\times10^6$, about $5\times10^6$, about $7.5\times10^6$, or about $9\times10^6$ CD8+ cells, and/or at least about $1\times10^6$, about $2.5\times10^6$, about $5\times10^6$, about $7.5\times10^6$, or about $9\times10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ $CD4^+$ cells, and/or between about $10^8$ and $10^{12}$ or between about $10^{10}$ and $10^{11}$ $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of $CD4^+$ to $CD8^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof.

In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent.

The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

In certain embodiments, the modified cells of the invention may be administered to a subject in combination with an immune checkpoint antibody (e.g., an anti-PD1, anti-CTLA-4, or anti-PDL1 antibody). For example, the modified cell may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVA®) or an antigen-binding fragment thereof. In certain embodiments, the modified cell may be administered in combination with an anti-PD-L1 antibody or antigen-binding fragment thereof. Examples of anti-PD-L1 antibodies include, but are not limited to, BMS-936559, MPDL3280A (TECENTRIQ®, Atezolizumab), and MEDI4736 (Durvalumab, Imfinzi). In certain embodiments, the modified cell may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the modified cell comprising the CAR. In certain embodiments, combination treatment comprising an immune checkpoint modulator may increase the therapeutic efficacy of a therapy comprising a modified cell of the present invention.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the subject is provided a secondary treatment. Secondary treatments include but are not limited to chemotherapy, radiation, surgery, and medications.

In some embodiments, the subject can be administered a conditioning therapy prior to CAR T cell therapy. In some embodiments, the conditioning therapy comprises administering an effective amount of cyclophosphamide to the subject. In some embodiments, the conditioning therapy comprises administering an effective amount of fludarabine to the subject. In preferred embodiments, the conditioning therapy comprises administering an effective amount of a combination of cyclophosphamide and fludarabine to the subject. Administration of a conditioning therapy prior to CAR T cell therapy may increase the efficacy of the CAR T cell therapy. Methods of conditioning patients for T cell therapy are described in U.S. Pat. No. 9,855,298, which is incorporated herein by reference in its entirety.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 $mg/m^2$/day and about 2000 $mg/m^2$/day (e.g., 200 $mg/m^2$/day, 300 $mg/m^2$/day, or 500 $mg/m^2$/day). In an exemplary embodiment, the dose of cyclophosphamide is about 300 $mg/m^2$/day. In some embodiments, the lymphodepletion step includes administration of fludarabine at a dose of between about 20 $mg/m^2$/day and about 900 $mg/m^2$/day (e.g., 20 $mg/m^2$/day, 25 $mg/m^2$/day, 30 $mg/m^2$/day, or 60 $mg/m^2$/day). In an exemplary embodiment, the dose of fludarabine is about 30 $mg/m^2$/day.

In some embodiment, the lymphodepletion step includes administration of cyclophosphamide at a dose of between about 200 $mg/m^2$/day and about 2000 $mg/m^2$/day (e.g., 200 $mg/m^2$/day, 300 $mg/m^2$/day, or 500 $mg/m^2$/day), and fludarabine at a dose of between about 20 $mg/m^2$/day and about 900 $mg/m^2$/day (e.g., 20 $mg/m^2$/day, 25 $mg/m^2$/day, 30 $mg/m^2$/day, or 60 $mg/m^2$/day). In an exemplary embodiment, the lymphodepletion step includes administration of cyclophosphamide at a dose of about 300 $mg/m^2$/day, and fludarabine at a dose of about 30 $mg/m^2$/day.

In an exemplary embodiment, the dosing of cyclophosphamide is 300 $mg/m^2$/day over three days, and the dosing of fludarabine is 30 $mg/m^2$/day over three days.

Dosing of lymphodepletion chemotherapy may be scheduled on Days −6 to −4 (with a −1 day window, i.e., dosing on Days −7 to −5) relative to T cell (e.g., CAR-T, TCR-T, a modified T cell, etc.) infusion on Day 0.

In an exemplary embodiment, for a subject having cancer, the subject receives lymphodepleting chemotherapy including 300 $mg/m^2$ of cyclophosphamide by intravenous infusion 3 days prior to administration of the modified T cells.

In an exemplary embodiment, for a subject having cancer, the subject receives lymphodepleting chemotherapy including 300 mg/m$^2$ of cyclophosphamide by intravenous infusion for 3 days prior to administration of the modified T cells.

In an exemplary embodiment, for a subject having cancer, the subject receives lymphodepleting chemotherapy including fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including fludarabine at a dose of 30 mg/m$^2$ for 3 days.

In an exemplary embodiment, for a subject having cancer, the subject receives lymphodepleting chemotherapy including cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including cyclophosphamide at a dose of about 300 mg/m$^2$/day, and fludarabine at a dose of 30 mg/m$^2$ for 3 days.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade ≥3 organ toxicity, aggressive clinical intervention, and/or potentially life threatening).

Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol Blood Marrow Transplant*, doi.org/10.1016/j.bbmt.2018.12.758; Neelapu et al. (2018)*Nat Rev Clin Oncology*, 15:47; Teachey et al. (2016) *Cancer Discov*, 6(6):664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

In certain embodiments, administration of the modified cell decreases HIV-induced loss of one or more of the following cells: CD4$^+$ T cells, CD4T cells, CD8$^+$ T cell, CD8$^-$ T cells, memory CD4$^+$ T cells, and CD14$^+$ macrophages as compared to a subject not having been administered the modified cell.

In certain embodiments, administration of the modified cell decreases incidence of HIV-infected cells in one or more of the following cells: CD4$^+$ T cells, CD4$^-$ T cells, CD8$^+$ T cell, CD8$^-$ T cells, central memory CD4$^+$ T cells, and CD14$^+$ macrophages as compared to a subject not having been administered the modified cell.

In certain embodiments, the subject's blood comprises at least about 100 modified cells/λL of blood by at least week three after a single administration of the modified T cell.

In certain embodiments, the subject's blood comprises at least about 100 modified cells/λL of blood by at least week three after a single administration of the modified T cell.

In certain embodiments, the modified cell binds to the first and second targets of a cell expressing the first and second targets, and kills the cell via granule-mediated cytolysis.

In certain embodiments, the method further comprises administering one or more anti-retroviral therapeutic agents. Examples of anti-retroviral therapeutic agents include, but are not limited to: a) Nucleoside/Nucleotide Reverse Transcriptase Inhibitors (NRTIs) such as Abacavir, or ABC (Ziagen), Didanosine, or ddl (Videx), Emtricitabine, or FTC (Emtriva), Lamivudine, or 3TC (Epivir), Stavudine, or d4T (Zerit)Tenofovir alafenamide, or TAF (Vemlidy), Tenofovir disoproxil fumarate, or TDF (Viread), Zidovudine or ZDV (Retrovir); b) Non-nucleoside Reverse Transcriptase Inhibitors (NNRTIs) such as Delavirdine or DLV (Rescripor), Doravirine, or DOR (Pifeltro), Efavirenz or EFV (Sustiva), Etravirine or ETR (Intelence), Nevirapine or NVP (Viramune), Rilpivirine or RPV (Edurant); c) Protease Inhibitors (PIs) such as Atazanavir or ATV (Reyataz), Darunavir or DRV (Prezista), Fosamprenavir or FPV (Lexiva), Indinavir or IDV (Crixivan), Lopinavir+ritonavir, or LPV/r (Kaletra), Nelfinavir or NFV (Viracept), Ritonavir or RTV (Norvir), Saquinavir or SQV (Invirase, Fortovase), Tipranavir or TPV (Aptivus); d) Integrase Inhibitors such as Bictegravir or BIC (combined with other drugs as Biktarvy), Dolutegravir or DTG (Tivicay), Elvitegravir or EVG (Vitekta), Raltegravir or RAL (Isentress); e) Fusion Inhibitors such as Enfuvirtide, or ENF or T-20 (Fuzeon); f) CCR5 Antagonist such as Maraviroc, or MVC (Selzentry); f) Post-Attachment Inhibitor or Monoclonal Antibody; g) Pharmacologic enhancers, or "Drug Boosters"; and the like, and any combination thereof.

In one aspect, the invention includes a method of treating cancer in a subject in need thereof, comprising administering to the subject any one of the modified immune or precursor cells disclosed herein.

In another aspect, the invention includes a method of treating HIV in a subject in need thereof, comprising administering to the subject any one of the modified immune or precursor cells disclosed herein.

In yet another aspect, the invention includes a method treating an HIV-1 infection in a subject in need thereof. The method comprises administering a modified immune cell or precursor cell thereof comprising a first chimeric receptor comprising the extracellular domains of a CD4 molecule, a CD8α transmembrane domain, a 4-1BB costimulatory domain, and a CD3z intracellular signaling domain; and a second chimeric receptor comprising the extracellular domains of a CD4 molecule, a CD28 transmembrane domain, a CD28 costimulatory domain, and a CD3z intracellular signaling domain.

In still another aspect, the invention includes a method of treating a cancer in a subject in need thereof. The method comprises administering a modified T cell comprising a first chimeric receptor comprising a first binding domain, a first transmembrane domain, a first costimulatory domain that confers enhanced pro-survival function, and a CD3z intracellular signaling domain; and a second chimeric receptor comprising a second binding domain, a second transmembrane domain, a second costimulatory domain that confers enhanced effector function, and a CD3z intracellular signaling domain.

Another aspect of the invention includes a method of treating an HIV-1 infection in a subject in need thereof, comprising administering a modified T cell comprising a first chimeric receptor comprising the extracellular domains of a CD4 molecule, a CD8α transmembrane domain, a 4-1BB costimulatory domain, and a CD3z intracellular signaling domain; and a second chimeric receptor comprising the extracellular domains of a CD4 molecule, a CD28 transmembrane domain, a CD28 costimulatory domain, and a CD3z intracellular signaling domain.

In certain embodiments, the modified cell is an autologous cell. In certain embodiments, the modified cell is an autologous cell obtained from a human subject. In certain embodiments, the modified cell is a modified T cell.

Another aspect of the invention includes a method of treating a disease or disorder in a subject in need thereof, comprising:

(a) administering any of the modified cells disclosed herein, or any of the pharmaceutical compositions disclosed herein; or
(b) administering a modified immune cell or precursor cell thereof comprising:
  (i) a first chimeric receptor comprising a first binding domain, a first transmembrane domain, a first costimulatory domain that confers enhanced pro-survival function, and a CD3z intracellular signaling domain; and
  (ii) a second chimeric receptor comprising a second binding domain, a second transmembrane domain, a second costimulatory domain that confers enhanced effector function, and a CD3z intracellular signaling domain.

In certain embodiments of the method:

(a) the disease or disorder is a viral disease; and/or
(b) the disease or disorder is a viral disease, wherein the viral disease is HIV-1 infection; and/or
(c) the disease or disorder is a cancer; and/or
(d) the disease or disorder is a cancer, wherein the cancer is a liquid tumor; and/or
(e) the disease or disorder is a cancer, wherein the cancer is a hematological malignancy; and/or
(f) the disease or disorder is a cancer, wherein the cancer is a solid tumor.

In certain embodiments of the method, the method is directed to treating an HIV-1 infection in a subject in need thereof, and comprises administering a modified immune cell or precursor cell thereof comprising:

(a) a first chimeric receptor comprising the extracellular domains of a CD4 molecule, a CD8α transmembrane domain, a 4-1BB costimulatory domain, and a CD3z intracellular signaling domain; and
(b) a second chimeric receptor comprising the extracellular domains of a CD4 molecule, a CD28 transmembrane domain, a CD28 costimulatory domain, and a CD3z intracellular signaling domain.

In certain embodiments of the method, the method is directed to treating a cancer in a subject in need thereof and comprises administering a modified T cell comprising: (a) a first chimeric receptor comprising a first binding domain, a first transmembrane domain, a first costimulatory domain that confers enhanced pro-survival function, and a CD3z intracellular signaling domain; and (b) a second chimeric receptor comprising a second binding domain, a second transmembrane domain, a second costimulatory domain that confers enhanced effector function, and a CD3z intracellular signaling domain.

In certain embodiments, the method is directed to treating an HIV-1 infection in a subject in need thereof, and comprises administering a modified T cell comprising: (a) a first chimeric receptor comprising the extracellular domains of a CD4 molecule, a CD8α transmembrane domain, a 4-1BB costimulatory domain, and a CD3z intracellular signaling domain; and (b) a second chimeric receptor comprising the extracellular domains of a CD4 molecule, a CD28 transmembrane domain, a CD28 costimulatory domain, and a CD3z intracellular signaling domain.

In certain embodiments of the method, (a) the modified cell is a modified immune cell; and/or
(b) the modified cell is a modified T cell; and/or
(c) the modified cell is an autologous cell; and/or
(d) the modified cell is an autologous cell obtained from a human subject; and/or
(e) the subject is human; and/or
(f) administration of the modified cell decreases HIV-induced loss of one or more of the following cells: $CD4^+$ T cells, $CD4^-$ T cells, $CD8^+$ T cell, $CD8^-$ T cells, memory $CD4^+$ T cells, and $CD14^+$ macrophages as compared to a subject not having been administered the modified cell; and/or
(g) administration of the modified cell decreases incidence of HIV-infected cells in one or more of the following cells: $CD4^+$ T cells, $CD4^-T^+$ cells, $CD8^+$ T cell, $CD8^-$ T cells, central memory $CD4^+$ T cells, and $CD14^+$ macrophages as compared to a subject not having been administered the modified cell; and/or
(h) the subject's blood comprises at least about 100 modified cells/L of blood by at least week three after a single administration of the modified T cell; and/or
(i) the modified cell binds to the first and second targets of a cell expressing the first and second targets, and kills the cell via granule-mediated cytolysis; and/or
(j) the method further comprises administering one or more anti-retroviral therapeutic agents.

F. Sources of Immune Cells

Prior to expansion, a source of immune cells may be obtained from a subject for ex vivo manipulation. Sources of target cells for ex vivo manipulation may also include, e.g., autologous or heterologous donor blood, cord blood, or bone marrow. For example, the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a $CD8^+$ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product.

Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps.

In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune are obtained cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker −) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO$^{+}$ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNABEADS® M-450 CD3/CD28 T Cell Expander).

In some embodiments, T cells are separated from a PBMC sample by negative selection of markers expressed on non-T cells, such as B cells, monocytes, or other white blood cells, such as CD 14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In some embodiments, memory T cells are present in both CD62L+ and CD62L− subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a $CD4^+$ T cell population and a $CD8^+$ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+ T helper cells are sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, $CD4^+$ T cells. In some embodiments, central memory CD4+ cells are CD62L+ and CD45RO+. In some embodiments, effector CD4+ cells are CD62L- and CD45RO. In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

G. Expansion of Immune Cells

Whether prior to or after modification of cells, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more. In one embodiment, human T regulatory cells are expanded via anti-CD3 antibody coated KT64.86 artificial antigen presenting cells (aAPCs). Methods for expanding and activating T cells can be found in U.S. Pat. Nos. 7,754,482, 8,722,400, and 9,555,105, contents of which are incorporated herein in their entirety.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

H. Pharmaceutical Compositions and Formulations

Also provided are populations of modified immune cells of the invention, compositions containing such cells and/or enriched for such cells, such as in which cells expressing dual chimeric receptors make up at least 50%, 60%, 70%, 80%, 90%, 91%, 92%, 93%, 94%, 95%, 96%, 97%, 98%, 99%, or more of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives.

Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

In certain aspects, the invention provides a pharmaceutical composition comprising a therapeutically effective amount of any of the modified cells disclosed herein.

In another aspect, the invention provides a pharmaceutical composition comprising a therapeutically effective amount of a modified immune cell or precursor cell thereof, wherein the modified cell comprises: a first chimeric receptor comprising a first binding domain, a first transmembrane domain, a first costimulatory domain that confers enhanced pro-survival function, and a CD3z intracellular signaling domain; and a second chimeric receptor comprising a second binding domain, a second transmembrane domain, a second costimulatory domain that confers enhanced effector function, and a CD3z intracellular signaling domain.

In yet another aspect, the invention provides a pharmaceutical composition comprising a therapeutically effective amount of a modified immune cell or precursor cell thereof, wherein the modified cell comprises: a first chimeric receptor comprising the extracellular domains of a CD4 molecule, a 4-1BB transmembrane domain, a 4-1BB costimulatory domain, and a CD3z intracellular signaling domain; and a second chimeric receptor comprising the extracellular domains of a CD4 molecule, a CD28 transmembrane domain, a CD28 costimulatory domain, and a CD3z intracellular signaling domain.

In another aspect, the invention provides a pharmaceutical composition comprising:

(a) a therapeutically effective amount any of the modified cells disclosed herein; and/or (b) a therapeutically effective amount of a modified immune cell or precursor cell thereof, wherein the modified cell comprises:

(i) a first chimeric receptor comprising a first binding domain, a first transmembrane domain, a first costimulatory domain that confers enhanced pro-survival function, and a CD3z intracellular signaling domain; and (ii) a second chimeric receptor comprising a second binding domain, a second transmembrane domain, a second costimulatory domain that confers enhanced effector function, and a CD3z intracellular signaling domain; and/or (c) a therapeutically effective amount of a modified immune cell or precursor cell thereof, wherein the modified cell comprises:

(i) a first chimeric receptor comprising the extracellular domains of a CD4 molecule, a CD8α transmembrane domain, a 4-1BB costimulatory domain, and a CD3z intracellular signaling domain; and (ii) a second chimeric receptor comprising the extra-cellular domains of a CD4 molecule, a CD28 transmembrane domain, a CD28 costimulatory domain, and a CD3z intracellular signaling domain.

I. Methods of Producing Genetically Modified Immune Cells

The present disclosure provides methods for producing or generating a modified immune cell or precursor thereof (e.g., a T cell comprising dual chimeric receptors) of the invention for tumor immunotherapy, e.g., adoptive immunotherapy or treatment of a disease, e.g. HIV.

One aspect of the invention includes a method for generating a modified immune cell comprising introducing into an immune cell any of the nucleic acids disclosed herein.

In certain embodiments, the immune cell is obtained from the group consisting of T cells, dendritic cells, and stem cells. In certain embodiments, the immune cell is a T cell selected from the group consisting of a $CD8^+$ T cell, a $CD4^+$ T cell, a naive T cell, a central memory T cell, a stem cell memory T cell, an effector memory T cell, a natural killer T cell, and a regulatory T cell.

In certain embodiments, the method further comprises expanding the T cell. In certain embodiments, the method further comprises expanding the T cell, wherein the T cell is expanded in the range of about 150 fold to about 500 fold. In certain embodiments, the method further comprises expanding the T cell, wherein the T cell is expanded by at least about 150 fold. In certain embodiments, the method further comprises expanding the T cell, wherein the T cell is expanded by at least about 300 fold. In certain embodiments, the method further comprises expanding the T cell, wherein the T cell expansion is in vivo.

In some embodiments, the dual chimeric receptor is introduced into a cell by an expression vector. Expression vectors comprising a nucleic acid sequence encoding the dual chimeric receptors of the present invention are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the dual chimeric receptors in the host cell. In some embodiments, the adenovirus genome is a 36 kb, linear, double stranded DNA, where a foreign DNA sequence (e.g., a nucleic acid encoding a dual chimeric receptor) may be inserted to substitute large pieces of adenoviral DNA in order to make the expression vector of the present invention (see, e.g., Danthinne and Imperiale, Gene Therapy (2000) 7(20): 1707-1714).

Another expression vector is based on an adeno associated virus (AAV), which takes advantage of the adenovirus coupled systems. This AAV expression vector has a high frequency of integration into the host genome. It can infect nondividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368. In some embodiments, the nucleic acid encoding the dual chimeric receptors is introduced into the cell via viral transduction. In certain embodiments, the viral transduction comprises contacting the immune or precursor cell with a viral vector comprising the nucleic acid encoding a dual chimeric receptor. In certain embodiments, the viral vector is an adeno-associated viral (AAV) vector. In certain embodiments, the AAV vector comprises a Woodchuck Hepatitis Virus post-transcriptional regulatory element (WPRE). In certain embodiments, the AAV vector comprises a polyadenylation (polyA) sequence. In certain embodiments, the polyA sequence is a bovine growth hormone (BGH) polyA sequence.

Retrovirus expression vectors are capable of integrating into the host genome, delivering a large amount of foreign genetic material, infecting a broad spectrum of species and cell types and being packaged in special cell lines. The retroviral vector is constructed by inserting a nucleic acid (e.g., a nucleic acid encoding a dual chimeric receptor) into the viral genome at certain locations to produce a virus that is replication defective. Though the retroviral vectors are able to infect a broad variety of cell types, integration and stable expression of the dual chimeric receptors requires the division of host cells.

Lentiviral vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are capable of infecting non-dividing cells and can be used for both in vivo and ex vivo gene transfer and expression, e.g., of a nucleic acid encoding dual chimeric receptors (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired.

Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell an immune cell or precursor thereof, e.g., a T cell, an NK cell, or an NKT cell.

The present invention also provides modified cells which include and stably express the dual chimeric receptors of the present disclosure. In some embodiments, the modified cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In certain embodiments, the genetically engineered cells are autologous cells.

Modified cells (e.g., comprising dual chimeric receptors) may be produced by stably transfecting host cells with an expression vector including a nucleic acid of the present disclosure. Additional methods for generating a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing the dual chimeric receptors of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). Compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, molecular biology assays well known to those of skill in the art, such as Southern and Northern blotting, RT-PCR and PCR; biochemistry assays, such as detecting the presence or absence of a particular peptide, e.g., by immunological means (ELISAs and Western blots) or by assays described herein to identify agents falling within the scope of the invention.

In one embodiment, the nucleic acids introduced into the host cell are RNA. In another embodiment, the RNA is mRNA that comprises in vitro transcribed RNA or synthetic RNA.

The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA may be, for example, genomic DNA, plasmid DNA, phage DNA, cDNA, synthetic DNA sequence or any other appropriate source of DNA.

PCR may be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers may also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. 5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

In some embodiments, the RNA is electroporated into the cells, such as in vitro transcribed RNA. Any solutes suitable for cell electroporation, which can contain factors facilitating cellular permeability and viability such as sugars, peptides, lipids, proteins, antioxidants, and surfactants can be included.

In some embodiments, a nucleic acid encoding the dual chimeric receptors of the present disclosure will be RNA, e.g., in vitro synthesized RNA. Methods for in vitro synthesis of RNA are known in the art; any known method can be used to synthesize RNA comprising a sequence encoding a chimeric receptor. Methods for introducing RNA into a host cell are known in the art. See, e.g., Zhao et al. Cancer Res. (2010) 15: 9053. Introducing RNA comprising a nucleotide sequence encoding the dual chimeric receptors into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding dual chimeric receptors.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

In some embodiments, the immune cells (e.g. T cells) can be incubated or cultivated prior to, during and/or subsequent to introducing the nucleic acid molecule encoding the dual chimeric receptors. In some embodiments, the cells (e.g. T cells) can be incubated or cultivated prior to, during or subsequent to the introduction of the nucleic acid molecule encoding the dual chimeric receptors, such as prior to, during or subsequent to the transduction of the cells with a viral vector (e.g. lentiviral vector) encoding the exogenous receptor.

One aspect of the invention includes a method for generating a modified immune cell, the method comprising introducing into an immune cell any of the nucleic acids disclosed herein.

In certain embodiments of the method, (a) the immune cell is obtained from the group consisting of T cells, dendritic cells, and stem cells; and/or (b) the immune cell is a T cell selected from the group consisting of a $CD8^{+}$ T cell, a CD4+ T cell, a naive T cell, a central memory T cell, a stem cell memory T cell, an effector memory T cell, a natural killer T cell, and a regulatory T cell; and/or (c) the method further comprises expanding the T cell; and/or (d) the method further comprises expanding the T cell, wherein the T cell is expanded in the range of about 150 fold to about 500 fold; and/or (e) the method further comprises expanding the T cell, wherein the T cell is expanded by at least about 150 fold; and/or (f) the method further comprises expanding the T cell, wherein the T cell is expanded by at least about 300 fold; and/or (g) the method further comprises expanding the T cell, wherein the T cell expansion is in vivo.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods used in the Experimental Examples are now described:

Humanized mice: Male and female NOD/SCID/IL2R$\gamma^{-/-}$ (NSG) mice (The Jackson Laboratory) were housed at in pathogen-free facilities at either the Ragon Institute of MGH, MIT and Harvard or the University of Pennsylvania. Mice were maintained in microisolator cages and fed autoclaved food and water. BLT humanized mice were generated at the Ragon Institute as previously described (Brainard et al. (2009) J Virol 83, 7305-7321). Briefly, 6 to 8-week-old NSG mice were sublethally whole-body irradiated (2 Gy), anesthetized, and implanted with 1-mm$^3$ fragments of human fetal thymus and liver tissue under the murine kidney capsule. Following, $10^5$ autologous fetal liver tissue derived human $CD34^+$ hematopoietic stem cells (HSCs) were injected intravenously (IV) within 6 hours of tissue transplantation. Human fetal tissues (17 to 19 weeks of gestational age) were made available through Advanced Bioscience Resources (ABR, Alameda, CA). BLT humanized mice were also generated at the University of Pennsylvania as previously described (Pardi et al. (2017) *Nat Commun* 8, 14630). Briefly, 1-1.5×$10^5$ human fetal liver-derived $CD34^+$ HSCs were administered IV into 7 to 10-week old NSG mice 24 hours after busulfan (30 mg kg$^1$) conditioning. 3 to 6 days following stem cell transplant, mice were surgically implanted with 3 to 5 fragments of autologous human fetal thymus tissue measuring 3 to 5 mm$^3$ under the murine kidney capsule. For all BLT humanized mice, human immune reconstitution was monitored over 12 to 17 weeks. Mice were generally considered reconstituted and included in experiments when greater than 50% of cells in the lymphocyte gate were human $CD45^+$ and, of those human cells, greater than 40% were $CD3^+$ T cells.

Figure 31A:
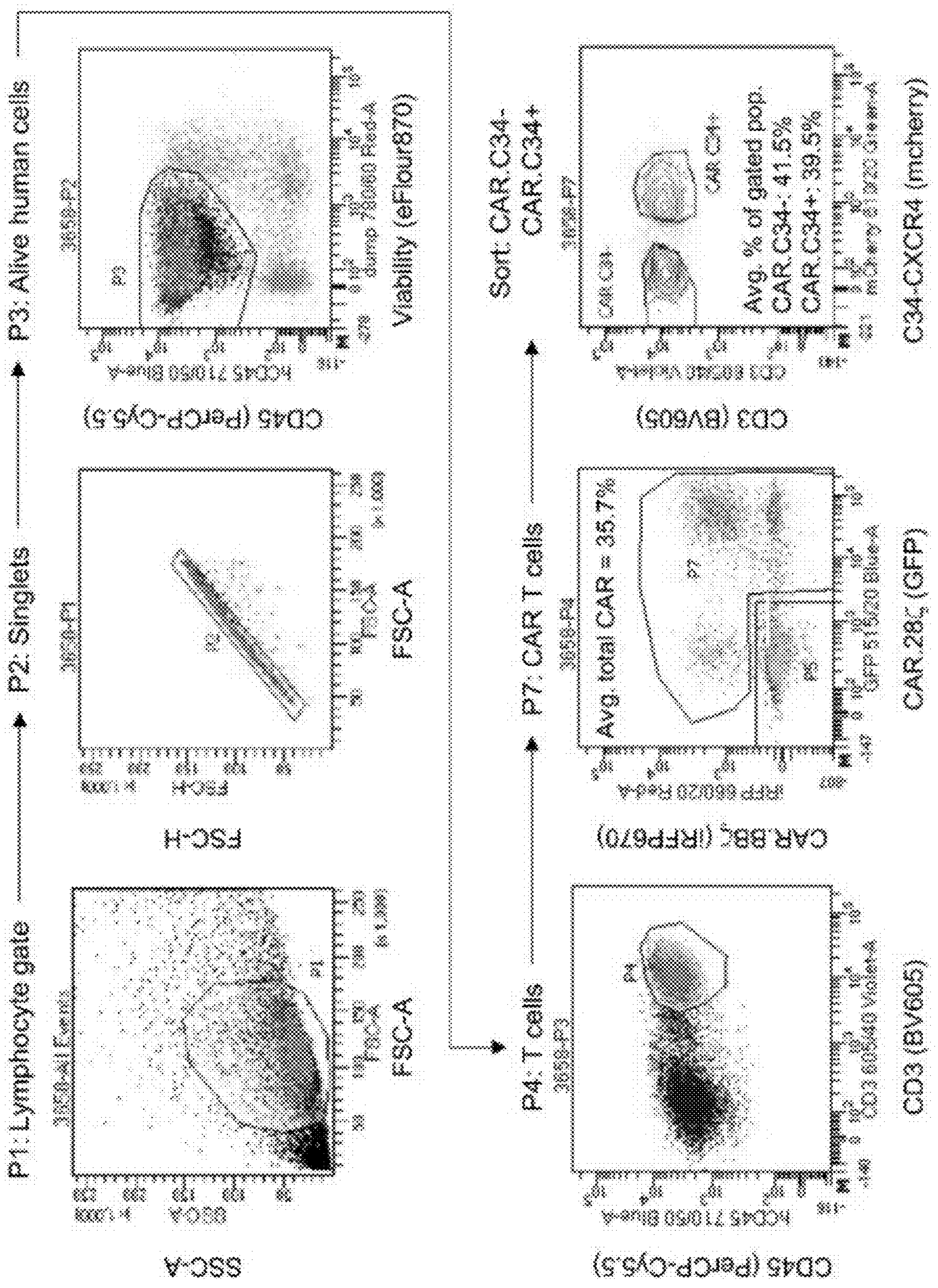
FIGS. 31A-31B illustrate a gating strategy for FACS sorting of CAR T cells and endogenous central memory $CD4^+$ T cells.
Figure 31B:
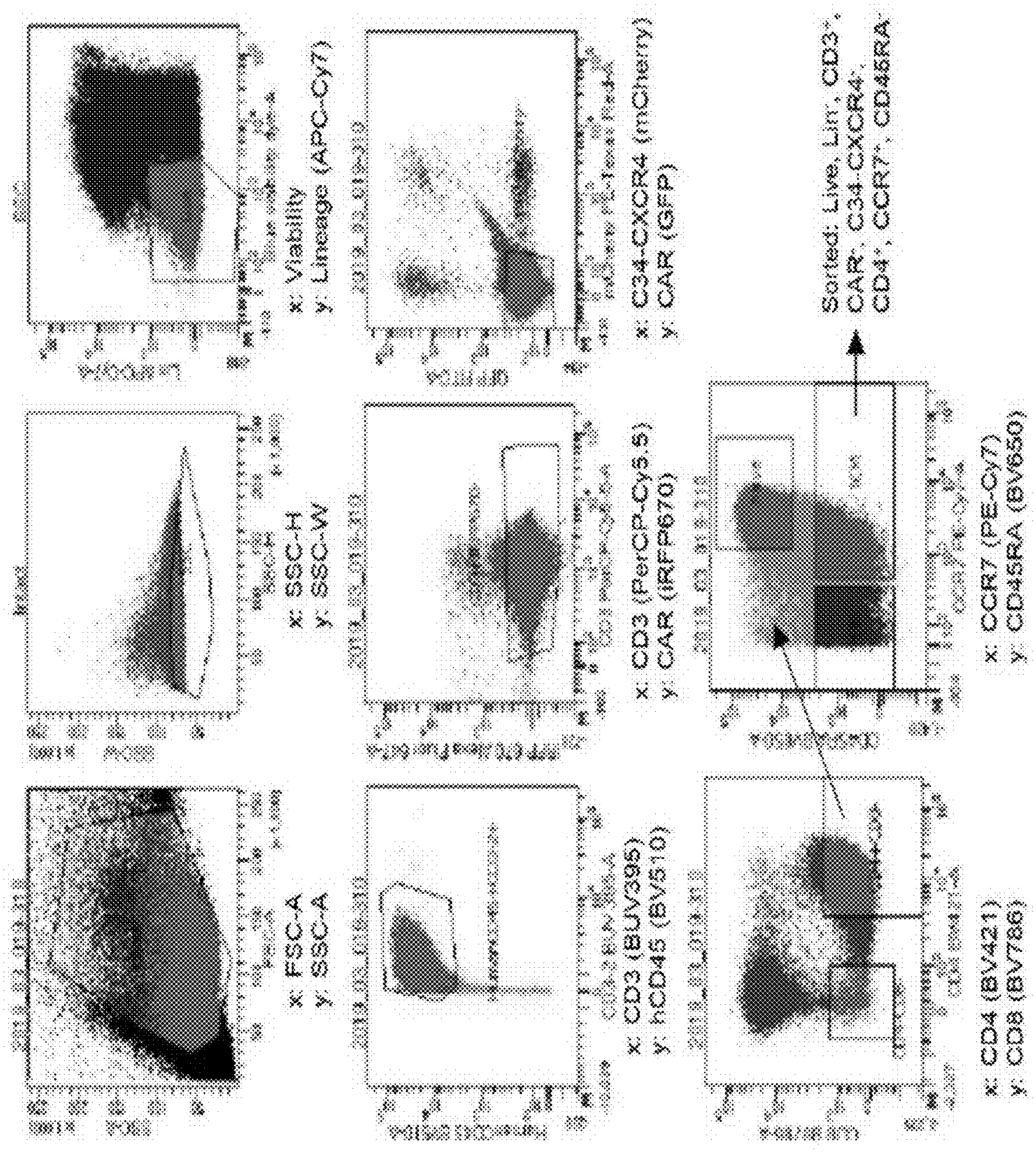

Flow Cytometry and Cell Sorting: Surface staining was performed in PBS containing 2% fetal calf serum and 2 mM EDTA using anti-human antibodies procured from the following sources: BioLegend: CD45 (HI30 and 2D1), CD19 (HIB19), CDS (OKT3), CD4 (OKT4), CDS (RPA-T8), CD45RA (HI100), CD27 (LG.3A10), CCR7 (G043H7), CCR5 (J418F1), CD271 (ME20.4), PD-1 (EH12.2H7), TIGIT (VSTM3), 2B4 (C1.7), CD107a (H4A3); BD Biosciences: CD45 (HI30), CDS (UCHT1), CDS (SKi), CD45RA (HI100), CCR7 (3D12); R&D: Human EGFR (Cetuximab Biosimilar, Hul). Live cells were discriminated by staining with either Fixable Viability Dye eFlour 780 (eBioscience) or LIVE/DEAD Fixable Blue (Invitrogen). Intracellular proteins were stained for with Cell Fixation & Cell Permeabilization Kit (Invitrogen) or True-Nuclear Transcription Factor Buffer Set (BioLegend) in accordance with the manufacture's protocol using antibodies from the following sources: BioLegend: IL-2 (MQH-17H12), Perforin (B-D48); BD Biosciences: TNF (Mab11), IFN-y (4S.B3), Granzyme B (GB11), MIP-1β (D21-1351), GM-CSF (BVD2-21C11), Active Caspase-3 (C92605); Beckman Coulter: HIV-1 Core Antigen (KC57); eBioscience: T-bet (4B10), EOMES (WD1928), TOX (TXRX10). Flow cytometry data were acquired on a BD LSR II, BD LSRFortessa, and BD FACS Symphony instruments. Data were analyzed using FlowJo software (TreeStar). Sorting of C34-CXCR+ and C34-CXCR4− CAR T cells for quantitation of viral burden by digital-droplet PCR was performed by sorting live C34-$CXCR4^+$ and C34-$CXCR4^-$ CAR T cells from splenocytes after surface staining with the following antibodies from BioLegend: CD45 (2D1), CDS (OKT3), CD4 (OKT4), CD8 (RPA-T8). Living CAR T cells were discriminated based on staining with Fixable Viability Dye eFlour 780 (FIG. 31A). Sorting of endogenous central memory $CD4^+$ T cell populations for quantitation of viral burden by droplet-digital PCR was performed by staining splenocytes with the following antibodies from BioLegend: anti-mouse CD45 (30-F11), antihuman CD45 (HI30), CD20 (2H7), CD14 (HCD14), CD56 (HCD56), CDS (OKT3), CD4 (RPA-T4), CDS (SKi), CCR7 (G043H7), CD45RA (H1100). Live cells were discriminated by staining with LIVE/DEAD Fixable Blue (Invitrogen). FACSAria II (BD Biosciences) was used for all cell sorting (FIG. 31B).

HIV inoculum preparation: Viral stocks of the $HIV_{JRCSF}$ and $HIV_{MJ4}$ molecular clones were generated through transfections of HEK293T cells (ATCC: CRL-3216) and tittered as previously described (Boutwell et al. (2009) *J Virol* 83, 2460-2468). $HIV_{BAL}$ virus stocks were generated by passage in anti-CD3/CD28 stimulated human $CD4^+$ T cells as previously described (Leibman et al. (2017) *PLoS Pathog* 13, e1006613).

HIV viral load quantitation: Viral RNA was isolated from plasma using the QiaAmp Viral RNA Mini Kit (Qiagen). Viral Loads were determined by quantitative RT-PCR using the QuantiFast Syber Green RT-PCR kit (Qiagen) as previously described (Boutwell et al. (2009) *J Virol* 83, 2460-2468). The limit of quantification for this assay is 1.81 log copies RNA $mL^{-1}$ plasma.

Plasmid construction: The amino acid sequence for the CD4-based CAR constructs containing the intracellular signaling domains: CD3-ζ, 4-1BB/CD3-ζ and CD28/CD3-ζ are described elsewhere (Leibman et al. (2017) *PLoS Pathog* 13, e1006613). In this study, each CAR was amplified from their original plasmid with 5'-CACGTCCTAGGATGGCCTTACCAGTG (SEQ ID NO: 38) and 5'-GTGGTCGACTTATGCGCTCCTGCTGAAC (SEQ ID NO: 39) and inserted into the Avril and Sall restriction enzyme sites of the pTRPE plasmid. In this orientation, the CAR is downstream of GFP, mCherry or iRFP670 and a T2A linker that permits expression of both proteins. To construct the plasmids for CAR T cell selection, double-stranded DNA fragments (IDT) encoding NGFR (CD271) (Johnson et al. (1986) Cell 47, 545-554) and truncated EGFR (Wang et al. (2011) Blood 118, 1255-1263) were custom synthesized, flanked with suitable restriction enzyme sites and cloned into the second position of the pTRPE plasmid preceded by the CAR-BBζ and CAR-28ζ gene and T2A linker. The amino acid sequence for the C34-CXCR4 construct is described elsewhere (Buggert (2014) *PLoS Pathog* 10, e1004251). A single Asp mutation was introduced in CXCR4 (D97N), which has been previously described (Brelot et al. (2000) *J Biol Chem* 275, 23736-23744) to impair SDF-1 binding and limit receptor internalization.

Lentivirus production and transfection: To generate lentiviral particles, expression vectors encoding VSV or Cocal glycoprotein, HIV Rev, HIV Gag and Pol (pTRPE pVSV-g, pCocal-g, pTRPE.Rev, and pTRPE g/p, respectively) were synthesized by DNA 2.0 or ATUM (Newark, CA) and transfected into HEK293T cells with pTRPE transfer vectors using Lipofectamine 2000 (Life Technologies) as previously described (Leibman et al. (2017) *PLoS Pathog* 13, e1006613). Transfected HEK293T cell supernatant was collected at 24 and 48 hours, filtered through a 0.45 μm nylon syringe filter and concentrated by ultracentrifugation for 2.5 hours at 25,000 rpm at 4° C. Supernatant was aspirated and virus pellet was resuspend in 800 μL total volume and stored at −80° C.

Cell Culture and Selection: For preparation of CAR T cells: T cells from healthy adult human donors were purified by negative selection using RosetteSep Human $CD3^+$ Enrichment Cocktails (Stem-Cell Technologies) according to the manufacturer's protocol. T cells from BLT humanized mice were purified by creating single-cell suspensions from spleen, bone marrow, and liver. Mononuclear cells were isolated by density gradient centrifugation using Lymphoprep (Stem-Cell Technologies). Human $CD2^+$ cells were purified by CD2 Microbeads (Miltenyi Biotec) according to the manufacturer's protocol. T cells were cultured at $10^6$ cells $mL^{-1}$ in either complete RPM: RPMI 1640, 1% Penicillin-Streptomycin, 2 mM GlutaMax and 25 mM HEPES buffer from Life Technologies, and 10% fetal calf serum (Seradigm), or CTS OpTmizer T-Cell Expansion SFM (Gibco) with 1% Penicillin-Streptomycin, 2 mM GlutaMax and 25 mM HEPES buffer. T cell expansion medium was supplemented with 10 ng $mL^{-1}$ human IL-7 (R&D) and 5 ng $mL^{-1}$ human IL-15 (BioLegend). T cells were stimulated with anti-CD3/CD28 coated Dynabeads (Life Technologies) at a 3:1 bead-to-cell ratio at 37° C., 5% CO2 and 95% humidity incubation conditions. 18 hours after stimulation half of the medium was removed and replaced with 200 to 300 μL of the appropriate lentivirus supernatant for CAR transduction. On day 5, the Dynabeads were removed from cell culture by magnetic separation. Medium was changed every other day throughout cell culture spanning 8 to 10 days, or as necessary to adjust cell counts to $0.5\times10^6$ cells $mL^1$.

Two-step immunomagnetic selection of CAR T cells during manufacturing: On day 4 after initial T cell activation, anti-CD3/CD28 Dynabeads were removed by magnetic bead separation. T cells were counted and then incubated at a 1:2 cell-to-bead ratio with CELLection Biotin Binder Dynabeads (Life Technologies) conjugated to anti-EGFR (Cetuximab) antibody. Truncated $EGFR^+$ T cells were isolated according to the manufacturer's protocol. The cell concentration was adjusted to $0.5\times10^6$ cells mL-1 with medium and expanded as described above. On day 7 after initial activation, $EGFRt^+$ T cells were counted and incubated with CD271 Microbeads (Miltenyi Biotec) to positively select for $NGFR^+$ T cells according to the manufacturer's instructions. The eluted fraction of T cells contained 85% to 95% $EGFR^+NGFR^+$ T cells. The T cells were placed in culture for one more day at the adjusted cell concentration prior to infusion into BLT humanized mice.

HIV treatment and ART discontinuation mouse model: For the study described in FIGS. 8A-8L, BLT humanized mice were administered 2 mg of medroxyprogesterone (McKesson) subcutaneously 1 week prior to intravaginal challenge with 20,000 $TCID_{50}$ $HIV_{RCSF}$ in 20 μL total volume. 75 to 100 μL of blood was obtained through puncture of the retro-orbital sinus weekly to quantify viral load and immunophenotype circulating blood cells. 3 weeks post-HIV challenge all infected mice were administered daily IP injections of antiretroviral therapy (ART) consisting of 10 mg $kg^{-1}$ EFdA (4'-ethynyl-2-fluoro-2'-deoxyadenosine, LeadGen Labs) and 50 mg $kg^{-1}$ Dolutegravir (Sigma) for 1 week and then every second day thereafter. Following 2 weeks of ART, four treatment groups were defined based on normalization of plasma viral load, body weight, and human reconstitution percentages. Group 1 (G1; n=6) and group 3 (G3; n=10) are treatment groups that were infused with $10^7$ CAR-BBζ T cells, while group 2 (G2; n=6) and group 4 (G4; n=9) are control groups that were infused with 107 CAR-BBΔζ T cells that express a defective CD3-ζ endodomain. T cells were administered in a 300 pL volume via tail vein injection. ART was interrupted immediately after adoptive T cell transfer for G1 and G2, while ART discontinuation was delayed for 3 weeks in G3 and G4. At necropsy, 17 weeks after HIV challenge, various tissues were collected to analyze the CAR T cells.

Figure 30B:
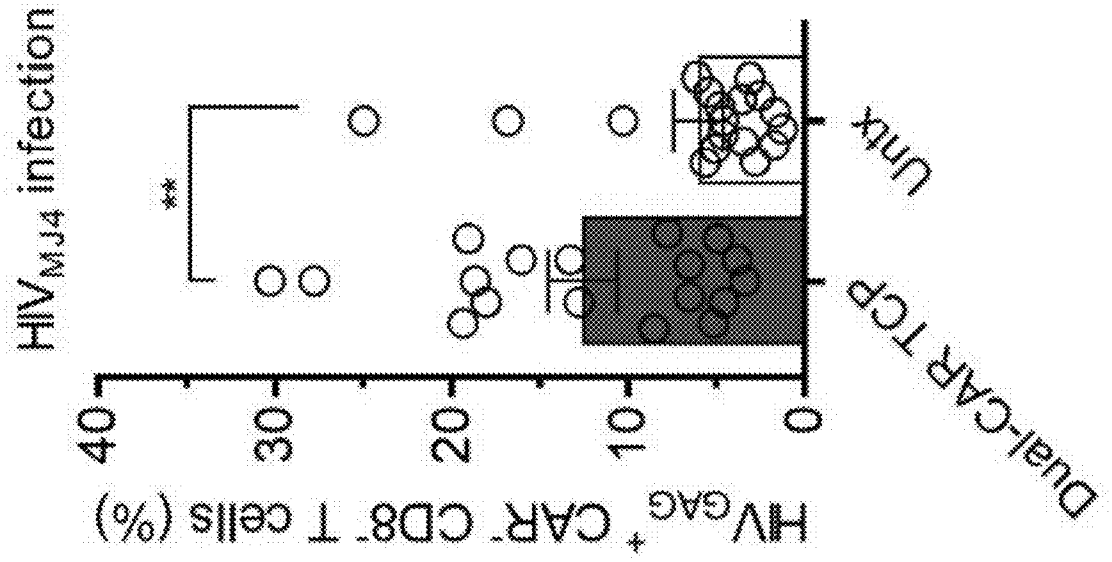
FIGS. 30A-30E illustrate HIV-resistant Dual-CAR TCP reduces virus replication in vivo.
Figure 30A:
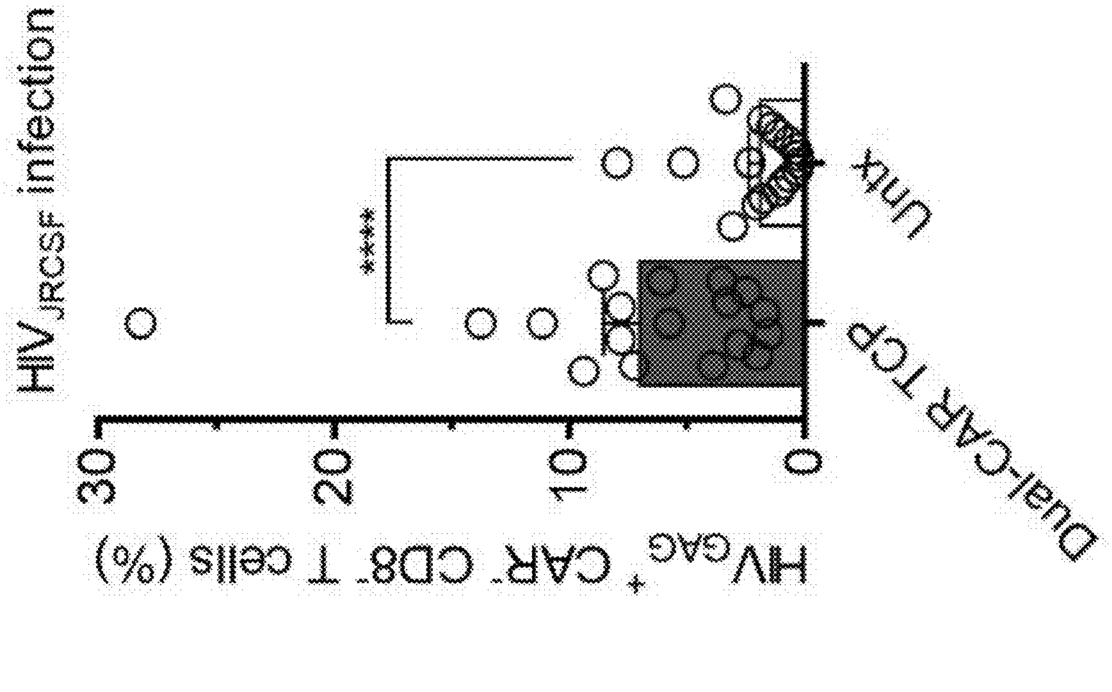
Figure 30C:
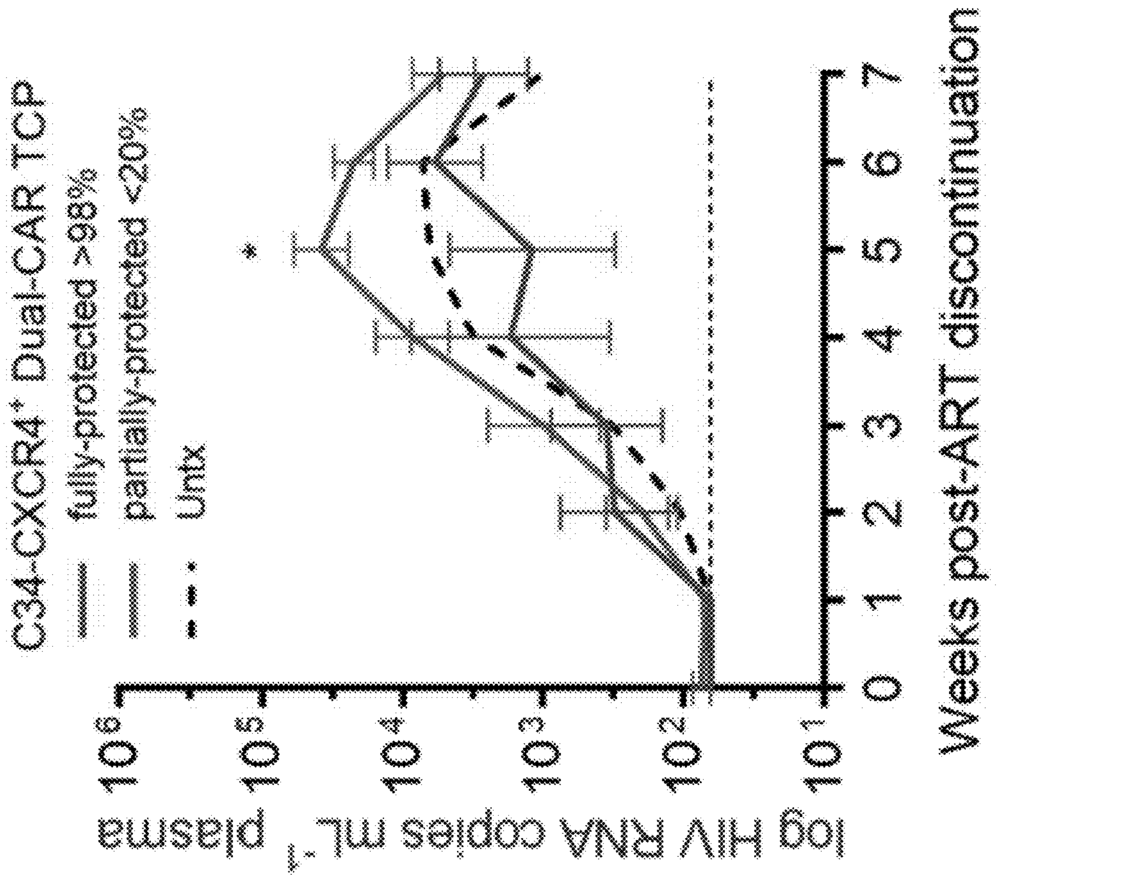

For the study described in FIG. 30C, BLT humanized mice were infected via the intraperitoneal (IP) route with 20,000 $TCID_{50}$ $HIV_{MJ4}$. At 3 weeks post-infection, all mice received ART and either an HIV-resistant (<20% C34-CXCR4+) Dual-CAR T cell product (n=7), an HIV-resistant Dual-CAR T cell product with further magnetic bead selection to obtain a >98% $C34\text{-}CXCR4^+$ transfer product (n=5), or no CAR T cells (n=9). After plasma viremia was fully suppressed in all 3 groups, ART was discontinued and virus rebound was monitored via weekly blood draws from the retro-orbital sinus.

Figure 19A:
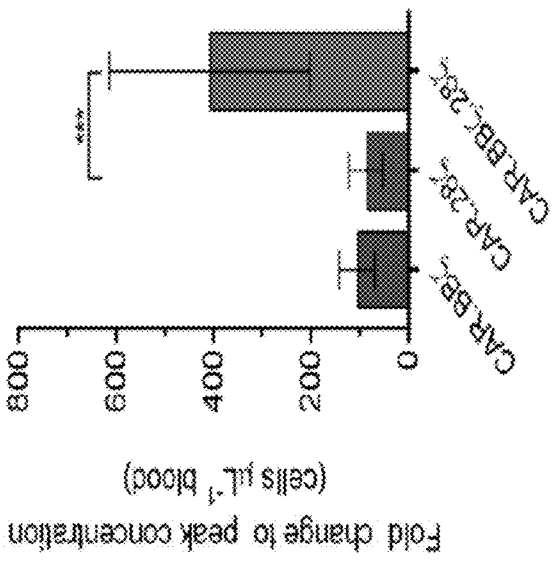
FIGS. 19A-19E illustrate the finding that Dual-CAR T cells exhibit superior in vivo expansion compared to 4-1BB, CD28, and 3rd-generation CAR T cells.
Figure 19B:
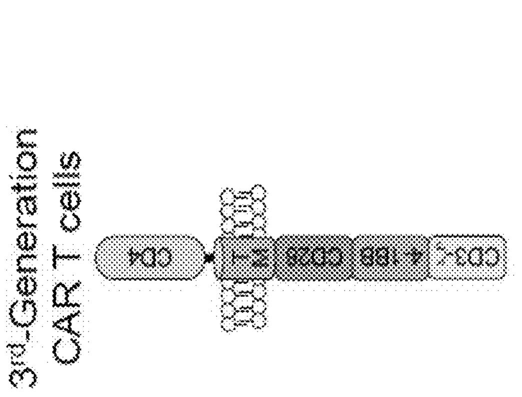
Figure 19C:
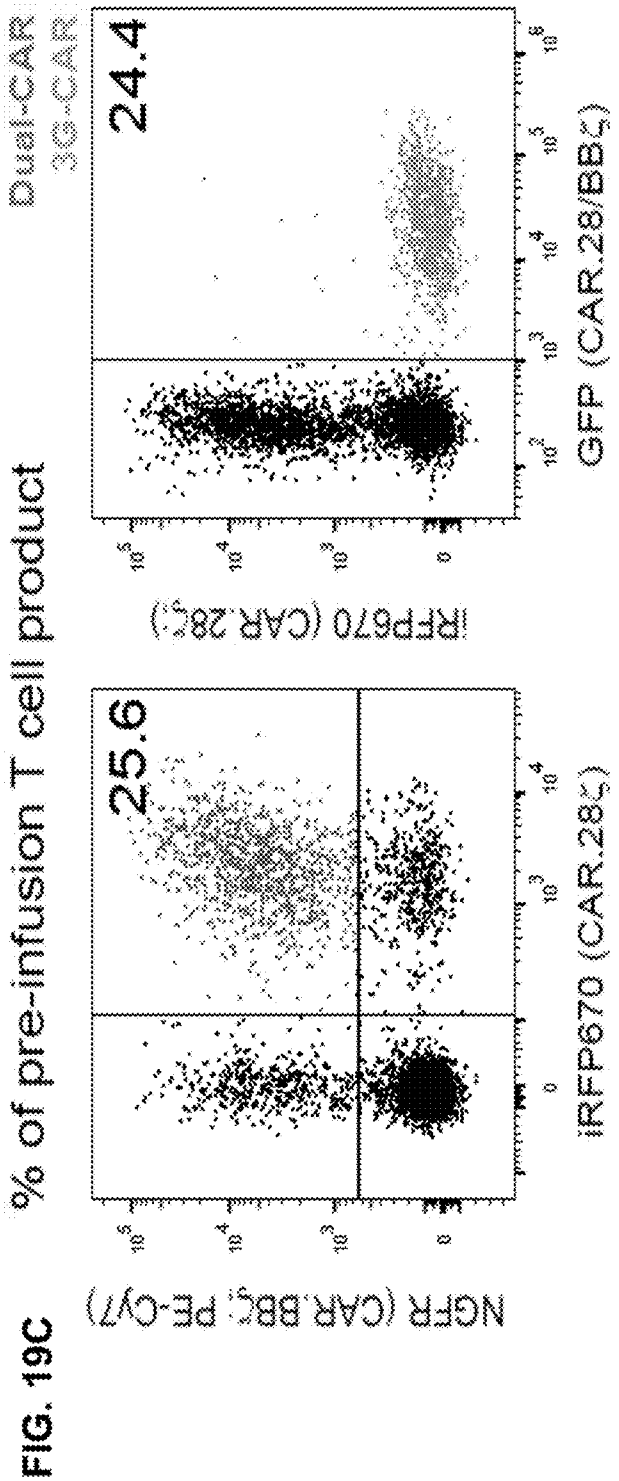
Figure 29A:
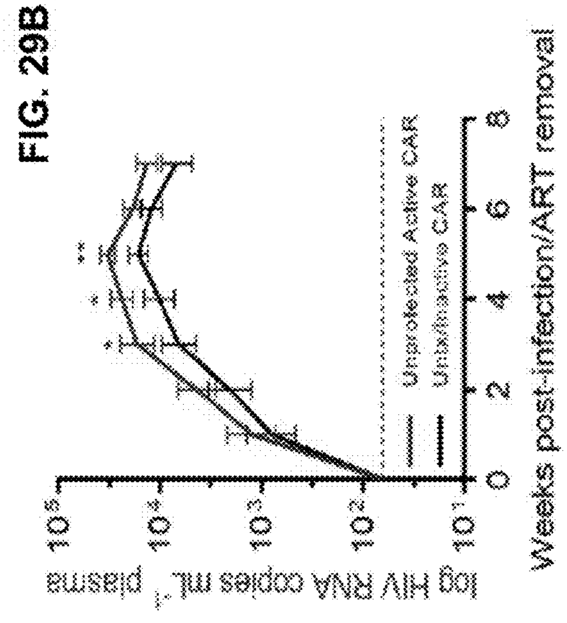
FIGS. 29A-29K illustrate the finding that mitigating CAR T cell infection improves control over HIV replication.

Acute HIV infection treatment model: BLT humanized mice were challenged with 20,000 $TCID_{50}$ $HIV_{JRCSF}$ or $HIV_{MJ4}$ via IP injection. For the study comparing the replication capacity of $HIV_{JRCSF}$ and $HIV_{MJ4}$ (FIGS. 14A-14J): $HIV_{JRCSF}$-infected mice (n=6) and $HIV_{MJ4}$-infected mice (n=6) were infused with the Dual-CAR T cell product consisting of $2\times10^7$ total CAR T cells. T cells were administered via tail vein injection 48 hours after HIV challenge. Control mice that were infected with $HIV_{JRCSF}$ (n=5) or $HIV_{MJ}4$ (n=6) received no T cells. For the study comparing Dual-CAR T cells and $3^{rd}$-generation (3G) CD4 based CAR T cells: Dual-CAR TCP was combined with 3G-CAR T cells, normalizing the frequency of Dual-CAR and 3G-CAR T cells prior to infusion into mice. 9 HIV-uninfected mice were infused with this mixture, where each mouse received $2.5\times10^6$ Dual-CAR T cells and $2.5\times10^6$3G-CAR T cells via tail vein injection. After 2 weeks, 6 mice were infused via IV injection with $10^7$ irradiated K.Env cells and 3 mice received $10^7$ irradiated K.WT cells (FIG. 19C). Additional mice (n=6) were challenged with 20,000 $TCID_{50}$ $HIV_{MJ4}$ and infused 48 hours later with same Dual-CAR TCP/3G-CAR T cell mixture described above (FIG. 14K). For the study in FIG. 21C, $HIV_{MJ4}$-infected mice were allocated into 4 groups. The groups were infused with $10^6$ $C34\text{-}CXCR4^+$, CAR.BBζ (n=6), CAR.28ζ (n=5), or purified Dual-CAR (n=4) T cells, while the remaining mice were untreated (n=6). For the study comparing purified Dual-CAR and double CAR-transduced BBζ.BBζ and 28ζ.28ζ T cell populations (FIG. 21F): $HIV_{MJ4}$-infected mice were allocated into 4 groups and normalized based on body weight and the absolute count of $CD4^+$ T cells in blood. The groups were infused with $10^6$ $C34\text{-}CXCR4^+$, purified CAR.BBζ.BBζ (n=5), CAR.28ζ.28ζ (n=5) or Dual-CAR (n=5) T cells via tail vein injection 48 hours after HIV challenge. Control mice did not receive T cells (n=5). For the study evaluating efficacy of enriched $C34\text{-}CXCR4^+$ (>98%) Dual-CAR T cells (FIGS. 29B-29D), $HIV_{MJ4}$-infected mice were divided into two groups that received $10^7$ C34-CXCR4-enriched Dual-CAR T cell product (TCP) (n=12) or were untreated (n=12). For all studies the mice were bled by retro-orbital puncture 1 day following adoptive T cell transfer, and then weekly thereafter until their respective endpoint and tissue collection.

CAR T cell therapy and ART combination model: For the study described in FIG. 29E, BLT humanized mice were challenged with 20,000 $TCID_{50}$ $HIV_{JRCSF}$ via IP injection. 3 weeks post-HIV challenge all infected mice were administered low-dose ART consisting of 1 mg $kg^{-1}$ EFdA and 25 mg $kg^{-1}$ Dolutegravir every other day by IP injection for 4 weeks. At the time of ART initiation, HIV-infected mice were allocated into 3 groups. Treated mice (n=11) were infused with an HIV-resistant ($C34\text{-}CXCR4^+$) Dual-CAR TCP consisting of $10^7$ total CAR T cells. Control mice were infused with either $10^7$ total CAR T cells from the HIV-resistant Dual-ACAR T cell product which expresses defective CD3-ζ signaling domains (n=5) or were untreated (n=7). The mice were euthanized and tissues were harvested for analysis 7 weeks post-infection. For the study described in FIG. 30D, BLT humanized mice were challenged with 20,000 $TCID_{50}$ $HIV_{BAL}$ via IP injection. 3 weeks post-HIV challenge all infected mice were administered ART consisting of 10 mg $kg^1$ EFdA and 25 mg $kg^{-1}$ Dolutegravir every other day by IP injection for 2 weeks. At the time of ART initiation, HIV-infected mice were allocated into 2 groups. Treated mice (n=6) were infused with an HIV-resistant ($C34-CXCR4^+$) Dual-CAR TCP consisting of $10^7$ total CAR T cells, or untreated (n=6).

Figures 21A, 21B, 21C, 21D:
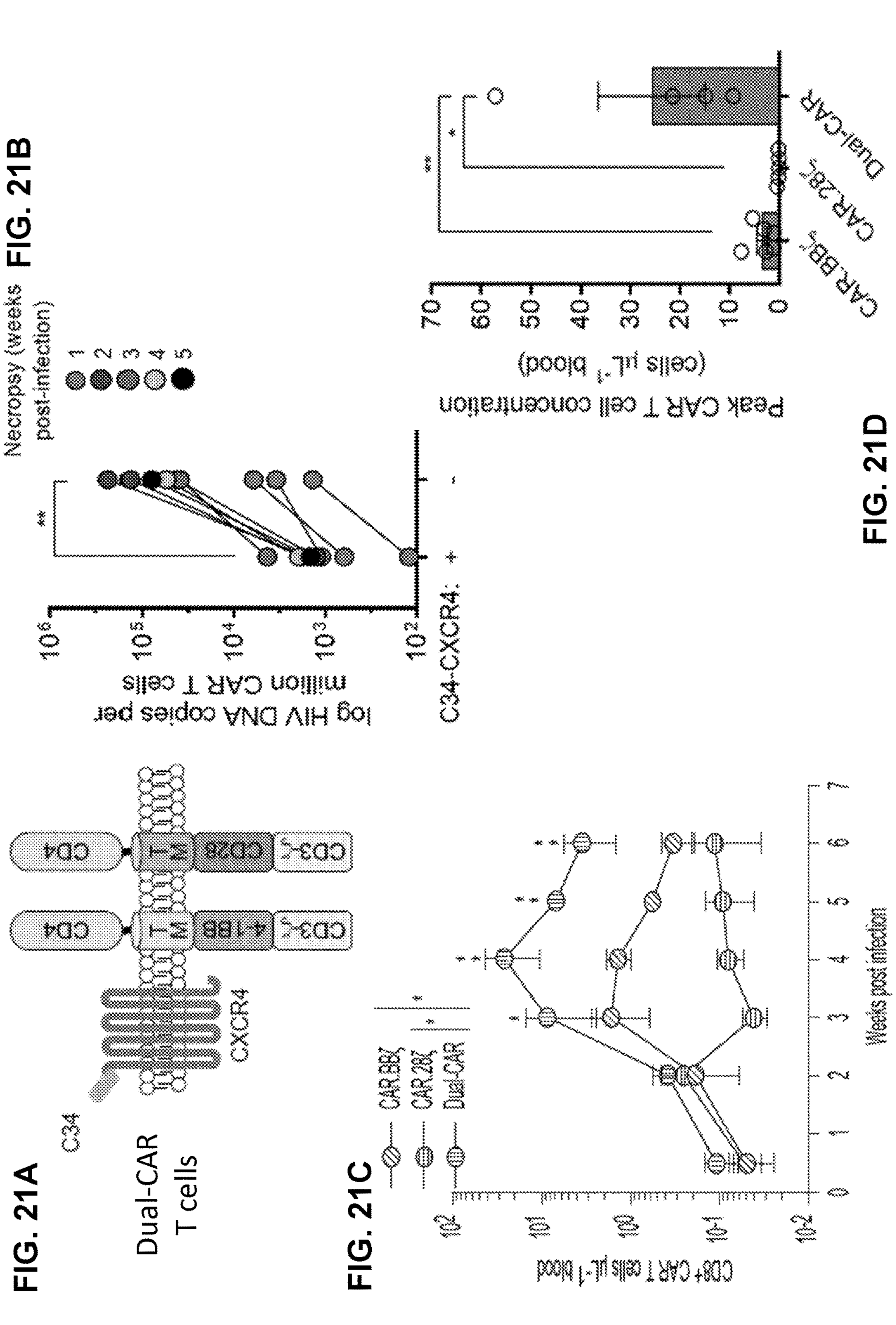
FIGS. 21A-21N illustrate the finding that HIV-resistant Dual-CAR T cells mediate superior virus-specific immune responses.
FIG. 21B illustrate experiments wherein $HIV_{JRCSF}$-infected BLT mice received $10^7$CAR T cells 48 hours post-challenge. HIV DNA load in sorted CAR T cells from individual mouse splenic tissue (n=8) is shown.
FIGS. 21C-21D illustrate experiments wherein $HIV_{MJ4}$-infected mice were infused 48 hours post-challenge with $10^6$ C34-$CXCR4^+$, CAR.BBζ (n=6), CAR.28ζ (n=5), or purified Dual-CAR (n=4) T cells.

C34-CXCR4 protection of CAR T cells in vivo: In FIG. 21B, BLT humanized mice were challenged with 20,000 $TCID_{50}$ $HIV_{JRCSF}$ via IP injection. 48 hours after challenge, mice were infused with the HIV-resistant (C34-CXCR4+) DualCAR T cell product consisting of $2\times10^7$ total CAR T cells. In one-week intervals after challenge, mice were euthanized and tissues were collected at necropsy. Splenocytes were prepared and freshly sorted; isolated cells were used to quantify the amount of cell-associated HIV DNA harbored within C34-CXCR4+ and $C34-CXCR4^-$ CAR T cells as described below.

In vitro HIV suppression assay: Two days after removing the anti-CD3/CD28 Dynabeads, primary $CD4^+$ T cells were infected with CCR5-tropic $HIV_{JRCSF}$ at a multiplicity of infection of 1.0. 24 hours later, HIV-challenged $CD4^+$ T cells were washed with complete RPMI supplemented with 100 U $ml^{-1}$ IL-2 and mixed with CAR.ζ or control untransduced (UTD) T cells at effector-to-target (E:T) ratios of 1:12.5, 1:25, 1:50, 1:100 and 1:200. The E:T ratios reflect the number of CAR.ζ T cells to HIV-challenged, $CD4^+$ T cells. Cell mixtures were plated in triplicate and the spread of HIV replication was assessed by flow cytometry by sampling 100 μL per well for intracellular staining for HIV-1 Core Antigen at 2, 4 and 6 days post-coculture. Fresh media was added to all wells after staining.

HIV-infected cell elimination assay: A similar HIV-infected target cell elimination assay was performed as described (Clayton et al. (2018) *Nat Immunol* 19, 475-486). Briefly, HIV-infected $CD4^+$ T cells were prepared as detailed above. When 30% of total T cells stained positive for HIV-1 Core Antigen the cells were labeled with CellTrace Violet (CTV) (ThermoFisher) to distinguish target cells from effector cells. For characterizing the cytotoxic function of the preinfusion T cell product, CAR-ζ and UTD T cells were cultured with CTV-labelled HIV-infected target cells at 0.25:1, 1:1 and 4:1 E:T ratios. For ex vivo stimulation, single cell suspensions of bone marrow from HIV-infected mice treated with the Dual-CAR T cell product were cultured with CTV-labelled HIV-infected target cells at 1:1, 5:1 and 10:1 E:T ratios. After 24 hours, target cells were analyzed for the induction of active caspase-3 by intracellular staining and flow cytometry. Active caspase-3 was identified in living $CTV^+$ $HIVgag^+$ T cells. Gating strategy is outlined in FIG. 4F.

In vitro cytotoxicity, CD107a degranulation, and cytokine assays: Functionality of CAR T cells was measured in vitro after stimulating $2\times10^5$ CAR-ζ or untransduced (UTD) T cells with $2\times10^5$ wild-type K562 cells (K.WT) or K562 cells transduced with the $HIV_{YU2}$GP160 (K.Env). Anti-CD107a antibody was added at the start of stimulation followed by the addition of 1× Brefeldin A and Monensin Solution (BioLegend) one hour later. Cells were incubated fora total of 6 hours at 37° C. Cytokine production was assessed by intracellular staining with antibodies specific for human IL-2, IFN-γ, MIP-1β, TNF and GM-CSF, while cytotoxic potential was measured by staining with antibodies specific for granyzme B and perforin. The percentage of cytokine-positive CAR T cells was calculated by subtracting production of cytokines after stimulation with K.WT cells.

Measurement of CAR T cell responses ex vivo: Functionality of CAR T cells from HIV-infected BLT humanized mice was measured after ex vivo stimulation with K562 target cells. Mononuclear cells were isolated by density gradient centrifugation after preparing a single-cell suspension from tissues. Between 0.5-$1\times10^6$ mononuclear cells were cultured with $2\times10^5$ K562.WT or K562.Env cells. The assessment of cytotoxic potential, degranulation and cytokine production was performed using the same protocol described above.

Cell-Associated HIV DNA quantitation: Mononuclear cell suspensions obtained from spleens were stained and sorted as described above. After sorting, samples were frozen as cell pellets and stored at −80° C. To obtain genomic DNA, cell pellets were thawed and total DNA was extracted using the QIAamp DNA Mini Kit (QIAGEN) per the manufacturer's protocol. Total HIV DNA was measured in each sample using a multiplexed droplet-digital PCR (ddPCR) assay specific for HIV gag and the human RPP30 gene. Gag forward and reverse amplification primer sequences were 5'-AGTGGGGGGACATCAAGCAGCCATGCAAAT (SEQ ID NO:40) and 5'-TGCTATGTCAGTTCCCCTTGGTTCTCT (SEQ ID NO: 41), respectively. Gag sequence was detected using a 5' HEX-labeled hydrolysis probe (HEX-CCATCAATGAGGAAGCTGCAGAATGGGA) (SEQ ID NO: 42). RPP30 forward and reverse amplification primer sequences were 5'-GATTTGGACCTGCGAGCG (SEQ ID NO: 43) and 5'-GCGGCTGTCTCCACAAGT (SEQ ID NO: 44), respectively. Human RPP30 sequence was detected with a 5' 6-FAM-labeled hydrolysis probe (6-FAM-CTGACCTGAAGGCTCT) (SEQ ID NO: 45). The RPP30 primer/probe set has been described previously (Hindson et al. (2011) *Anal Chem* 83, 8604-8610). ddPCR reactions were performed using the manufacturer recommended consumables and the ddPCR supermix for probes (No DTP) (Bio-Rad). Thermal cycling conditions are as follows: 1 cycle of 95° C. for 10 minutes, 45 cycles of 94° C. for 30 seconds followed by 60° C. for 1 minute, 1 cycle of 98° C. for 10 minutes. Droplets were generated using a QX100 droplet generator and subsequently analyzed on a QX200 droplet reader (Bio-Rad). All samples were run in duplicate.

Viral replication capacity assay: In vitro replication assays were performed essentially as previously described (Deymier et al. (2015) *PLoS Pathog* 11, 1659 e1005154). Human PBMCs were isolated from whole blood by density gradient centrifugation using Histopaque-1077 (Sigma). PBMCs were stimulated with 3 μg $mL^{-1}$ PHA in complete RPMI (1% Penicillin-streptomycin, 2 mM L-Glutamine, 25 mM HEPES buffer, and 10% fetal calf serum) supplemented with 20 U $mL^{-1}$ of recombinant human IL-2 at a concentration of $1\times10^6$ cells $mL^{-1}$. After 72 hours of stimulation, PBMCs were washed twice with complete RPMI, and resuspended in complete RPMI supplemented with 50 U $mL^{-1}$ IL-2 at a concentration of $5\times10^6$ cells $mL^1$. Cells were infected by combining 1000 $TCID_{50}$ $HIV_{JRCSF}$ or $HIV_{MJ}4$ with $5\times10^5$ cells and a final concentration of 5 μg $mL^{-1}$ polybrene in 200 μL total volume. Cells were infected by spinoculation at 1200 rpm and 25° C. for 2 hours. Cells were then washed 5 times to remove excess virus, and plated in 500 μL of complete RPMI supplemented with 50 U $mL^{-1}$ IL-2 in a 48-well plate. Infections were incubated at 37° C. and 5% CO2, and 50 pL of media was removed every 2 days and frozen. Gag p24 levels were measured in the supernatant using the Alliance HIV-1 p24 antigen ELISA kit per the manufacturer's instructions (Perkin Elmer). All infections were carried out in triplicate.

Statistical analysis: All statistical analysis was performed using JMP Pro, version 12 (SAS Institute Inc., Cary, NC)

and GraphPad Prism, version 7 (San Diego, CA). All bivariate continuous correlations were performed using Spearman's rank correlation. One-way comparison of means from unmatched samples was performed using the Wilcoxon rank sum test, comparison of means from matched samples was performed using Wilcoxon matched pairs signed rank test. Kaplan-Meier survival curves were performed using an endpoint defined as the limit of detection of the viral load quantification assay (1.81 log RNA copies $mL^{-1}$), and statistics were generated from the log-rank test. K-means clustering was performed using the JMP Pro version 12 statistical package to generate principal component plots with circles denoting where 90% of the observations would fall. Area under the curve calculations were performed in GraphPad Prism version 7 using cell concentration data normalized to one microliter of blood.

The results of the experiments are now described.

Example 1

A CD4 CAR T cell infusion product was generated comprising CD4 CAR T cells that express either an intracellular 4-1BB costimulatory domain and an active signaling domain (FIG. 1A, left) or an intracellular 4-1BB costimulatory domain and an inactive signaling CD3ζ domain (FIG. 1A, right). The inactive signaling CAR T cells (FIG. 1A, left) do not induce T cell activation following recognition of a HIV-infected cell.

CD4 CAR T cells expressing active and inactive signaling domains were infused into humanized BLT mice 48 hours after HIV challenge (FIG. 1). Mice were bled at the indicated time points to measure 1) the level of virus and 2) the number of CAR T cells in peripheral blood (FIG. 1). Quantification of HIV in peripheral blood demonstrated that active CAR T cells (FIG. 1C) were incapable of preventing early virus replication relative to inactive CAR T cells (FIG. 1C). Active CAR T cells (FIG. 1D, red) were expanded in peripheral blood to a greater extent relative to inactive CAR T cells (FIG. 1D). These data demonstrated that signaling competent CAR T cells that express 4-1BB signaling domain are capable of robust cellular proliferation and survival after encountering HIV-infected cells.

Figures 2A, 2B, 2C, 2D:
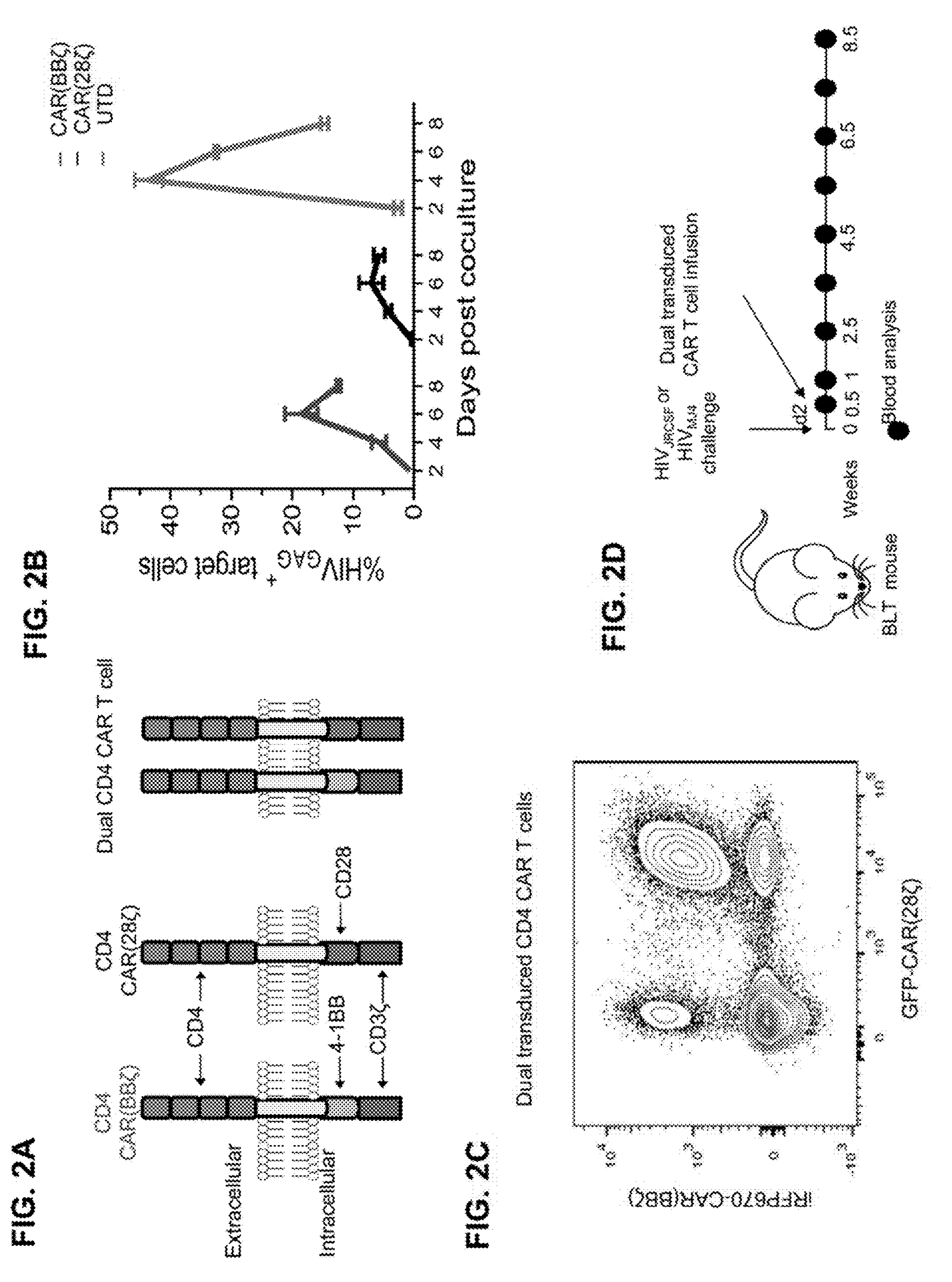
FIG. 2A is a schematic of T cells expressing HIV-specific CARs: 4-1BBζ CD4 CAR (left), CD28 CD4 CAR (middle) and dual CD4 CARs (4-1BBζ and CD28 CARs, right).
FIG. 2B depicts results from an in vitro HIV suppression experiment where HIV-infected $CD4^+$ T cells were mixed with the indicated T cell populations. These data show that both CD4
FIG. 2C illustrates a CAR T cell product that combines the functional attributes of 4-1BB (pro-survival) and CD28 (effector function) signaling. T cells were co-transduced with viruses that separately expressed the 4-1BB and CD28 CAR. This created a dual transduced CD4 CAR T cell product, where a portion of cells express the 4-1BB CAR (upper left), the CD28 CAR T cells (bottom right) or both the 4-1BB CAR and the CD28 CAR (upper right).
FIG. 2D illustrates an experimental design wherein a dual transduced CAR T cell product was infused into humanized BLT mice 48 hours after infection with one of two HIV strains: JR-CSF and MJ4. Mice were bled at the indicated time points to measure 1) the level of virus and 2) the number of CAR T cells in peripheral blood.

T cells expressing HIV-specific CARs: 4-1BBζ CD4 CAR (FIG. 2A, left), CD28 CD4 CAR (FIG. 2A, middle), and dual CD4 CARs (4-1BBζ and CD28 CARs)(FIG. 2A, right) were generated herein. HIV-infected $CD4^{+}$ T cells were mixed with 4-1BBζ CD4 CAR T cells, CD28 CD4 CAR T cells, or untransduced cells, and in vitro HIV suppression was measured (FIG. 2B). The data showed that both CD4 CAR T cell populations were capable of suppressing HIV replication compared to untransduced T cells (UTD), but CD28 CAR T cells exerted greater control over HIV at the indicated time points than 4-1BBζ CAR T cells. This demonstrates that CD28 CAR T cells exert greater effector function than 4-1BB CAR T cells.

In order to create a CAR T cell product that combines the functional attributes of 4-1BB (pro-survival) and CD28 (effector function) signaling T cells were co-transduced with viruses that separately expressed the 4-1BB and CD28 CAR.ζ This created a dual transduced CD4 CAR T cell product, where a portion of cells expressed the 4-1BB CAR (FIG. 2C, upper left), the CD28 CAR T cells (FIG. 2C, bottom right) or both the 4-1BB CAR and the CD28 CAR (FIG. 2C, upper right).

Figure 2E:
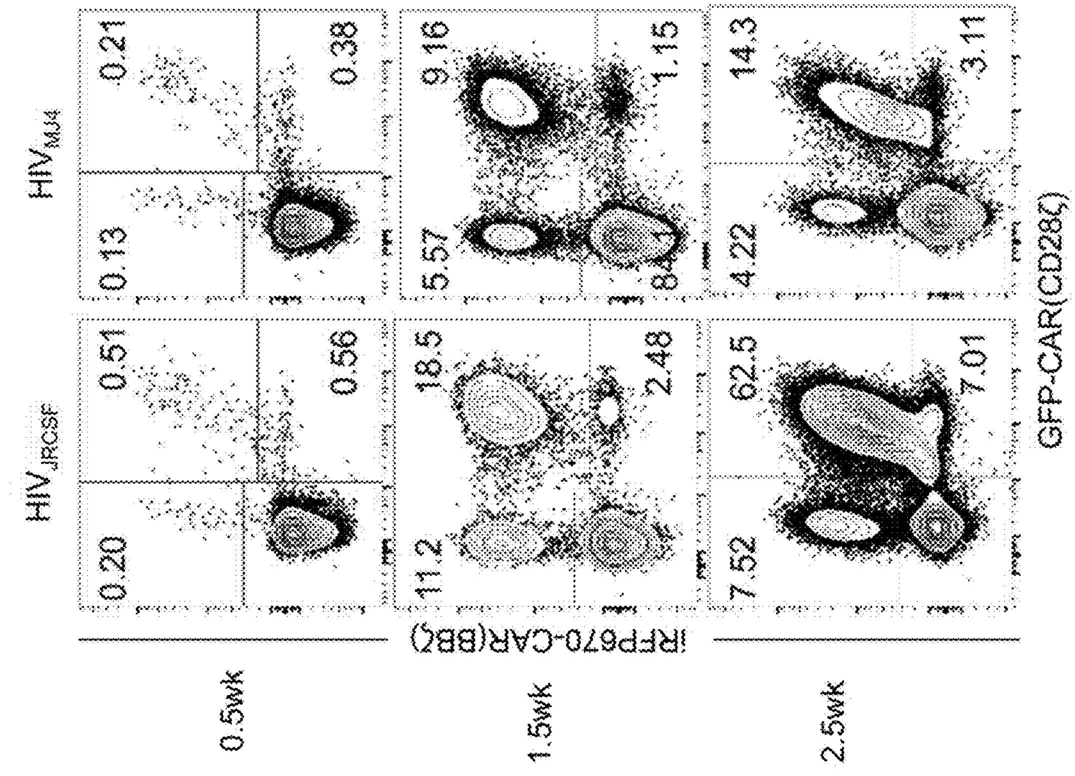
FIG. 2E illustrates expansion of all CAR T cell populations in peripheral blood over time. The dual transduced CAR T cells, which express both 4-1BB and CD28 CARs, proliferate to a greater extent than single transduced CAR T cells. In HIV JRCSF and MJ4 infected mice, dual transduced CAR T cells reached greater than 60% and 14% of total T cells, respectively.

The dual transduced CAR T cell product was infused into humanized BLT mice 48 hours after infection with one of two HIV strains: JR-CSF and MJ4. Mice were bled at 0.5, 1, 2.5, 4.5, 6.5, and 8.5 weeks to measure 1) the level of virus and 2) the number of CAR T cells in peripheral blood (FIG. 2D). In peripheral blood, expansion of all CAR T cell populations was seen over time (FIG. 2E). However, the dual transduced CAR T cells, which expressed both 4-1BB and CD28 CARs, proliferated to a greater extent than single transduced CAR T cells. In HIV JRCSF and MJ4 infected mice, dual transduced CAR T cells reached greater than 60% and 14% of total T cells, respectively (FIG. 2E).

Figure 2F:
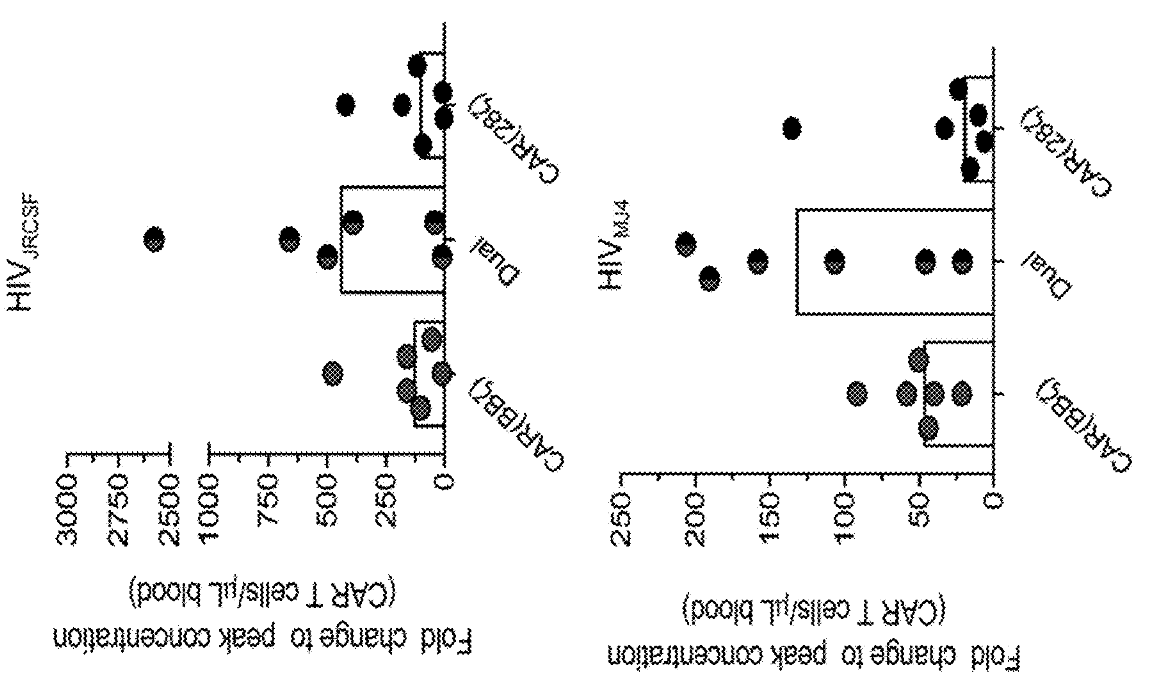
FIG. 2F depicts results showing the expression of dual CARs on T cells confers greater proliferative capacity than single-transduced CAR T cells. Nearly a 500- and 150-fold change in cell concentration in HIV JRCSF and MJ4 infected mice was detected in dual-transduced CAR T cells, whereas on average single-transduced CAR T cells only demonstrate a 125-fold (JRCSF) and 50-fold (MJ4) expansion.

Proliferation was normalized by calculating the fold change in individual CAR T cell concentration (cell per microliter blood) from baseline (one day post infusion) to peak (2.5 weeks post infusion) concentration (FIG. 2F). The expression of dual CARs on T cells conferred greater proliferative capacity, as nearly a 500- and 150-fold change in cell concentration in HIV JRCSF and MJ4 infected mice was detected, whereas on average single-transduced CAR T cells only demonstrated a 125-fold (JRCSF) and 50-fold (MJ4) expansion (FIG. 2F).

Figures 3A, 3B:
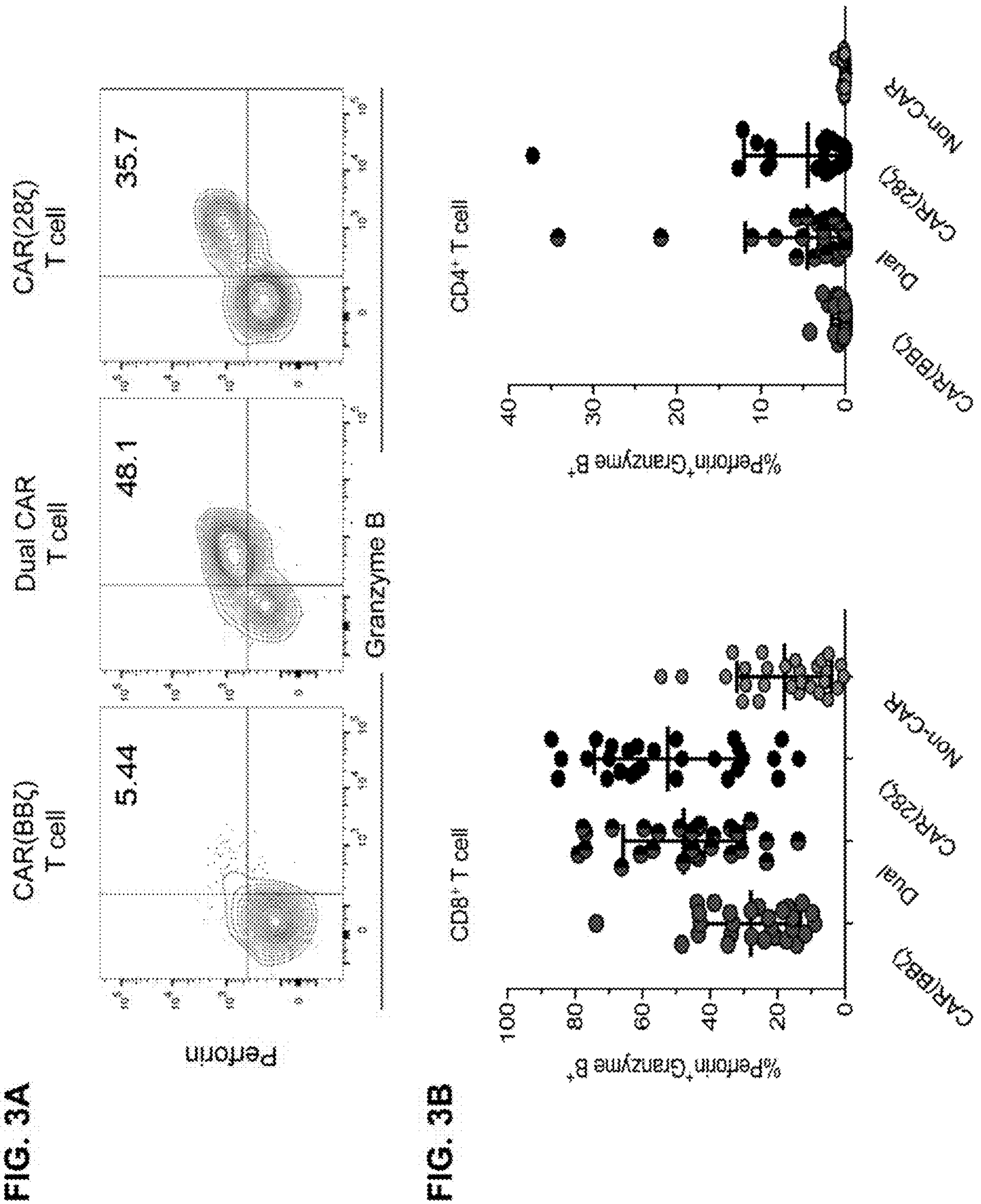
FIG. 3A illustrates the cytotoxic potential of the individual CAR T cell populations by measuring the co-expression of perforin and granzyme B, two critical molecules that mediate T cell killing of target cells.
FIG. 3B depicts results showing 4-1BB CAR T cells of both $CD8^+$ and $CD4^+$ T cell lineage express low levels of both perforin and granzyme B, but dual transduced CAR T cells co-express substantially more, and nearly to the same extent as CD28 CAR T cells.

The cytotoxic potential of the individual CAR T cell populations was assessed by measuring the co-expression of perforin and granzyme B, two critical molecules that mediate T cell killing of target cells (FIGS. 3A-3B). 4-1BB CAR T cells of both CD8+ and $CD4^{+}$ T cell lineage expressed low levels of both molecules, but dual transduced CAR T cells co-expressed substantially more, and nearly to the same extent as CD28 CAR T cells (FIGS. 3A-3B).

Figure 3C:
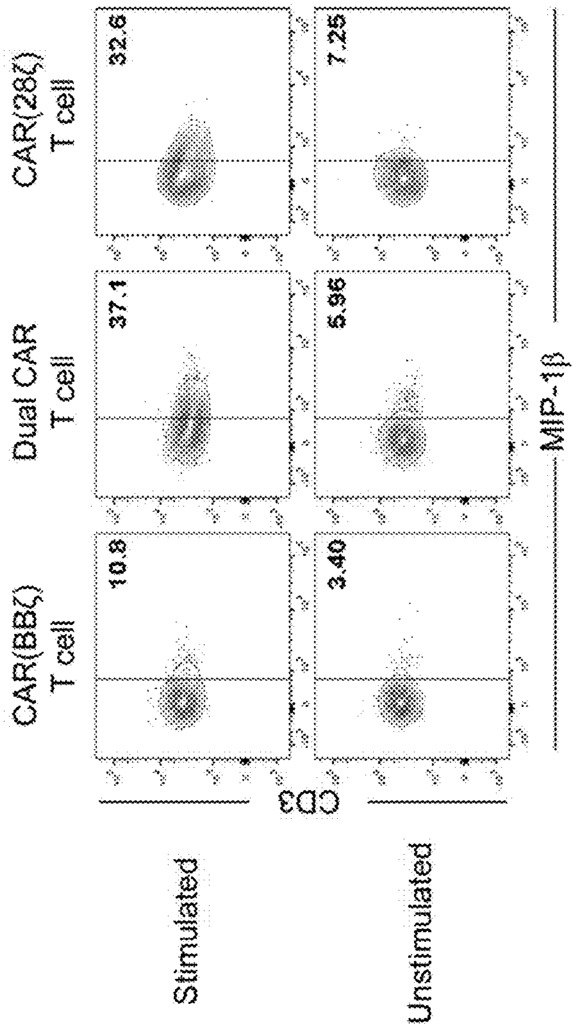
FIG. 3C depicts results from CAR T cells isolated from tissue of HIV-infected mice and stimulated with HIV antigen to detect production of MIP-1b, an antiviral chemokine.
Figure 3D:
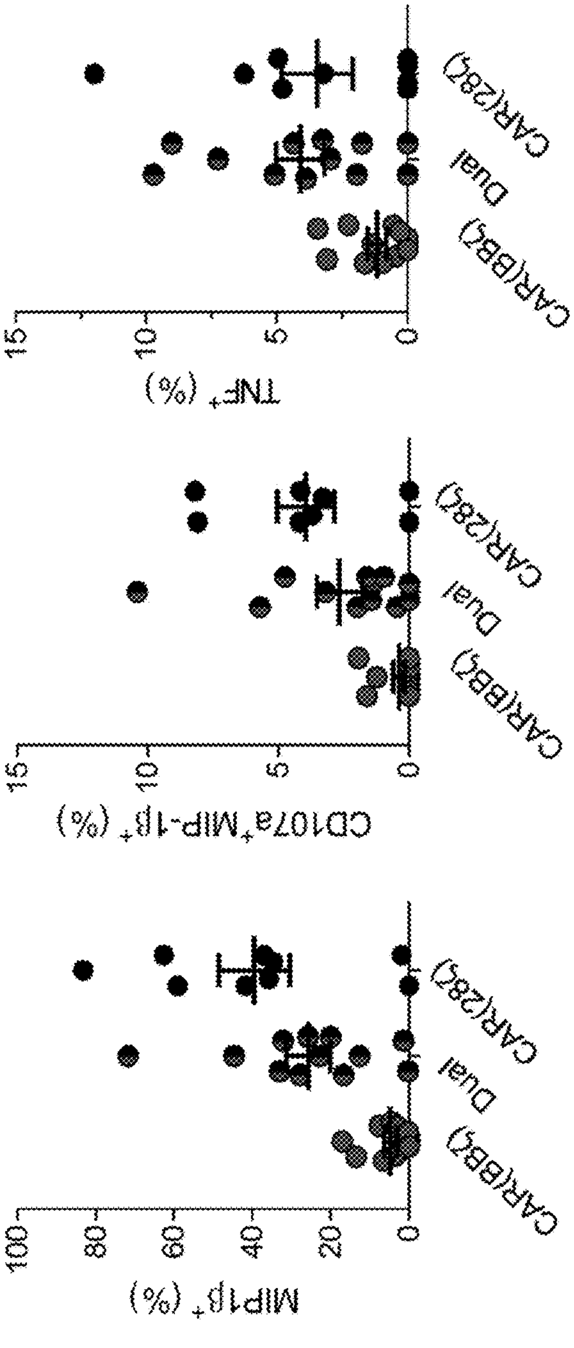
FIG. 3D depicts data showing 4-1BB CAR T cells produce relatively low amounts of molecules associated with effector function including: MIP-1b, an antiviral chemokine, CD107a, a marker for cytotoxicity, and TNF, a pro-inflammatory cytokine, but dual-transduced CAR T cells upregulate MIP-1b, CD107a and TNF to levels comparable with CD28 CAR T cells.

CAR T cells were isolated from the tissue of HIV-infected mice and stimulated with HIV antigen to detect production of multiple molecules associated with effector function including: MIP-1b, an antiviral chemokine, CD107a, a marker for cytotoxicity, and TNF, a pro-inflammatory cytokine (FIGS. 3C-3D). 4-1BB CAR T cells produced relatively low amounts of these molecules, but dual-transduced CAR T cells upregulated MIP-1b, CD107a and TNF to levels comparable with CD28 CAR T cells (FIGS. 3C-3D).

Taken together, these data indicate that the simultaneous expression of two HIV-specific receptors (4-1BB and CD28 CAR) endows T cells with superior proliferative capacity in response to HIV infection compared to single-transduced CAR T cells. Furthermore, these cells displayed enhanced effector function defined by cytotoxic potential and upregulation of antiviral molecules compared to 4-1BB CAR T cells. This shows that dual-transduced cells represent a novel population of CAR T cells that integrate signals from 4-1BB and CD28 to endow T cells with both pro-survival and effector functions.

Figure 4A:
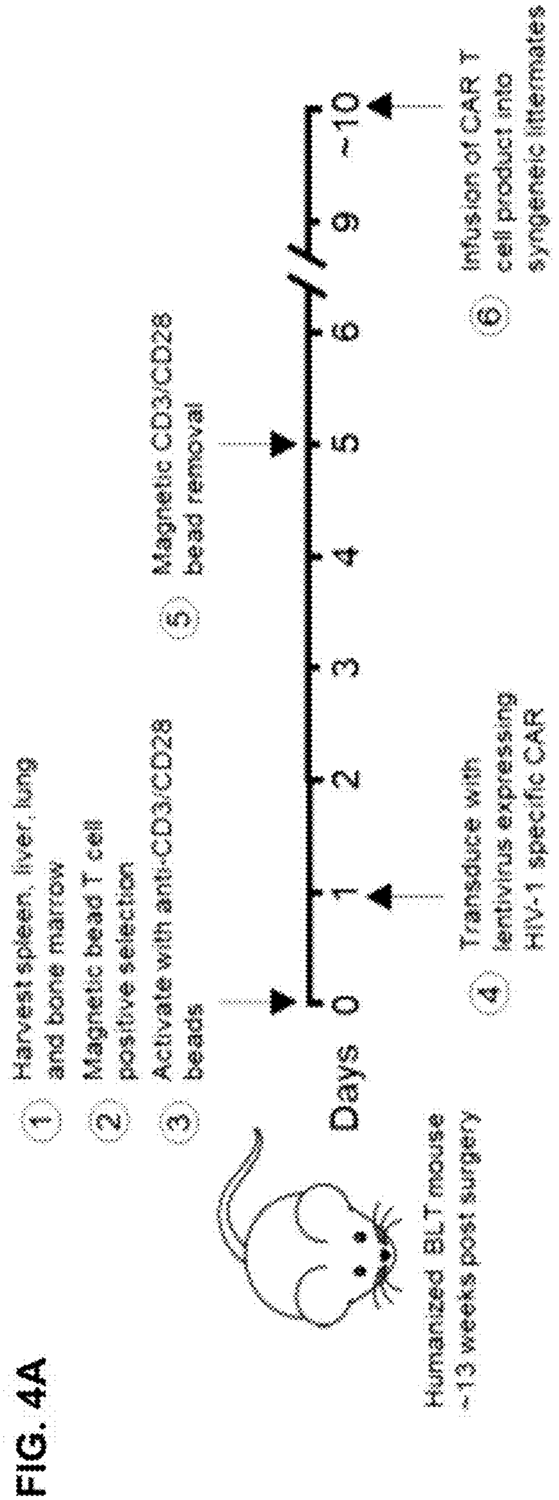
FIGS. 4A-4H illustrate the finding that BLT-mouse derived HIV-specific CAR T cells are multifunctional in vitro.
Figure 4B:
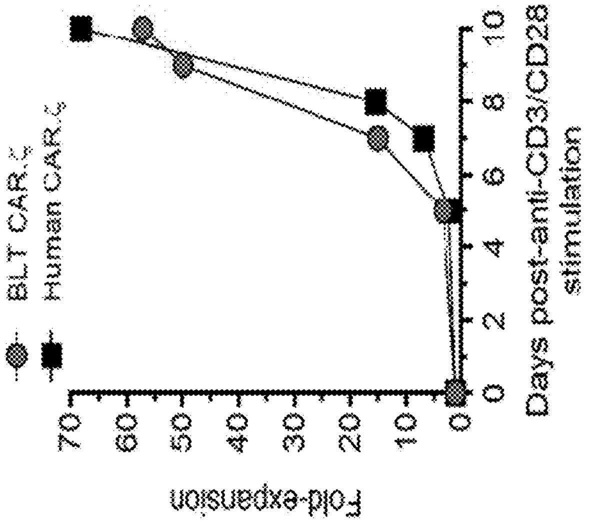
Figure 4C:
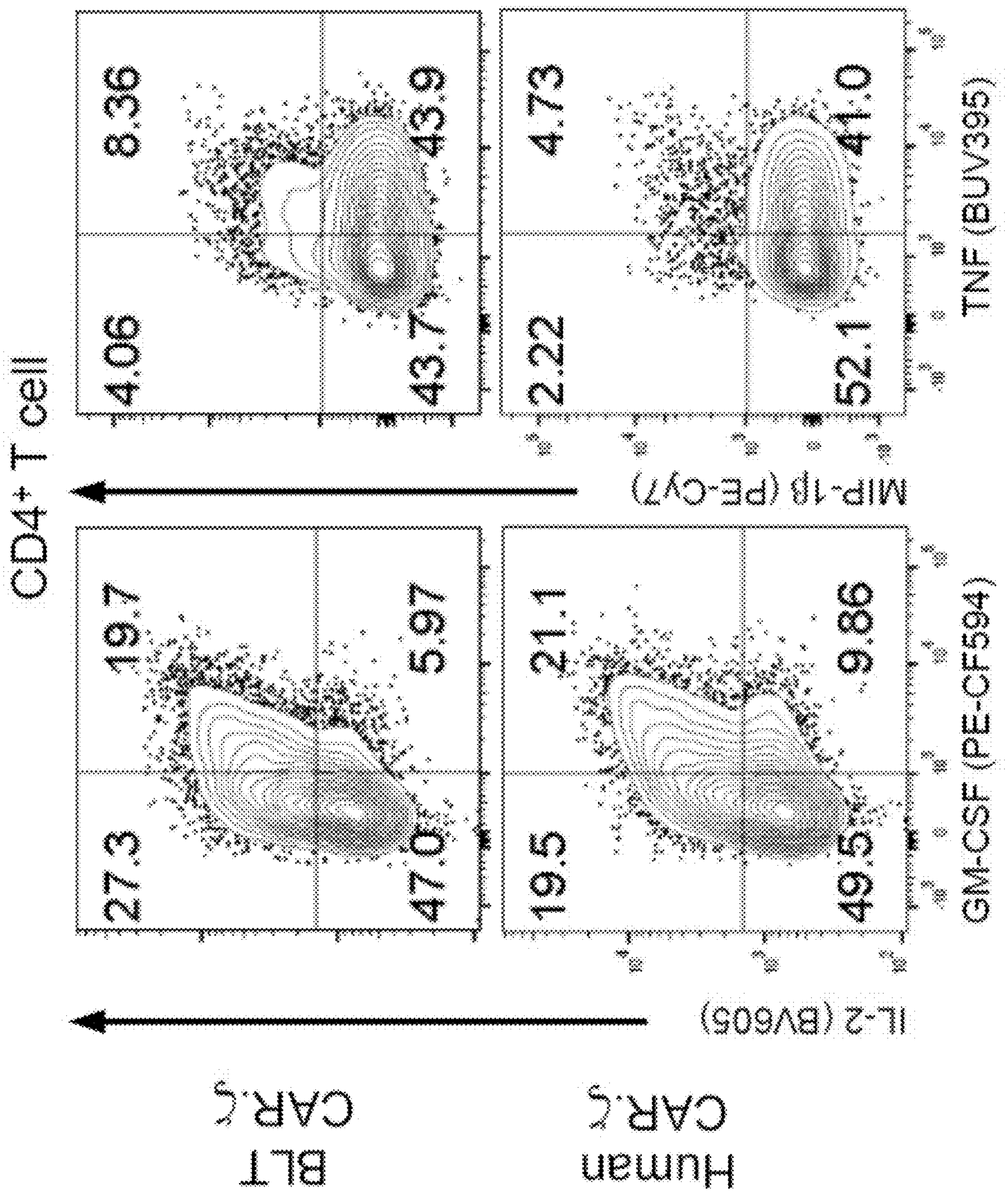
Figure 4E:
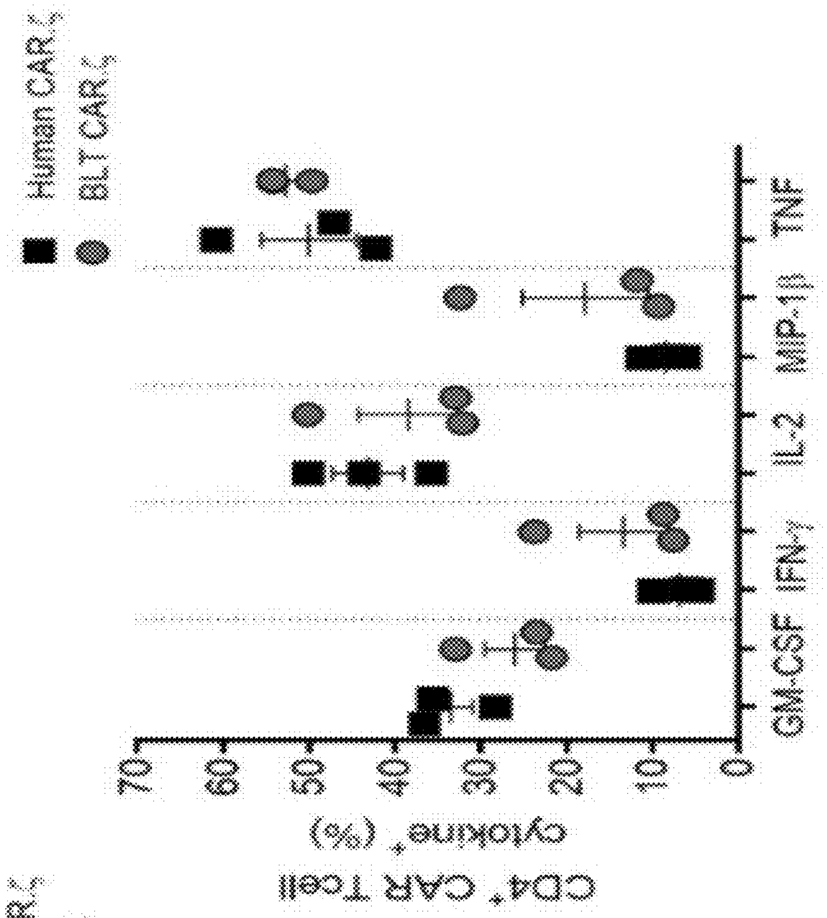
Figure 4D:
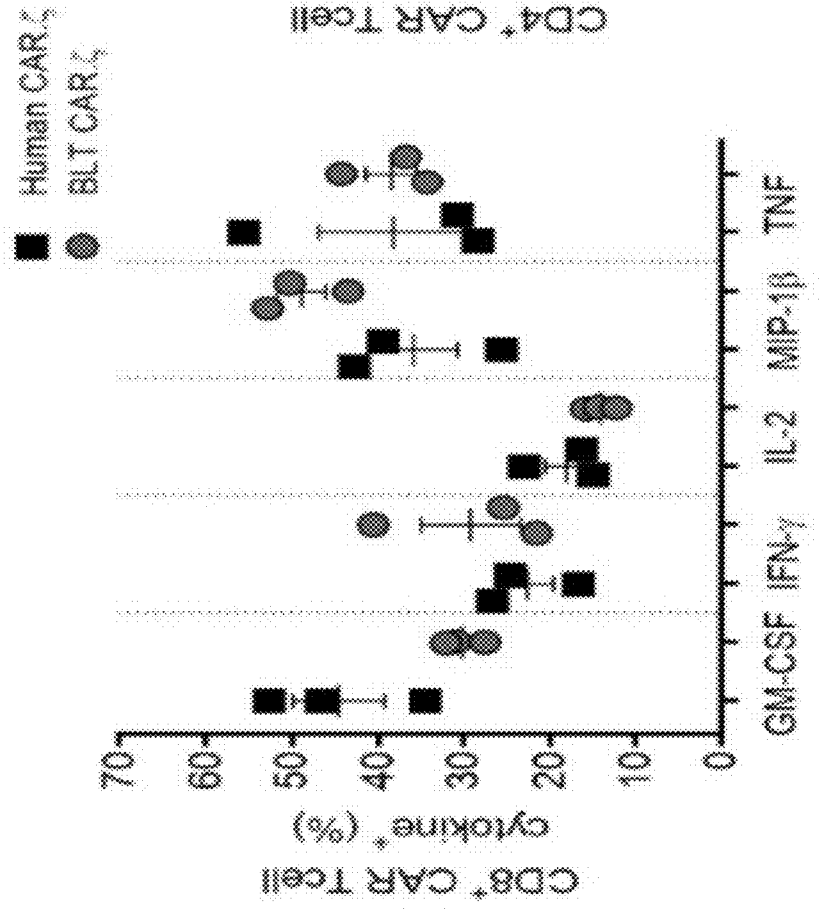
Figure 4F:
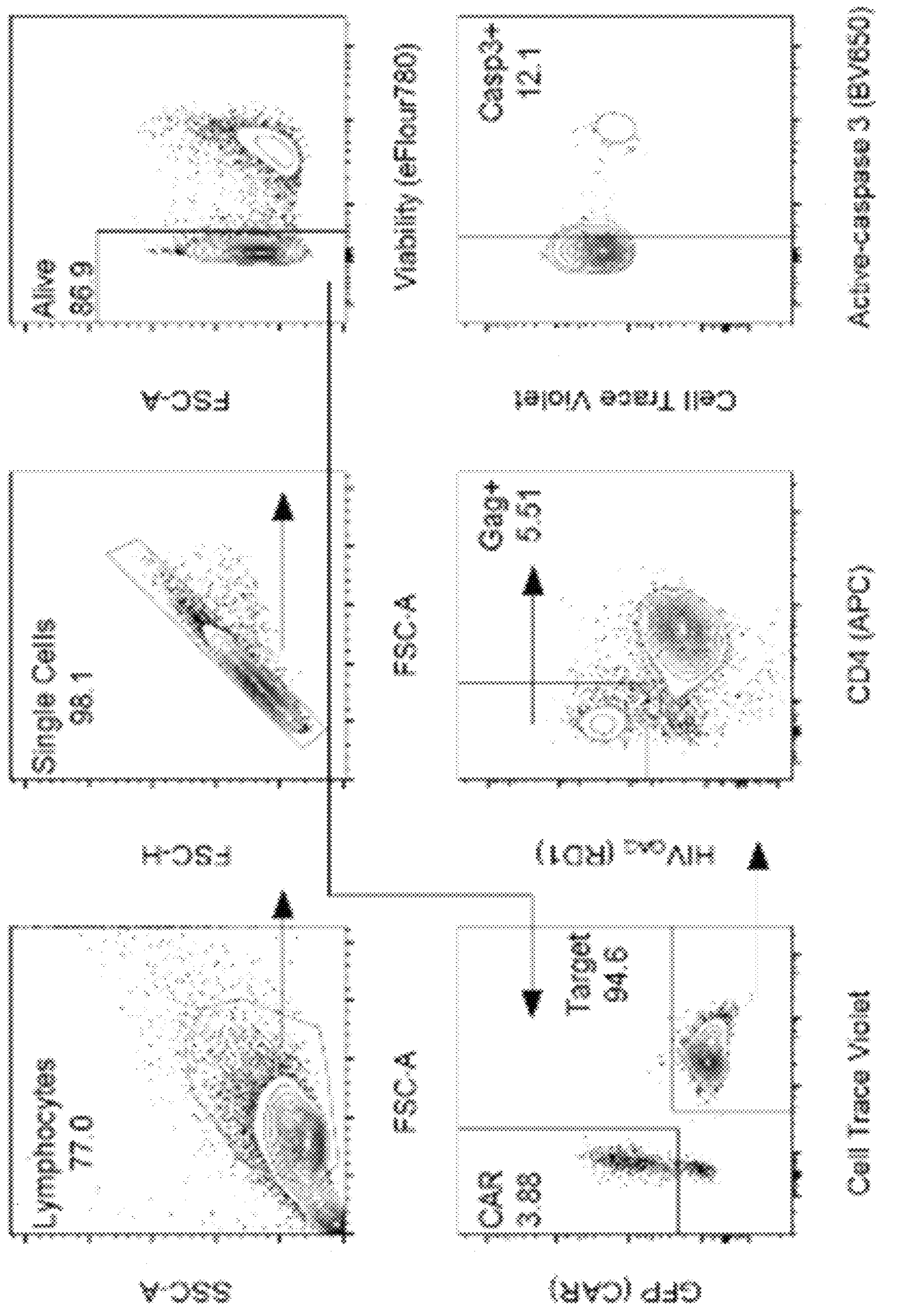
Figure 4G:
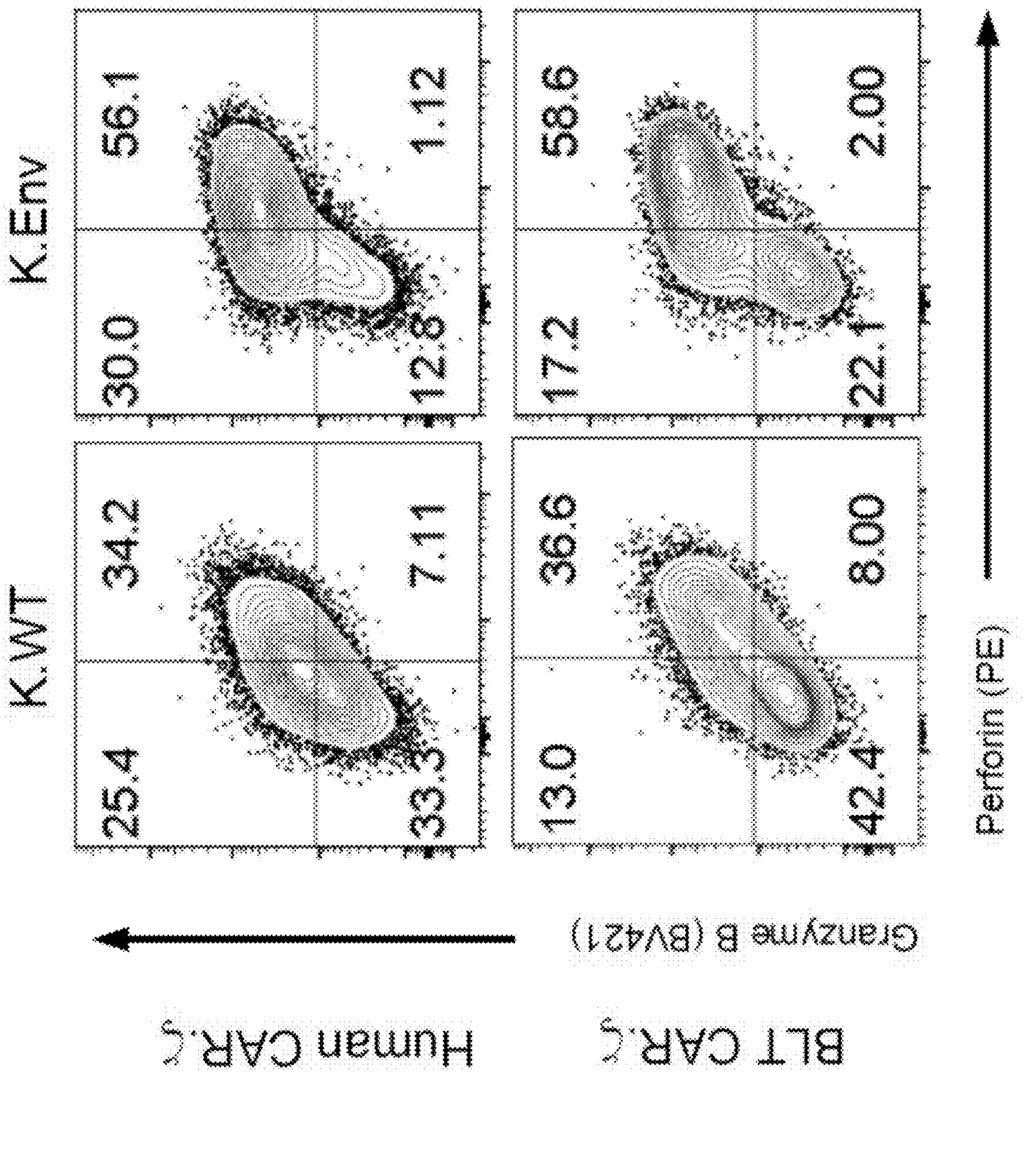
Figure 4H:
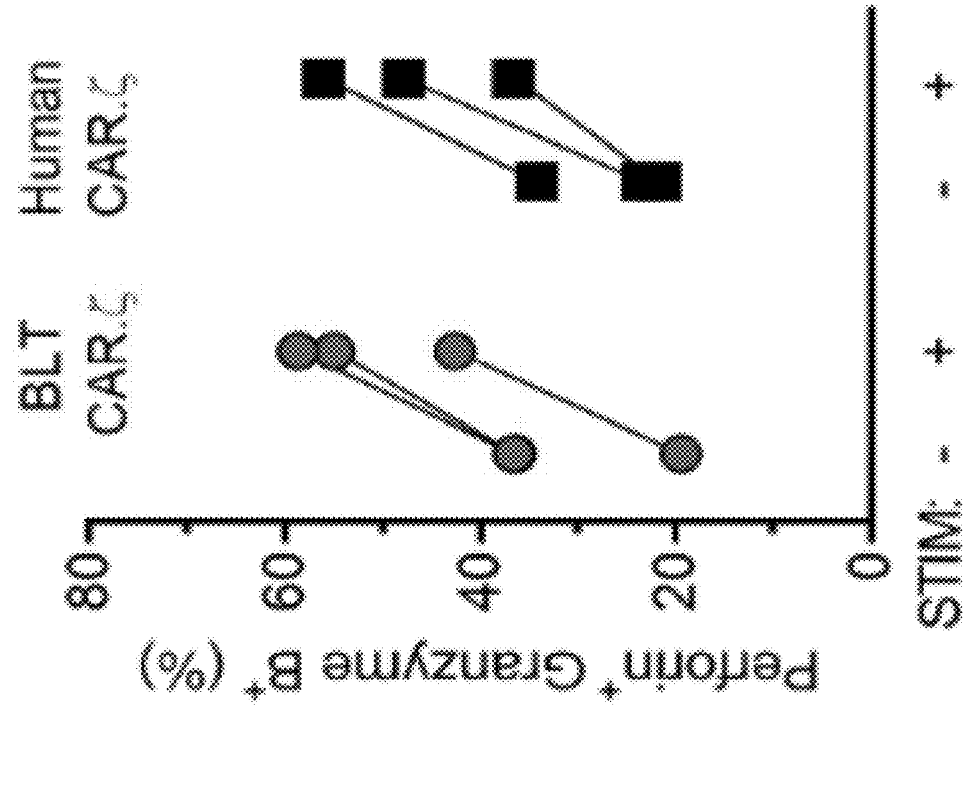
Figure 5A:
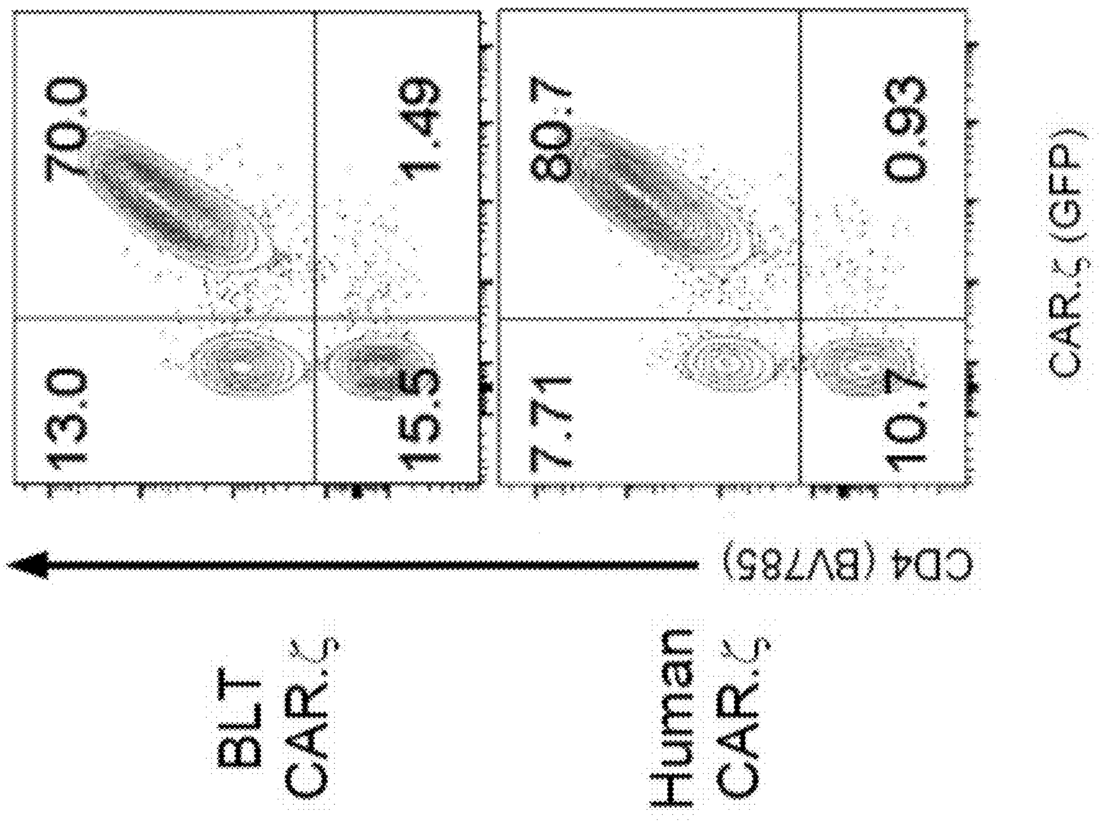
FIGS. 5A-5H illustrate BLT mouse-derived HIV-specific CAR T cells are functionally indistinguishable from human-derived CAR T cells in vitro. Purified human T cells from a BLT mouse and PBMCs from a healthy human donor were activated with αCD3/CD28 Dynabeads and transduced with the CD4-based CAR.ζ construct co-expressing GFP.
Figure 5B:
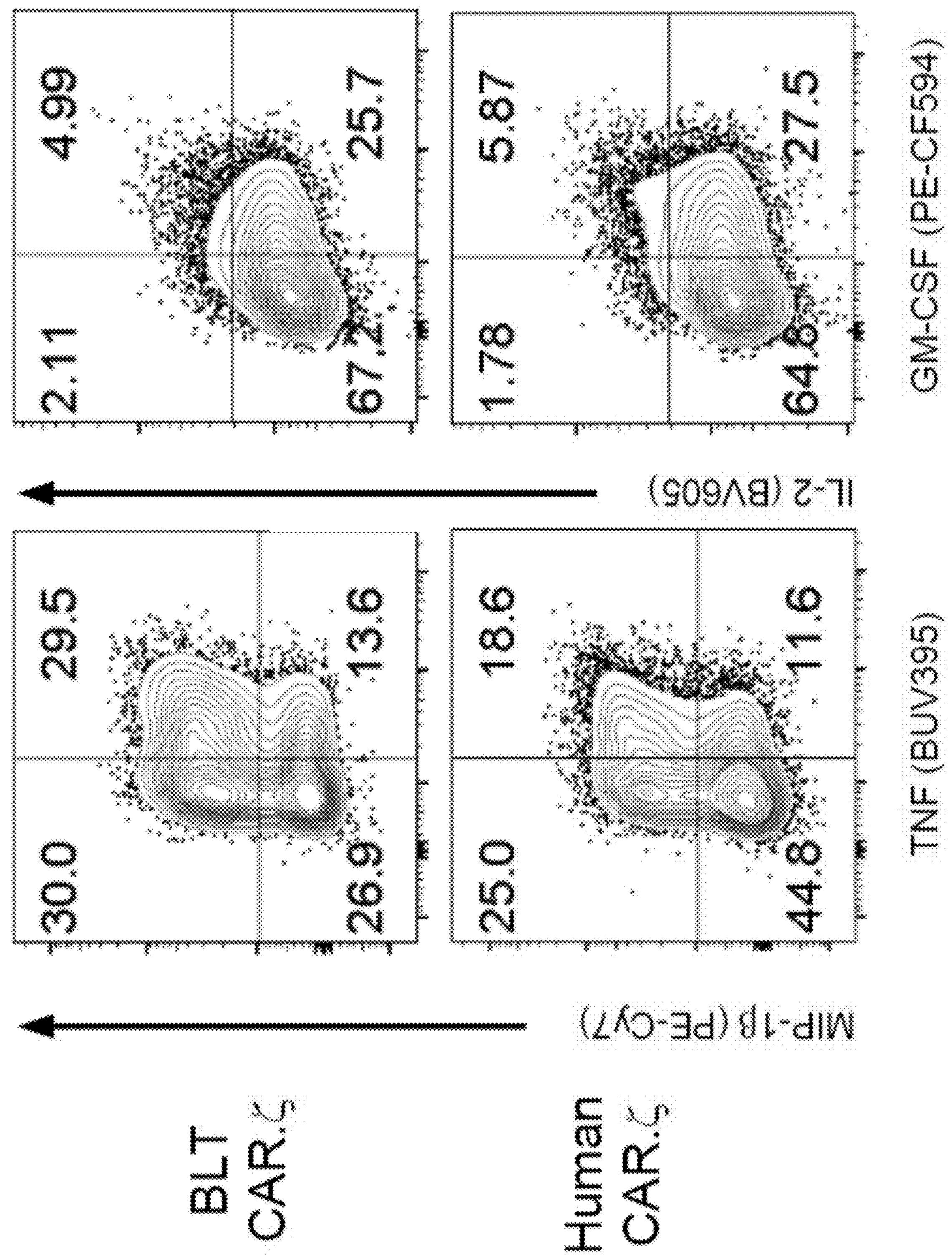
Figure 5C:
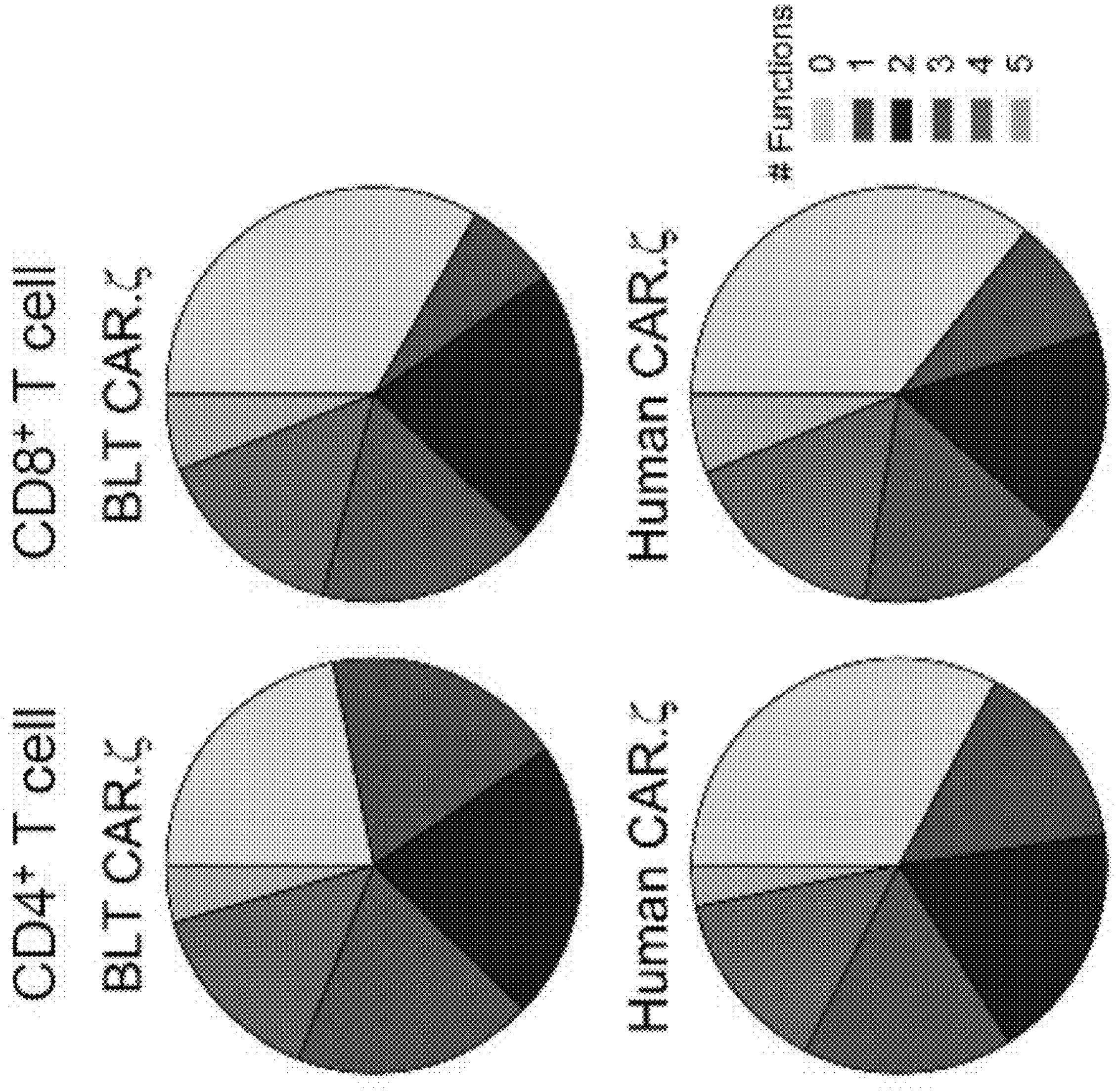
Figure 5D:
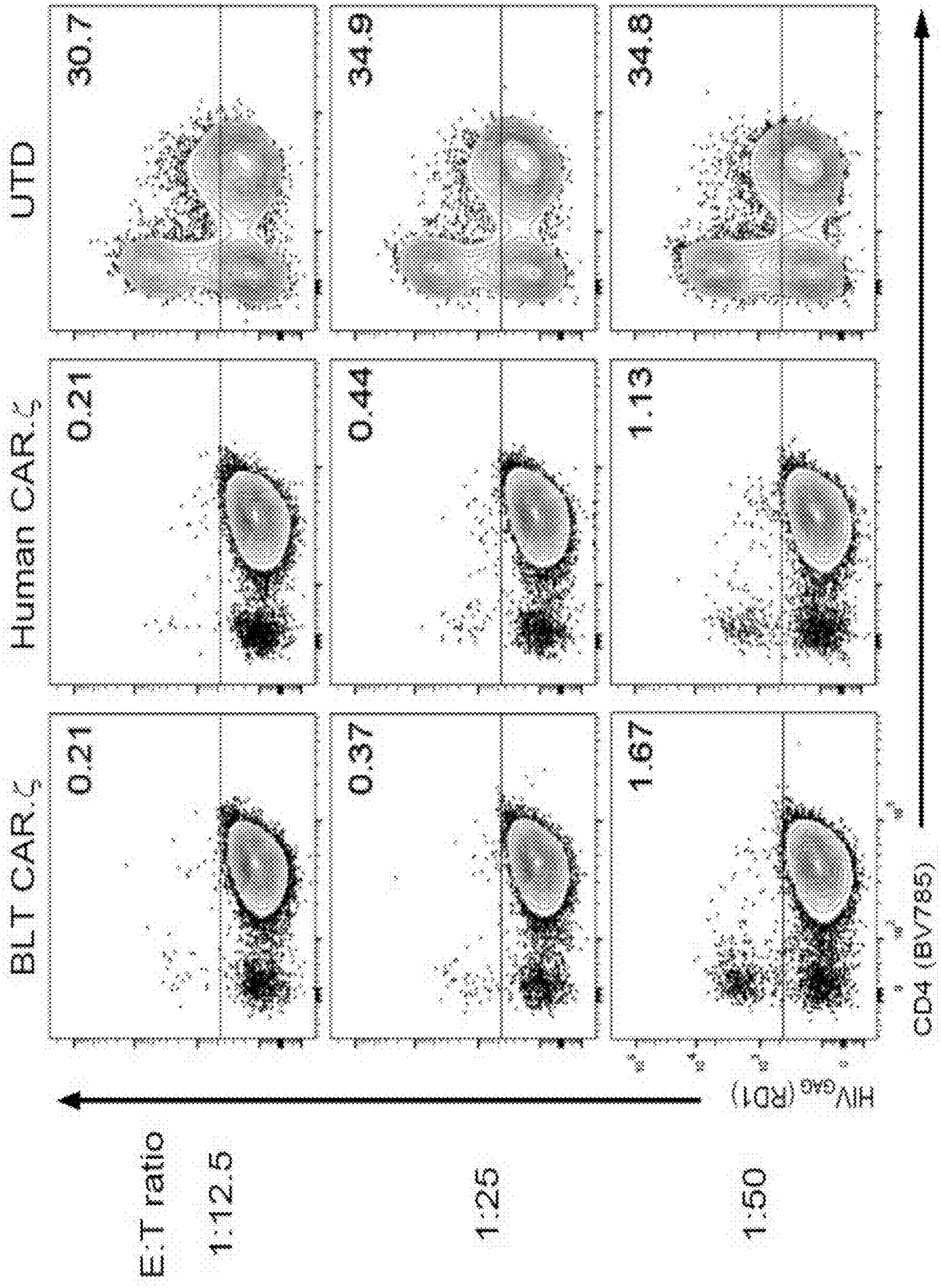
Figure 5F:
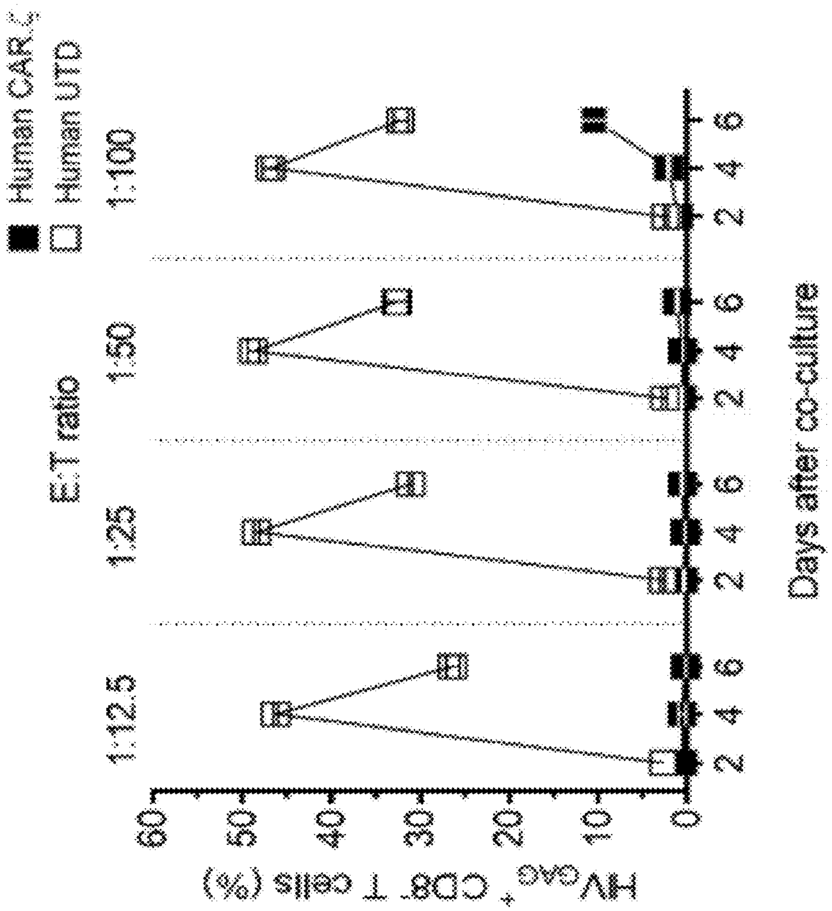
Figure 5E:
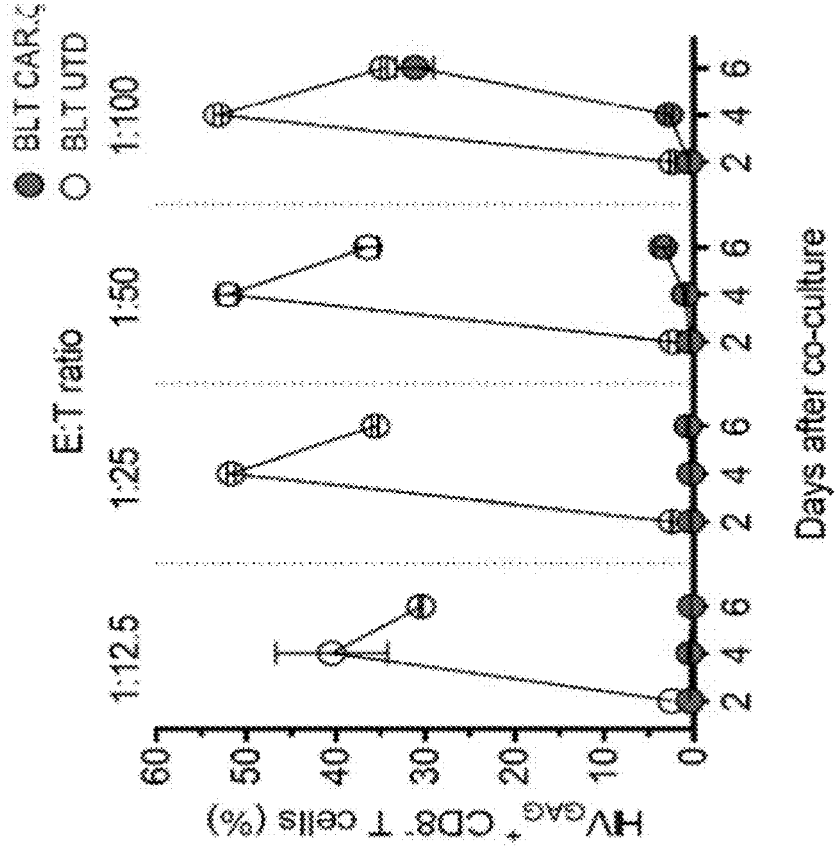
Figure 5G:
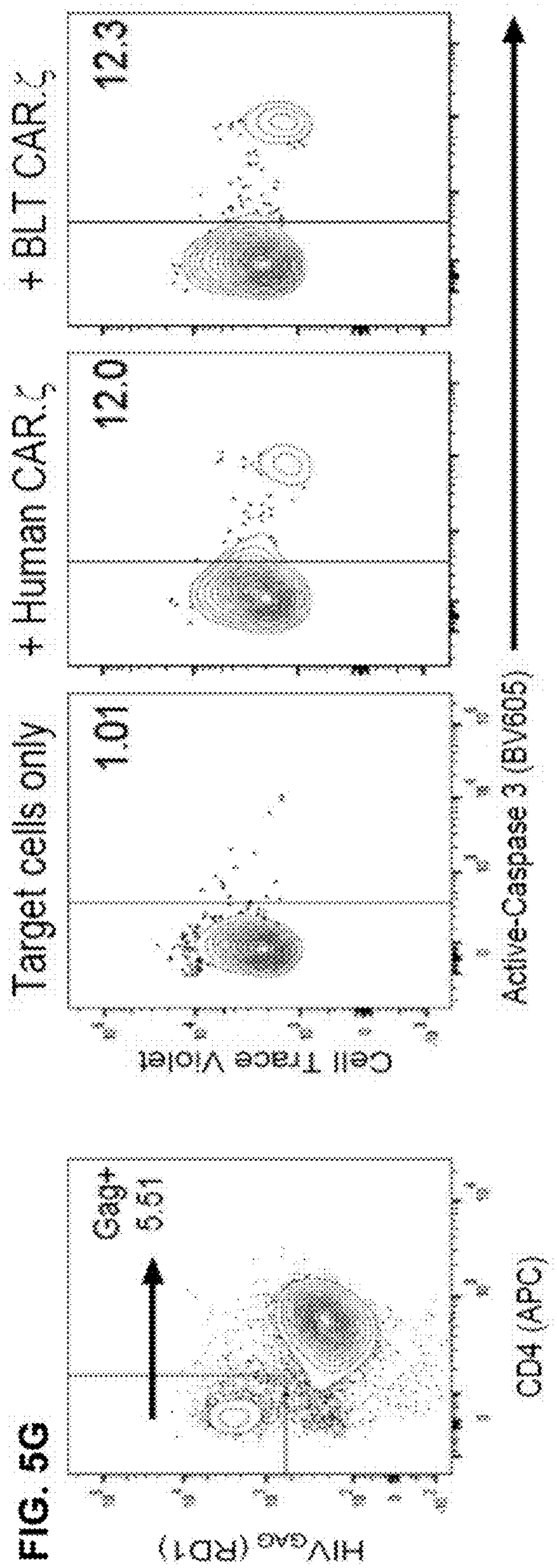
Figure 5H:
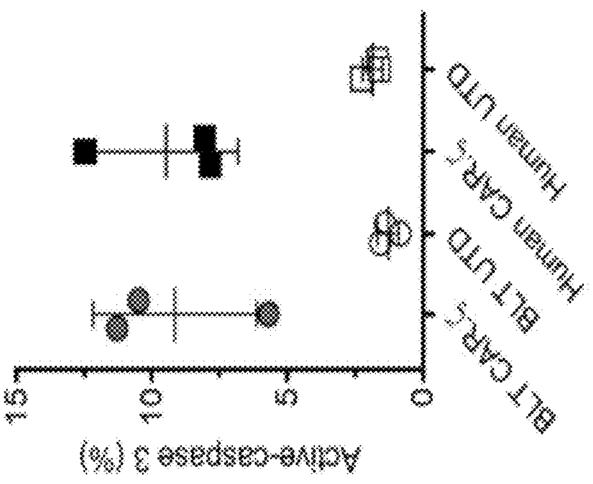

Example 2: BLT Mouse-Derived CAR T Cells are Multifunctional and Suppress HIV Replication In Vitro To determine whether T cells isolated from BLT mice generate potent CAR T cell products, HIV-specific (CD4-based) CAR T cells expressing the CD3-ζ endodomain (CAR.ζ) from BLT mouse tissues and adult human PBMCs were manufactured using a process similar to one being used in clinical trials (Wang & Riviere (2016), Mol Ther Oncolytics 3, 16015; Fesnak et al. (2016) Nat Rev Cancer 16, 566-581) (FIG. 4A). BLT mouse- and human-derived CAR.ζ T cells exhibited comparable in vitro expansion kinetics and CAR surface expression levels (FIG. 4B and FIG. 5A). Antigen-specific stimulation with K562 cells expressing $HIV_{YU2}$GP160 (K.Env) induced similar cytokine expression and polyfunctionality profiles between the CAR T cell sources (FIGS. 4C-4E and FIGS. 5B-5C). Furthermore, CAR.ζ T cells from both donors suppressed viral outgrowth down to a 1:50 effector-to-target ratio in vitro (FIGS. 5D-5F), and induced similar levels of cleaved caspase-3 in HIV-infected $CD4^+$ T cells (FIGS. 5G-5H). The induction of caspase 3 combined with the co-upregulation of granzyme B and perforin by CAR.ζ T cells (FIGS. 4G-4H) indicated that elimination of virus-infected cells likely occurred via granule-mediated cytolysis. In total, the in vitro functional profile of BLT mouse-derived CAR. T cells was indistinguishable from that of human-derived CAR.ζ T cells, demonstrating that highly functional engineered CAR T cells can be manufactured from BLT mice.

Figure 6A:
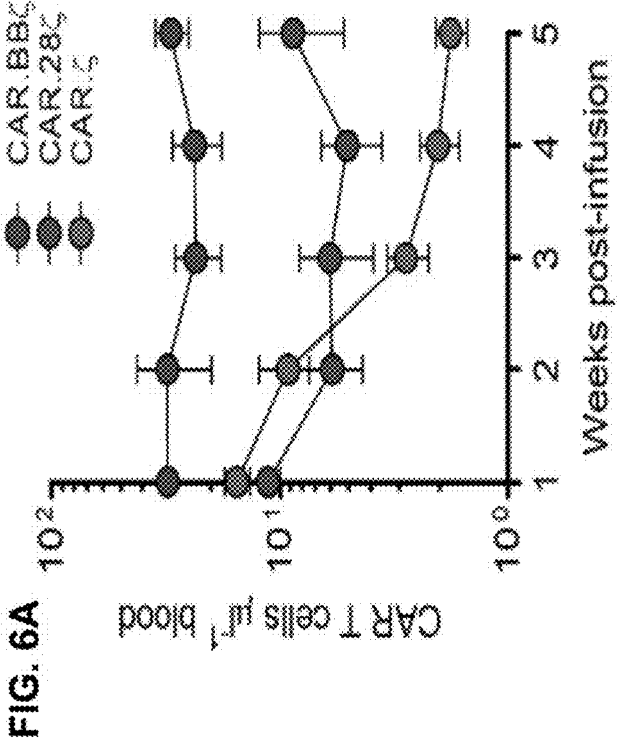
FIGS. 6A-6K depict CAR T cells expressing the 4-1BB costimulatory domain exhibit a proliferative advantage and induce B cell aplasia in vivo.
Figure 6C:
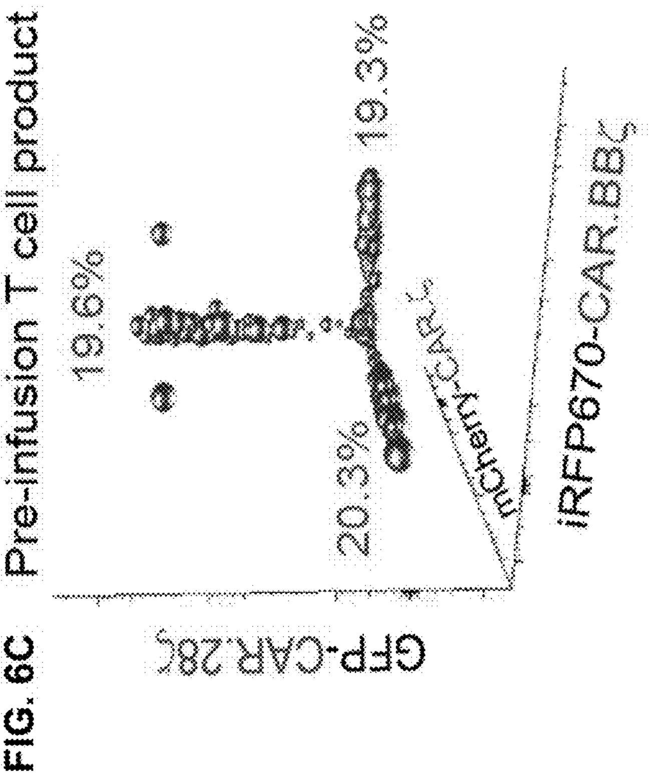
Figure 6B:
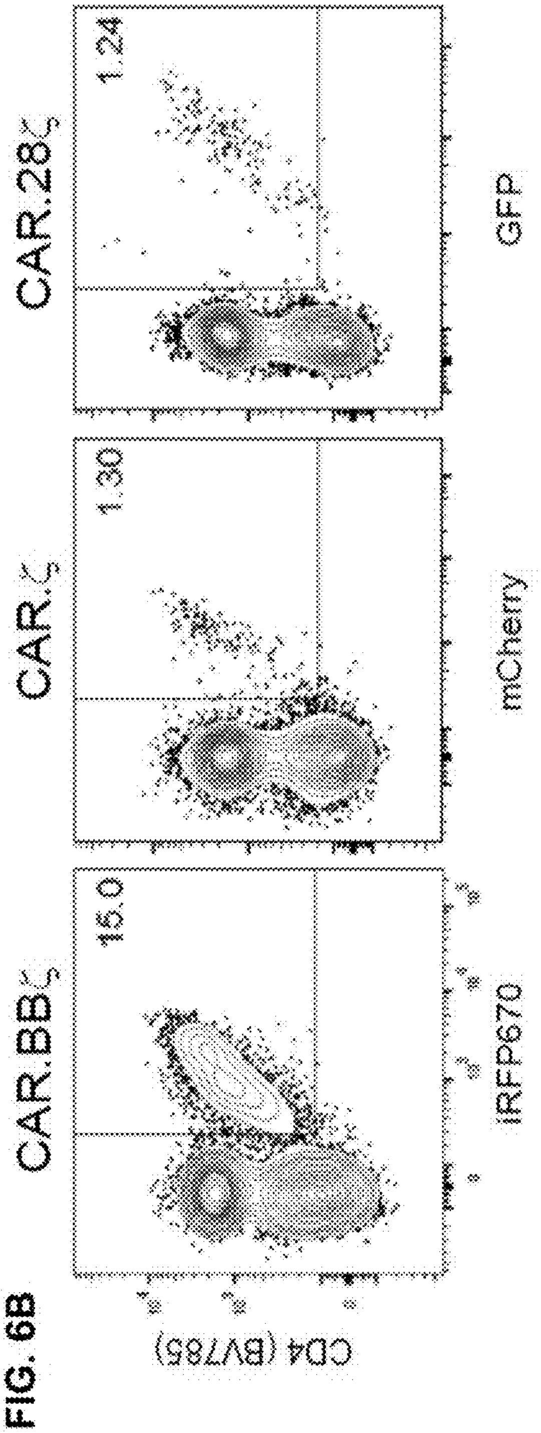
Figure 6A:
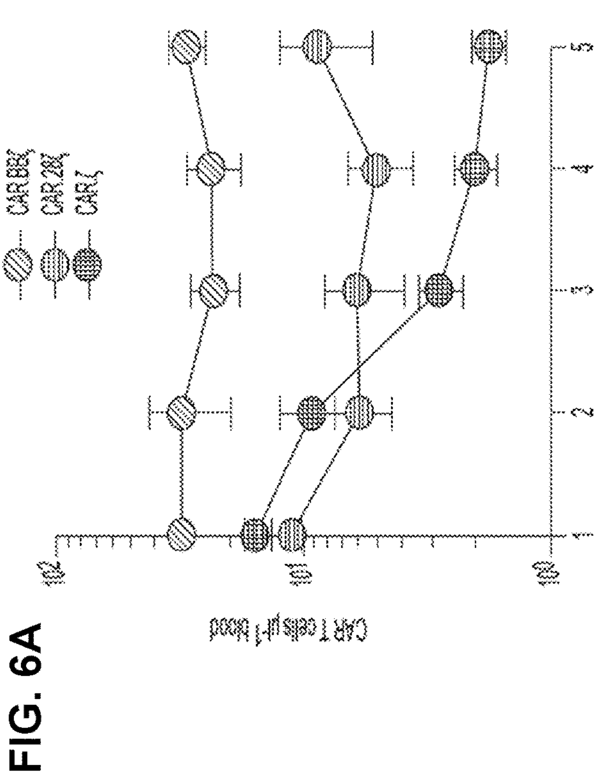
Figure 6B:
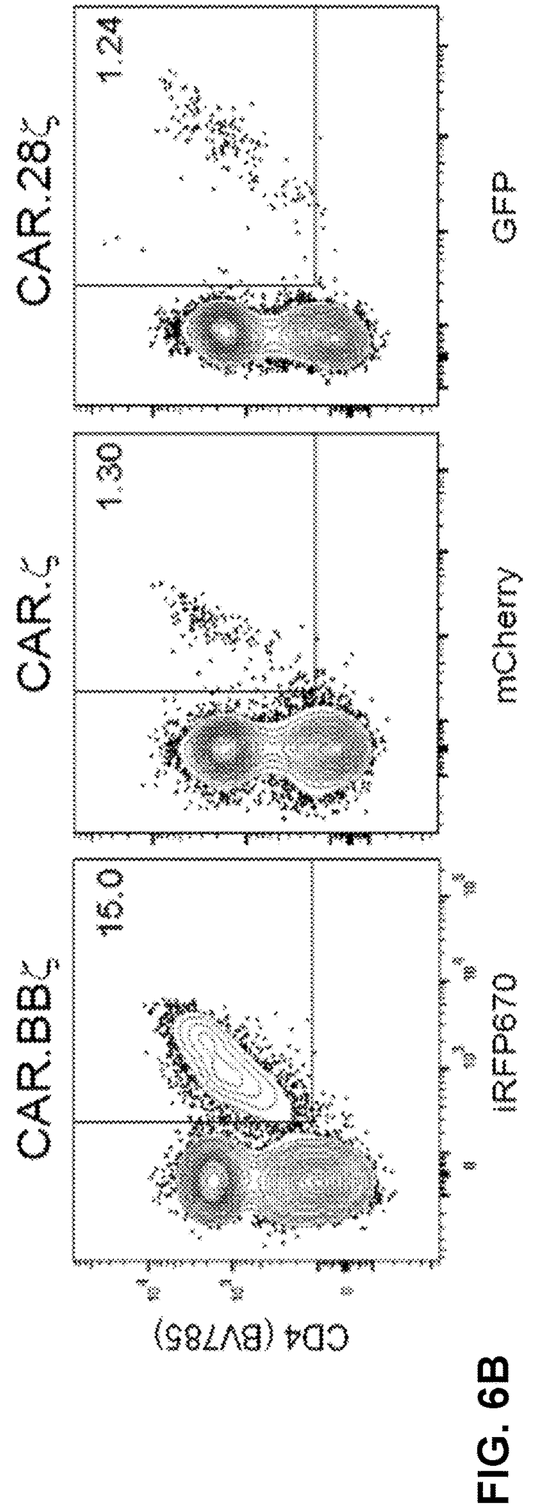
Figure 6C:
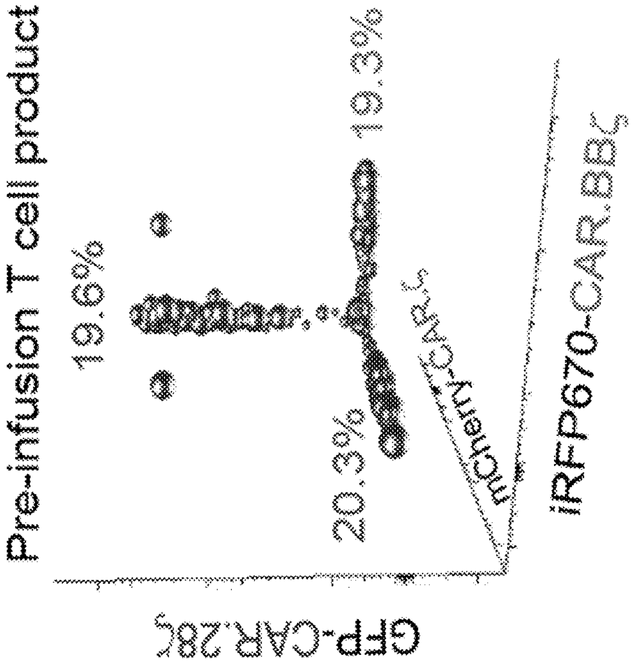
Figure 6D:
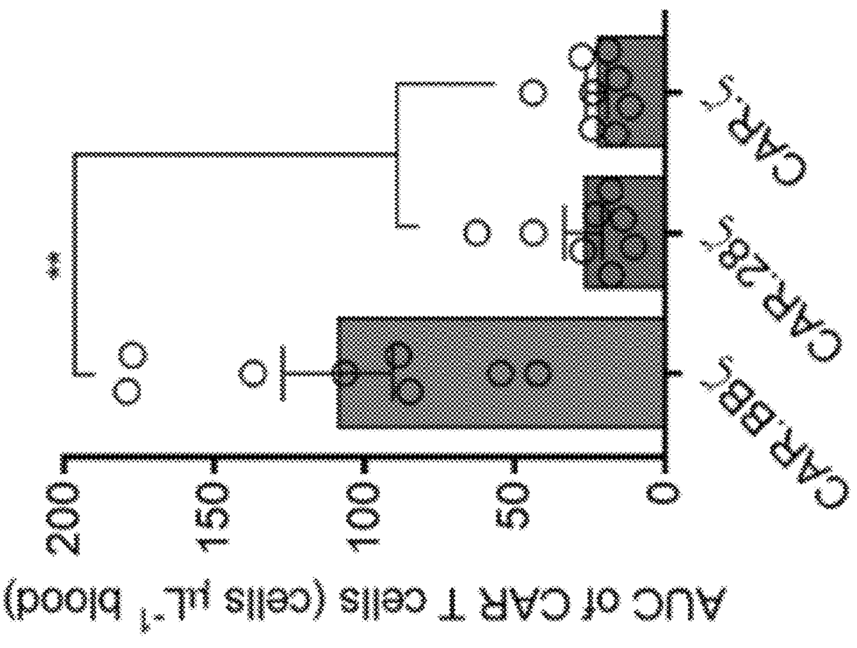
Figure 6E:
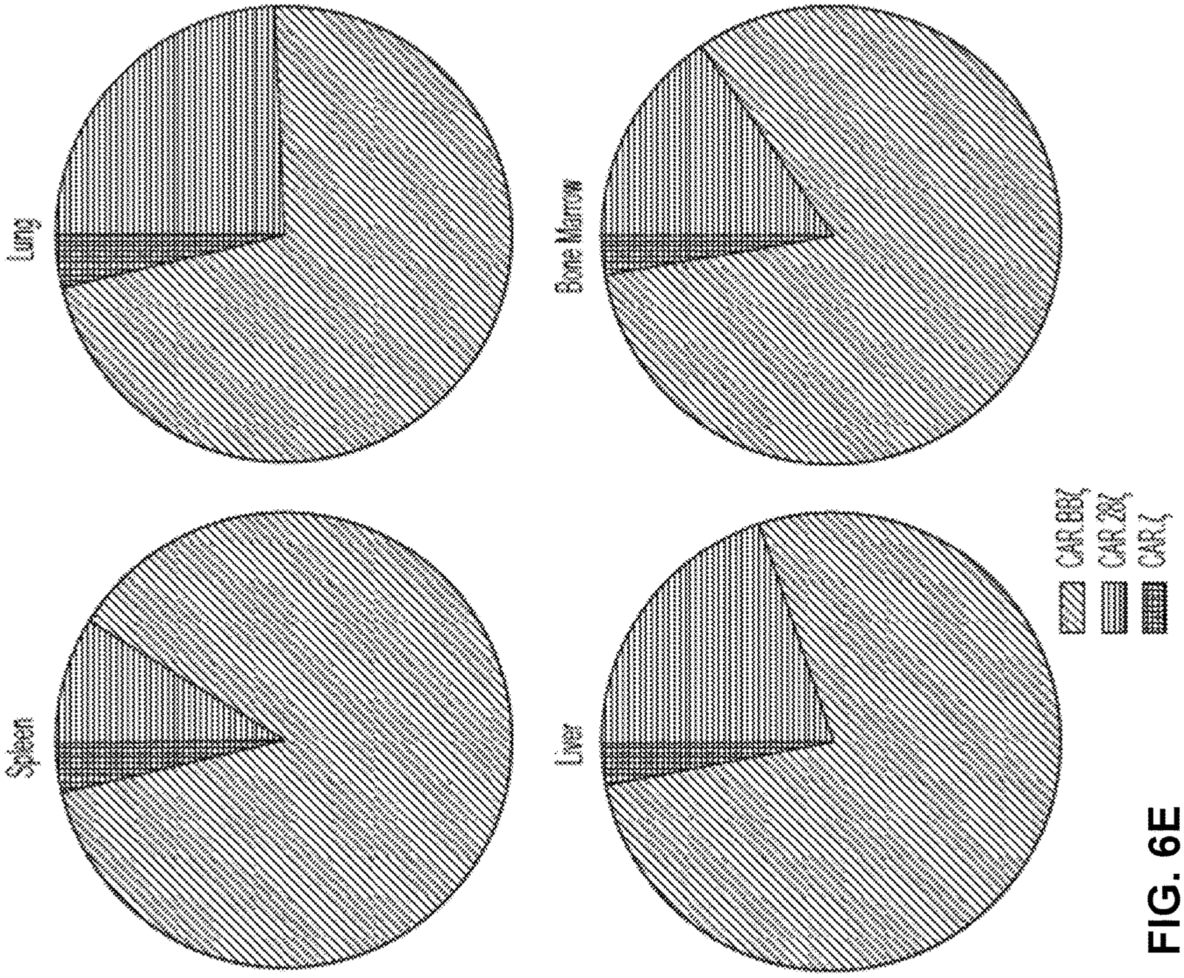
Figure 6F:
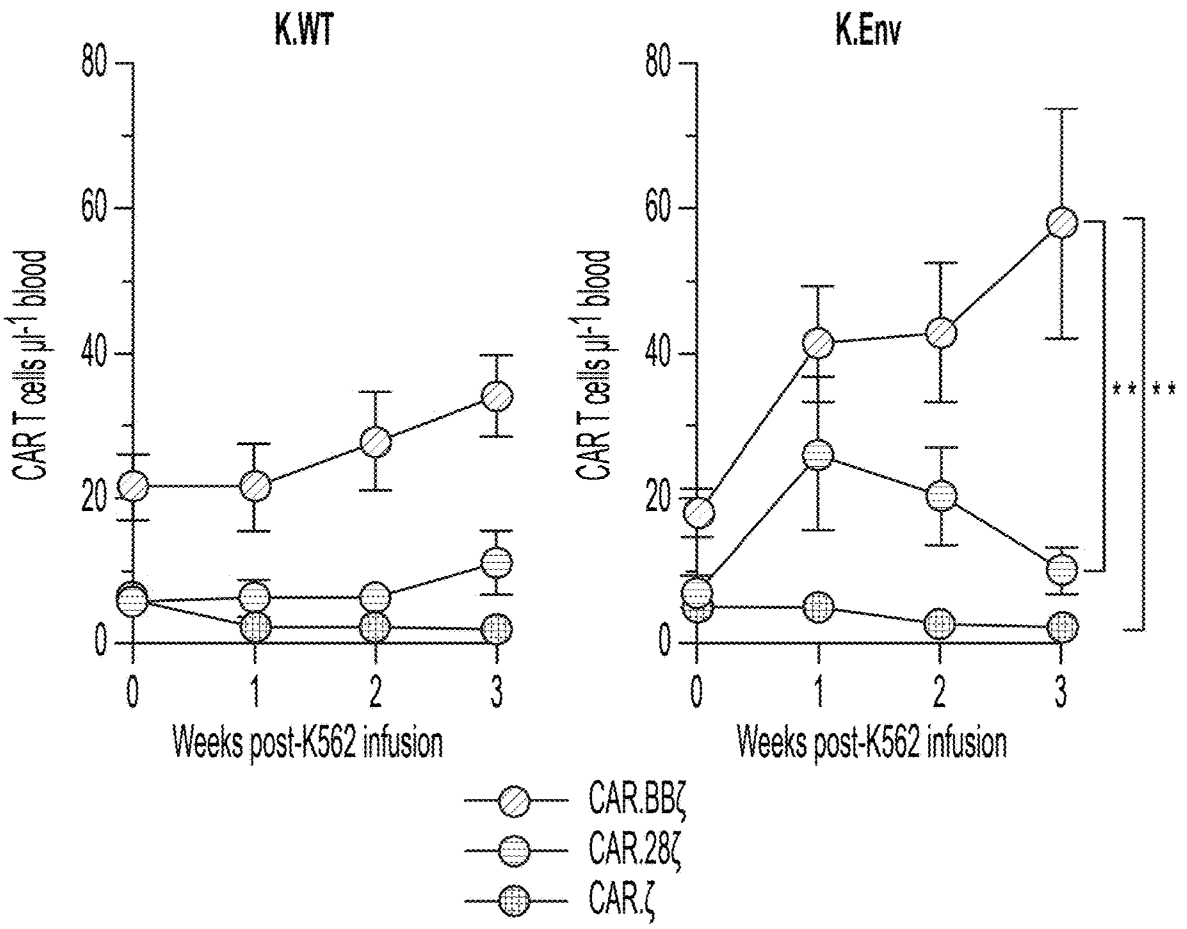
Figure 6G:
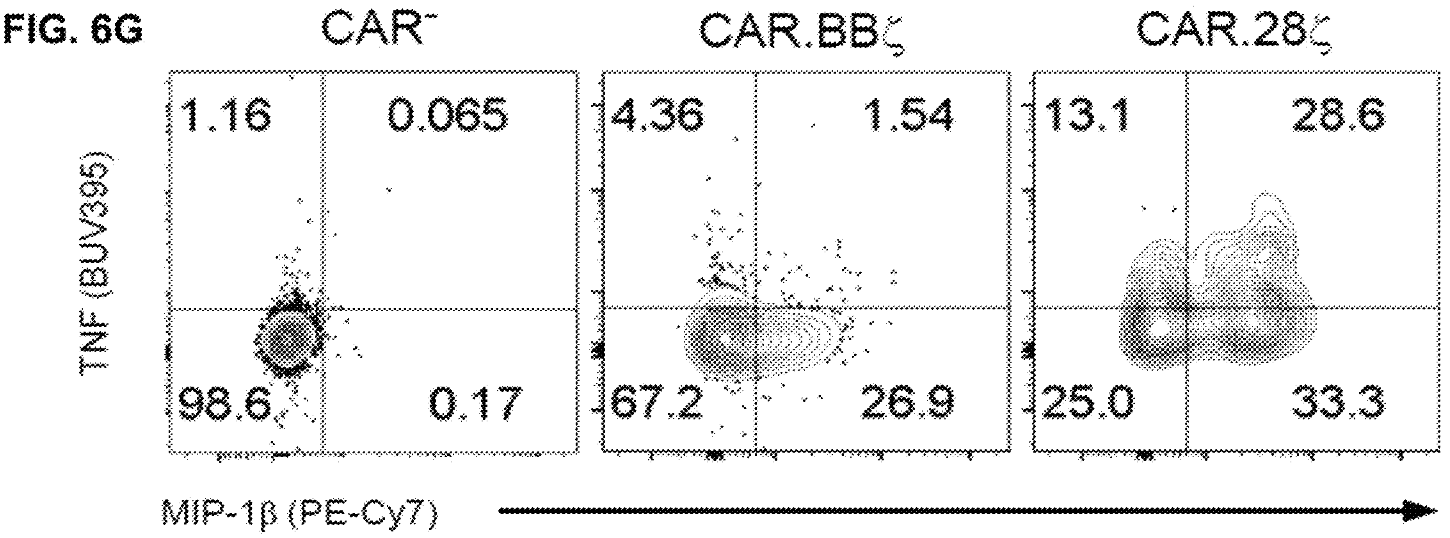
Figure 6H:
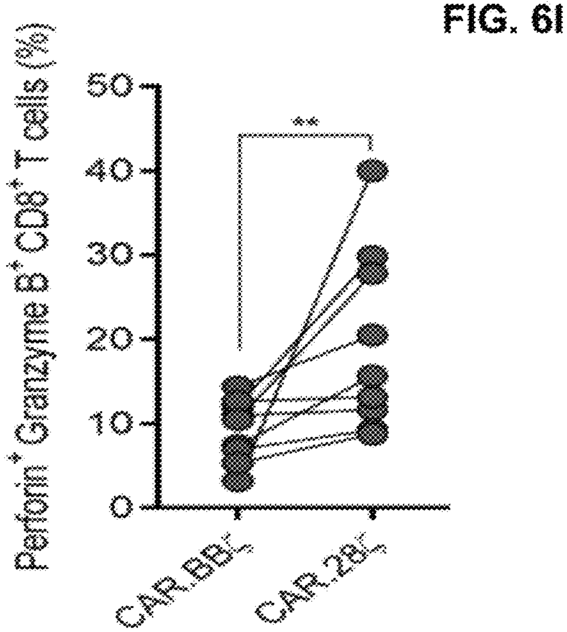
Figure 6I:
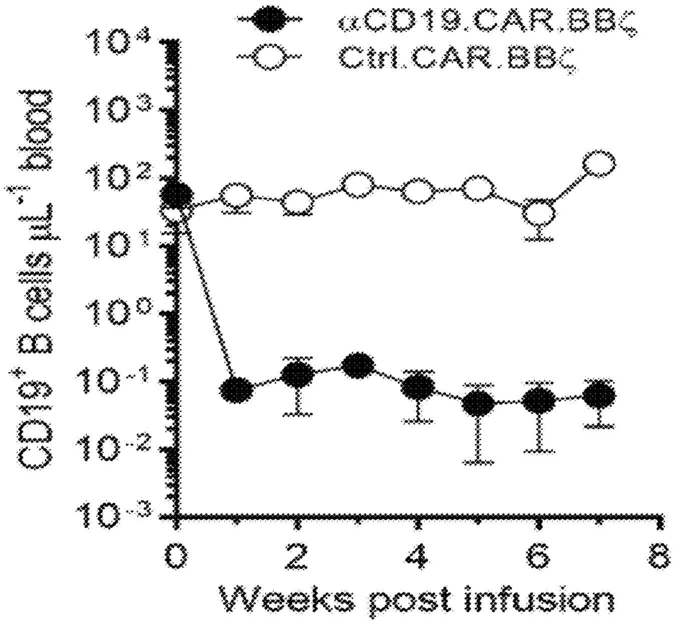
Figure 6J:
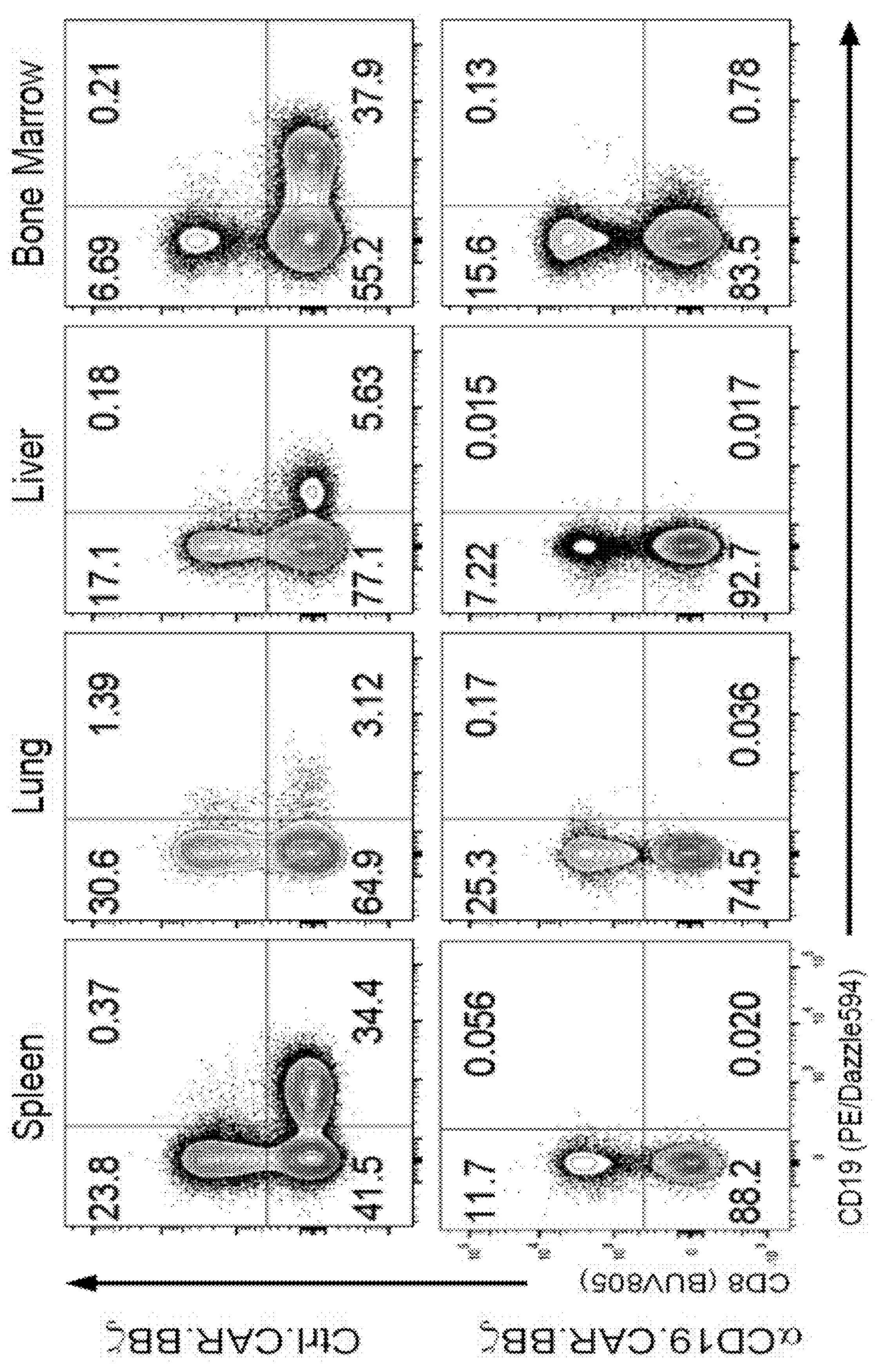
Figure 6K:
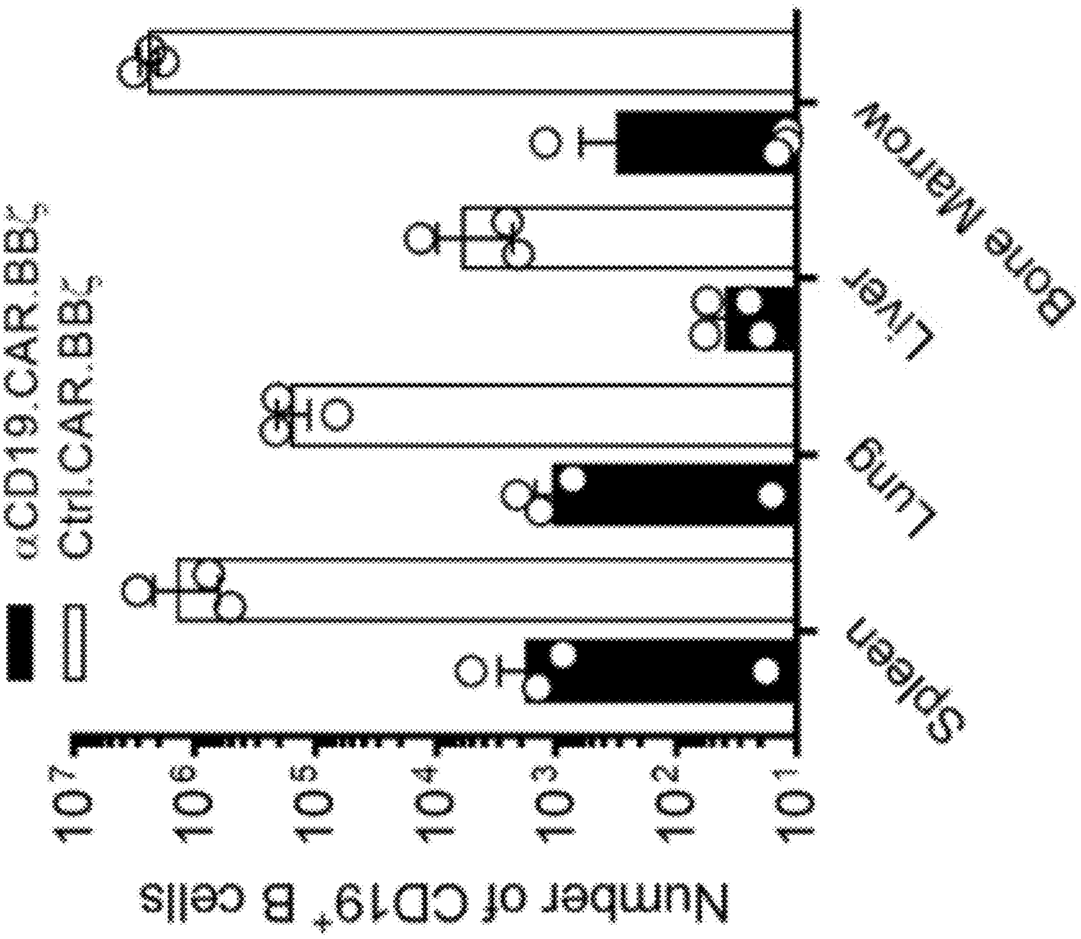
Figure 7:
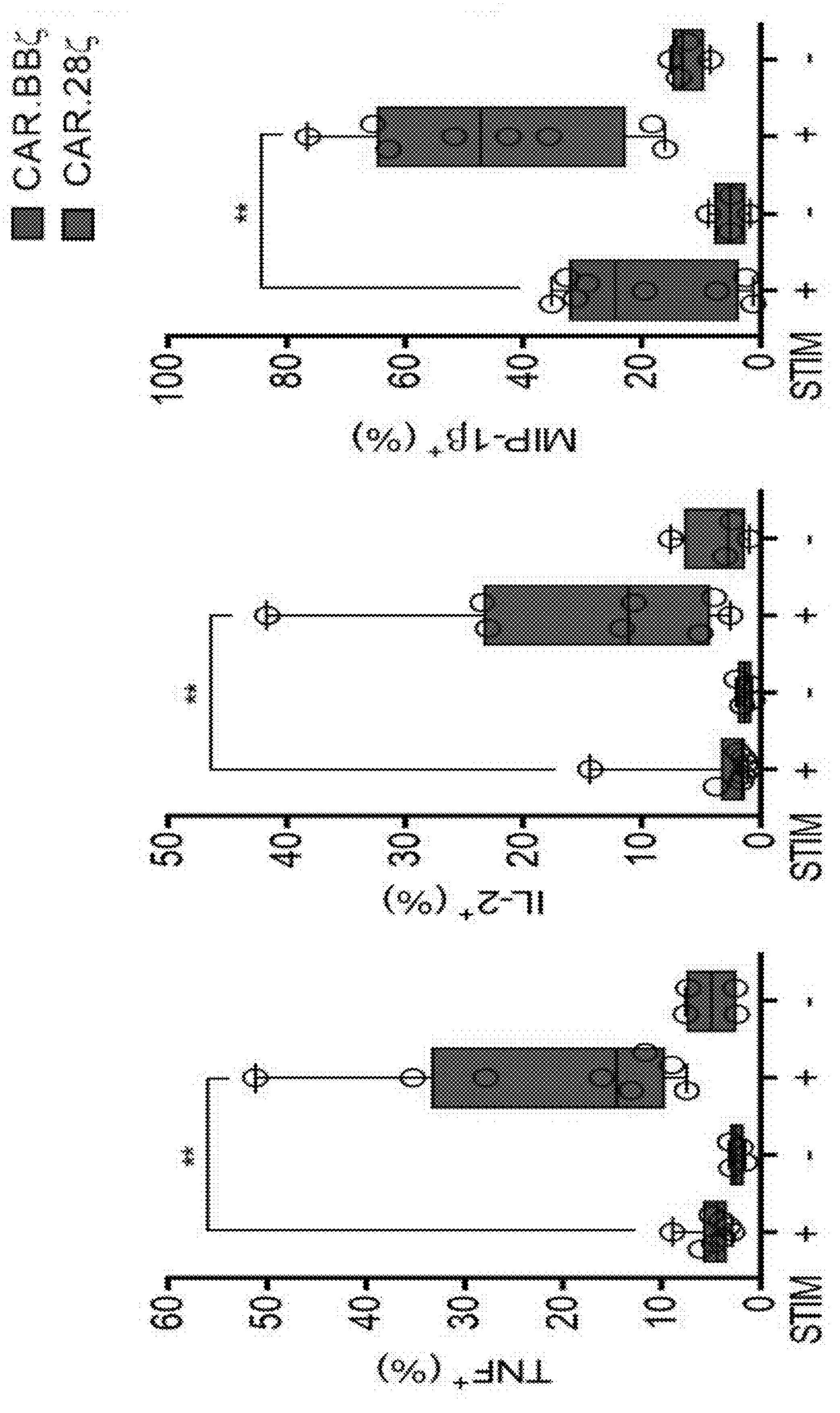
FIG. 7 illustrates CD28 costimulation enhances the ex vivo effector function of CAR T cells. HIV-uninfected mice were infused with an equal mixture of CD4-based CAR T cells expressing either CD3-ζ, 4-1BB/CD3-ζ and CD28/CD3-ζ costimulatory domains linked to unique fluorescent proteins to facilitate identification in vivo as described in FIGS. 6A-6K. Cumulative data indicating the frequency of $TNF^+$, $IL\text{-}2^+$ and MIP-1$\beta^+$ CAR.BBζ and CAR.28ζ T cells within the same mice after ex vivo stimulation with K.Env (stim) or K.WT (unstim) cells. Data represents the aggregate of cytokine producing cells from liver and terminal blood (n=8). CAR.ζ cells were too infrequent for analysis. Data shows box and whisker plots and bars indicate min and max values. Significance was calculated using Wilcoxon matched-pairs signed rank test (**P<0.07). Symbols represent individual mice.

Example 3: Costimulation Modulates CAR T Cell Persistence and Function In Vivo The generation of an effective cell-mediated immune response against HIV requires the long-term persistence of functional T cells. To this end, the contribution of costimulatory domains was compared to in vivo engraftment of T cells by creating an infusion product comprising equal frequencies of HIV-specific CAR CD3-ζ (ζ), 4-1BB/CD3-ζ (BBζ), and CD28/CD3-ζ (28ζ) T cells, each of which was linked to a distinct fluorescent protein (FIG. 6A). After infusion, CAR.BBζ T cells exhibited significantly greater survival in the absence of HIV antigen (FIGS. 6B-6D), and constituted approximately 80% of total CAR T cells across numerous tissues (FIG. 6E). Consistent with reports from the cancer field, CAR.BBζ T cells also demonstrated superior in vivo antigen-driven proliferation upon infusion of irradiated K.Env target cells (FIG. 6F). In contrast, CAR.28ζ T cells only exhibited a transient expansion followed by a progressive decline, and CAR.ζ T cells were seemingly non-responsive. Notably, however, CAR.28ζ T cells exhibited greater ex vivo effector functions, upregulating more MIP-1β, TNF and IL-2, and co-expressing greater levels of granzyme B and perforin than CAR.BBζ T cells from the same mice (FIGS. 6G-6H and FIG. 7). Finally, the in vivo cytotoxic potential of BLT mouse-derived CAR T cells was confirmed by infusing CD19-specific CAR.BBζ T cells into recipient mice. Rapid and profound B cell aplasia was observed in the blood (FIG. 6I) with significant clearance of B cells from the spleen, lung, liver, and bone marrow, consistent with a sustained cytotoxic CAR T cell response (FIG. 6J-6K). Together, these data demonstrate the suitability of BLT mice for studying in vivo CAR T cell function, and the degree to which costimulation can differentially modulate CAR T cell activity.

Figure 8A:
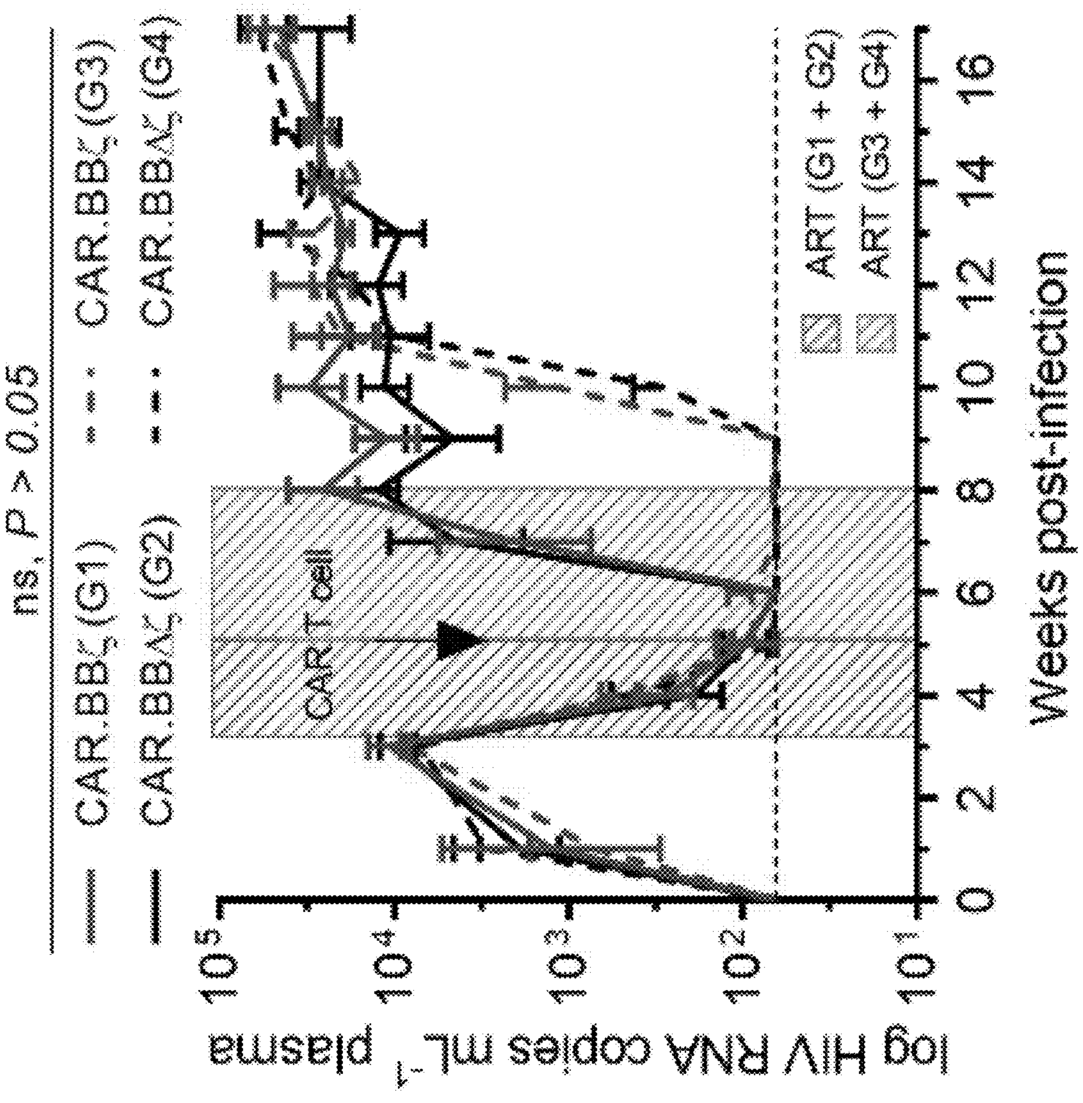
FIGS. 8A-8L illustrate HIV-specific CAR.BBζ T cells display features of T cell exhaustion after failing to control viral rebound.
Figure 10B:
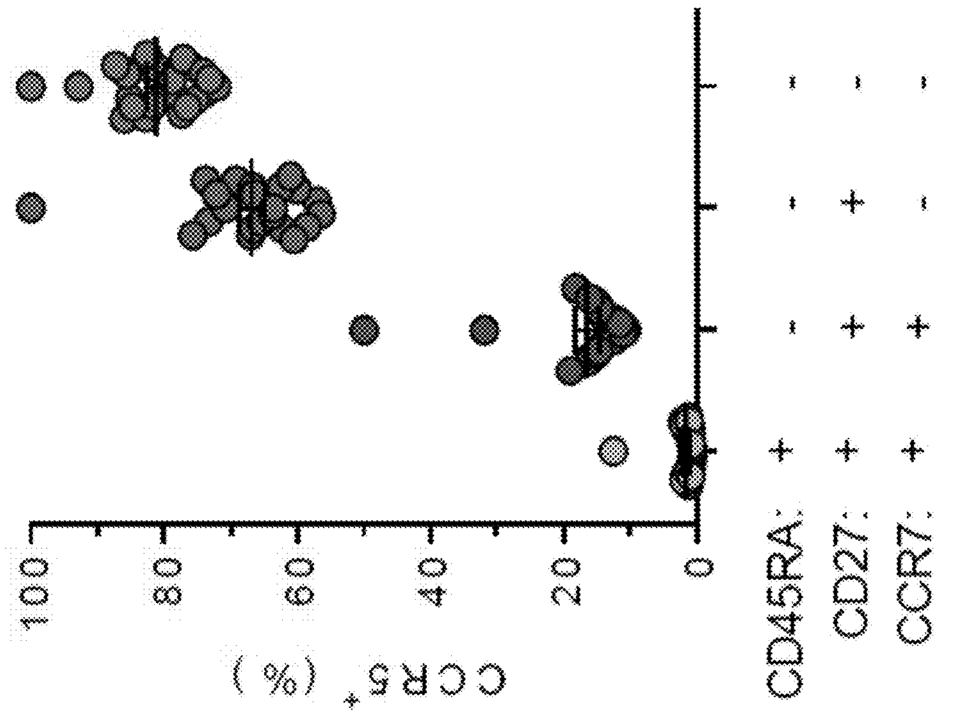
FIGS. 10A-10B illustrates the finding that HIV infection preferentially depletes memory $CD4^+$ T cells in BLT mice.
Figure 10A:
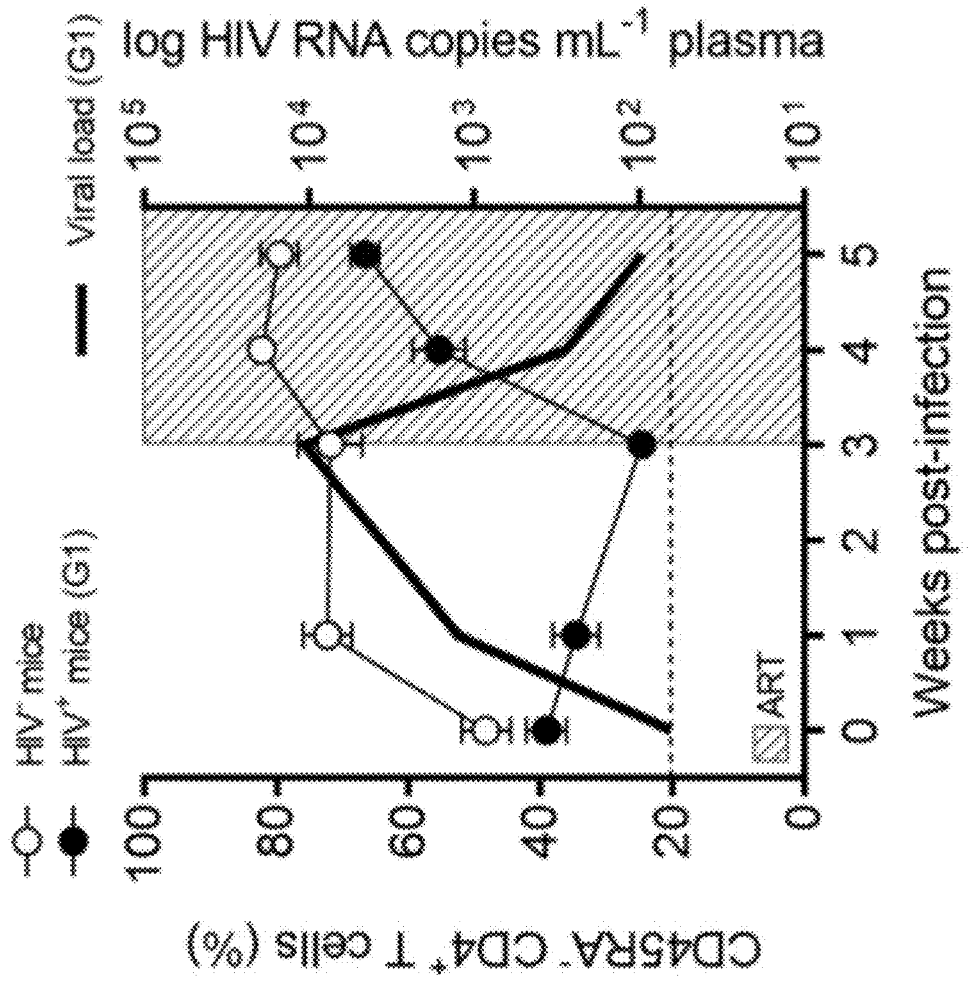

Example 4: CAR.BBζ T Cells Fail to Control HIV Rebound Upon ART Discontinuation After it was determined that the 4-1BB/CD3-ζ endodomain confers superior in vivo antigen-driven CAR T cell expansion and persistence, the therapeutic potential of CAR.BBζ T cells was tested in the context of ART-suppressed HIV infection. To do so, BLT mice were infected with CCR5-tropic $HIV_{JRCSF}$ and after 3 weeks ART was initiated. Two weeks later ART-suppressed mice were allocated into groups that received an infusion of either active CAR.BBζ T cells (G1 and G3), or inactive control CAR.BBΔζ T cells (G2 and G4), which express a truncated CD3-ζ chain. In G1 and G2, ART was ceased immediately after infusion, whereas in G3 and G4 ART was continued for an additional 3 weeks to test whether the timing of ART interruption impacted the efficacy of CAR T cell therapy. In all groups, HIV rebounded by 2 weeks after treatment interruption, regardless of timing, and there were no observable differences in the kinetics or magnitude of viremia in CAR.BBζ-treated mice compared to matched control mice (FIG. 8A). Moreover, CAR.BBζ T cell therapy did not prevent memory $CD4^+$ T cell loss in peripheral blood or tissues (FIGS. 8B-8C and FIGS. 9A-9C), which in BLT mice represent the $CD4^+$ T cell subset preferentially infected and depleted by HIV due to high levels of CCR5 expression (FIGS. 10A-10B). Together, these data indicate that CAR.BBζ T cell therapy did not impact HIV progression.

Figure 8B:
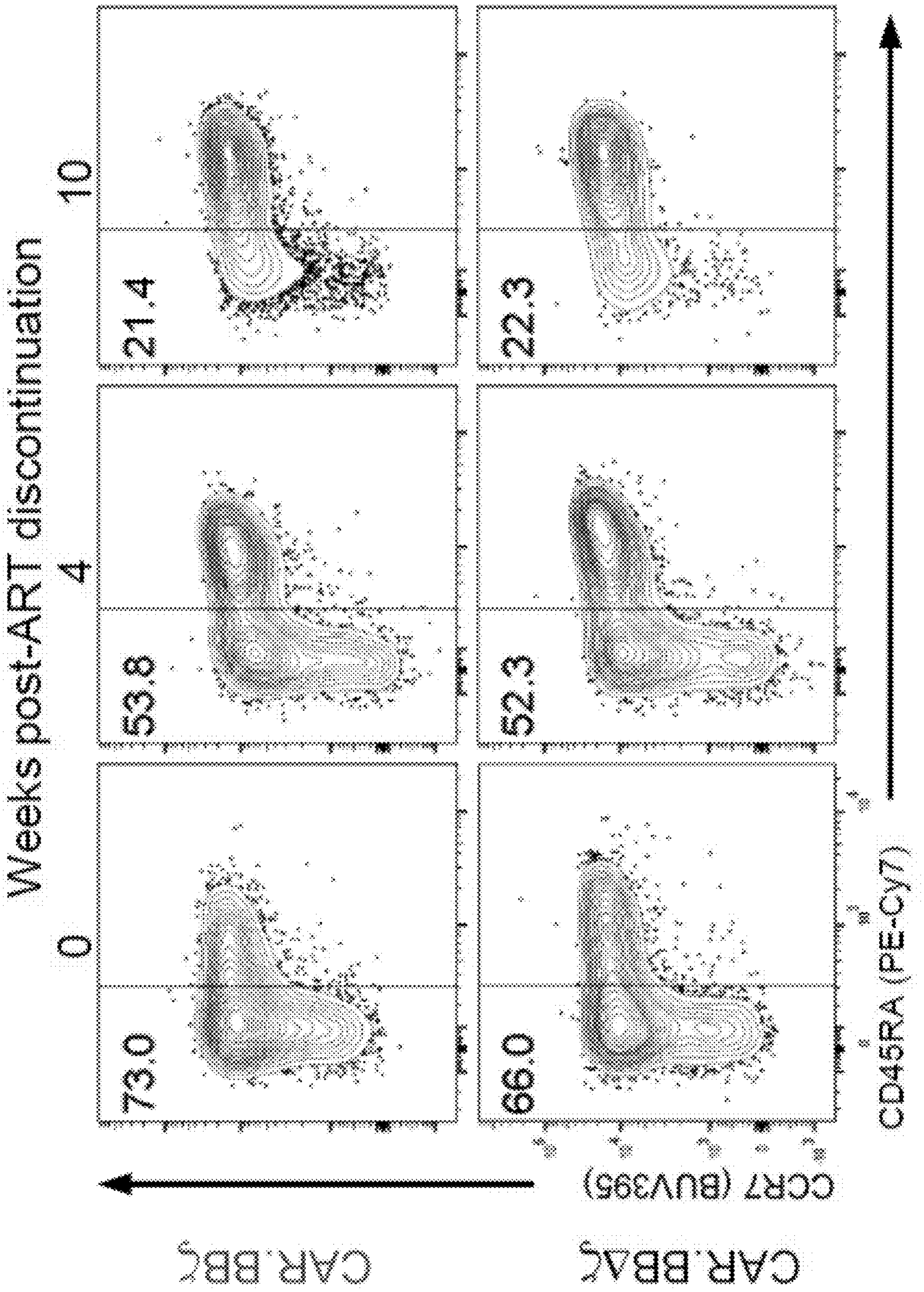
Figures 8C, 8D, 8E, 8F:
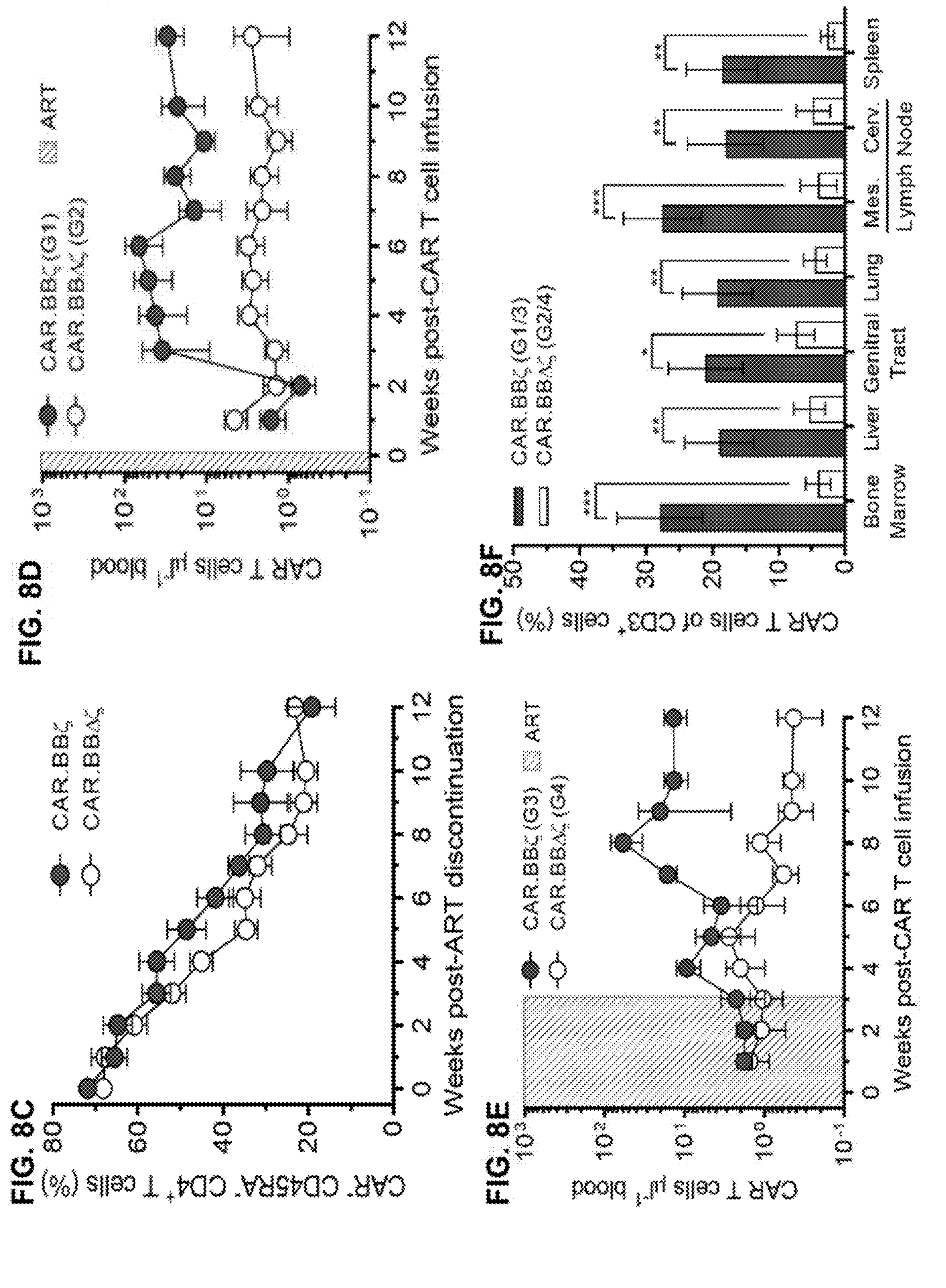
Figure 8G:
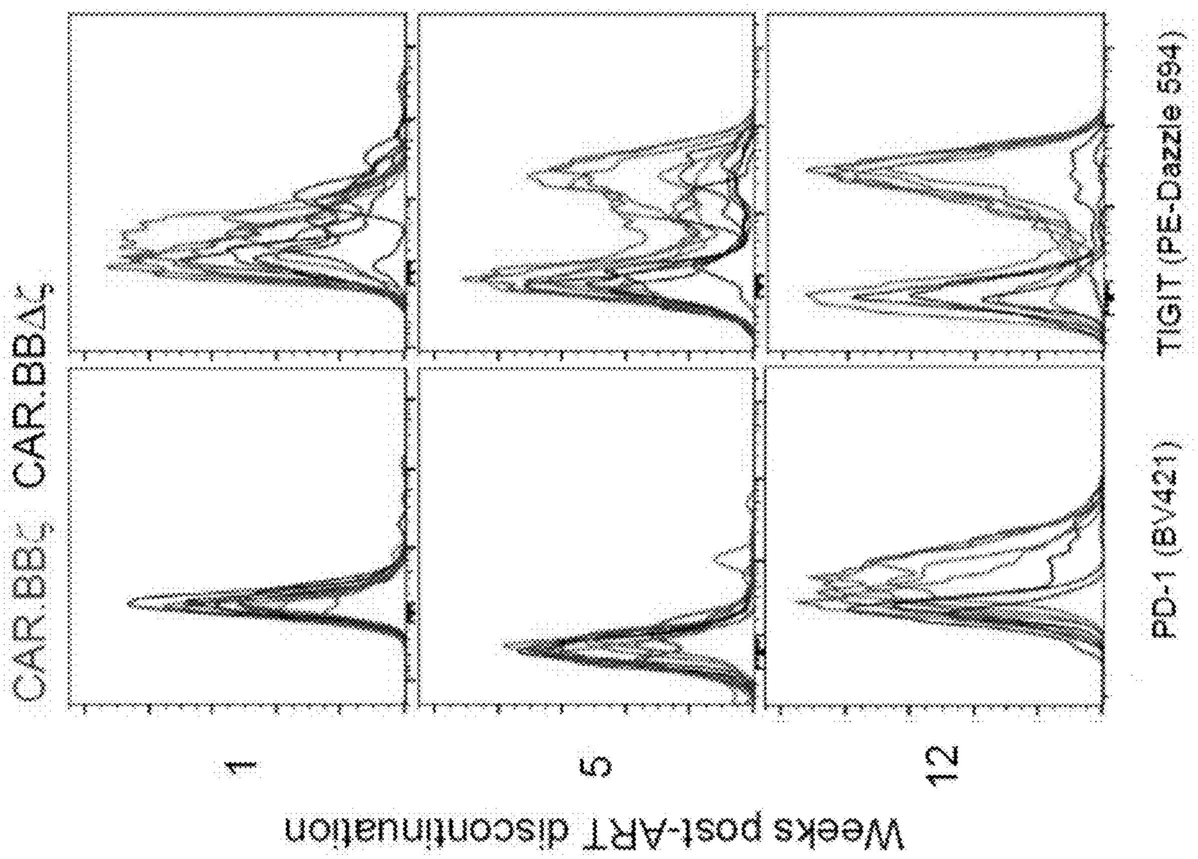
Figure 8H:
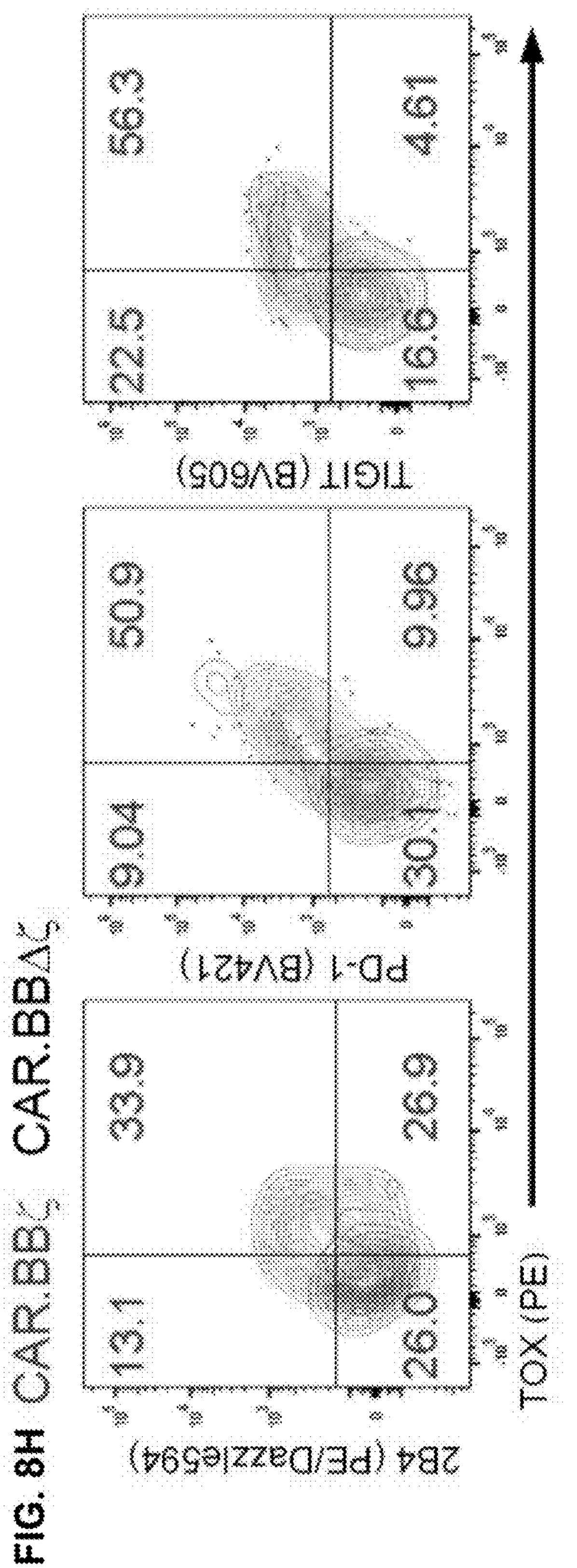
Figure 8I:
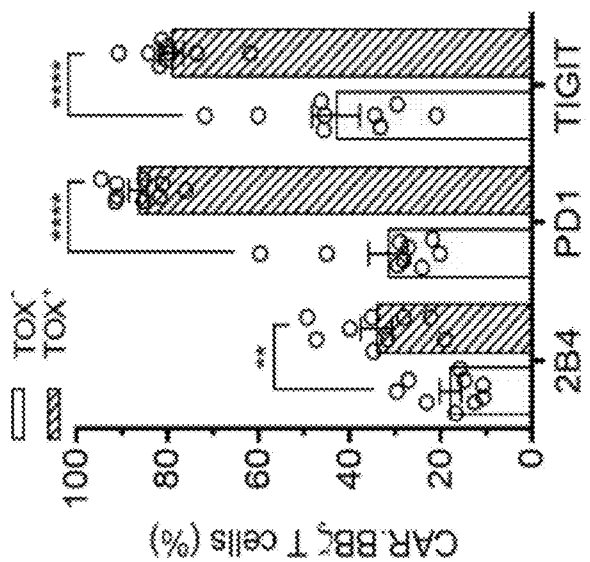
Figure 8J:
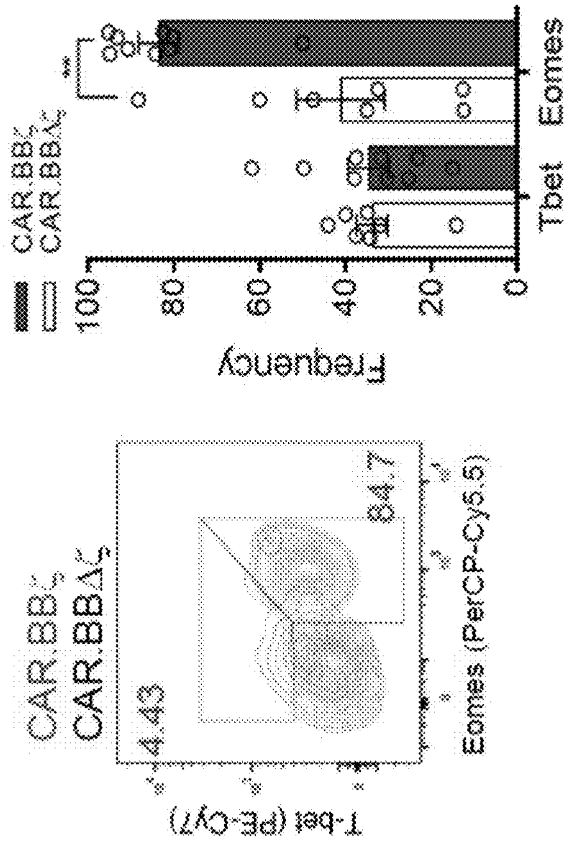
Figure 8K:
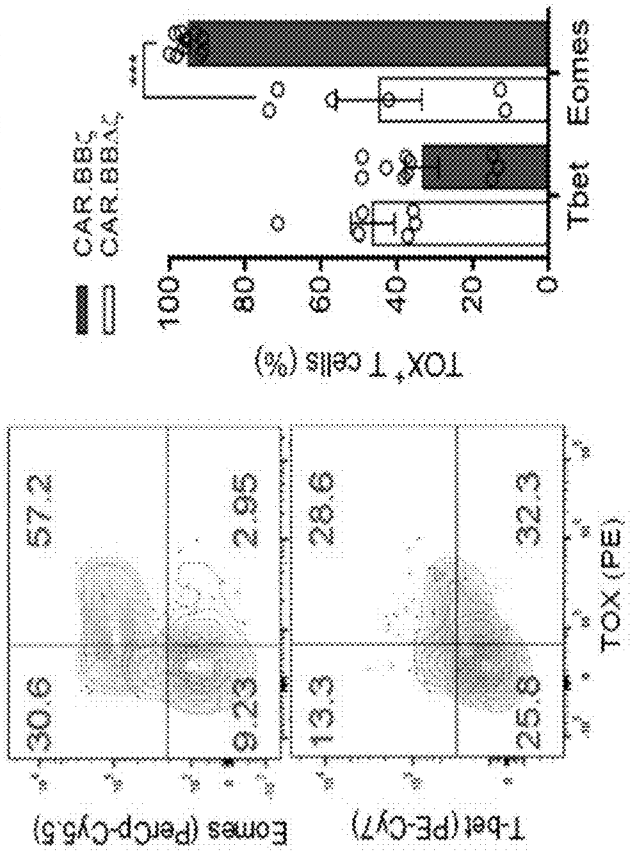
Figure 8L:
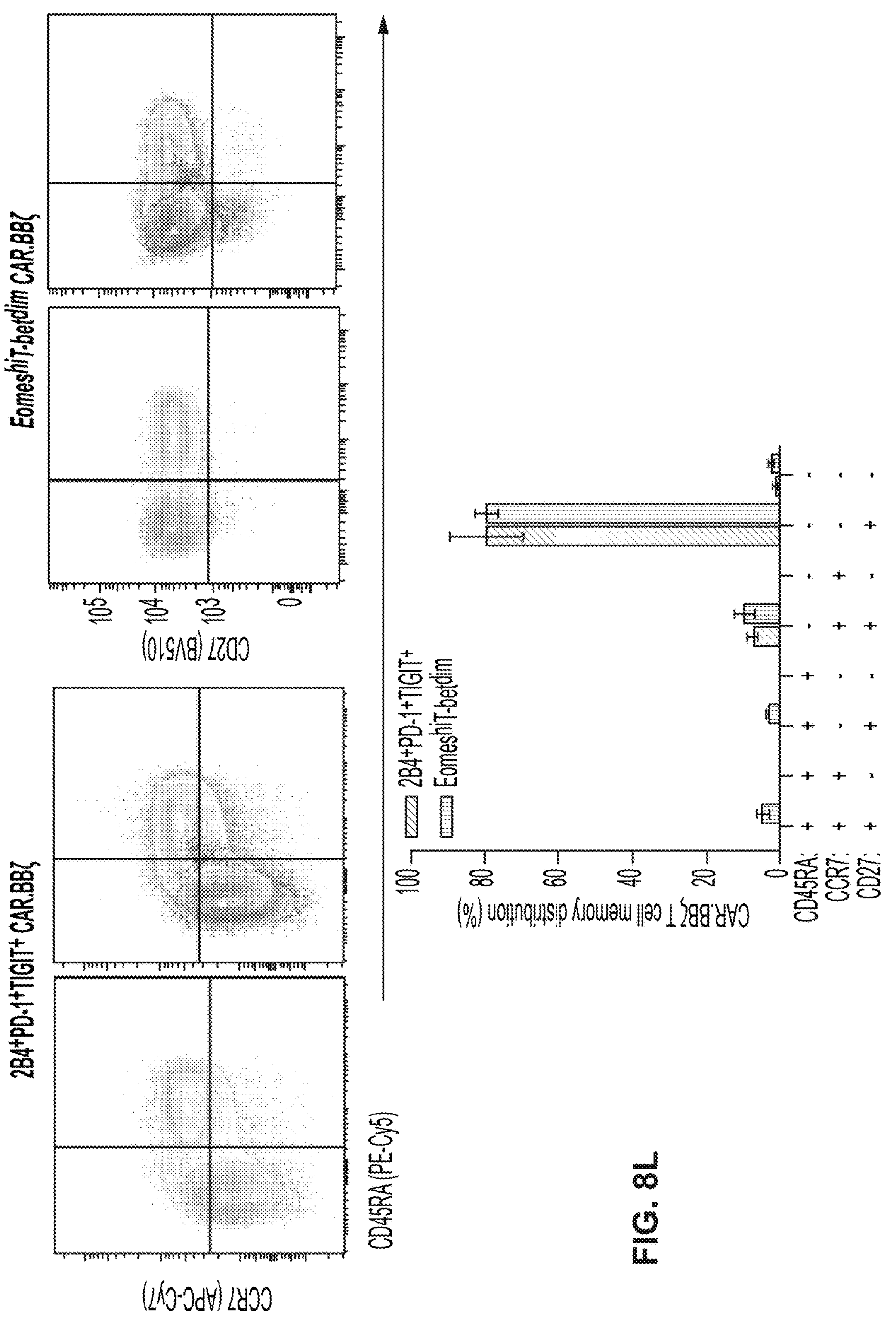
Figure 9A:
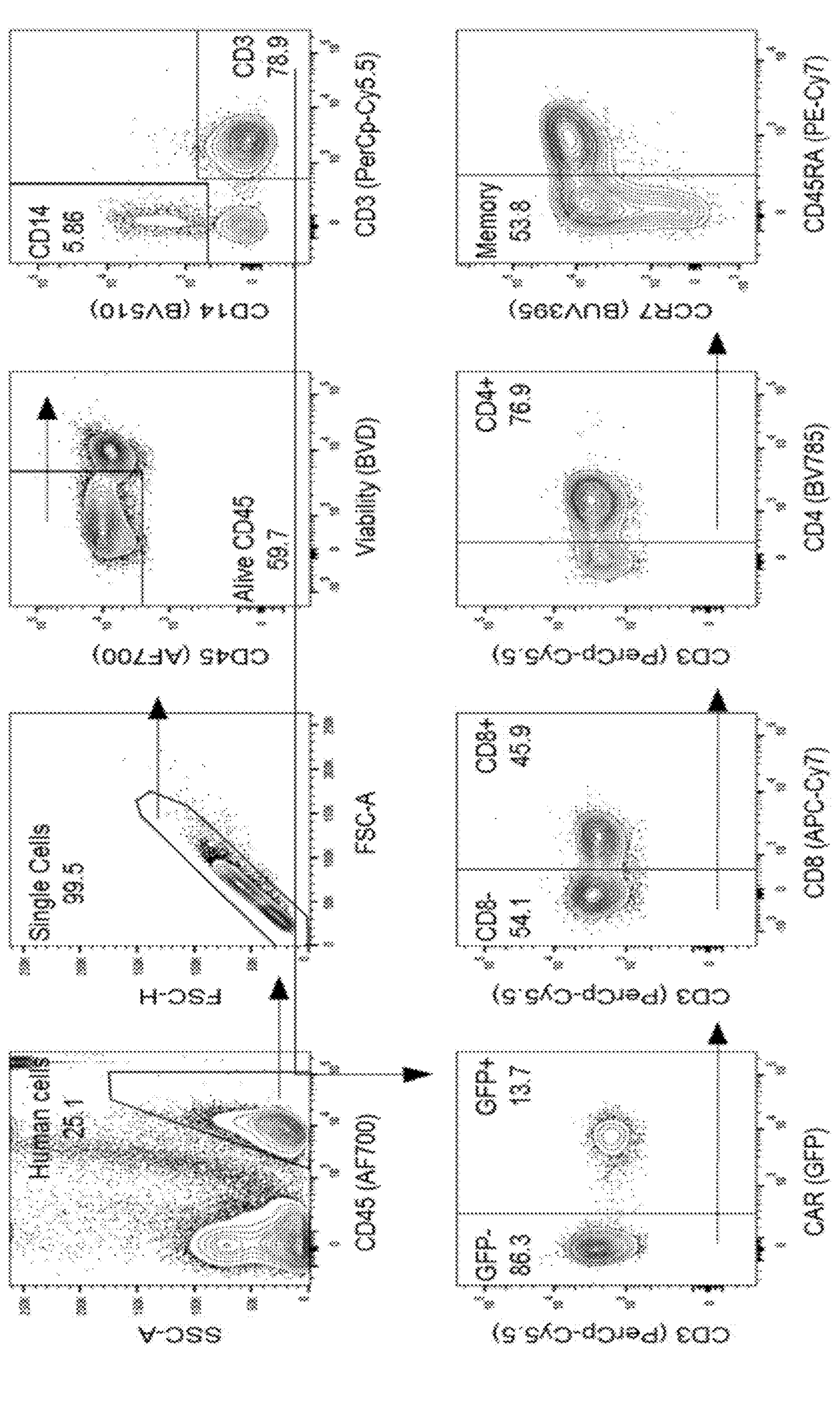
FIGS. 9A-9C illustrate CAR.BBζ T cells fail to prevent $CD4^+$ T cell loss after the discontinuation of ART.
Figure 9B:
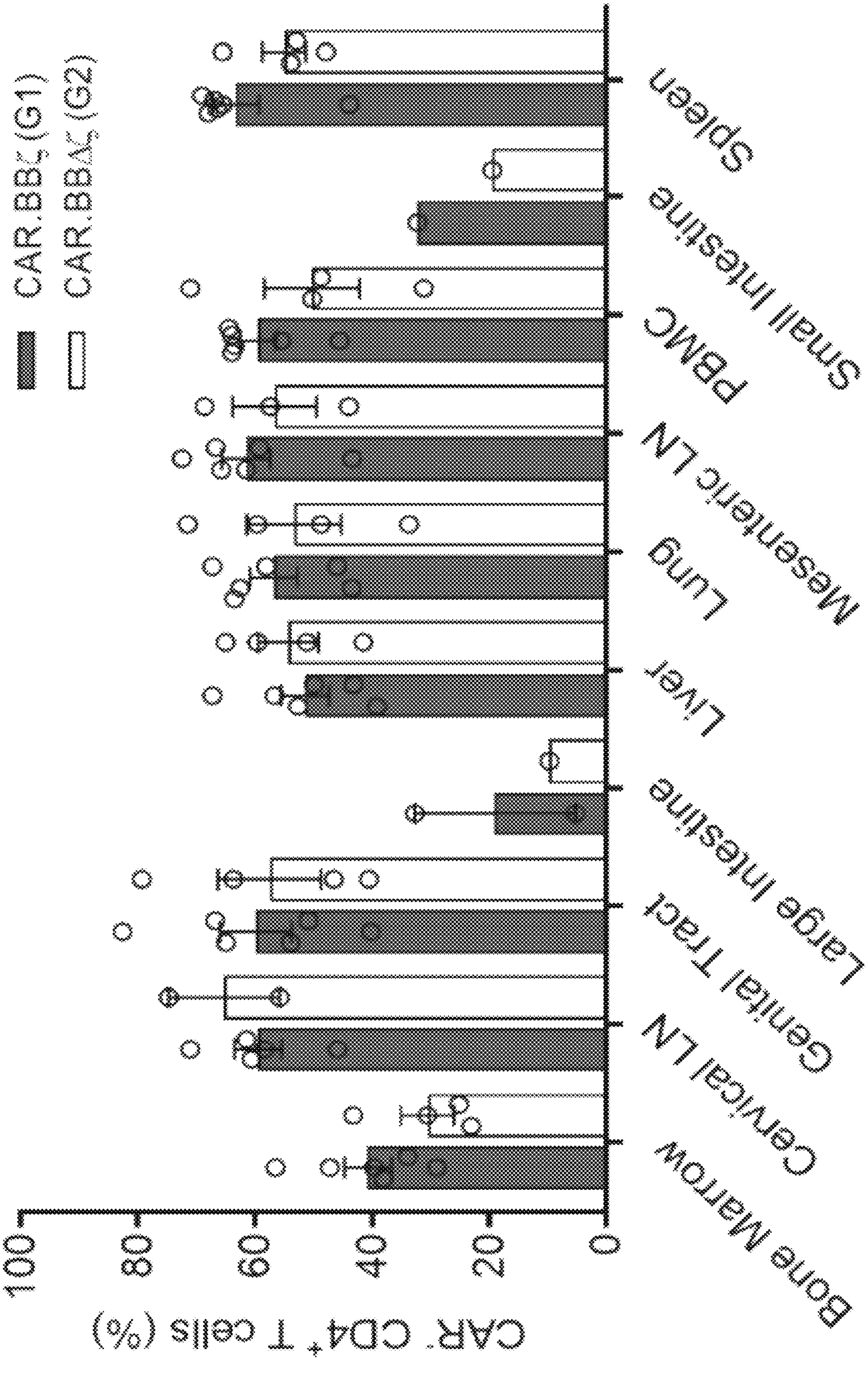
Figure 9C:
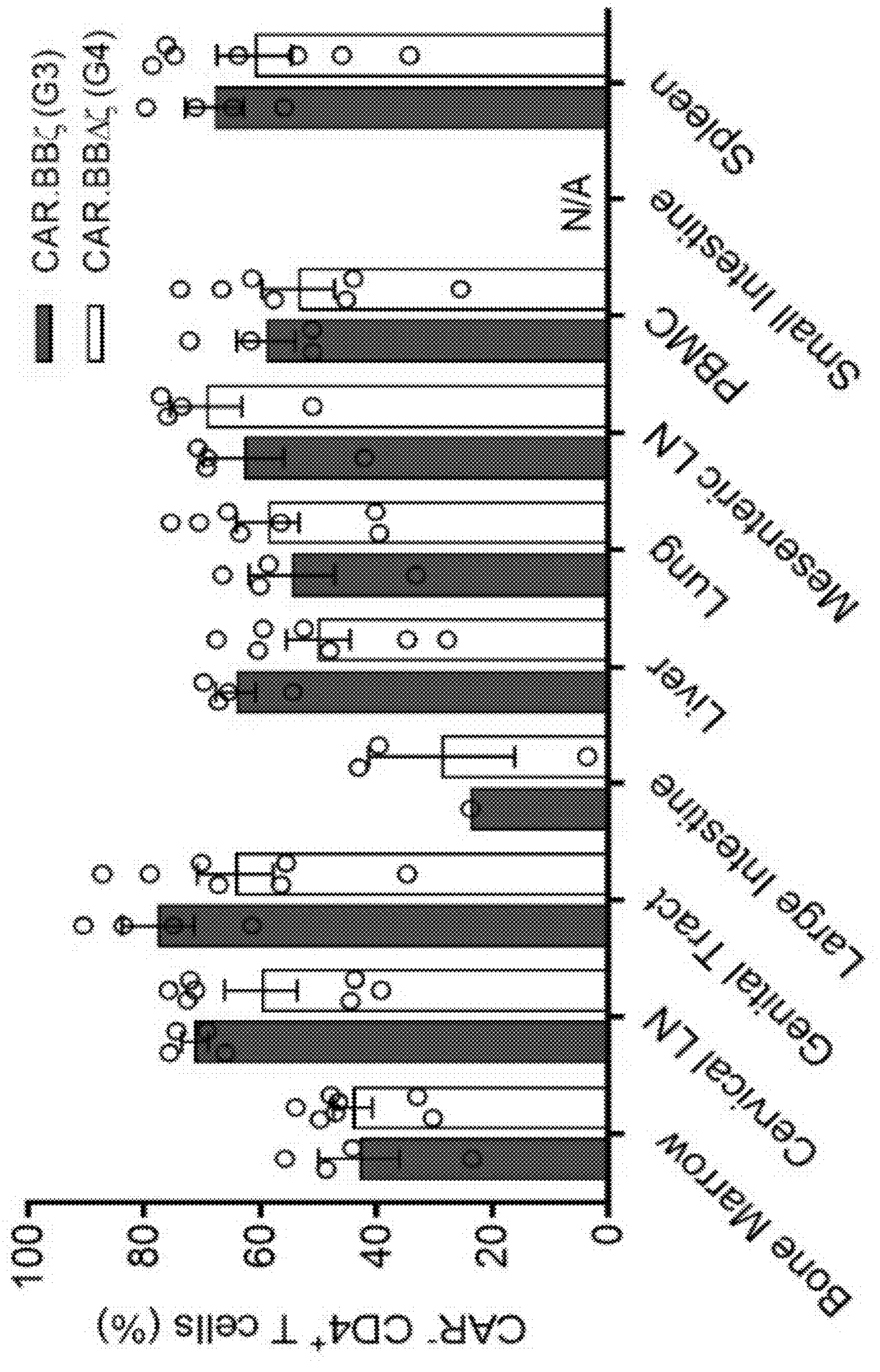

Example 5: CAR.BBζ T Cells Display Features of T Cell Exhaustion During Uncontrolled HIV Replication Despite the lack of efficacy following ART discontinuation, profound CAR.BBζ T cell expansion was observed during viral recrudescence with a median 75-fold increase in the blood (FIGS. 8D-8E). As expected, the inactive control T cells did not expand in response to viral rebound (FIGS. 8D-8E), and the CAR.BBζ T cells were substantially more abundant throughout the body 12 weeks after infusion (FIG. 8F). These findings suggested that the inability of CAR.BBζ T cells to control viremia and HIV pathogenesis was not the result of poor proliferation, persistence, or lack of migration to relevant anatomical compartments of virus replication.

Figure 11B:
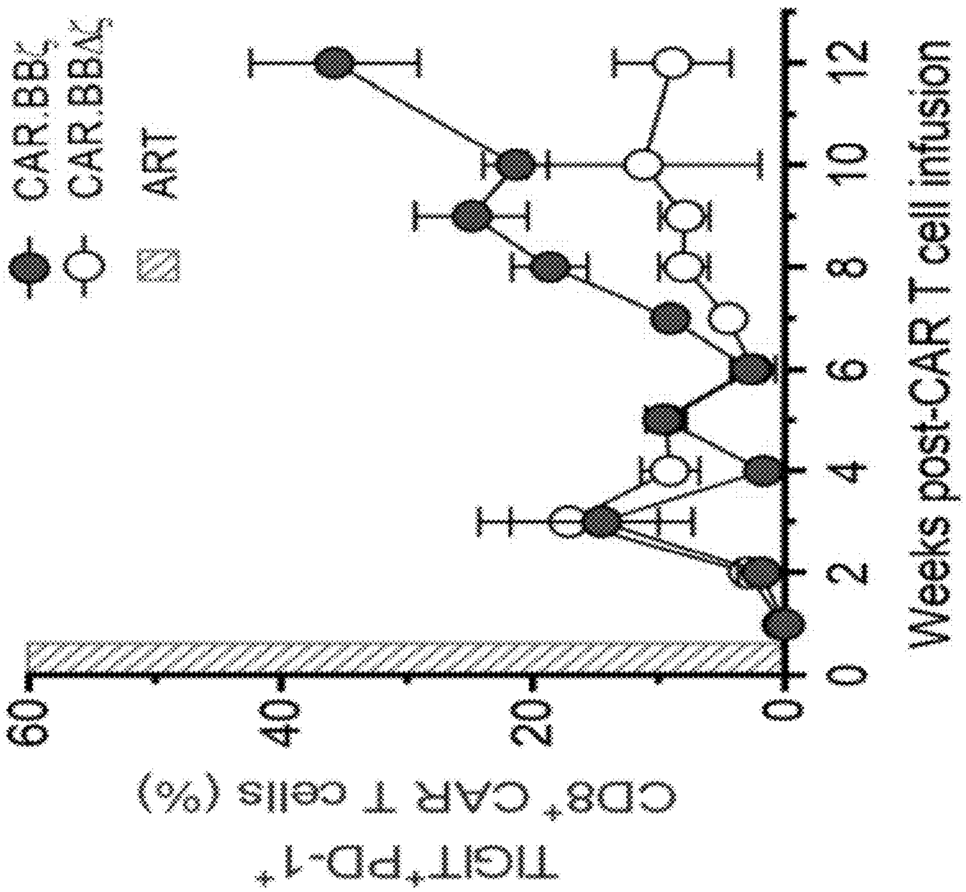
FIGS. 11A-11F illustrate CAR.BBζ T cells accumulate multiple inhibitory receptors as disease progresses.
Figure 11A:
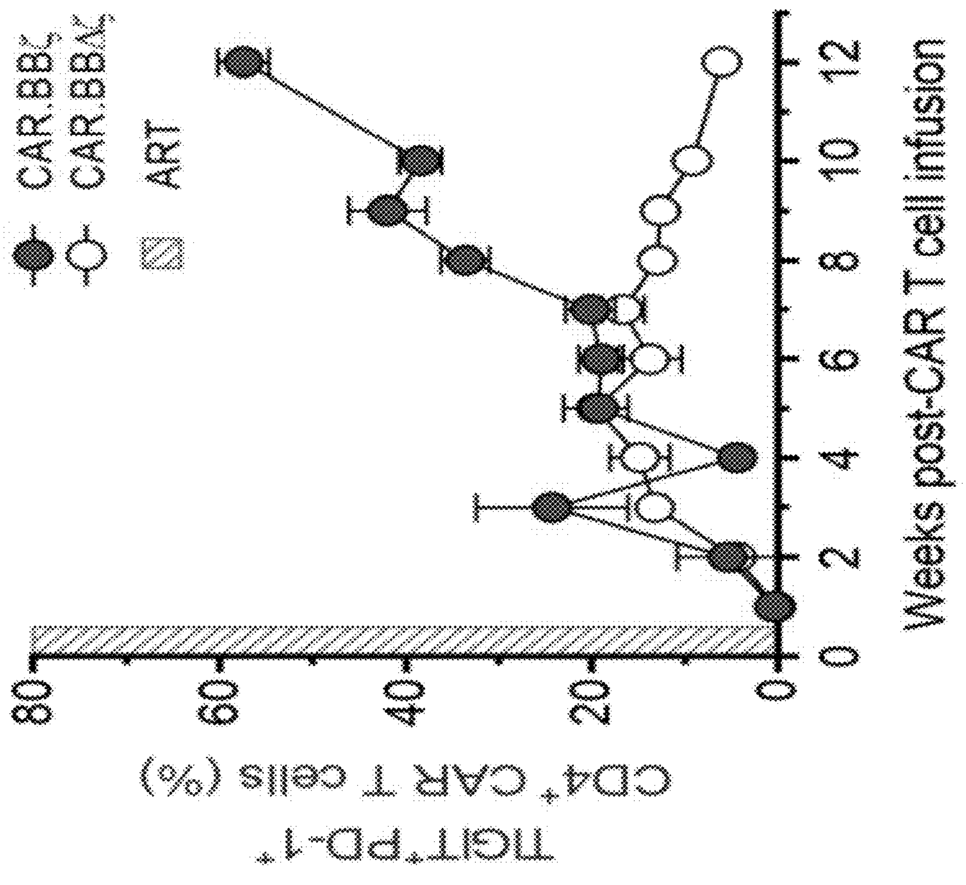
Figure 11D:
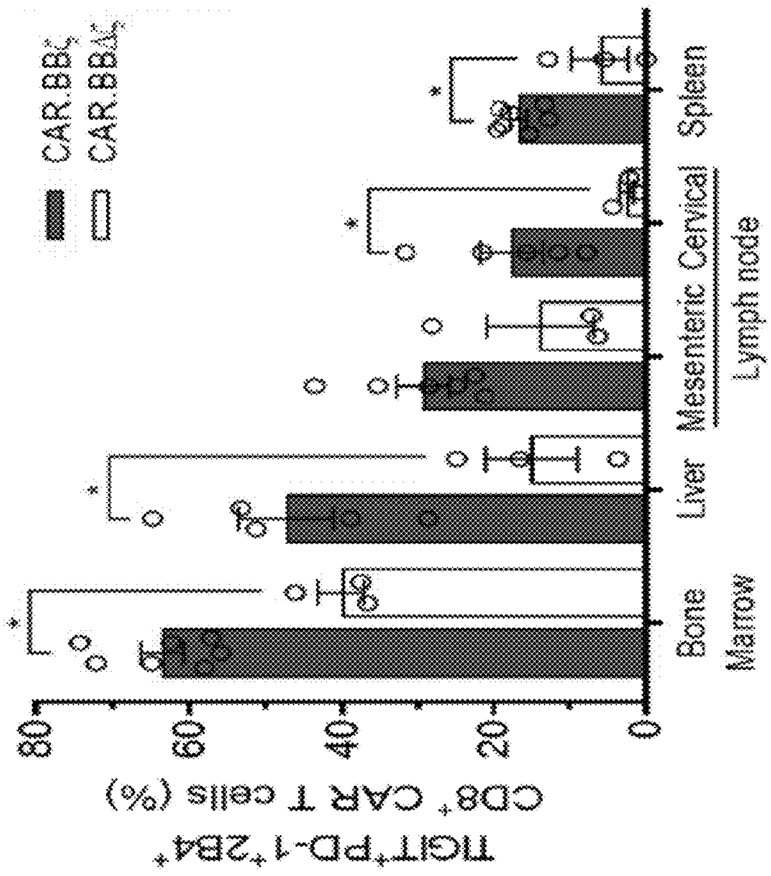
Figure 11C:
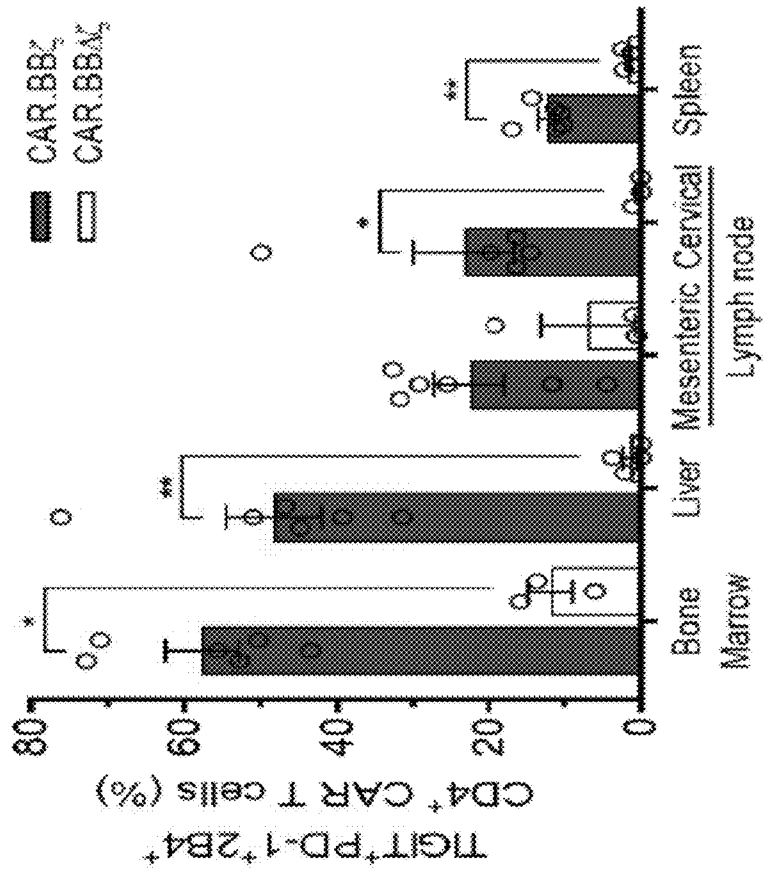
Figure 11F:
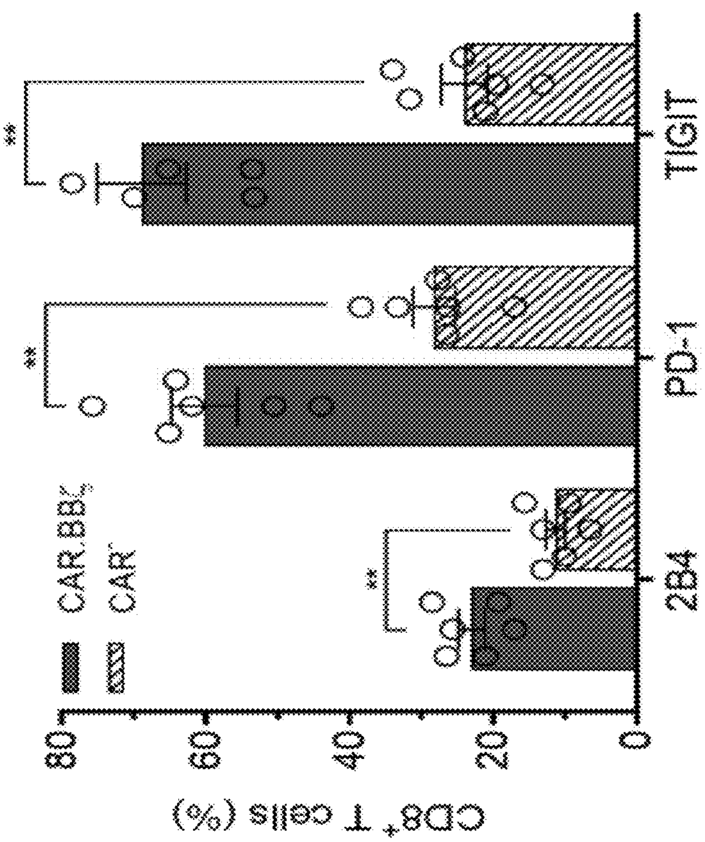
Figure 11E:
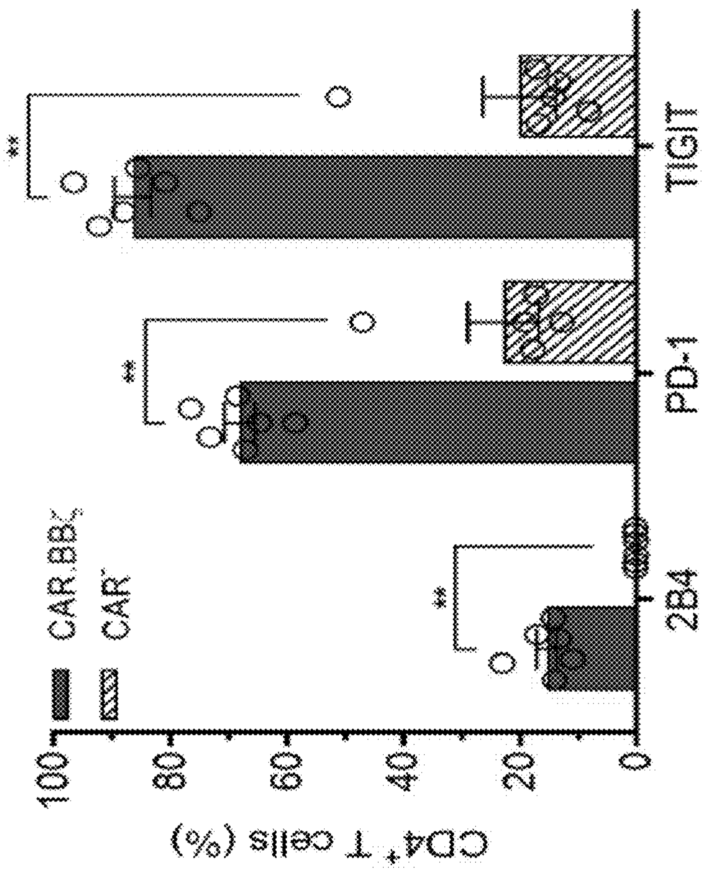
Figure 12A:
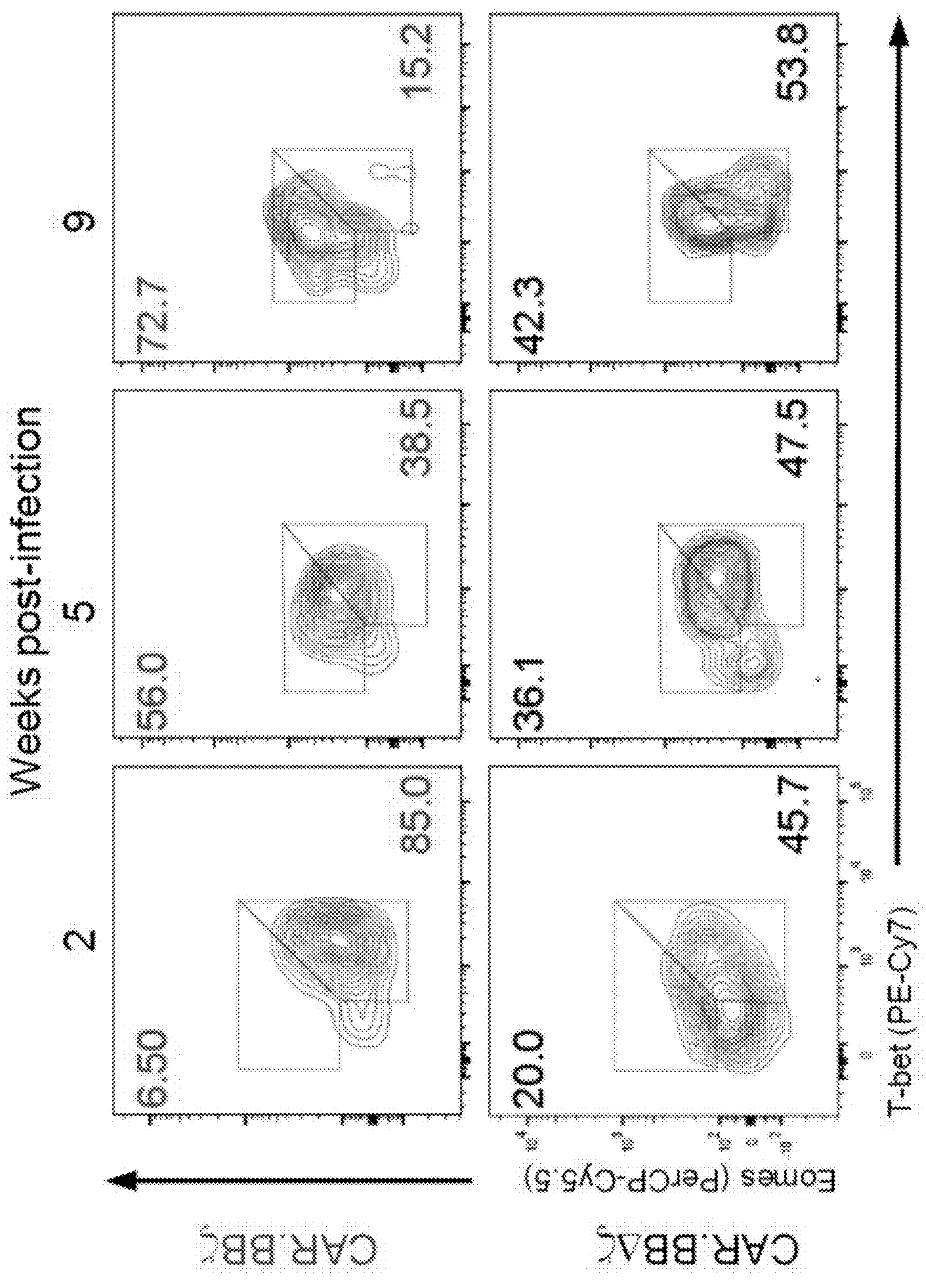
FIGS. 12A-12C illustrate $Eomes^{hi}T\text{-}bet^{dim}$ CAR.BBζ T cells accumulate from acute to chronic phases of infection. Mice were infected with $HIV_{JRCSF}$ and infused 48 hours later with either $2\times10^7$ CAR.BBζ T cells (n=5) or inactive control CAR.BBΔζ T cells (n=3).
Figure 12B:
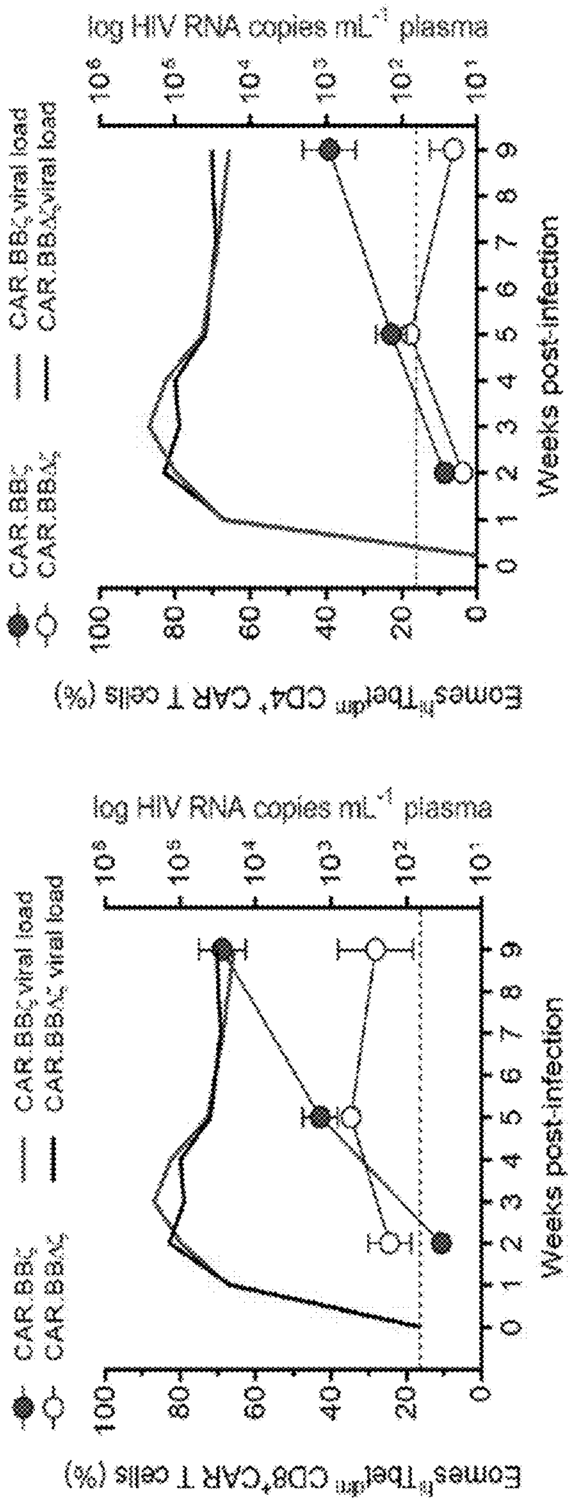
Figure 12C:
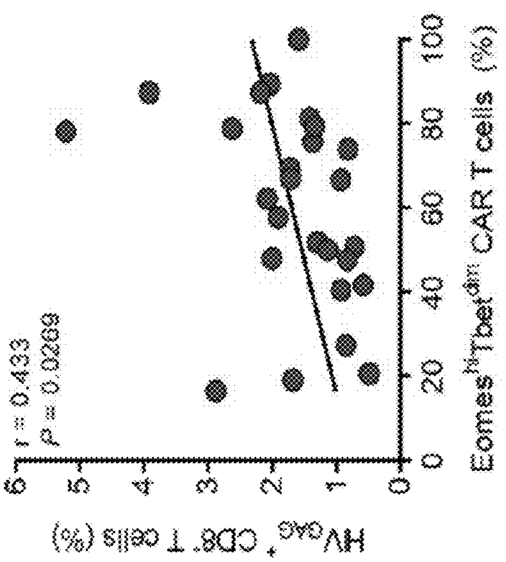

The proliferation of CAR.BBζ T cells was associated with upregulation of inhibitory receptors including PD-1, TIGIT, and 2B4, which increased over time (FIG. 8G and FIGS. 11A-11D). Importantly, these inhibitory receptors were not expressed to the same extent on endogenous CAR T cells within the same mice, suggesting a CAR T cell-specific effect rather than generalized T cell activation from inflammation or viral load (FIGS. 11E-11F). Notably, elevated inhibitory receptor expression on CAR.BBζ T cells from chronically infected mice was associated with the expression of TOX (FIGS. 8H-3I), a transcription factor that regulates the T cell exhaustion program linked to disease settings. Further supporting the gradual emergence of a dysfunctional CAR T cell phenotype, T-bet expression in CAR.BBζ T cells waned as HIV infection progressed culminating in a population of $Eomes^{hi}T\text{-}bet^{dim}$ CAR T cells that were enriched in TOX expression and accumulated in tissues with higher viral burden (FIGS. 8J-8K and FIGS. 12A-12C). In addition, expression of multiple inhibitory receptors on CAR.BBζ T cells from chronic infection was linked to a transitional memory state displaying an $Eomes^{hi}T\text{-}bet^{dim}$ phenotype (FIG. 8I), all of which is congruent with prior studies identifying dysfunctional HIV-specific $CD8^+$ T cells within this compartment in chronic human HIV infection.

Figure 13A:
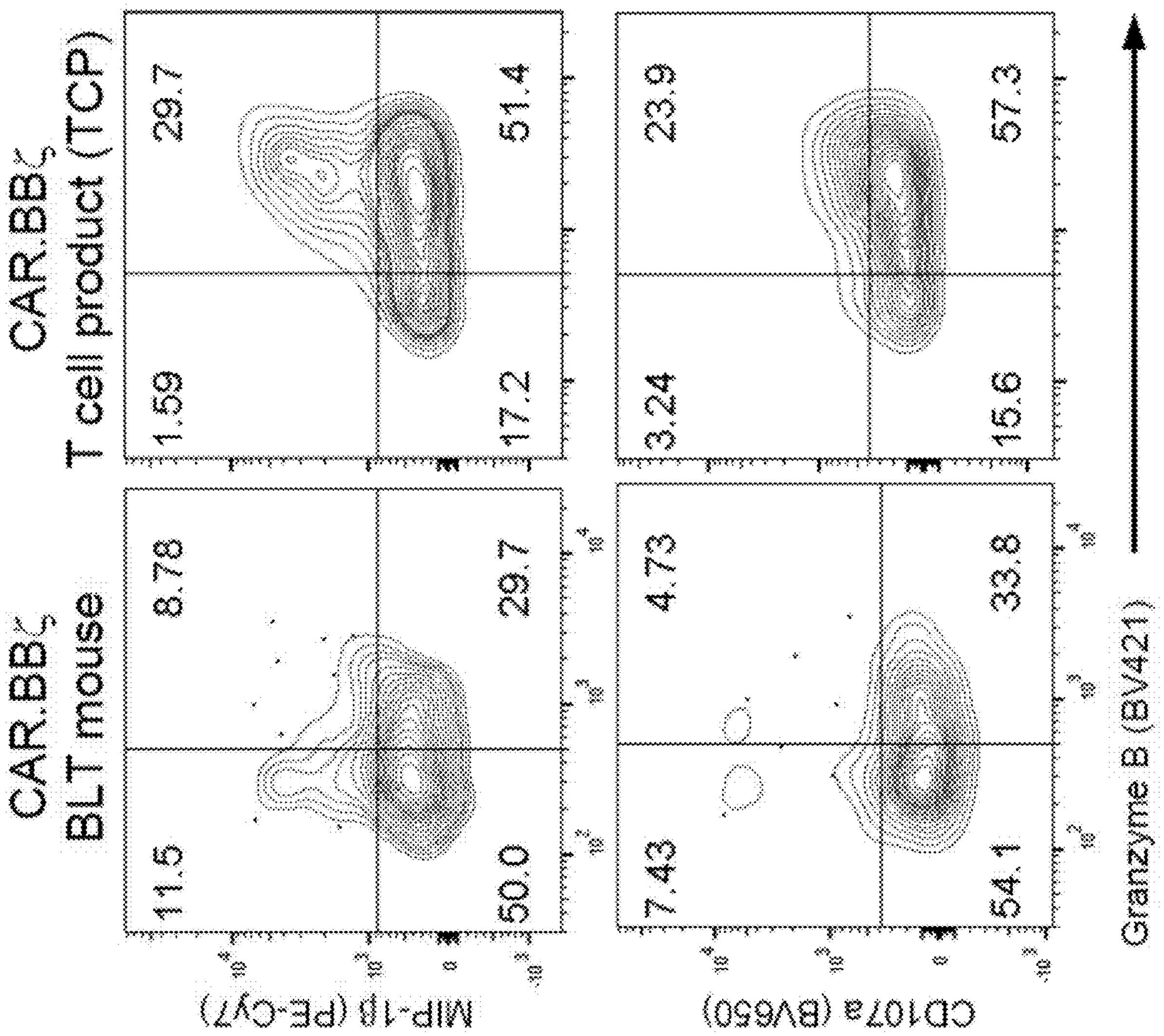
FIGS. 13A-13B illustrate CAR.BBζ T cells from chronic infection exhibit attenuated ex vivo function compared to CAR T cell product. CAR.BBζ T cells (n=14) and inactive control CAR.BBΔζ T cells (n=10) were isolated from the livers of chronically infected mice 12 weeks post-infusion, and the pre-infusion CAR.BBζ T cell product (TCP) were ex vivo stimulated.
Figure 13B:
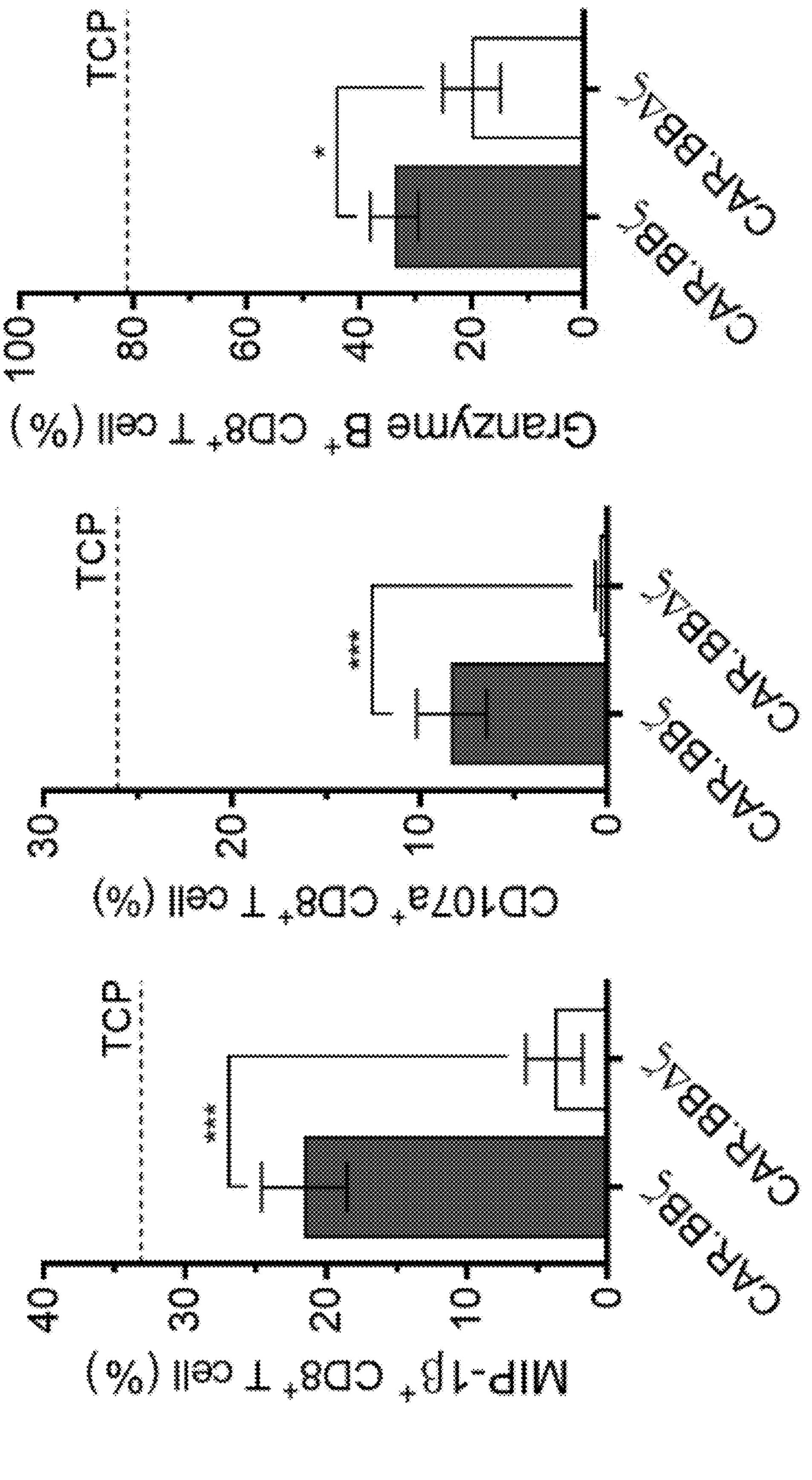

The ex vivo functional capacity of CAR.BBζ T cells isolated during chronic infection was compared to the pre-infusion CAR T cell product (TCP). Although the $CD8^+$ CAR.BBζ T cells from chronic infection retained the ability to upregulate MIP-1β and granzyme B, and degranulate based on CD107a expression, the degree of β-chemokine production and cytotoxic potential was attenuated (FIGS. 13A-13B). Taken together, these data indicate that CAR.BBζ T cells recognize HIV-infected cells, rapidly expand and upregulate markers of cellular activation, but that uncontrolled virus replication ultimately drives an exhaustion program that may attenuate T cell function and subvert efficacy.

Figures 14A, 14B, 14C:
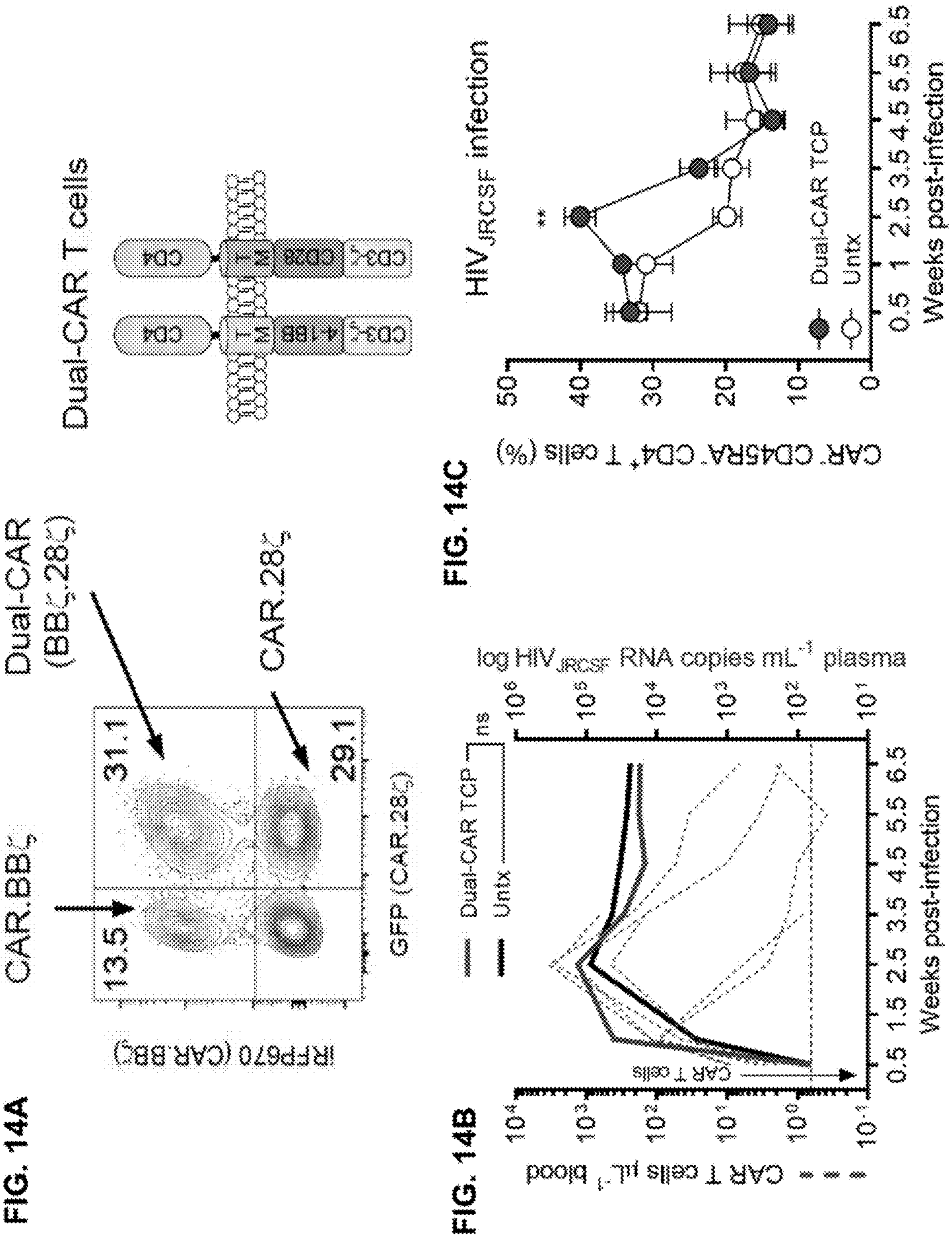
Figure 15:
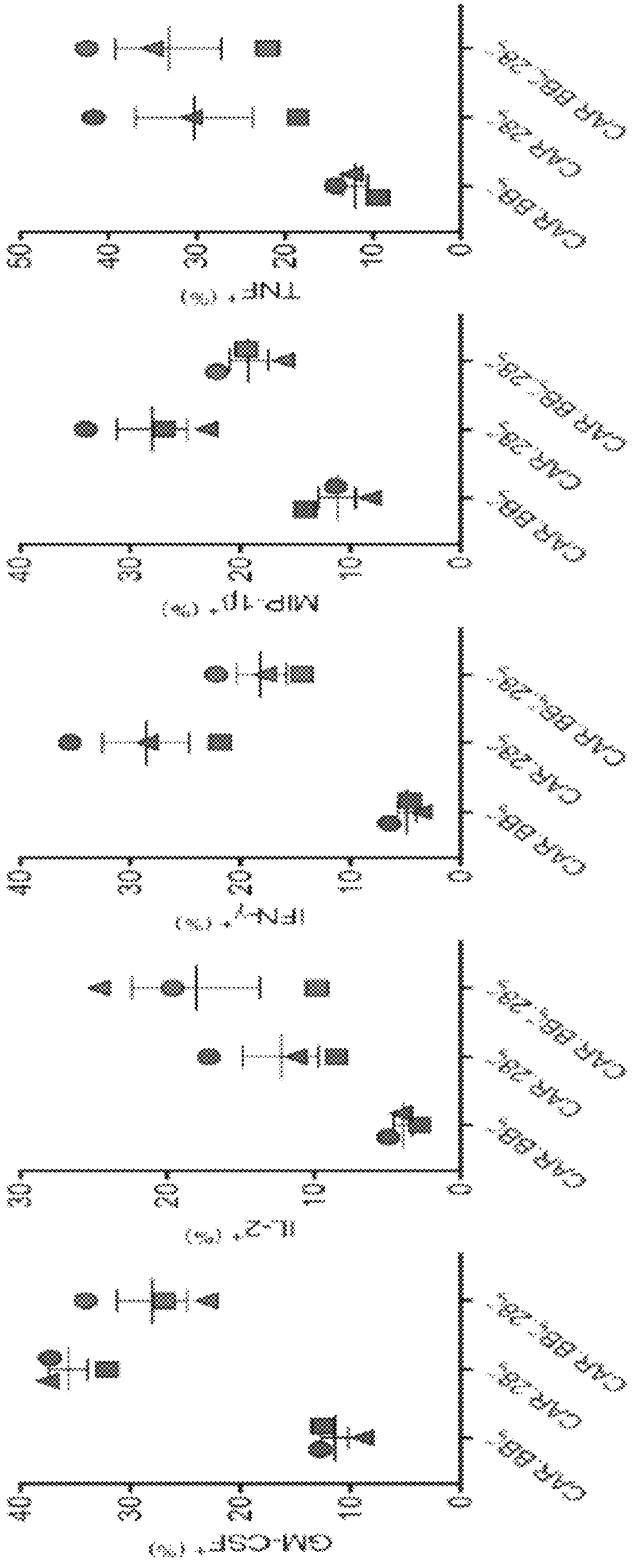
FIG. 15 illustrates the finding that Dual-CAR T cells exhibit similar in vitro effector functions as CAR.28ζ T cells. The Dual-CAR T cell product comprises CAR.BBζ, CAR.28ζ, and Dual-CAR T cells, where each population is identified by a unique fluorescent protein. Upregulation of cytokines was measured after in vitro stimulation with K.Env and K.WT cells. Each symbol represents a unique donor.
Figure 16A:
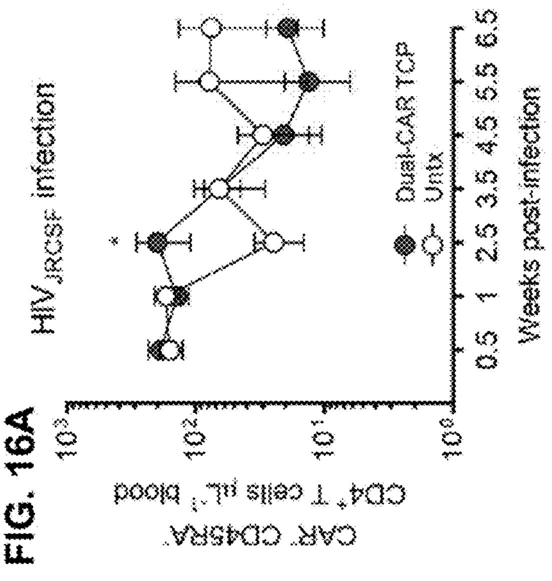
FIGS. 16A-16C illustrates dual-CAR T cell product transiently delays $CD4^+$ T cell loss despite persistent $HIV_{JRCSF}$ infection. Mice received Dual-CAR T cell product (TCP) (n=6) 48 hours post-$HIV_{JRCSF}$ challenge, while control mice were untreated (Untx) (n=5).
Figure 16B:
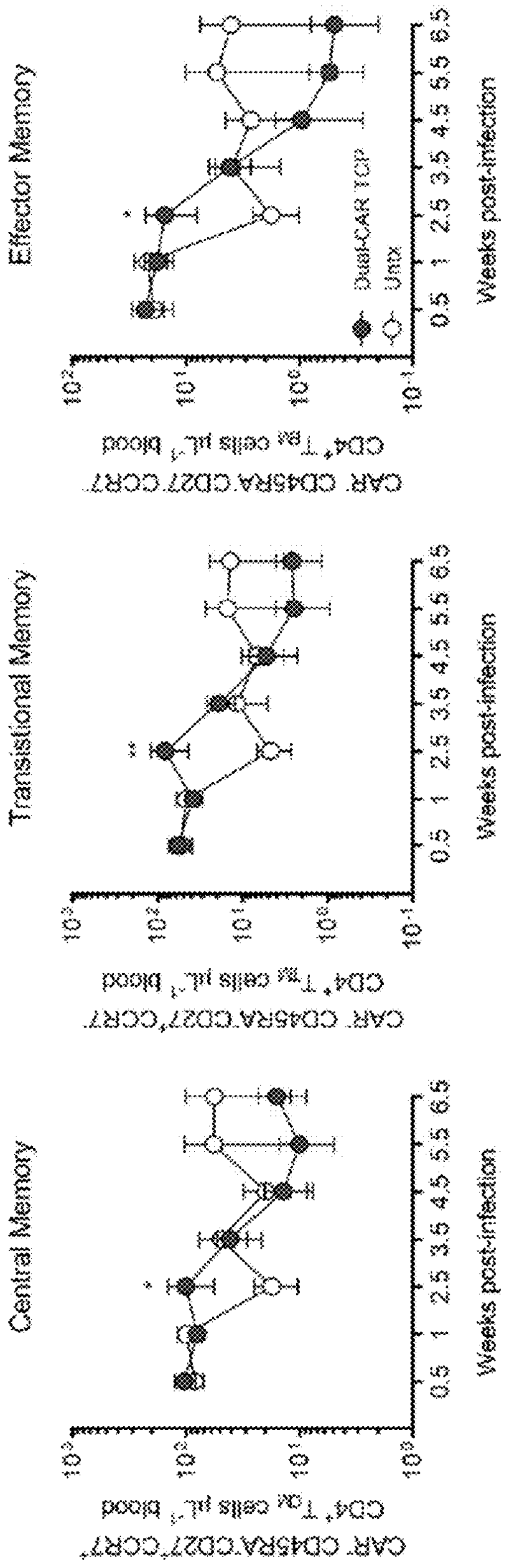

Example 6: Augmented HIV-Specific CAR T Cell Product Reduces $CD4^+$ T Cell Loss During Acute Infection It was hypothesized that combining the superior in vivo expansion and persistence of CAR.BBζ T cells with enhanced effector function could provide the necessary improvement to control HIV replication. To this end, CAR.BBζ T cells were co-transduced with the CD4-based, CD28-costimulated CAR that exhibited notable effector function (FIGS. 6A-6K) to create a novel Dual-CAR T cell product (TCP). Due to co-transduction probabilities, the Dual-CAR TCP comprised three populations: CAR.BBζ, CAR.28ζ and Dual-CAR T cells, the latter of which independently expresses both CD4-based CARs (FIG. 14A), which was hypothesized to combine the pro-survival attributes of 4-1BB with the effector functions of CD28 costimulation. Indeed, inclusion of the CD28-costimulated CAR increased in vitro cytokine production of Dual-CAR T cells over CAR.BBζ T cells (FIG. 15). To evaluate the Dual-CAR TCP in vivo, an acute infection model was used in which mice received a CAR T cell infusion 48 hours after $HIV_{JRCSF}$ challenge. This approach simulates the previous ART cessation model where CAR T cells are present only after infection is established, but plasma viremia is undetectable, and thus provides a rapid model to test therapeutic efficacy. Although no differences in acute viremia were observed between the Dual-CAR TCP-treated and untreated control groups (FIG. 14B), CAR T cell-treated mice exhibited a significant, albeit transient delay in the loss of peripheral memory $CD4^+$ T cells ($CAR^-$), which coincided with peak expansion of total CAR T cells in peripheral blood (FIG. 14B-14C and FIG. 16A). Notably, this delay in $CD4^+$ T cell loss was observed in central, transitional, and effector memory subsets (FIG. 16B), an effect that was not observed after ART discontinuation in the CAR.BBζ-treated mice in the prior study (FIG. 8B-8C).

Figures 14D, 14E, 14F, 14G:
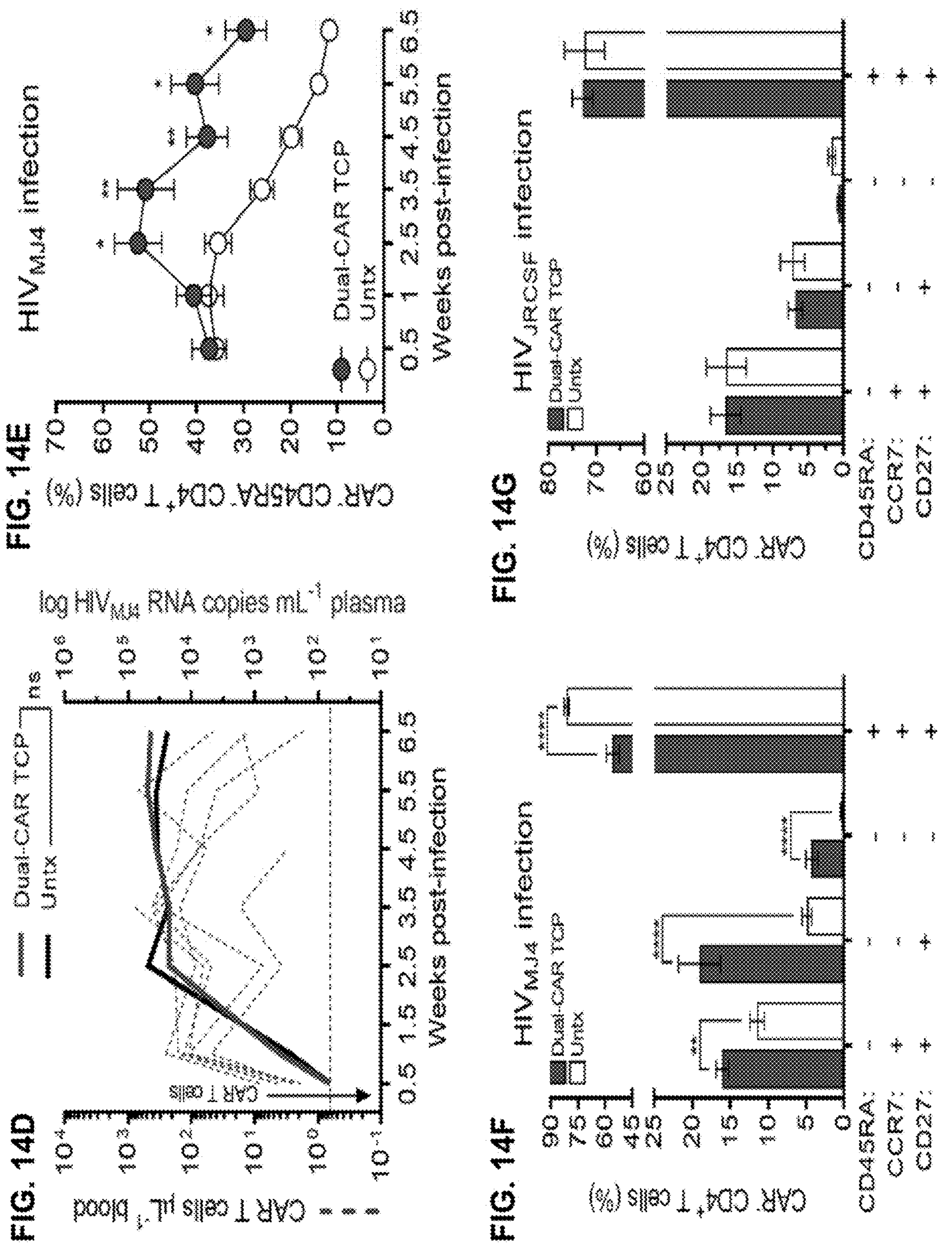
Figure 14H:
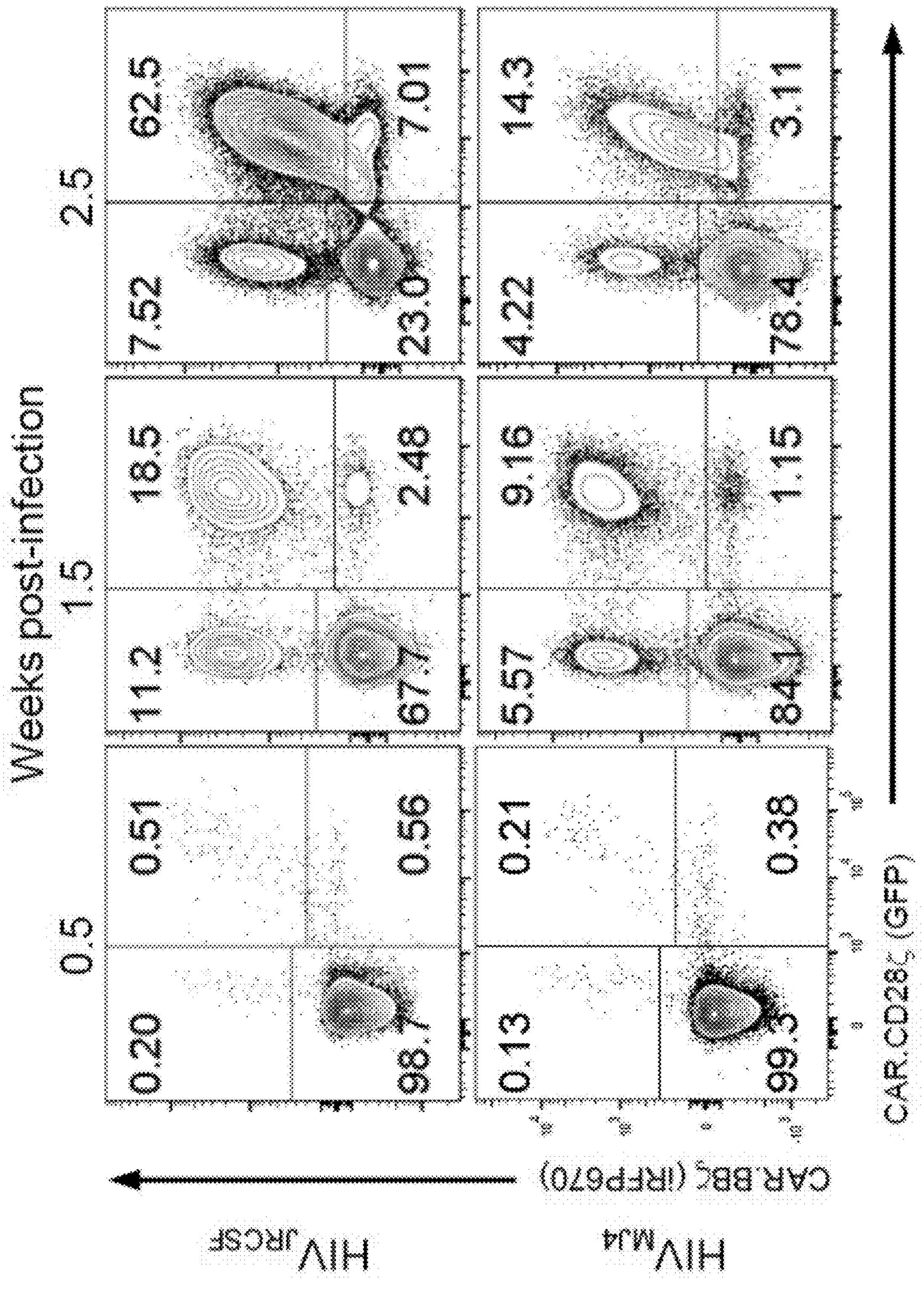
Figure 14I:
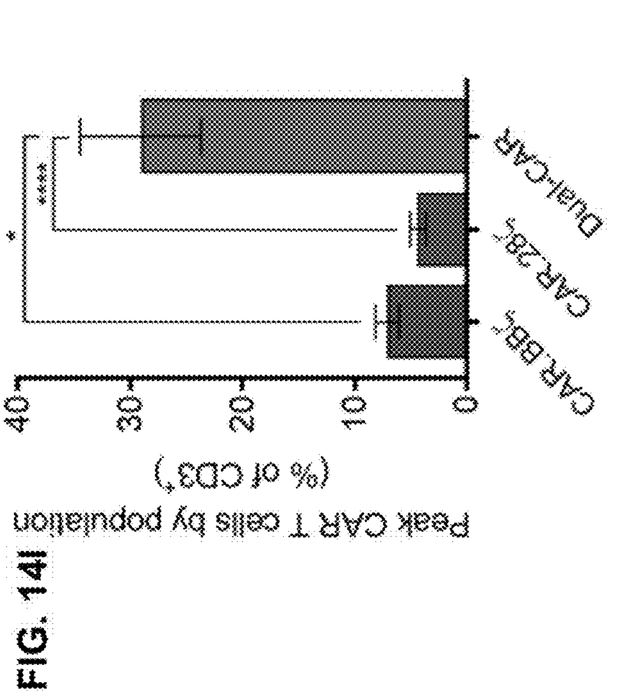
Figure 14J:
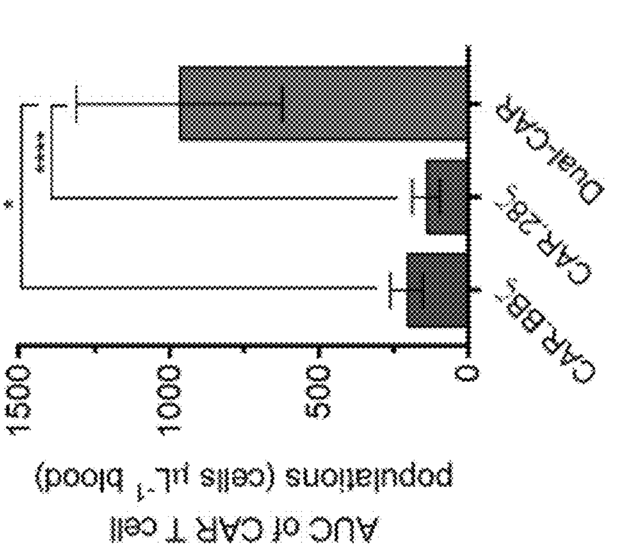
Figure 14K:
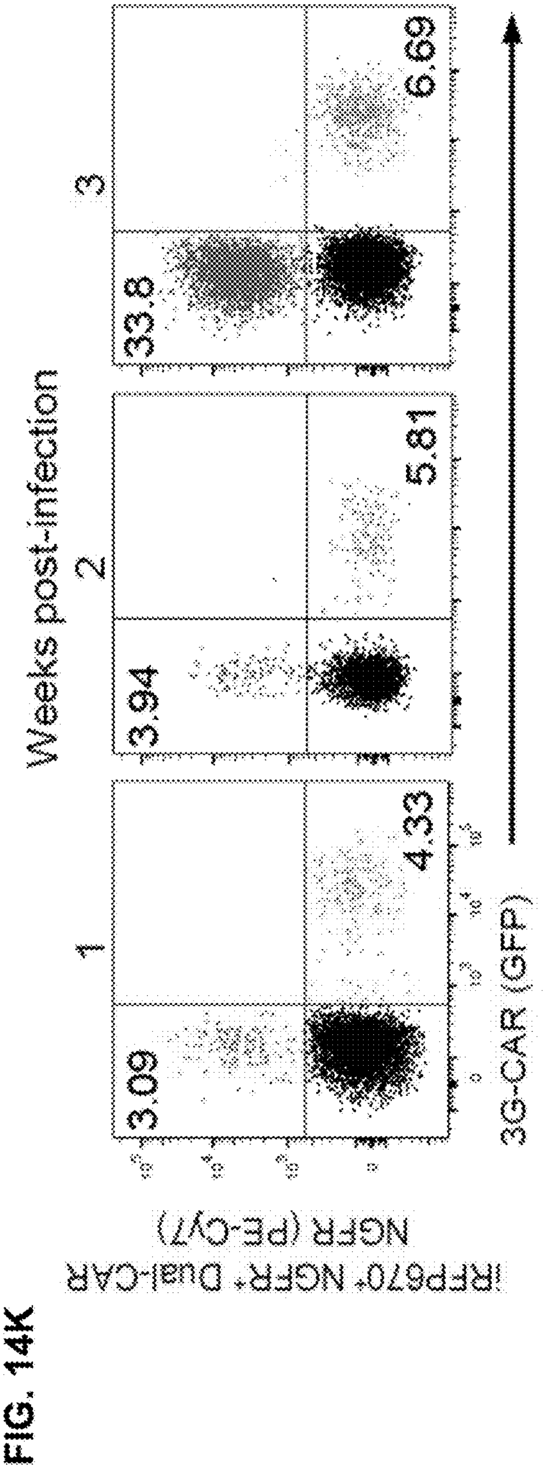
Figure 16C:
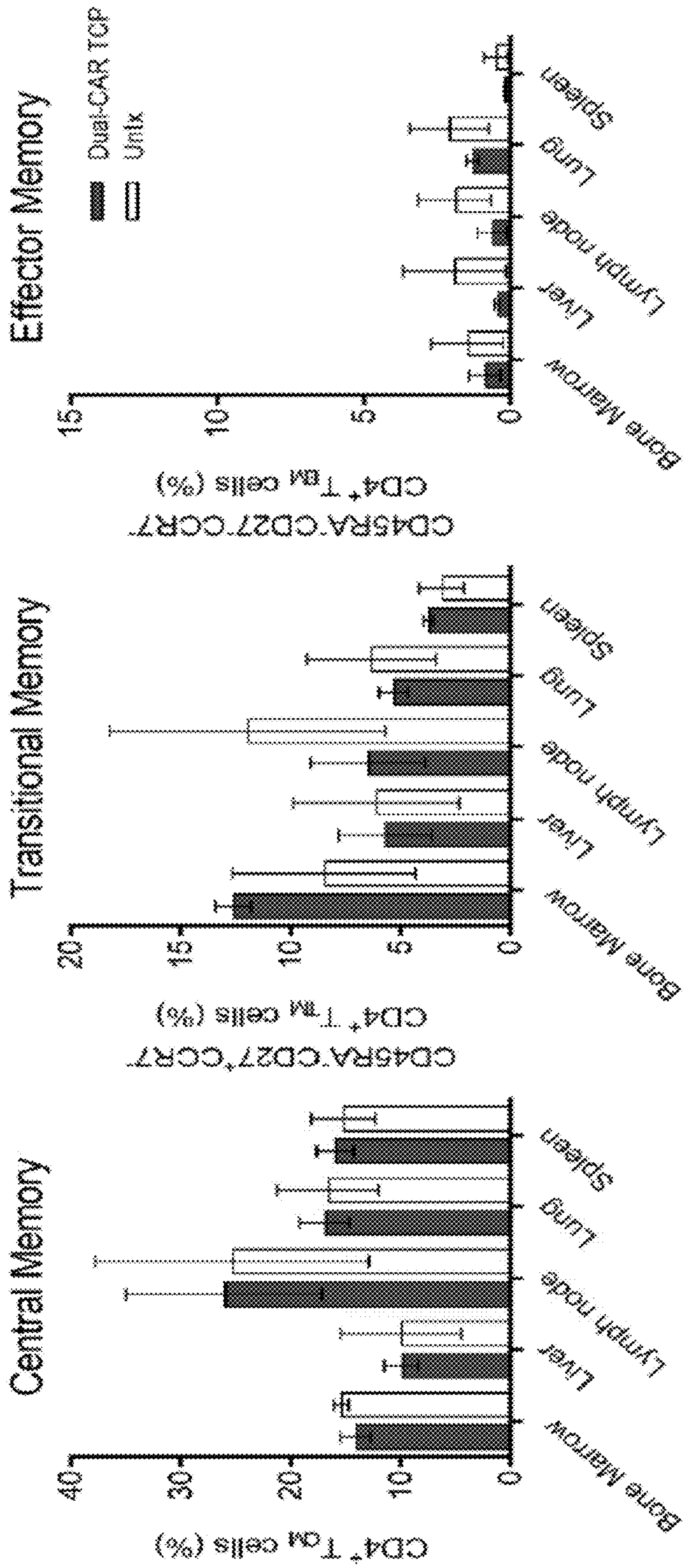
Figure 17B:
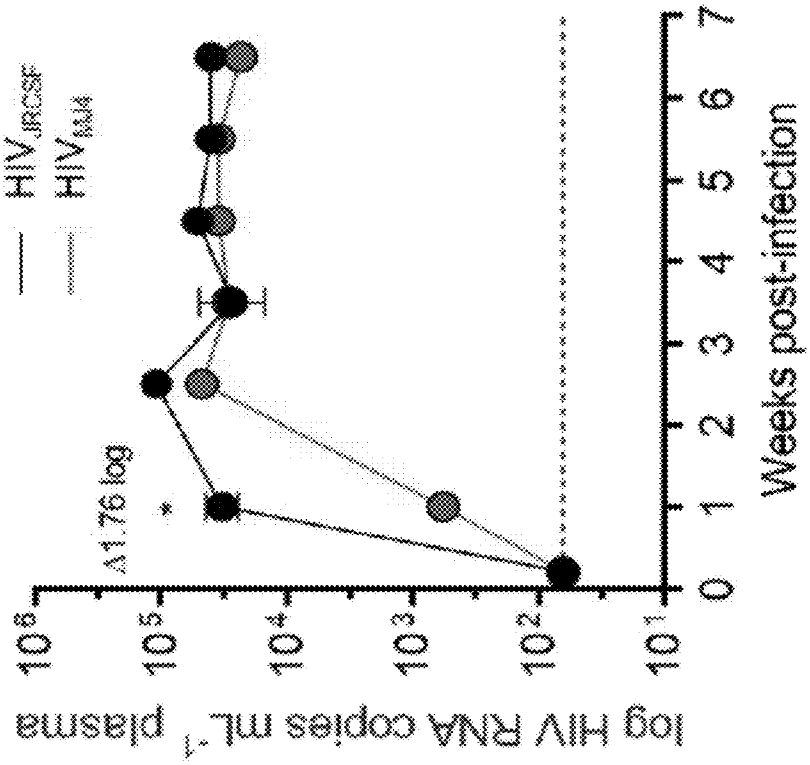
FIGS. 17A-17B illustrated the finding that $HIV_{JRCSF}$ and $HIV_{MJ4}$ exhibit different replication kinetics in vitro and in vivo.
Figure 17A:
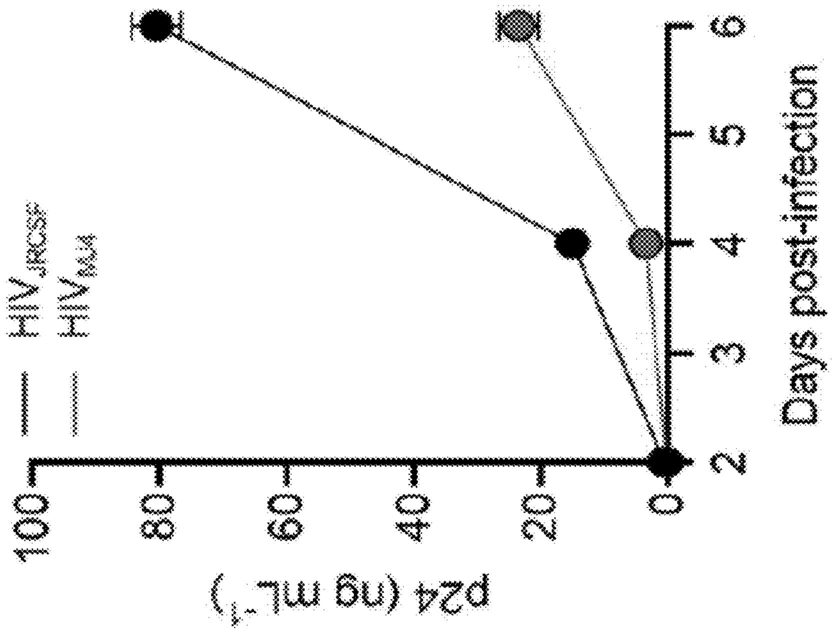
Figure 18A:
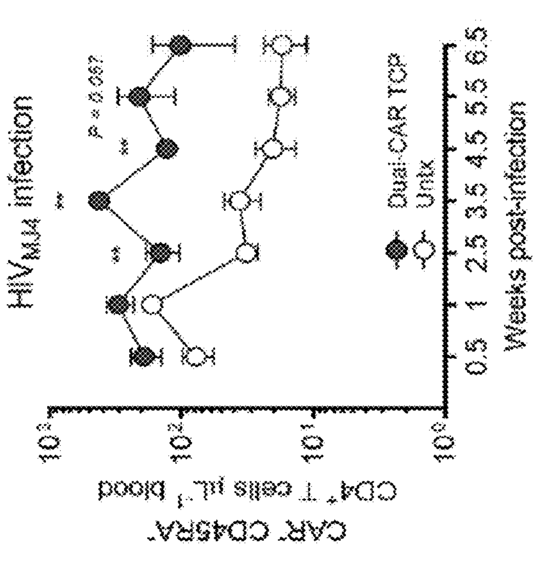
FIGS. 18A-18C illustrate the finding that Dual-CAR T cell product prevents $CD4^+$ T cell loss despite persistent $HIV_{MJ4}$ infection. Mice were infused with Dual-CAR T cell product (TCP) (n=6) 48 hours post-$HIV_{MJ4}$ challenge, while control mice were untreated (Untx) (n=6).
Figure 18B:
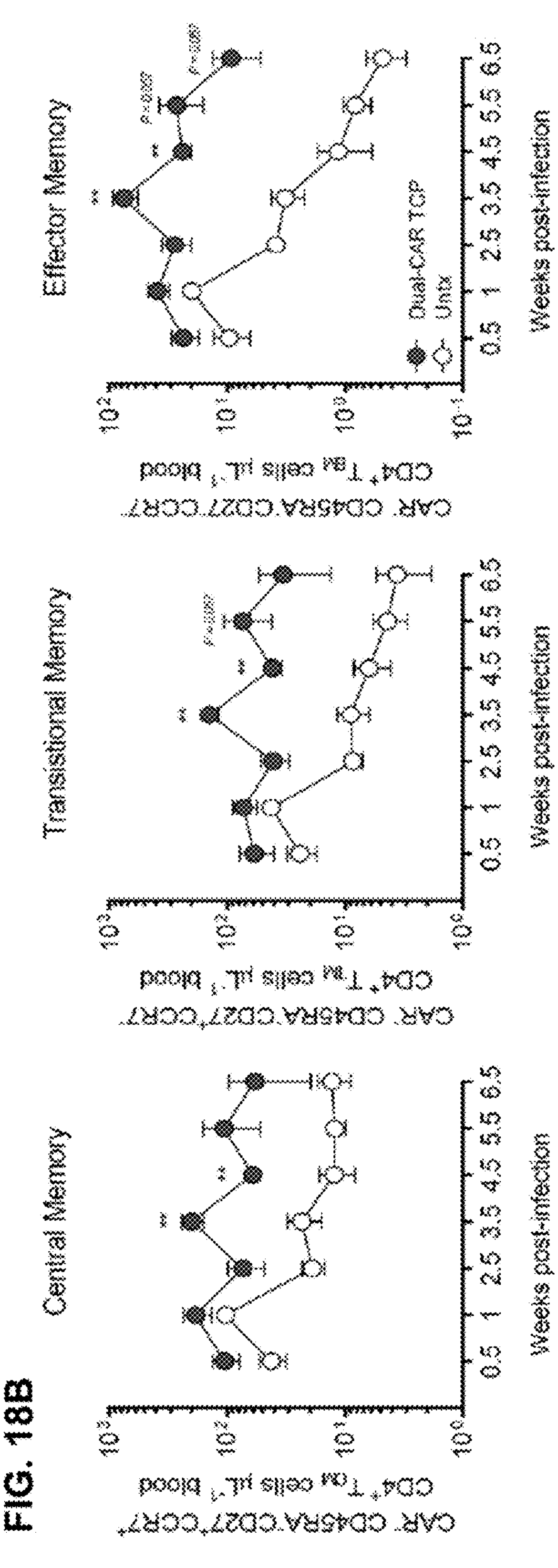
Figure 18C:
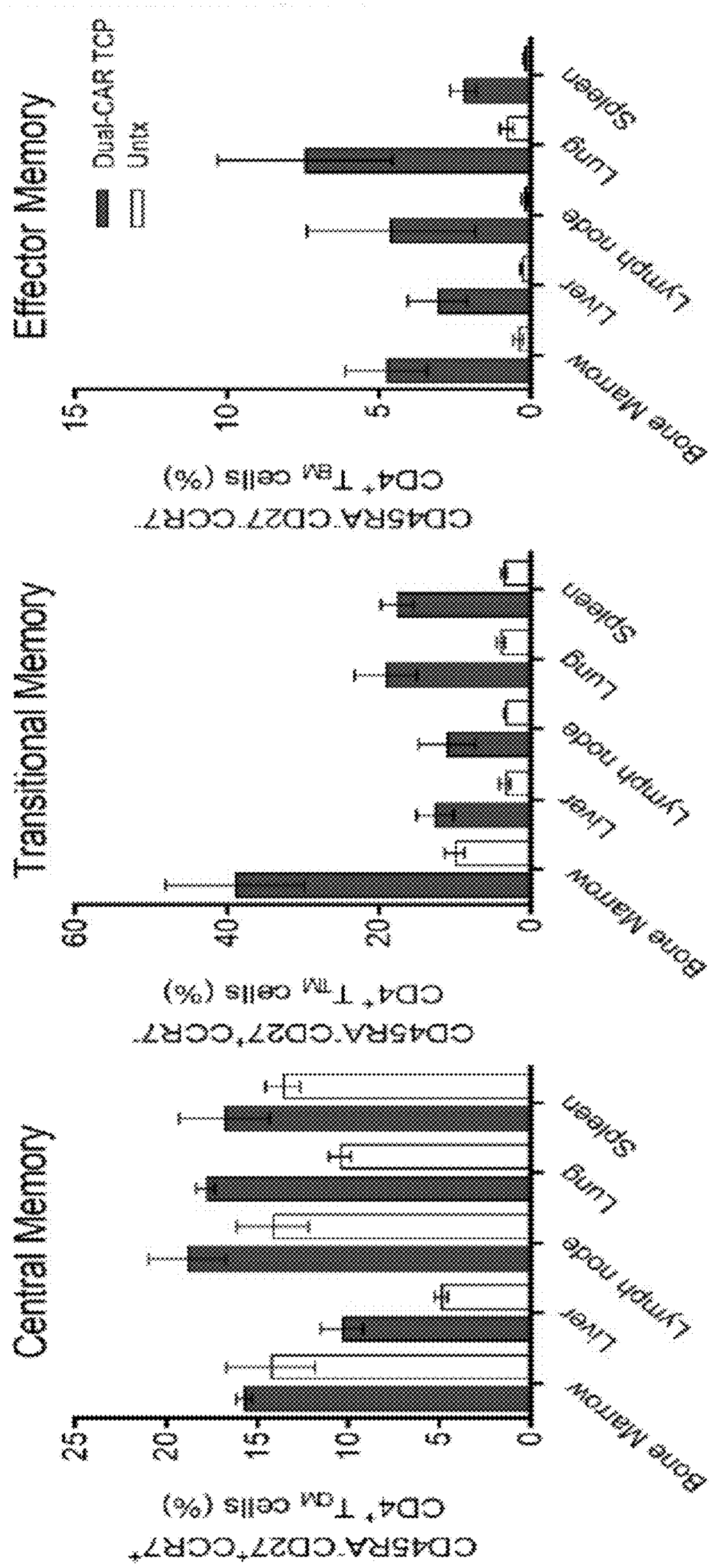

Next, the efficacy of the Dual-CAR TCP was assessed in the context of a more physiologically relevant strain of HIV. To do so, additional mice from the same cohort as above were infected with $HIV_{MJ4}$, which exhibits slower acute phase replication kinetics than $HIV_{RCSF}$, but ultimately achieves equivalent set-point viremia (FIGS. 17A-17B). Although the infusion of CAR T cells 48 hours post-infection, again, did not alter viremia (FIG. 14D), a more profound $CD4^+$ T cell preservation and maintenance of the Dual-CAR TCP in peripheral blood as compared to the CAR T cell-treated mice infected with $HIV_{RCSF}$ was observed (FIGS. 14D-14E and FIG. 18A). The preservation of $CD4^+$ T cells was particularly accentuated in transitional and effector memory populations, which express greater levels of the HIV coreceptor CCR5 (FIG. 18B). Similarly, the percentage of all memory $CD4^+$ T cell subsets in the tissues at necropsy were substantially preserved in Dual-CAR TCP-treated compared to untreated $HIV_{MJ4}$-infected mice (FIG. 14F and FIG. 18C), whereas there was no difference between CAR T cell-treated and control $HIV_{JRCSF}$-infected mice (FIG. 14G and FIG. 16C). These data demonstrate that treatment with the Dual-CAR TCP can effectively limit HIV-induced depletion of memory $CD4^+$ T cells and that this effect is modulated by the pathogenicity of the infecting virus.

Figure 14N:
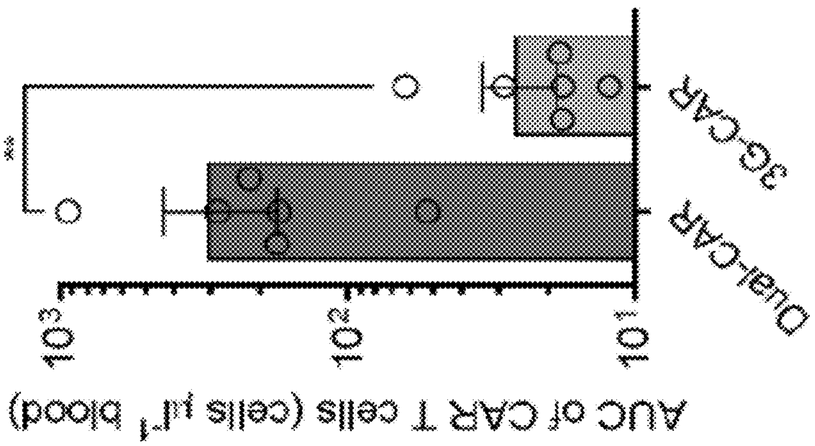
Figure 14M:
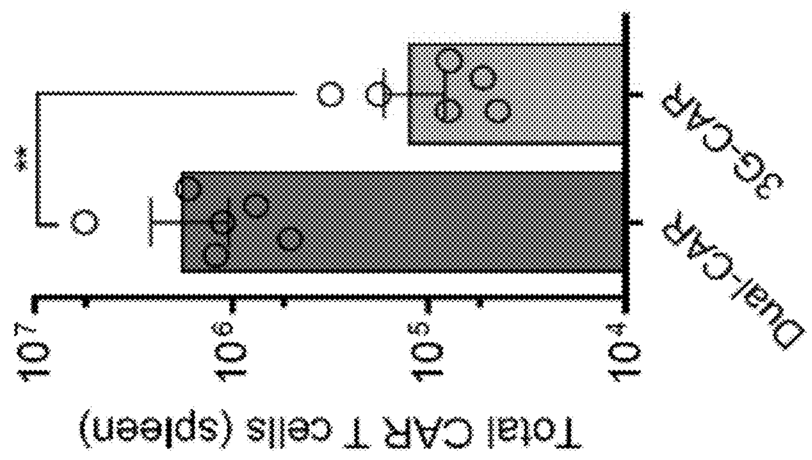
Figure 14L:
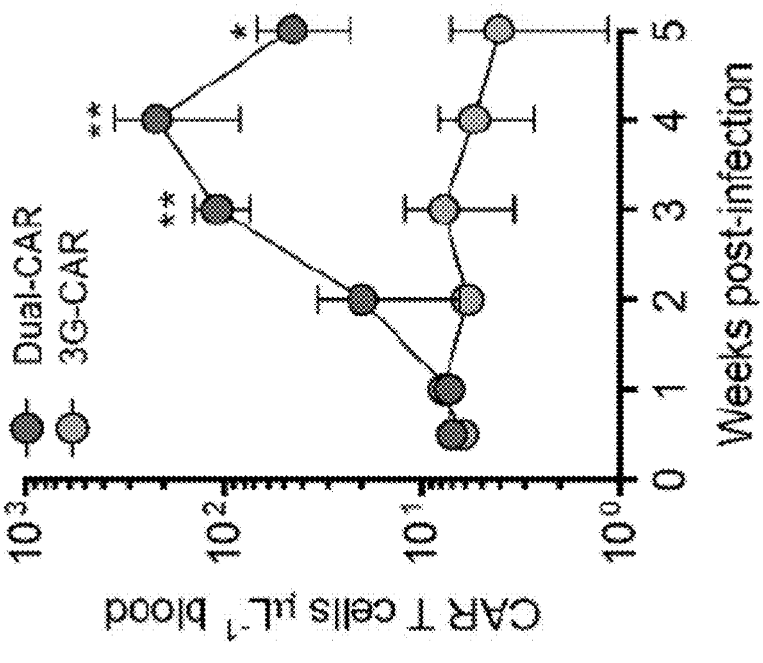
Figure 19E:
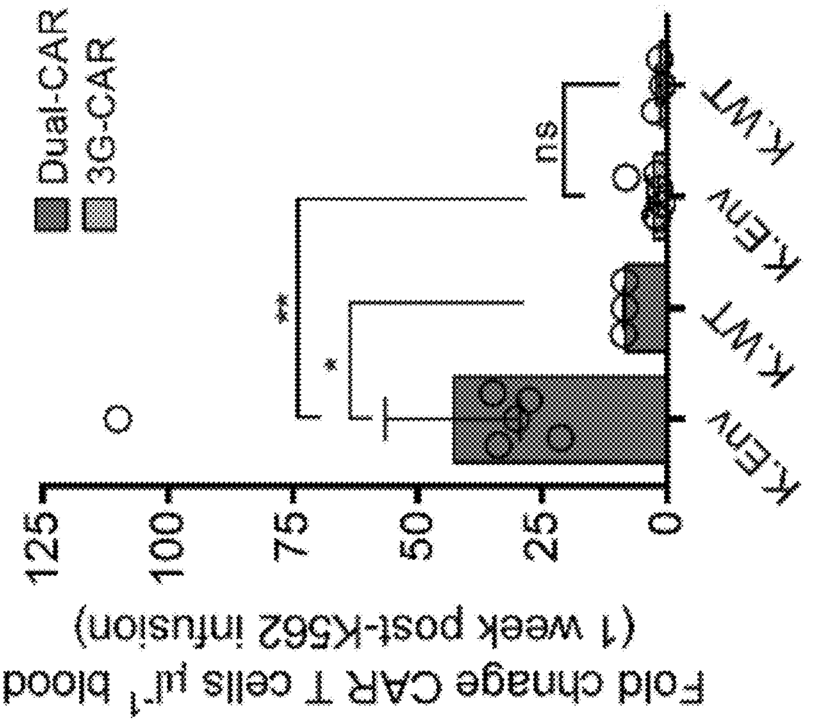
Figure 19D:
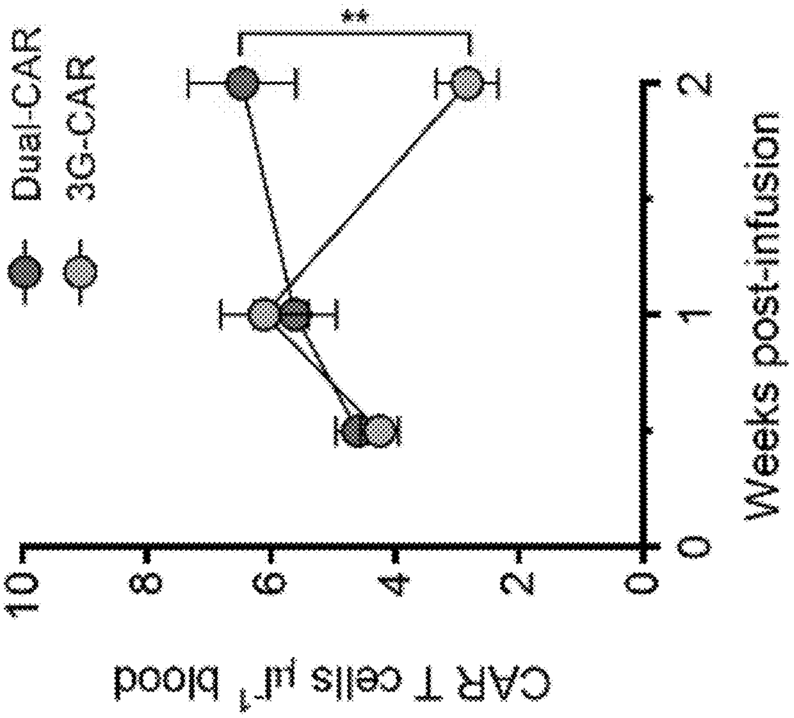

Example 7: Dual-CAR T Cells Exhibit Vigorous In Vivo Proliferation in a Competitive Environment Next, the specific immunologic response of the three CAR T cell components of the Dual-CAR TCP was interrogated. The linkage of each CAR to a unique fluorescent protein allowed for independent quantification of each CAR T cell type and revealed increased in vivo expansion of Dual-CAR T cells relative to either of the single costimulatory domain-expressing CAR T cell types (FIG. 14H), with significant differences observed in peak expansion and cumulative proliferation of Dual-CAR T cells (FIG. 14I-14J), which remained significant after correcting for the baseline absolute count of each population (FIG. 19A). In addition, the proliferative capacity of Dual-CAR T cells was compared to $3^{rd}$-generation (3G) CAR T cells, which express CD28 and 4-1BB linearly in the same construct (FIG. 19B). Here, an equal amount of Dual-CAR and 3G-CAR T cells were combined prior to adoptive transfer into recipient mice (FIG. 19C) After infusion, Dual-CAR T cells showed significantly greater antigen-independent engraftment (FIG. 19D), and also demonstrated superior antigen-driven proliferation after infusion of irradiated K.Env cells (FIG. 19E). In contrast, 3G-CAR T cells marginally expanded and then progressively declined. Notably, during $HIV_{MJ4}$ infection, Dual-CAR T cells exhibited profound proliferation (FIGS. 14K-14L) and long term survival (FIG. 14M-14N) relative to 3G-CAR T cells within the same mice. Together, these studies reveal the striking proliferative capacity exhibited by Dual-CAR T cells in a competitive setting under both antigen scarce and abundant in vivo environments.

Figure 20A:
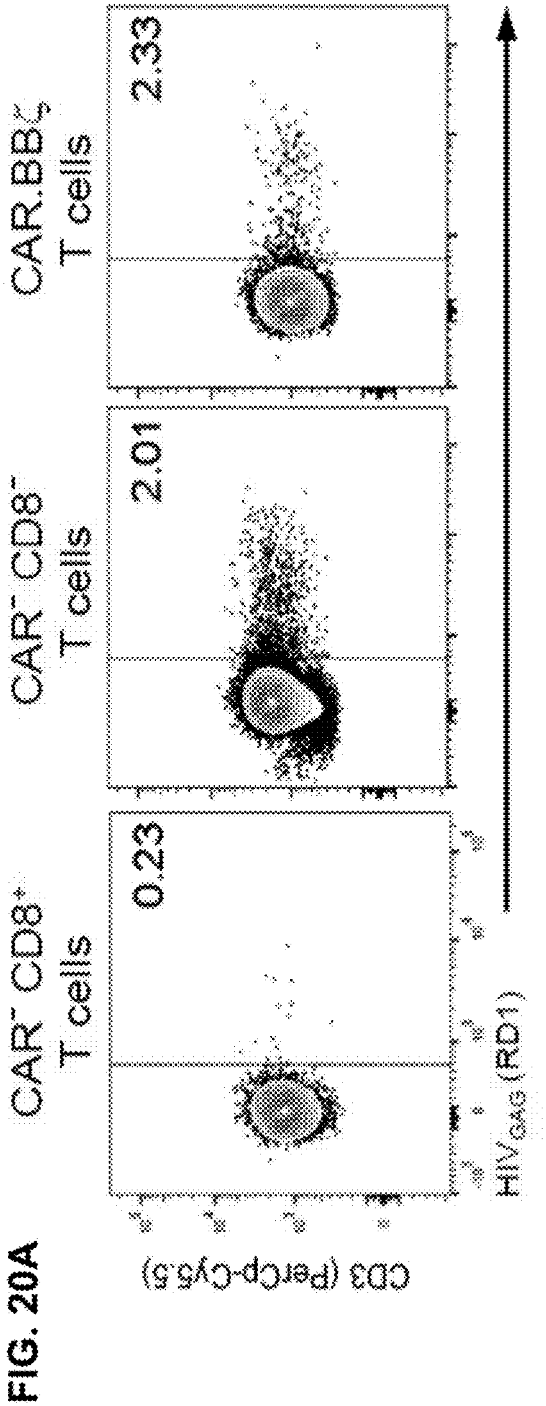
FIGS. 20A-20D illustrate the finding that CD4-based CAR T cells are susceptible to infection in vivo.
Figure 20B:
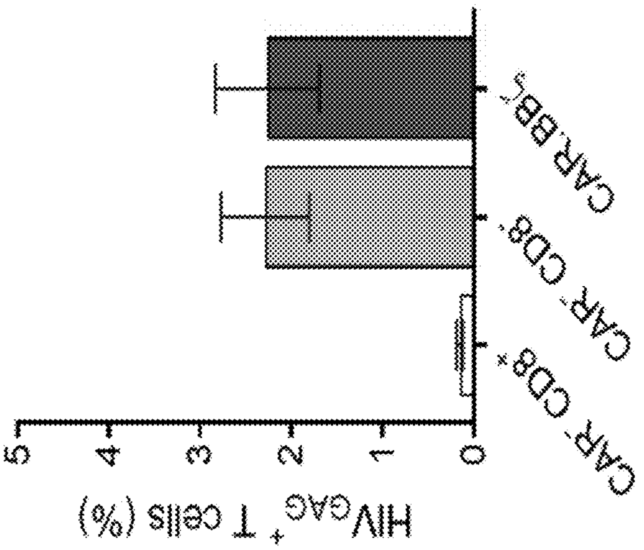
Figure 20D:
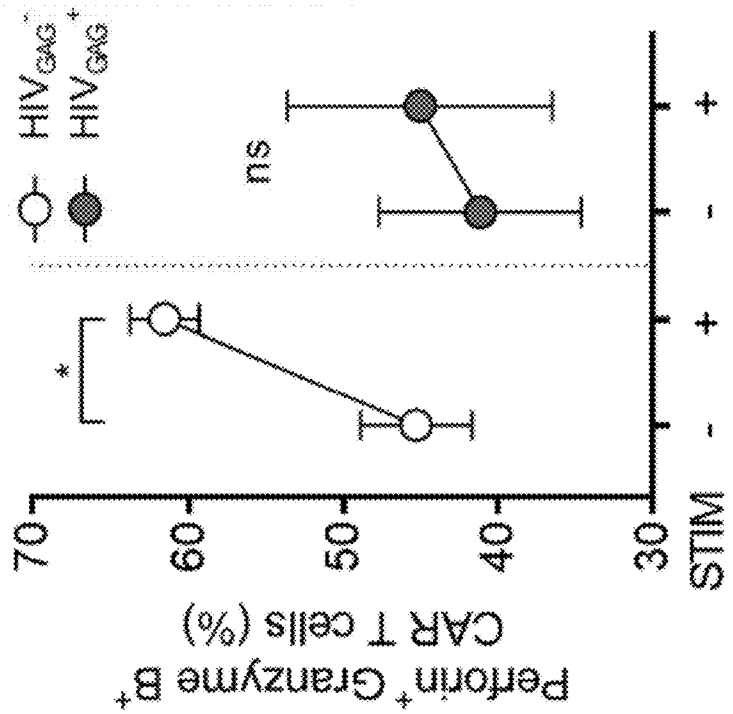
Figure 20C:
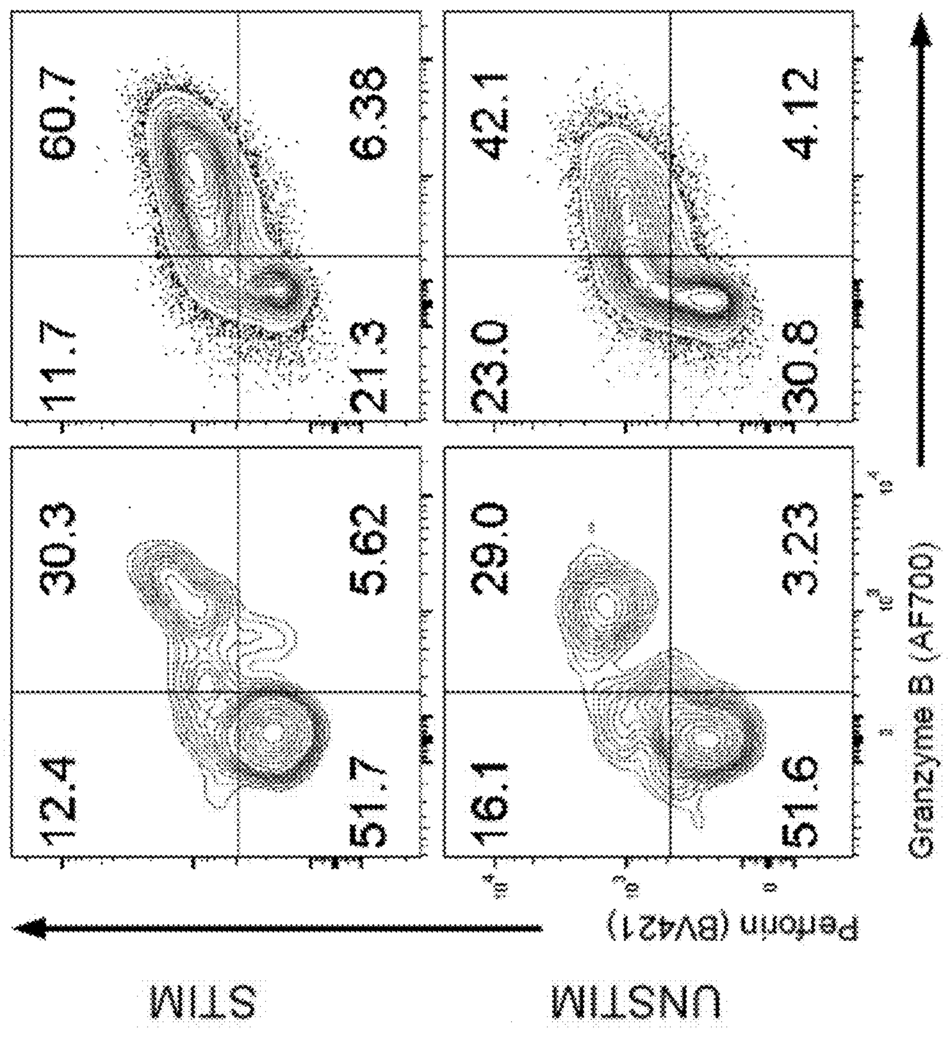
Figure 21I:
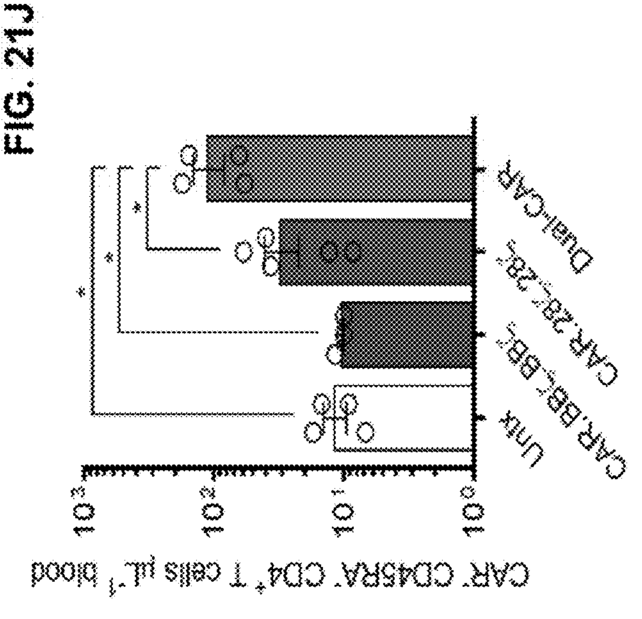
Figure 22A:
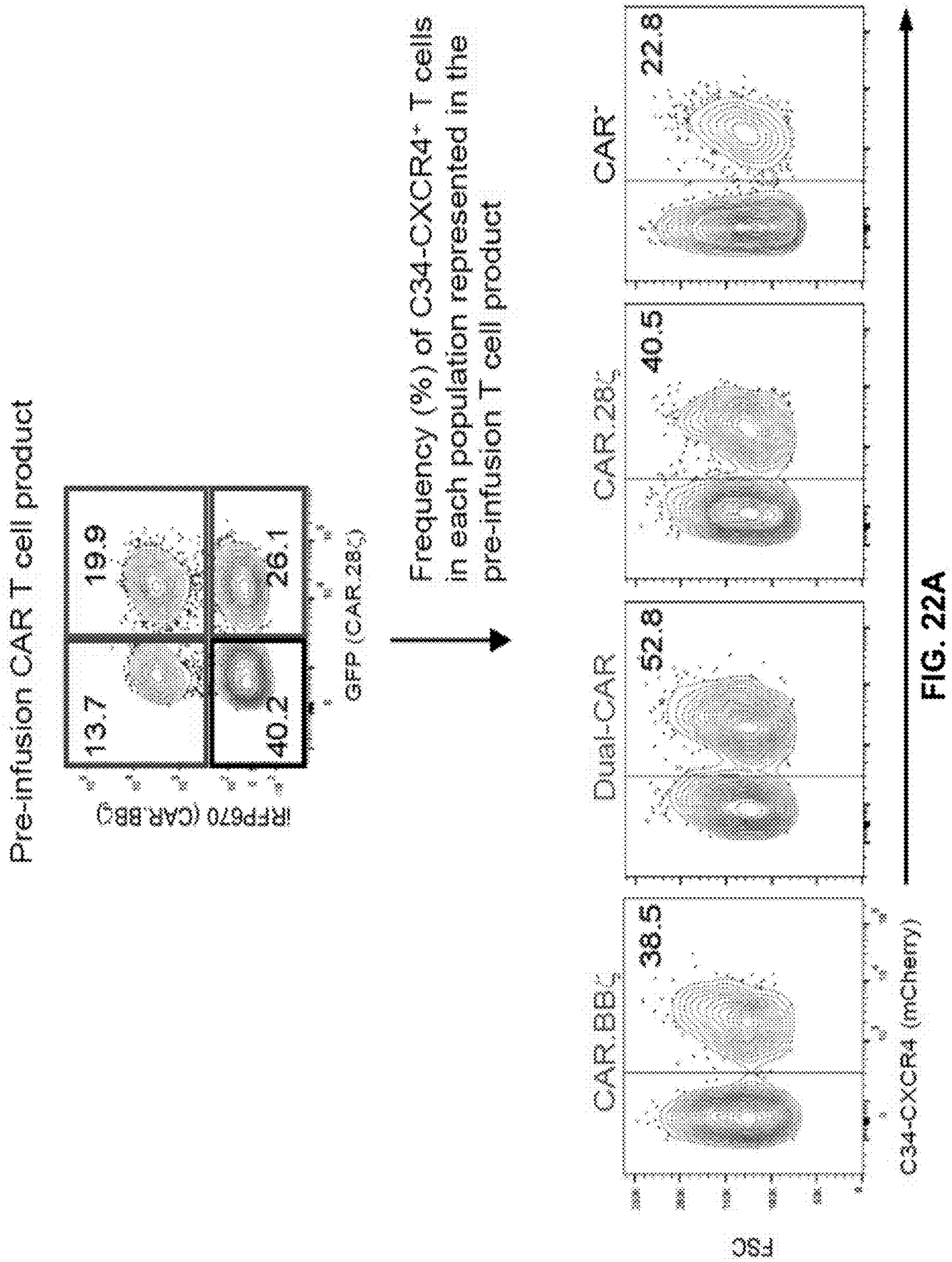
FIGS. 22A-22B illustrate the finding that HIV-resistant Dual-CAR T cell product fails to inhibit acute HIV replication.
Figure 22B:
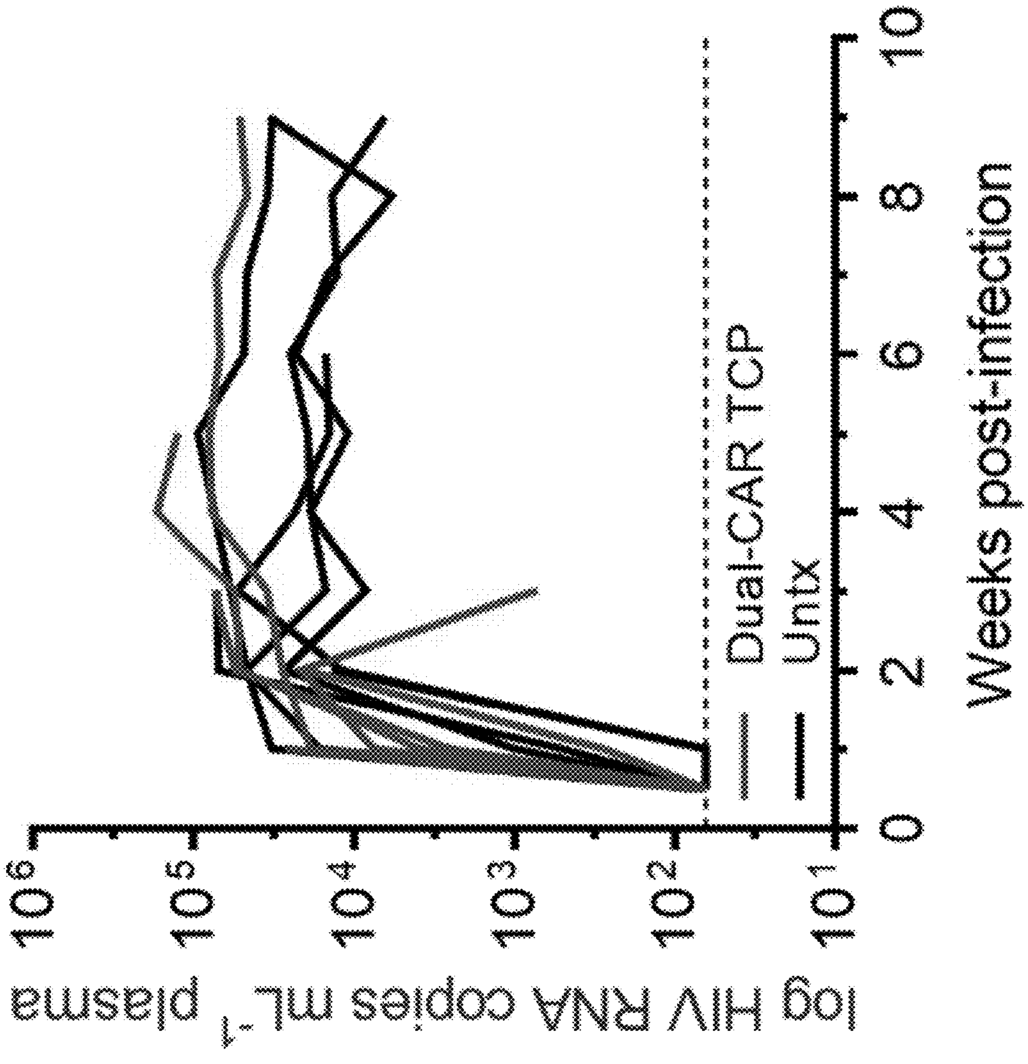
Figure 23A:
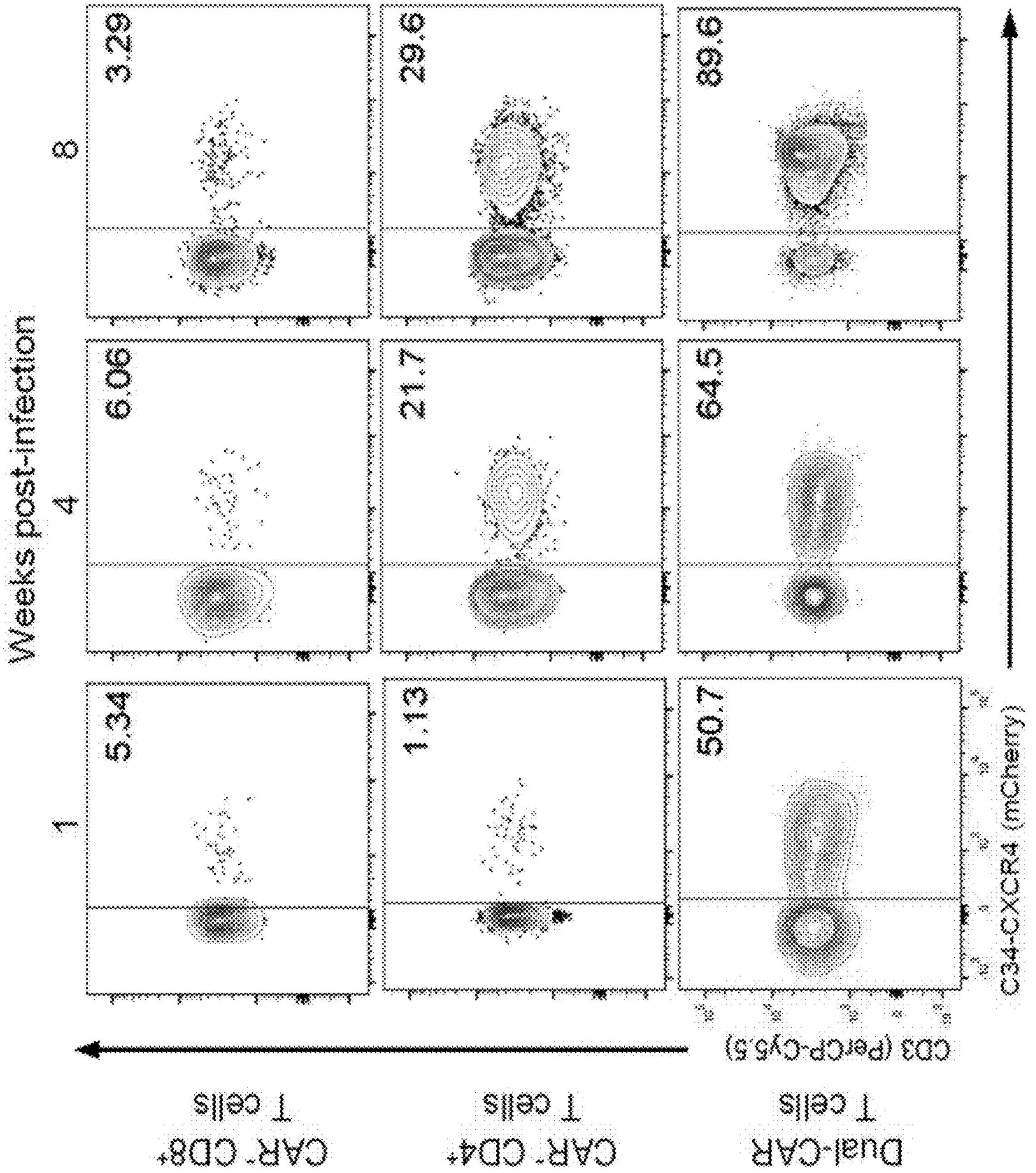
FIGS. 23A-23D illustrate C34-$CXCR4^+$ CAR T cells are selected for during chronic infection and exhibit superior ex vivo effector functions.
Figure 23C:
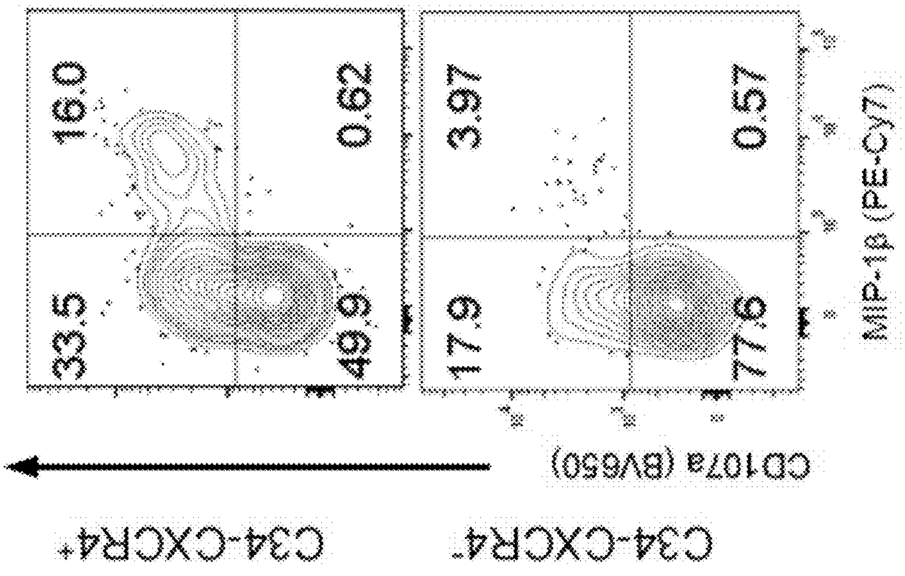
Figure 23B:
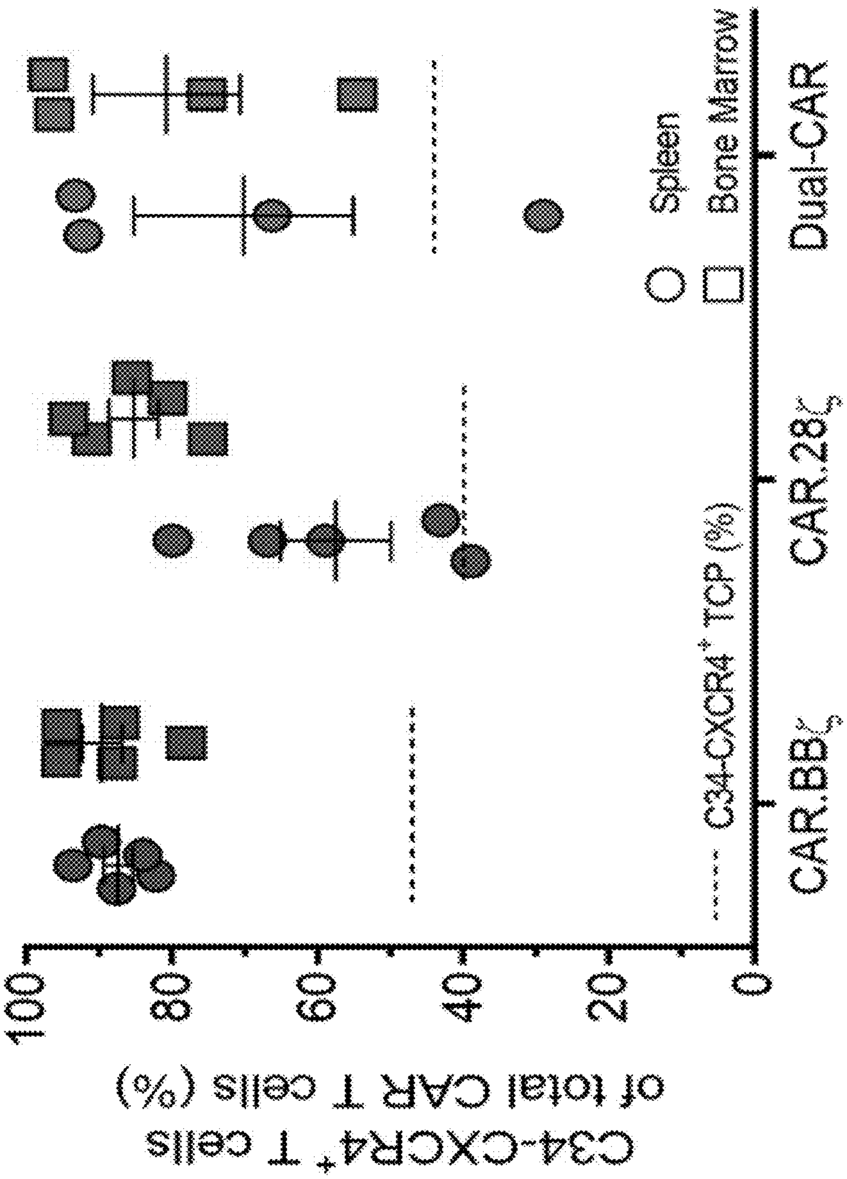
Figure 23D:
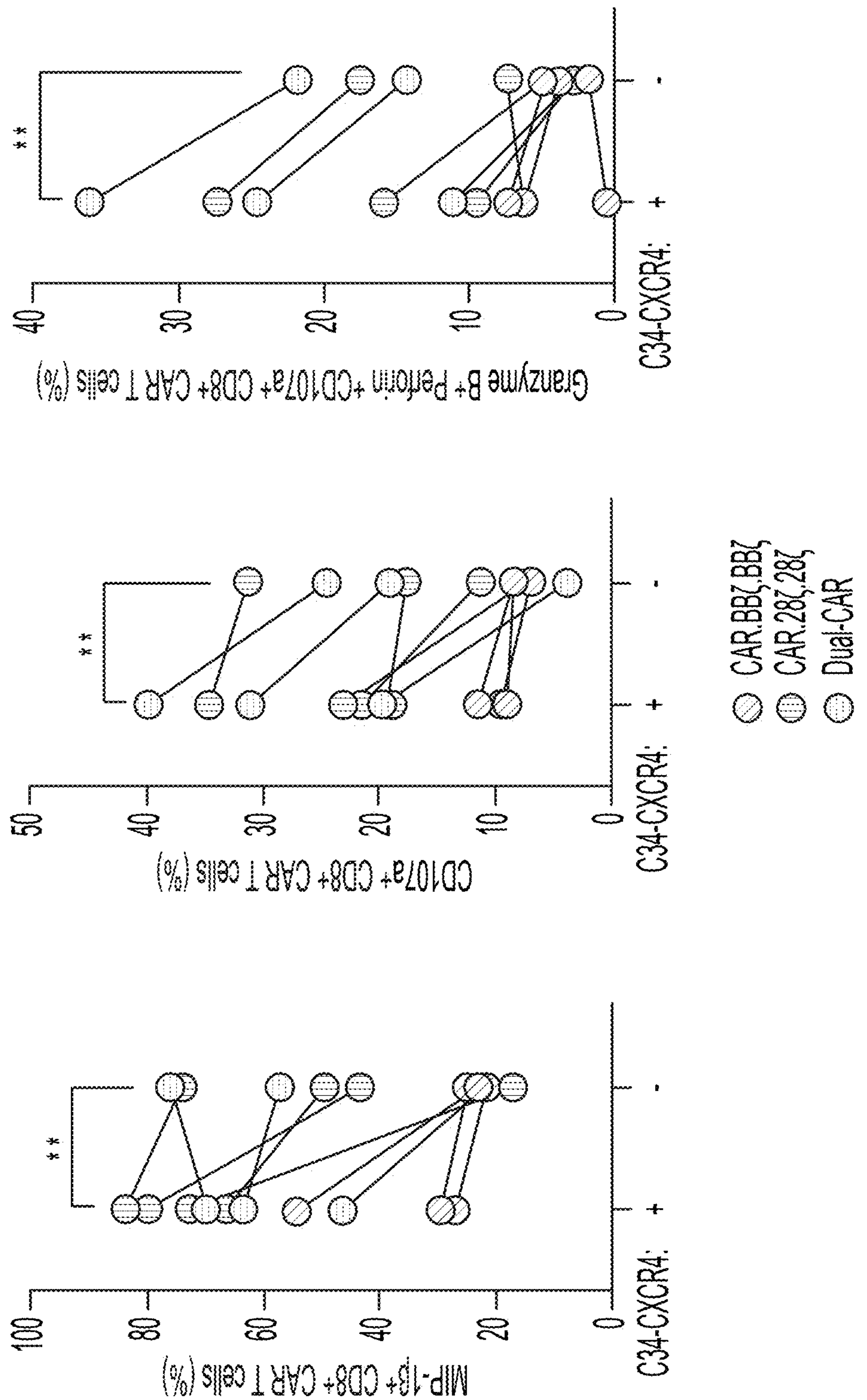

Example 8: Engineering HIV-Resistance Augments CAR T Cell Persistence and Function A CD4-based CAR was chosen to target HIV-infected cells because of this CAR's ability to suppress in vitro HIV replication better than several HIV-specific antibody-based CARs (Leibman et al. (2017) *PLoS Pathog* 13, e1006613), and the reduced likelihood for viral escape due to the requirement for HIV to bind CD4 for infection. However, this CAR results in the over-expression of CD4 on the T cell surface potentially increasing their susceptibility to infection. Indeed, HIV-infected CAR T cells were detected in vivo, although the extent of total infection appeared to be indistinguishable from endogenous CAR T cells (FIG. 20A-20B). More importantly, ex vivo stimulation revealed functional deficits in the capacity of HIV-infected CAR T cells to co-upregulate granzyme B and perforin (FIG. 20C-20D). To confer HIV resistance, the Dual-CAR TCP was co-transduced with the surface-expressed HIV fusion inhibitor C34-CXCR4 (Buggert (2014) *PLoS Pathog* 10, e1004251) (FIG. 21A and FIG. 22A) and evaluated in the acute HIV infection model. C34-CXCR4 was expressed on up to 50% of cells in the Dual-CAR TCP and provided protective benefit as the C34-$CXCR4^+$ CAR T cells harbored significantly less HIV DNA than their unprotected counterparts (FIG. 21*i*), and were selected for over time in chronically infected mice (FIGS. 23A-23B). Importantly, C34-$CXCR4^+$ CAR T cells from chronic infection had markedly improved cytotoxic potential and MIP-1β expression relative to unprotected CAR T cells within the same mice (FIGS. 23C-23D). Somewhat paradoxically, however, infusion of a Dual-CAR TCP where 50% of all cells were HIV-resistant was still insufficient to reduce acute virus replication (FIG. 22B). These results demonstrate that CD4-based CAR T cells can be protected from HIV infection by the C34-CXCR4 fusion inhibitor and that such protection can preserve CAR T cell functionality during persistent exposure to HIV.

Figure 21E:
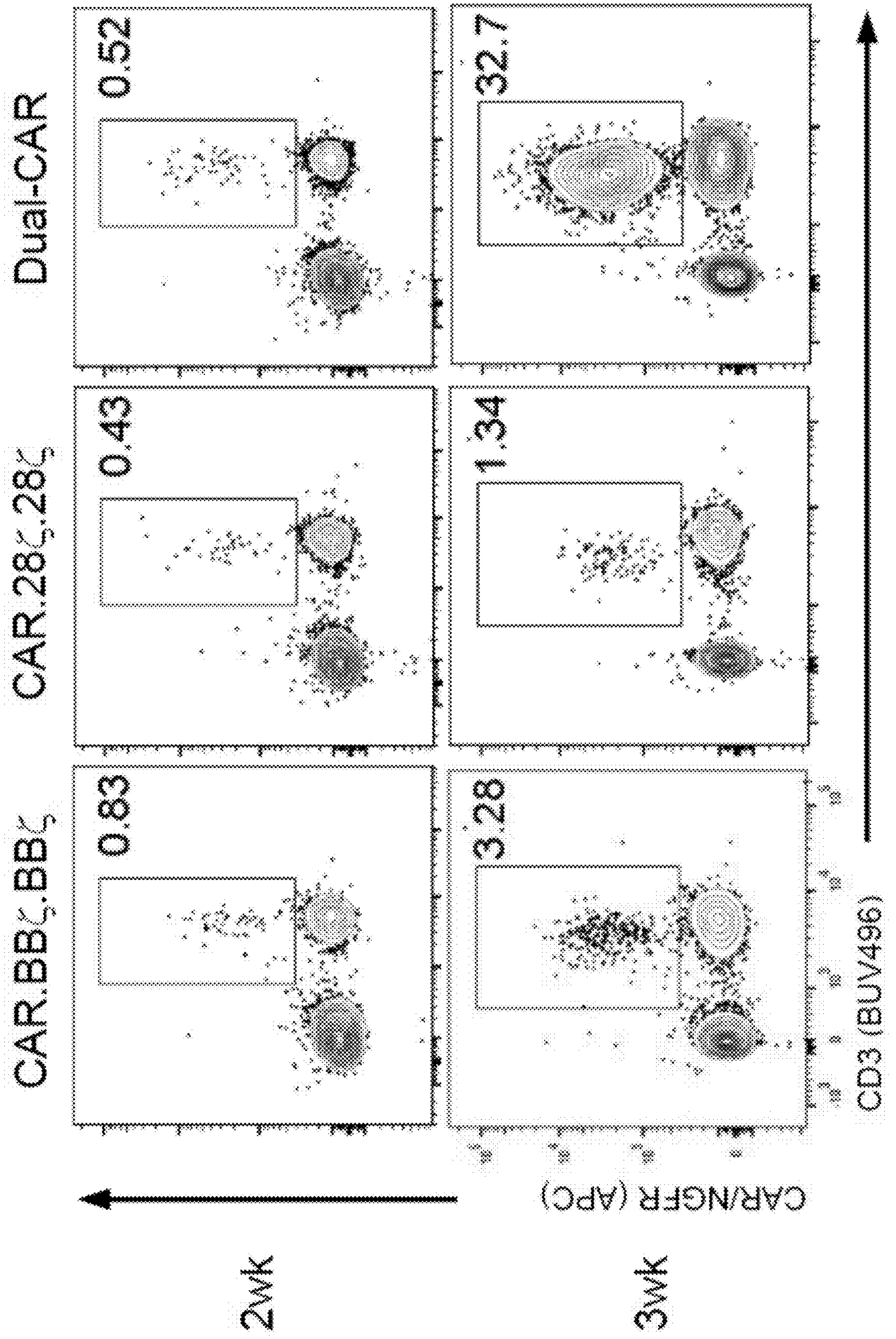
Figure 21G:
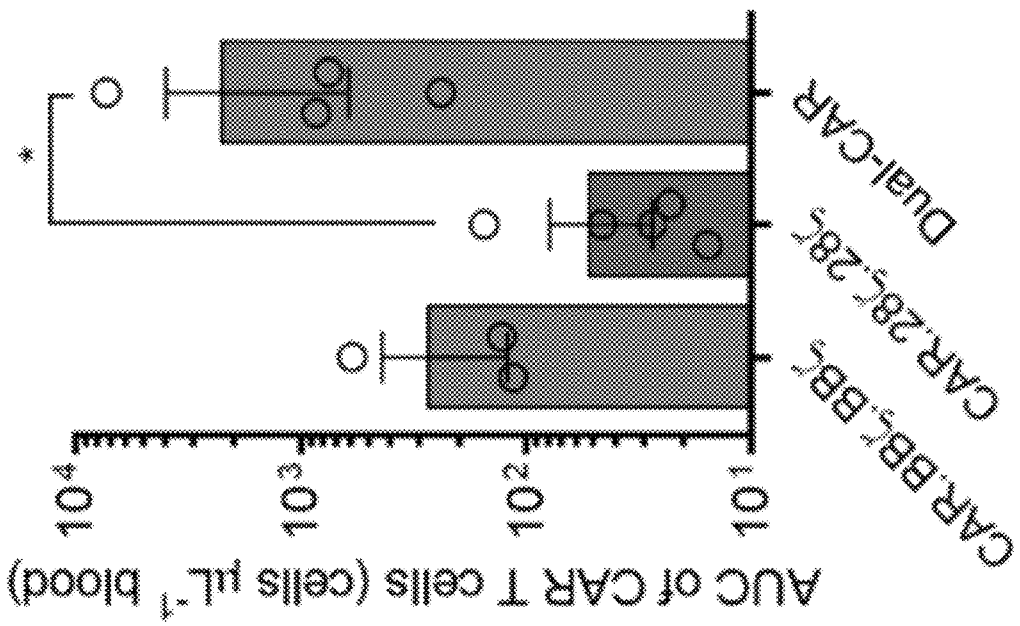
Figure 21F:
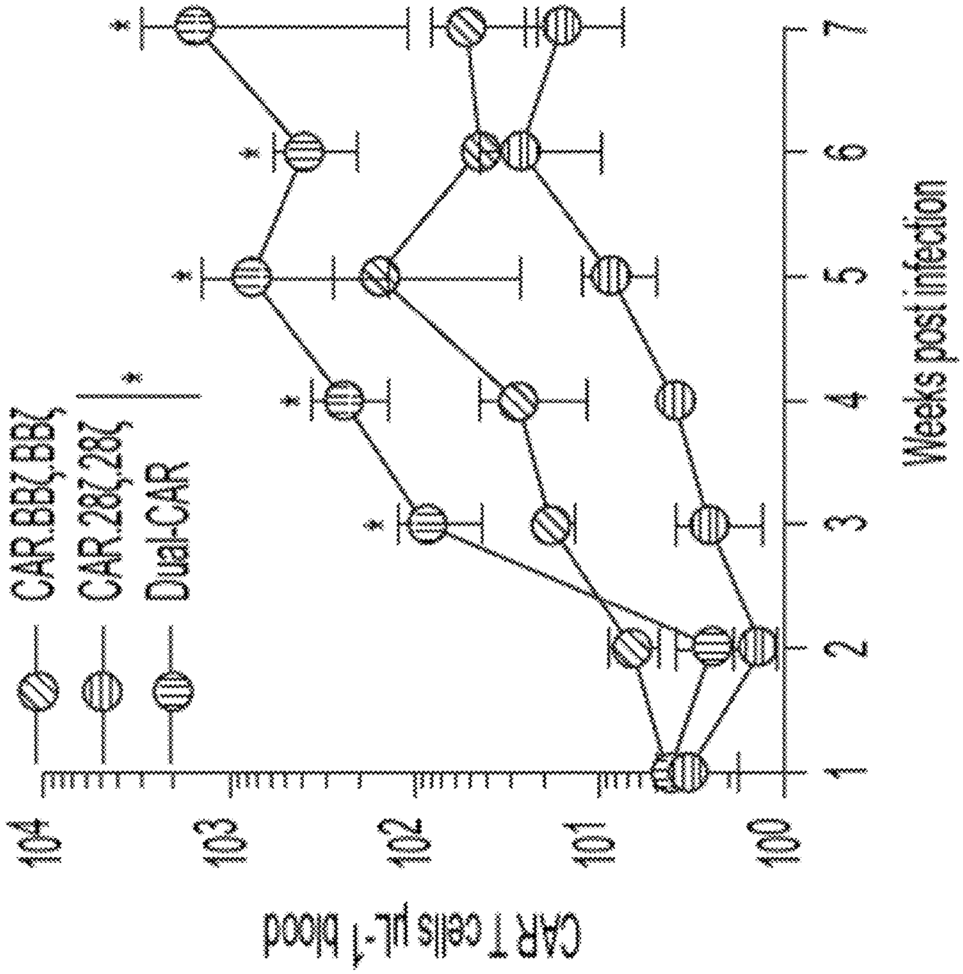
Figure 21H:
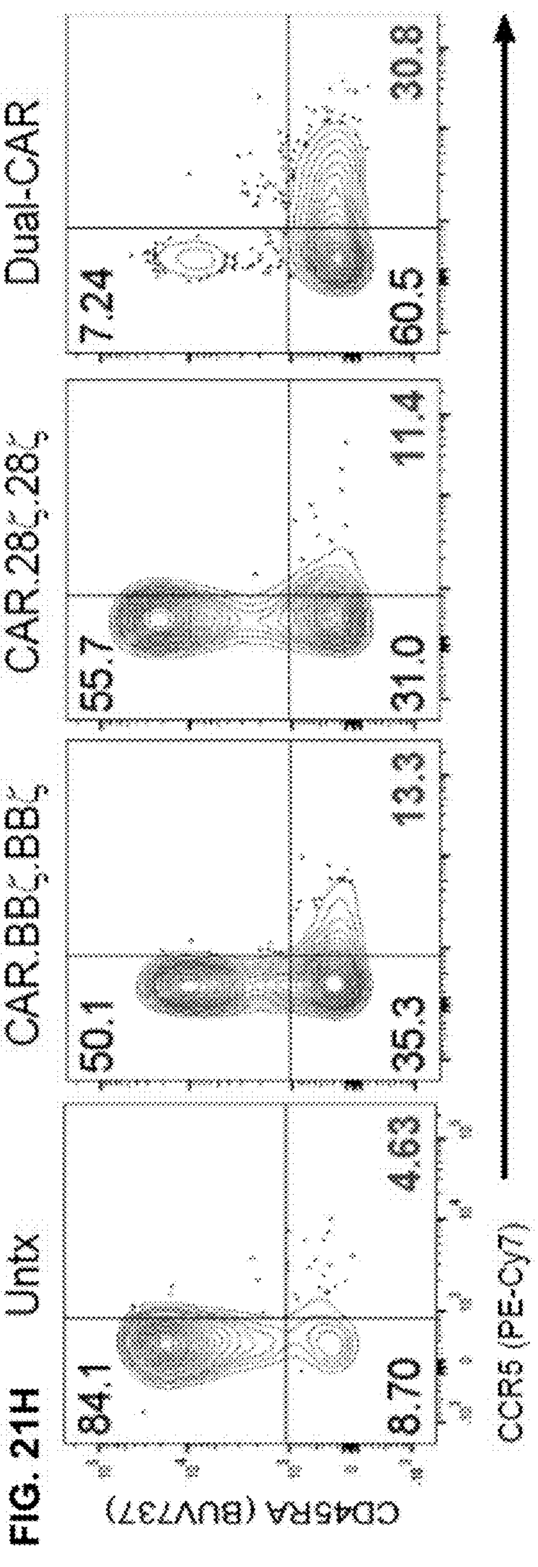
Figure 21J:
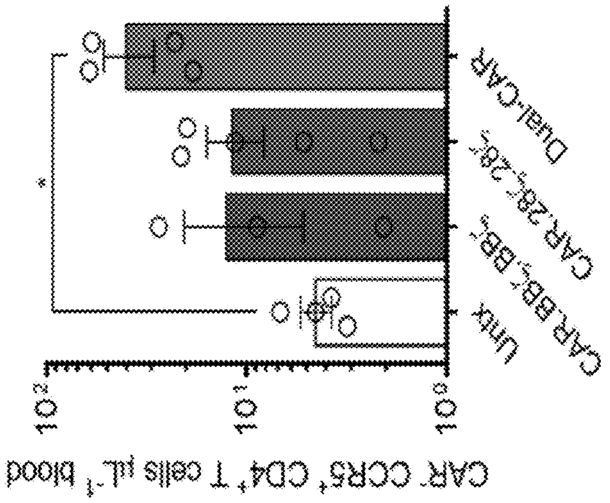
Figure 24:
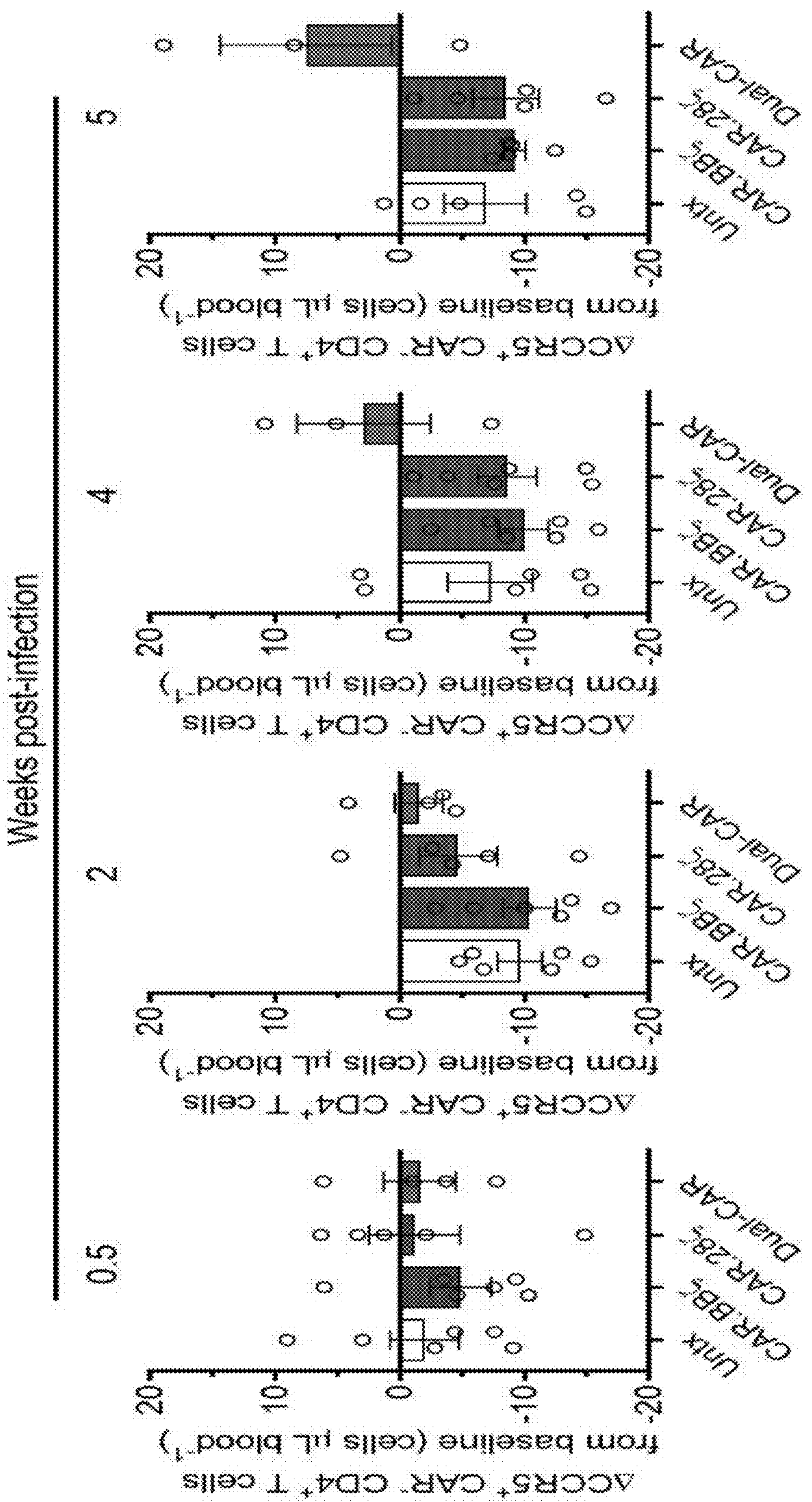
FIG. 24 illustrates the finding that low dose Dual-CAR T cells mitigate CD4+ T cell loss during $HIV_{MJ4}$ infection. $HIV_{MJ4}$-infected mice were infused 48 hours post-challenge with $10^6$ C34-$CXCR4^+$, CAR.BBζ (n=6), CAR.28ζ (n=6), or purified Dual-CAR (n=4) T cells. For each group of mice, the change in peripheral cell concentration of $CCR5^+$ $CD4^+$ T cells ($CAR^-$) was measured from the indicated time post-infection to pre-infection levels. Bars indicate mean and error bars show ±SEM. Symbols represent individual mice.
Figure 25A:
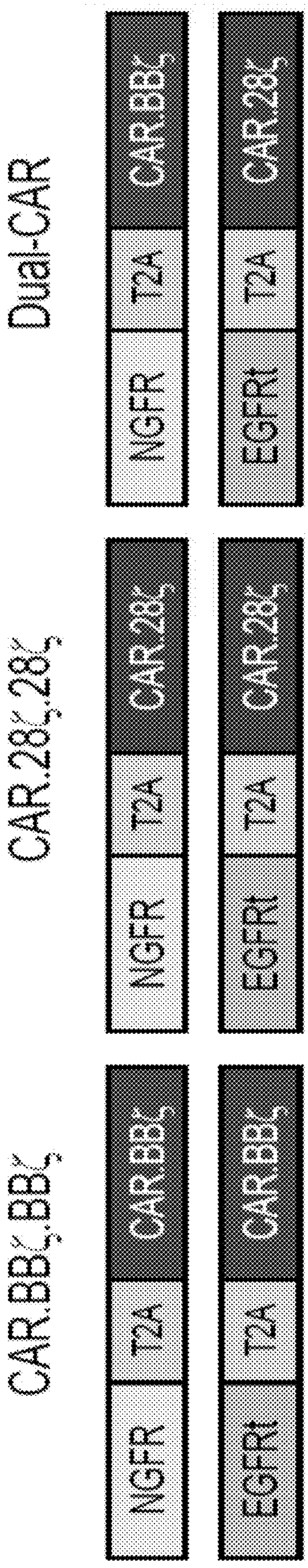
FIGS. 25A-25D illustrate a two-step immunomagnetic selection process that yields purified T cells expressing two independent CARs.
Figure 25B:
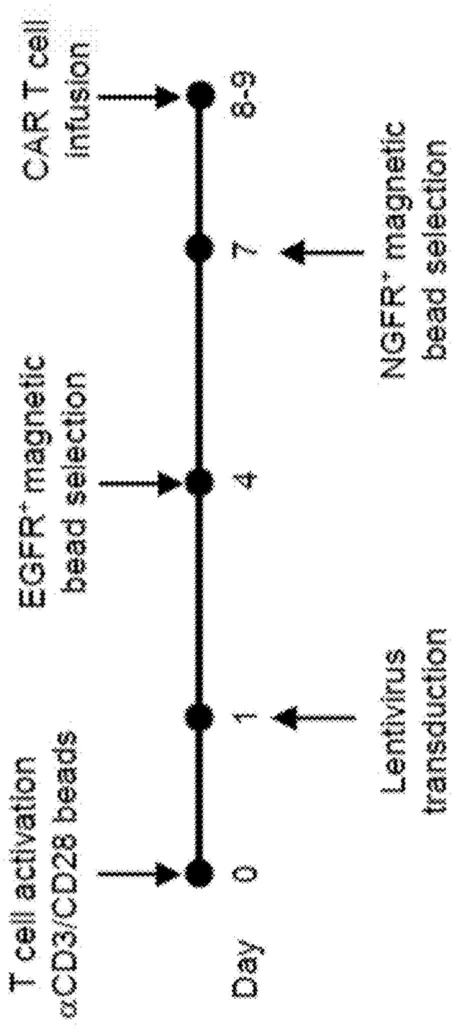
Figure 25C:
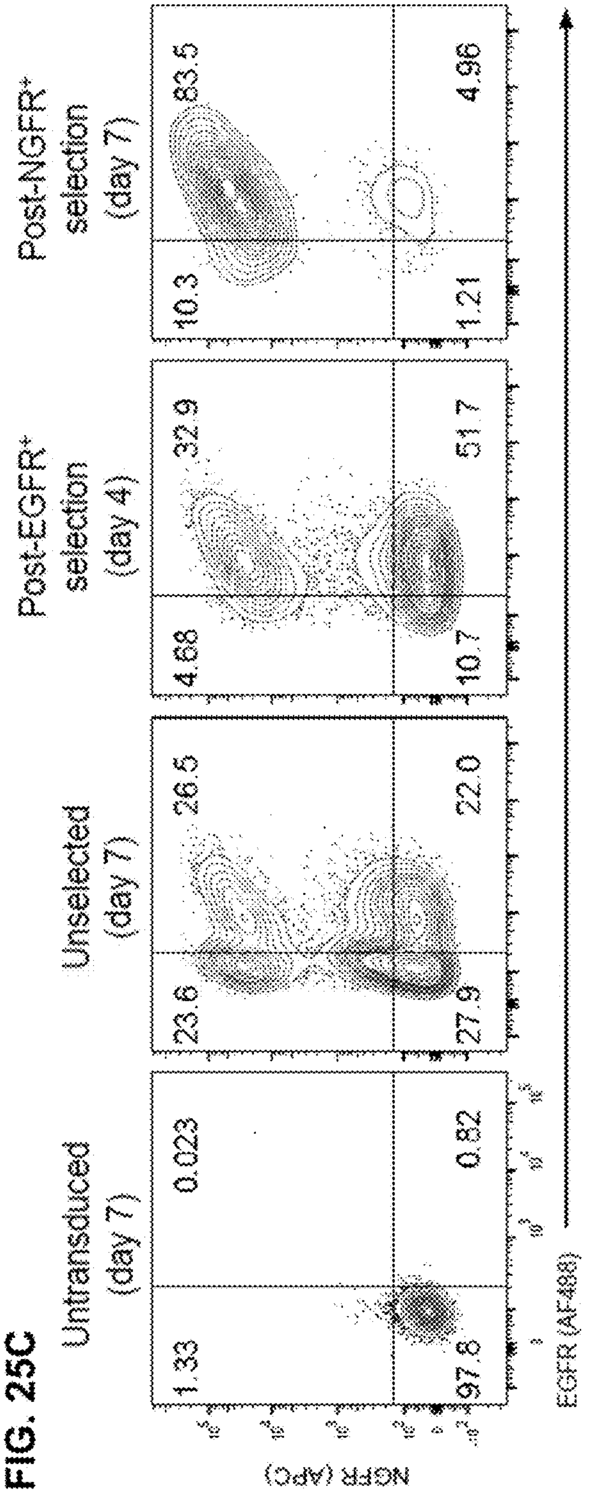
Figure 25D:
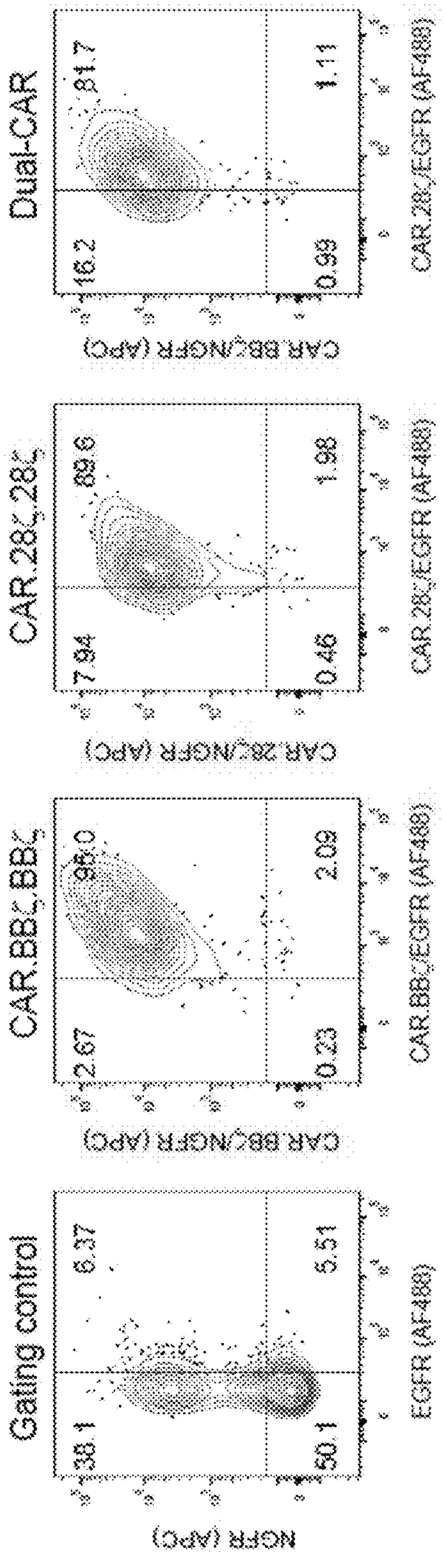
Figure 26B:
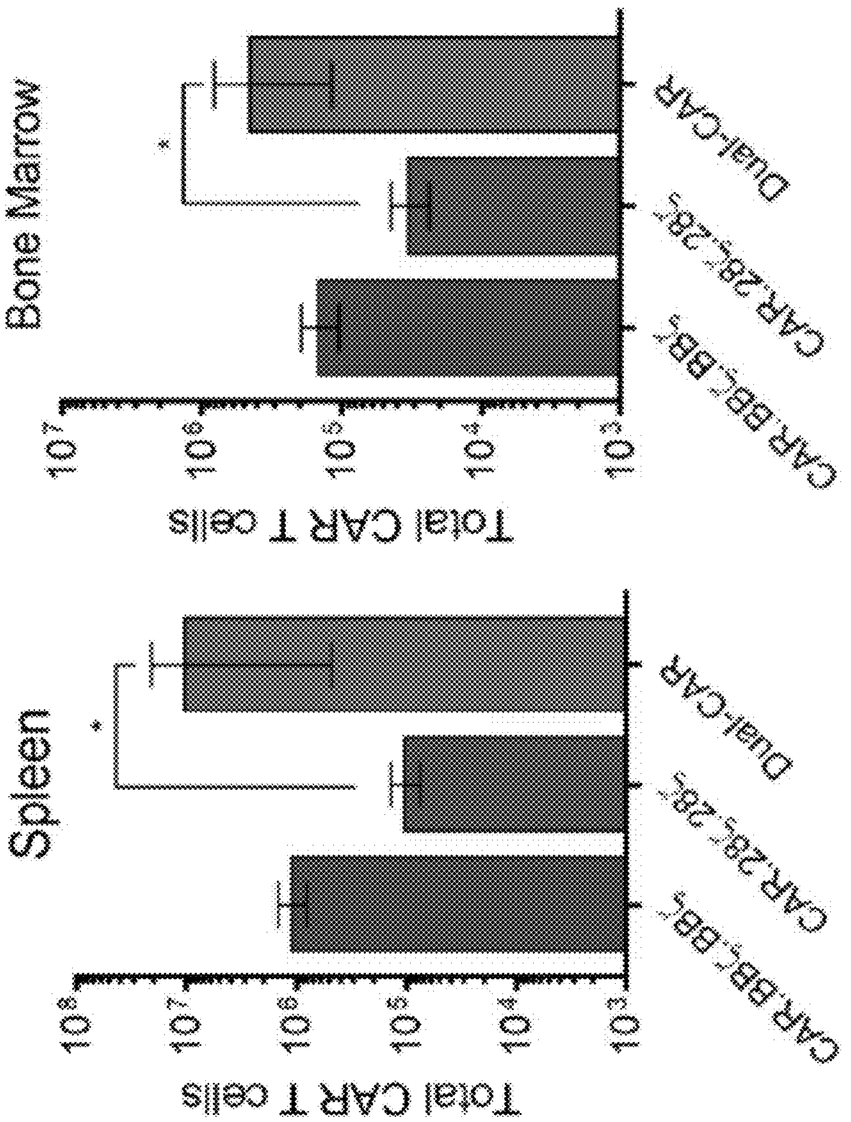
Figure 26A:
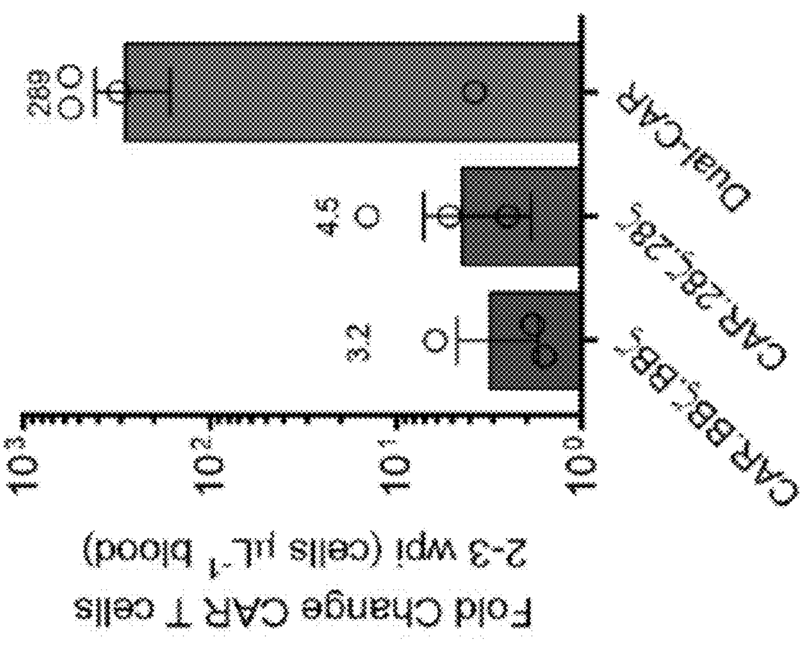

Example 9: HIV-Resistant Dual-CAR T Cells are Responsible for Mitigating HIV-Induced $CD4^+$ T Cell Loss It was next investigated whether an infusion product of Dual-CAR T cells alone exhibit enhanced virus-specific responses during HIV infection. To do so, a low dose of C34-CXCR4$^+$, purified Dual-CAR, CAR.BBζ or CAR.28ζ T cells were infused into separate groups of $HIV_{MJ4}$-infected mice. Dual-CAR T cells exhibited notable in vivo expansion kinetics that exceeded both single CAR transduced T cell populations (FIG. 21C-21D), and mitigated HIV-induced CCR5$^+$ CD4$^+$ T cell loss (FIG. 24). However, in order to more stringently control for CAR surface expression an additional study was performed in another cohort of mice where HIV-resistant, purified Dual-CAR T cells were compared to HIV-resistant, purified CAR T cells transduced with two independent CAR.BBζ or CAR.28ζ constructs (FIG. 25A-25D). Dual-CAR T cells again demonstrated remarkable sensitivity to acute virus replication expanding 300-fold to represent 30% of total human cells in blood 3 weeks post-infection, whereas CAR.BBζ.BBζ and CAR.28ζ.28ζ T cells reached only 3% and 1%, respectively (FIG. 21E and FIG. 26A). In addition, Dual-CAR T cells sustained greater long-term proliferation and maintenance in blood and tissues than their CAR.28ζ.28ζ T cell counterparts (FIG. 21F-21G and FIG. 26B). Importantly, the infusion of purified Dual-CAR T cells resulted in the greatest protection against CD4$^+$ T cell loss during $HIV_{MJ}4$ infection (FIG. 21H-21J), reflected in the preservation of total memory and CCR5$^+$ CD4$^+$ T cells especially late in the infection (FIG. 26C-26D). Furthermore, the magnitude of early CAR T cell expansion across all groups, but exemplified by Dual-CAR T cells, was positively correlated with CD4$^+$ T cell preservation (FIG. 26E). Together, these data indicate that after controlling for CAR surface expression, Dual-CAR T cells exhibit the greatest in vivo antiviral effect.

Figure 21K:
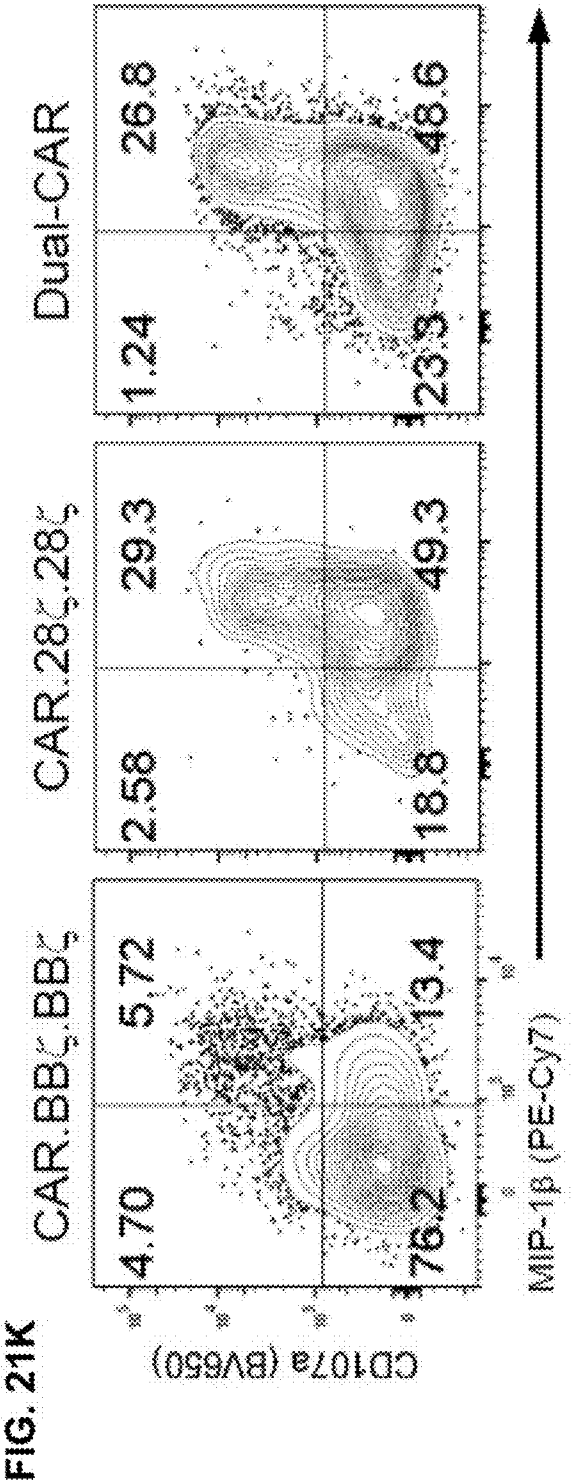
Figure 21L:
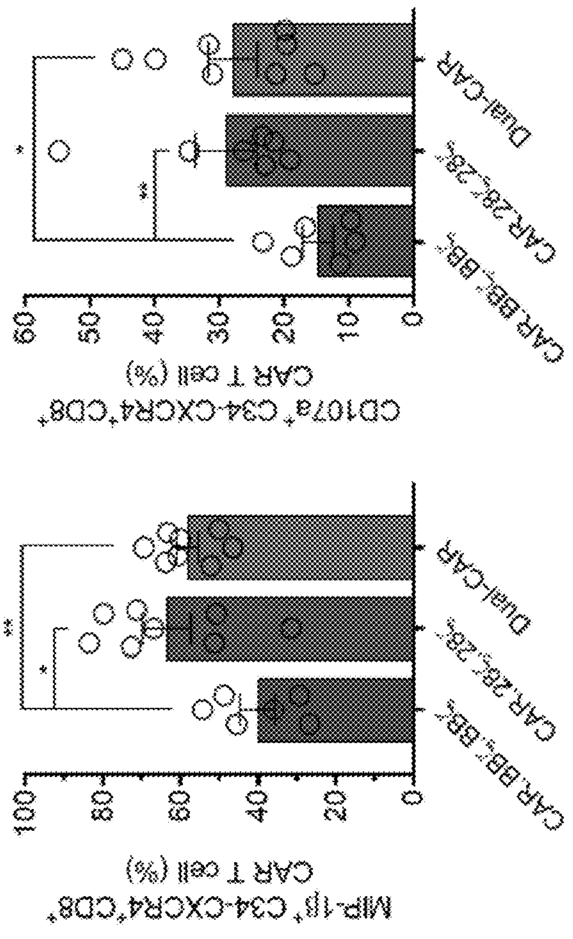
Figure 21M:
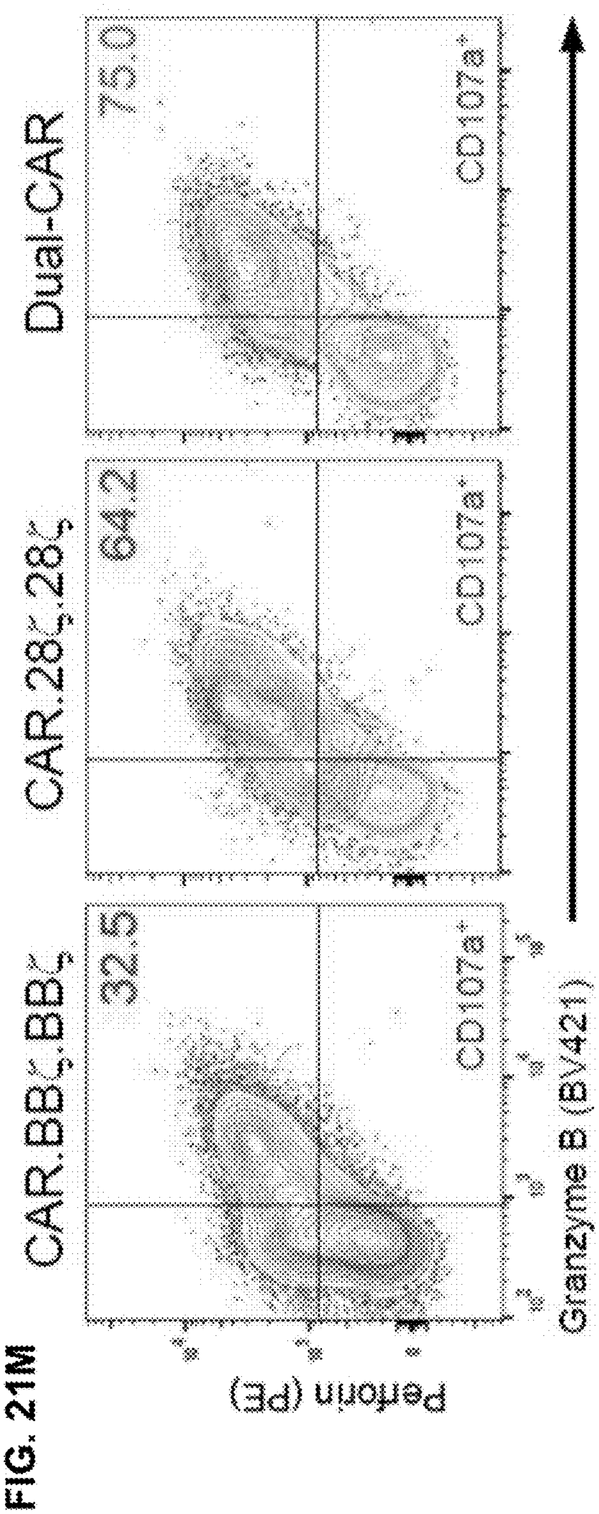
Figure 21N:
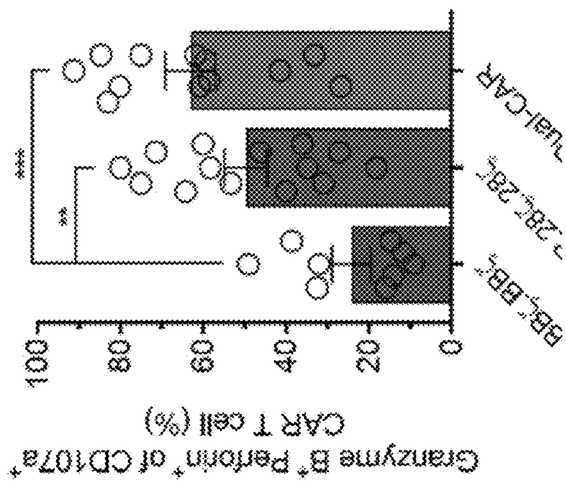

Example 10: Ex Vivo Effector Function of Dual-CAR T Cells Exceeds 4-1BB-Costimulated CAR T Cells The ex vivo effector functions of CAR T cells from chronically infected mice were interrogated. Dual-CAR T cells were superior to CAR.BBζ.BBζ T cells and equivalent to CAR.28ζ.28ζ T cells in their ability to produce MIP-1β and degranulate based on CD107a expression (FIG. 21K-21L). Notably, a majority of CD107a$^+$ Dual-CAR T cells co-expressed granzyme B and perforin compared to CAR.BBζ.BBζ T cells, indicating these cells possess cytotoxic potential (FIG. 21M-21N).

Figure 27A:
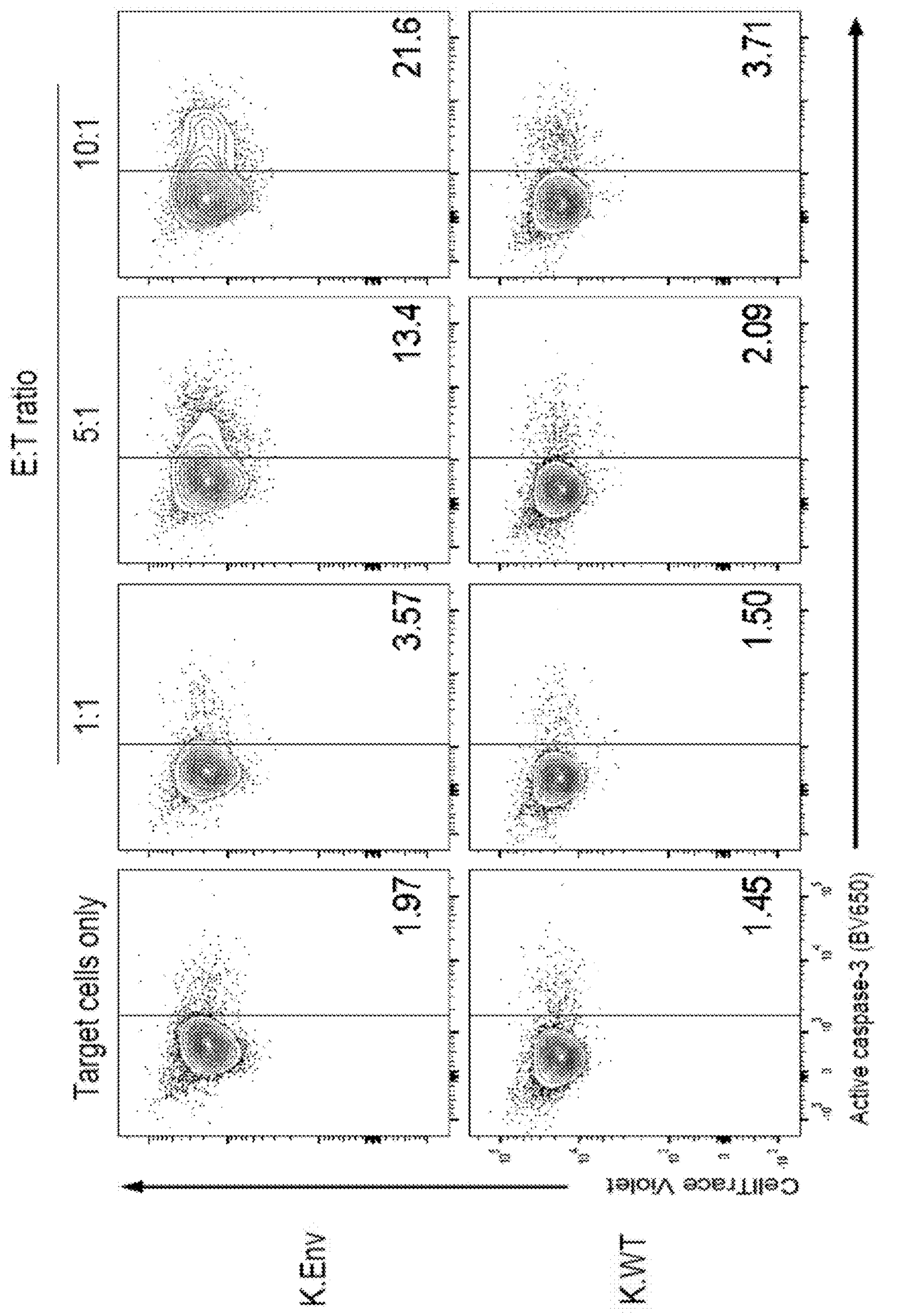
FIGS. 27A-27B illustrate CAR T cells from HIV-infected mice exhibit ex vivo cytotoxic function. $HIV_{JRCSF}$-infected mice (n=3) treated with the Dual-CAR TCP were euthanized and the bone marrow cells were ex vivo stimulated with K.Env or K.WT cells for 24 hours at the indicated E:T ratios.
Figure 27B:
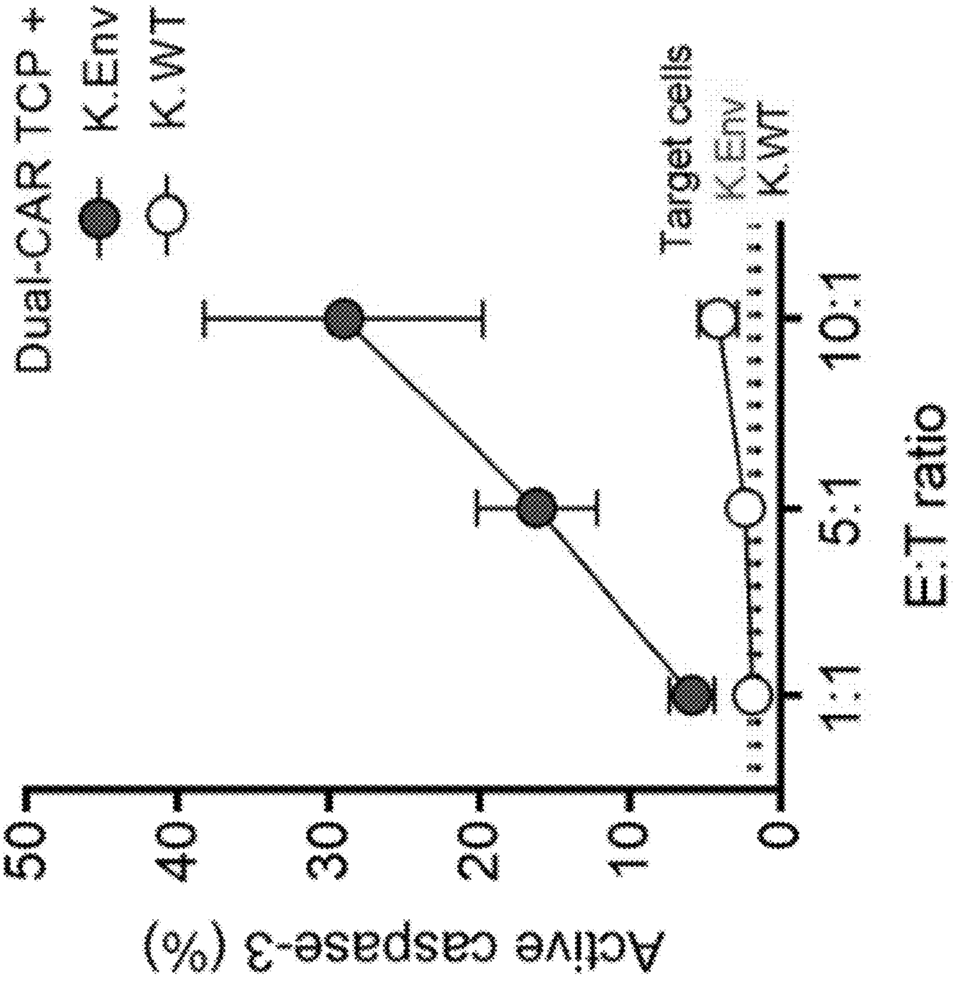
Figure 28A:
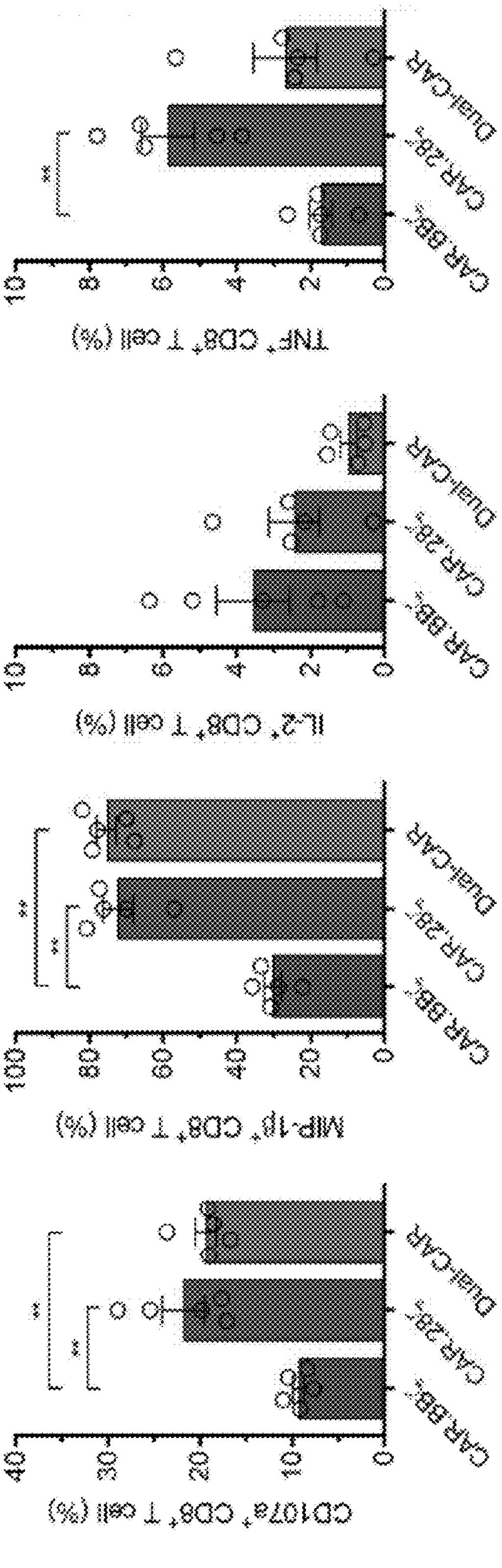
FIGS. 28A-28C illustrate Dual-CAR and CAR.28ζ T cells exhibit similar ex vivo functional profiles. Mice were challenged with $HIV_{JRCSF}$ (n=5) and infused with $2\times10^7$ Dual-CAR T cell product (TCP) 48-hour post infection.
Figure 28B:
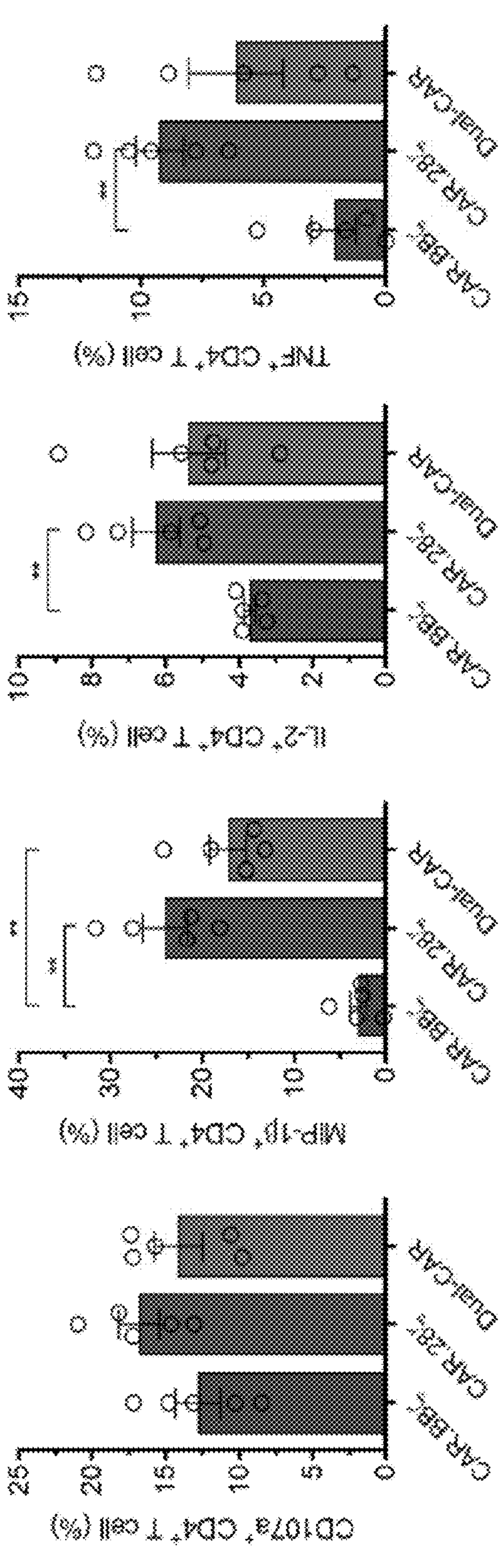
Figure 28C:
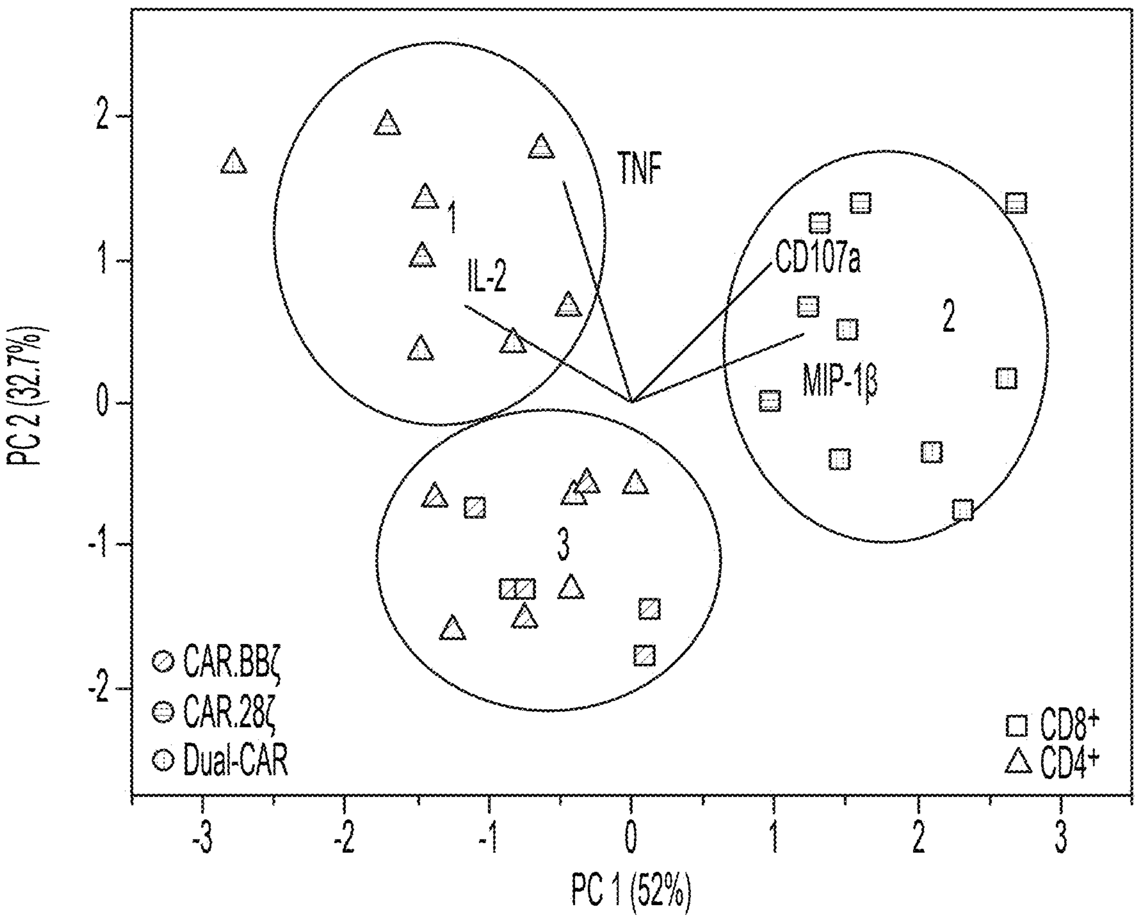

In further support of cytolytic function, CAR T cells comprising the Dual-CAR TCP induced active caspase-3 expression in K.Env cells after ex vivo stimulation (FIGS. 27A-27B). Moreover, comparison of IL-2, TNF, MIP-1β and CD107a expression revealed distinct effector profiles between these CAR T cell populations (FIGS. 28A-28B). Dual-CAR and CD28-costimulated CAR T cells clustered in a similar fashion, with CD4$^+$ CAR T cells expressing more TNF and IL-2, and CD8$^+$ CAR T cells upregulating more CD107a and MIP-1β. In contrast, CD4$^+$ and CD8$^+$ 4-1BB-costimulated CAR T cells clustered together and exhibited attenuated levels of effector molecules (FIG. 28C). Together, these findings support the hypothesis that Dual-CAR T cells co-expressing independent 4-1BB/CD3-ζ and CD28/CD3-ζ endodomains represent a novel CAR T cell population that accentuates antigen-driven proliferation mediated by 4-1BB costimulation and preserves the effector functions mediated by CD28 costimulation.

Figure 29B:
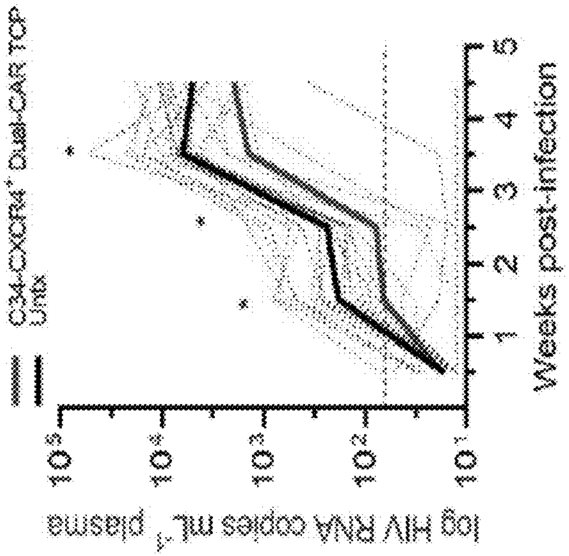
Figure 29C:
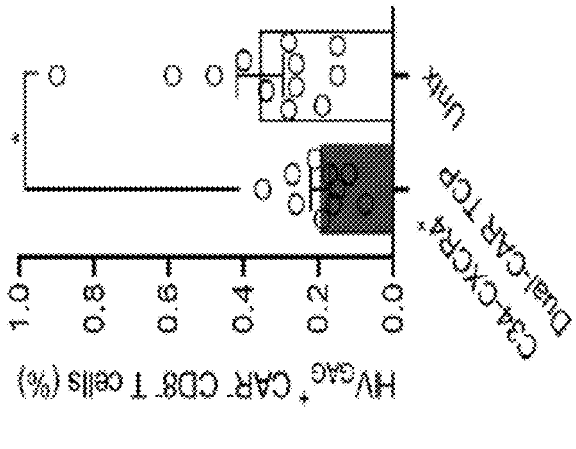
Figure 29D:
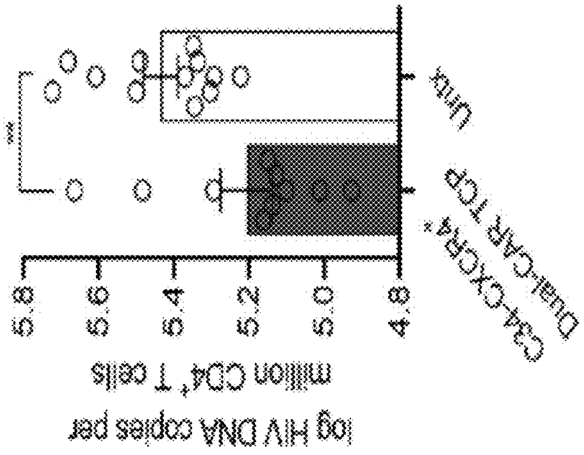

Example 11: Protecting CAR T Cells from HIV Infection Improves Control Over Virus Replication It was hypothesized that the contribution of HIV-infected CAR T cells to viremia may be significant, in that virus secreted from infected CAR T cells could mask reductions in viral load caused by clearing infected CD4$^+$ T cells. Indeed, after aggregating the data from all infection studies, it was observed that infusion of HIV susceptible CAR T cells significantly magnifies plasma viremia (FIG. 29A), as well as viral burden in tissues (FIGS. 30A-30B). Thus, to test the extent to which HIV infection of CD4-based CAR T cells negates CAR T cell-mediated reductions in viremia, the outcomes of infusing a fully-protected (>98% C34-CXCR4$^+$) or a partially-protected (<20% C34-CXCR4$^+$) Dual-CAR TCP into $HIV_{MJ4}$-infected, ART-suppressed mice followed by ART cessation were compared. Strikingly, infusion of the partially-protected Dual-CAR TCP increased rebound viremia over untreated mice to an average peak rebound of 4.6 log HIV RNA copies/mL versus 3.8 log copies/mL, whereas the fully-protected Dual-CAR TCP significantly reduced viral load to 3.0 log copies/mL (FIG. 30C). This result was confirmed by infusing the fully-protected, CXCR4$^+$ Dual-CAR TCP into a larger cohort of BLT mice. Significant reductions in acute viremia compared to untreated mice were observed (FIG. 29B). Notably, treatment with the HIV-resistant Dual-CAR TCP reduced the frequency of HIV-infected cells in tissues (FIGS. 29C-29D), contrasting the effect of unprotected CAR T cells on tissue viral burden in viremic mice (FIGS. 30A-30B). Together, these data demonstrate the importance of safeguarding CAR T cells as HIV infection of unprotected CAR T cells can contribute to plasma viremia and potentially overwhelm CAR T cell-mediated control over virus replication.

Figure 29E:
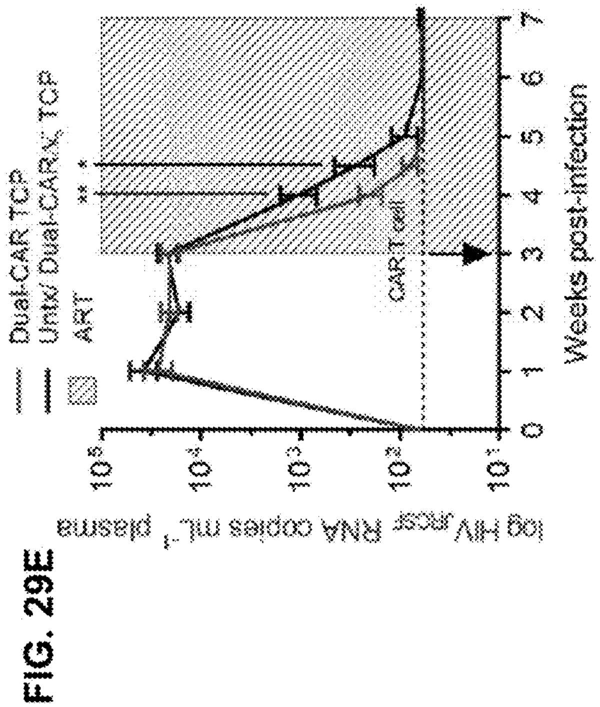
Figure 29F:
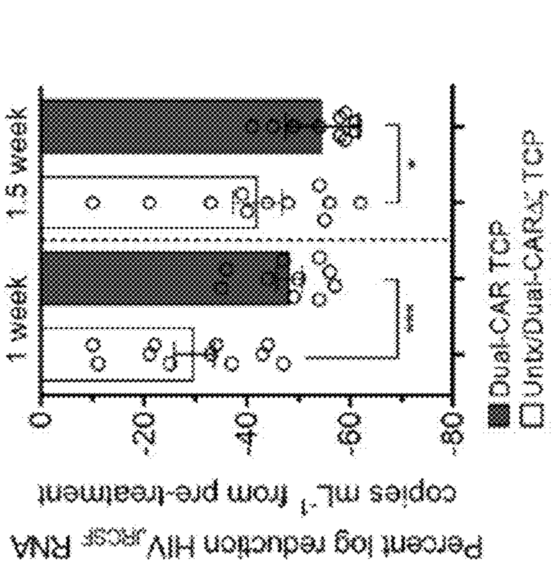
Figure 29G:
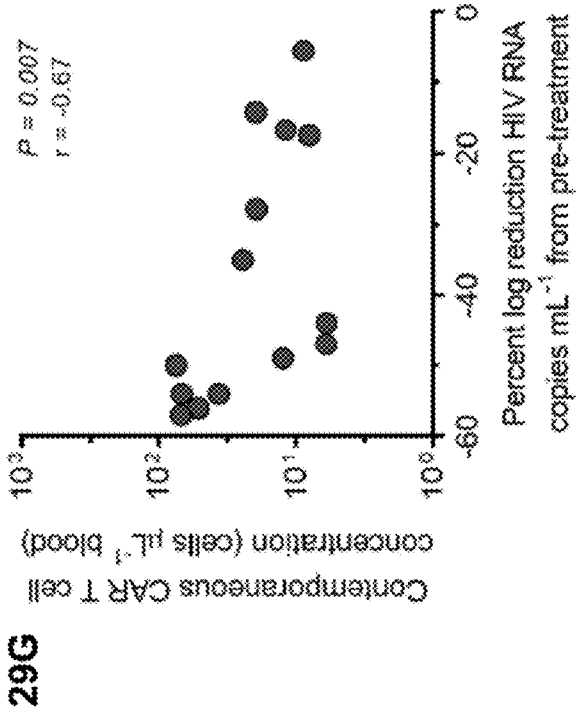
Figure 29H:
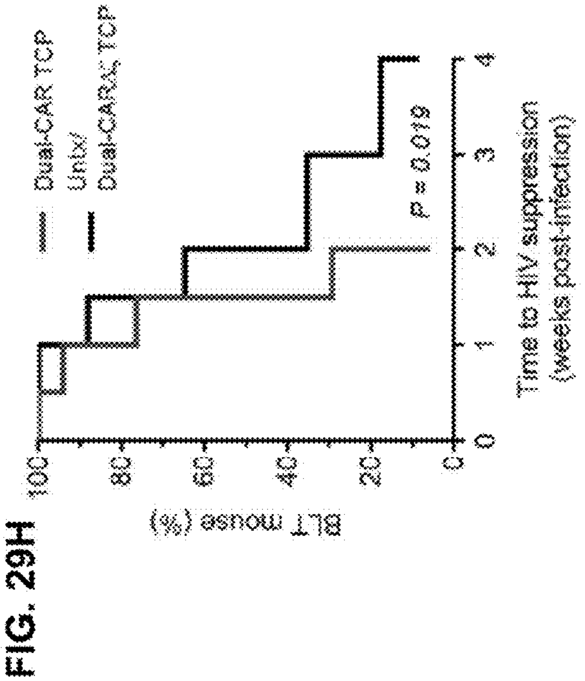
Figure 29K:
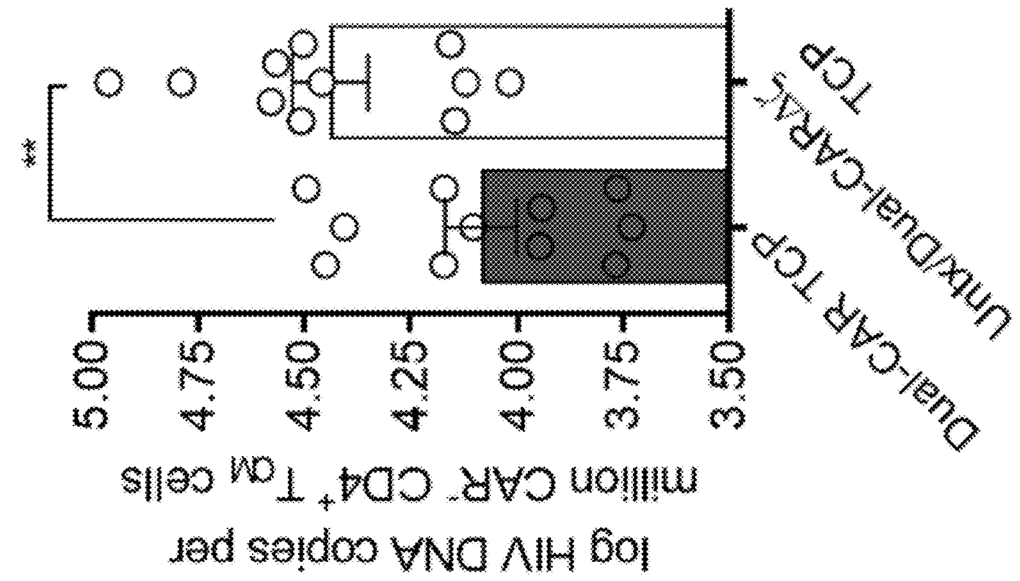
Figure 29J:
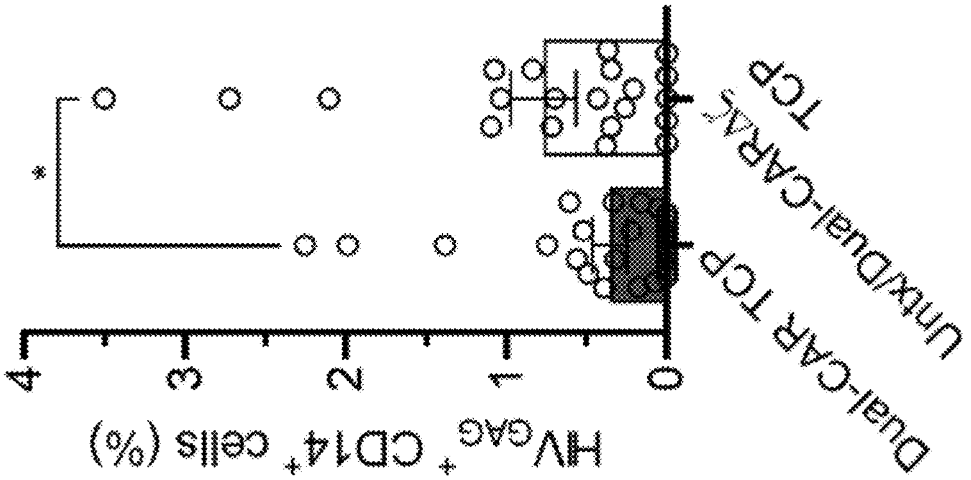
Figure 29I:
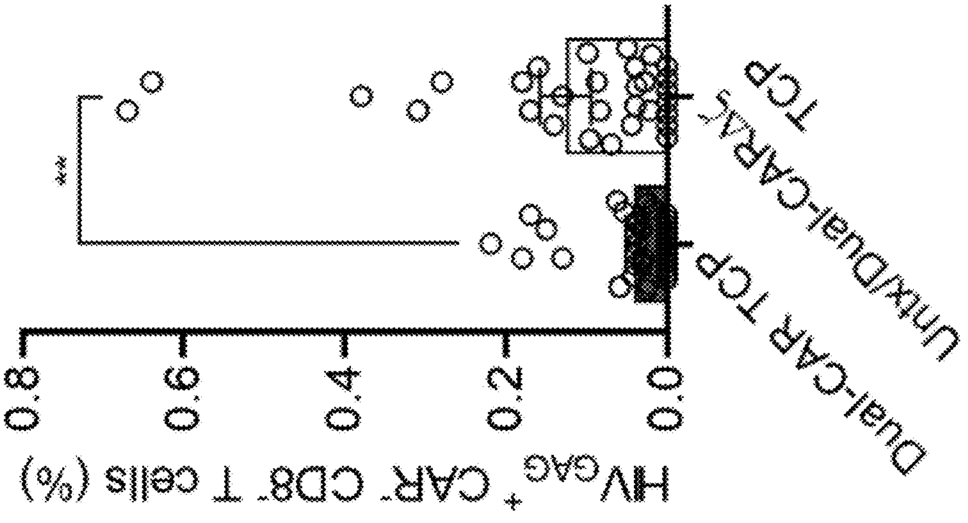
Figure 30E:
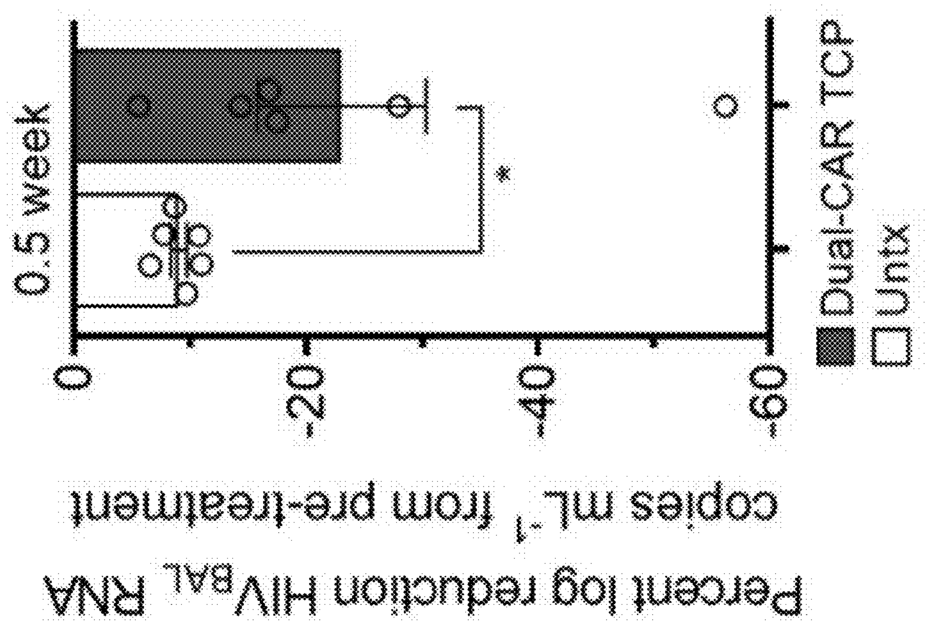
Figure 30D:
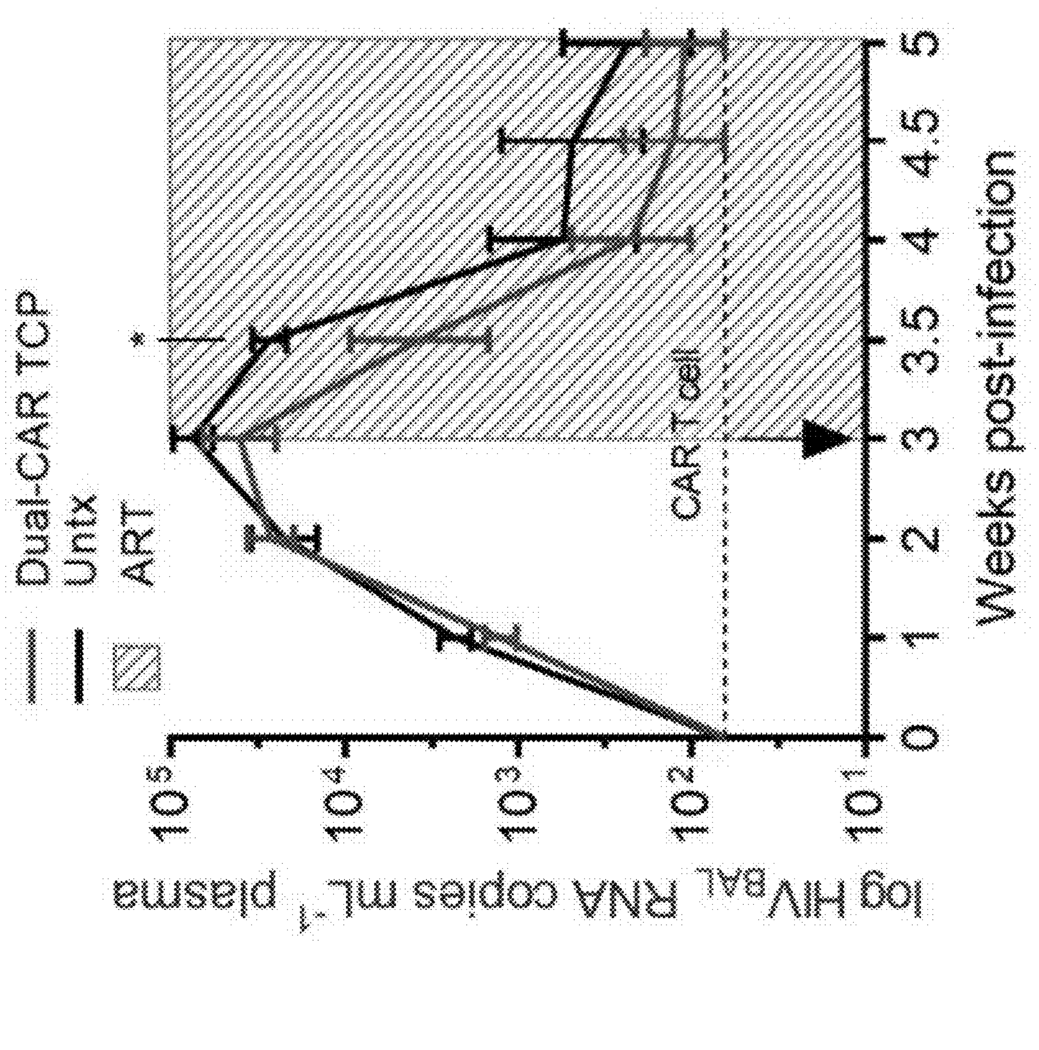

Although C34-CXCR4 reduces HIV infection of CAR T cells, it was shown that the protection is not sterilizing in the presence of persistent viremia (FIG. 2B). Thus, it was hypothesized that providing ART to prevent new rounds of infection at the time of CAR T cell infusion could further reveal CAR T cell-mediated viral load reduction. To test this, mice were challenged with $HIV_{JRCSF}$ and combination therapy (ART and Dual-CAR TCP) initiated at peak viremia. After one week of combination therapy, the Dual-CAR TCP-treated mice achieved approximately a 1-log greater reduction in viral load relative to the ART only control group, which corresponded to a 50% reduction in viremia from pre-treatment levels (FIGS. 29E-29F). The suppressive effect of the Dual-CAR TCP was confirmed in a separate cohort of mice infected with a different HIV strain ($HIV_{BAL}$) (FIGS. 30D-30E). Aggregation of the data from the two studies showed that the magnitude of early viral load reduction was associated with the contemporaneous concentration of CAR T cells in peripheral blood (FIG. 29G), and that CAR T cell treatment significantly accelerated HIV suppression, with nearly all combination therapy-treated mice reaching full suppression by 2 weeks after treatment initiation versus 4 weeks for ART-treated control mice (FIG. 29H). Furthermore, the Dual-CAR TCP reduced tissue viral burden in mice with suppressed plasma viremia, evidenced by fewer HIV-infected CD8$^-$ T cells (CAR$^-$) and CD14$^+$ macrophages in the tissues (FIGS. 29I-29J). Notably, central memory CD4$^+$ T cells (CAR$^-$) sorted from mice treated with the Dual-CAR TCP exhibited a significant, albeit modest, reduction in cell-associated HIV DNA load compared to the control group (FIG. 29K), suggesting that CAR T cell therapy is capable of reducing the size of the virus reservoir that forms during ART. Together, these findings highlight the potential for the HIV-resistant Dual-CAR TCP to mediate direct antiviral activity to clear infected cells in vivo.

Example 12: Discussion

Herein, extensive studies were performed using the BLT humanized mouse model of HIV infection to interrogate the therapeutic potential of CD4-based CAR T cells. This model system proved to be stringent and robust, identifying unique challenges presented by HIV infection and facilitating iterative in vivo testing to overcome these hurdles. It was initially reasoned that long-term stability of CAR T cells would be essential to engender durable control over HIV, given the remarkable persistence of latently-infected cells. Congruent with findings from the cancer field, 4-1BB costimulation was integral for in vivo antigen-driven proliferation and survival of CAR T cells. However, these cells were insufficient to alter HIV pathogenesis after ART cessation. Notably, failure to control viremia also induced a phenotype of T cell exhaustion similar to virus-specific T cells in the settings of other chronic infections. Additionally, it was observed that the high expression levels of CD4 on CAR T cells rendered them susceptible to infection, resulting in significant contribution to plasma viremia and deficiencies to their in vivo survival and function. These findings highlight critical hurdles facing CAR T cell immunotherapy in the setting of HIV infection.

To enhance the efficacy of HIV-specific CAR T cells, a novel CD4-based CAR T cell was created that independently expresses both 4-1BB/CD3-ζ and CD28/CD3-ζ costimulated CARs on the same cell. These Dual-CAR T cells demonstrated extraordinary sensitivity to antigen by exhibiting proliferation kinetics superior to those of 4-1BB-costimulated CAR T cells, while the incorporation of the CD28 costimulatory domain conferred cytotoxic potential and cytokine expression profiles consistent with CD28-costimulated CAR T cells. These findings support a mechanism whereby both endodomains contribute individually to CAR T cell costimulation and activation. These data contrast the in vivo phenotype of $3^{rd}$-generation (3G) CD4-based CAR T cells, which exhibited expansion kinetics similar to CAR.28ζ T cells despite expressing a 4-1BB costimulatory domain within the same construct. This suggests that the CD28 membrane proximal domain in the 3G-CAR has a dominant effect on T cell function, consistent with findings from the cancer field. Furthermore, to address the functional deficits associated with HIV infection of CAR T cells, the fusion inhibitor C34-CXCR4 was co-expressed in Dual-CAR T cells. Although not sterilizing, C34-CXCR4 expression resulted in significantly improved in vivo survival of the Dual-CAR T cells during HIV infection and reduced dysfunction in cytokine production and cytotoxic potential. Overall, the tractability of the BLT mouse model of HIV infection allowed iterative testing that led to the engineering of an enhanced HIV-resistant, CD4-based Dual-CAR T cell product with greater potency.

HIV infection is characterized by a steady decline in $CD4^+$ T cells, concomitant with overt immune activation and dysfunction, ultimately leading to a state of profound immunodeficiency. After the infusion of Dual-CAR T cells, striking protection of memory and $CCR5^+$ $CD4^+$ T cells from HIV-induced depletion despite persistent viremia was observed. Interestingly, the extent of $CD4^+$ T cell protection was greatly affected by the viral replication capacity (vRC) of the infecting HIV strain, as CAR T cells were capable of durably preventing $CD4^+$ T cell loss in mice infected with the lower vRC $HIV_4$, but not the high vRC isolate $HIV_{JRCSF}$. This is consistent with prior findings that vRC affects many aspects of HIV-associated pathogenesis, including the magnitude of immune activation and the kinetics of $CD4^+$ T cell loss in acute infection. The impact of vRC on CAR T cell efficacy may be an important clinical consideration as the vRC of transmitted/founder viruses can vary by orders of magnitude among infected individuals.

Although Dual-CAR T cell therapy during HIV infection failed to durably suppress acute viremia, ART-suppressed mice treated with HIV-resistant Dual-CAR T cells exhibited a striking reduction in early post-ART viral rebound when compared to mice treated with unprotected CAR T cells. These data suggested that HIV infection of the CAR T cells themselves may mask reductions in viral load caused by CAR T cell-mediated clearance of infected cells. This concept was supported by the observation that infusion of CAR T cells concomitant with ART initiation, which serves to prevent CAR T cell infection, reproducibly accelerated the kinetics of HIV suppression. It was also observed for the first time that CAR T cells decrease tissue viral burden in a variety of cell types, including long-lived memory $CD4^+$ T cells, suggesting that when combined with ART initiation, CAR T cells can ameliorate the formation of the latent reservoir. This finding underscores that sufficient antigen is necessary to activate the CAR T cell response. As such, employing CAR T cells in a traditional "shock and kill" strategy to target the latent reservoir will likely require the inclusion of a powerful HIV inducer to reactivate an adequate level of viral antigen. Taken together, these results support that Dual-CAR T cells are capable of mediating direct antiviral activity and reducing viremia, but protection of the CAR T cells against HIV infection is essential and may require the development of additional protection modalities such as deletion of CCR5.

BLT humanized mice recapitulate key aspects of HIV infection and pathogenesis, but the model may actually provide an overtly stringent test of CAR T efficacy to control viremia. Most notably, the timing of CAR T therapy and ART initiation in these studies occurred earlier than the development of endogenous HIV-specific T cells. This together with the general inability of BLT mice to develop affinity-matured antibodies suggests that the CAR T cells are likely functioning without the benefit of robust, endogenous antiviral immunity. However, this stringency proved to be critical for highlighting the insufficient potency of 4-1BB-costimulated CAR T cells and the importance of HIV-resistance, as 4-1BB-costimulated and unprotected CD4-based CAR T cells are capable of suppressing viral replication at favorable effector-to-target ratios in vitro and in less complex humanized mouse models of HIV infection.

In summary, the use of BLT mice, which are capable of supporting high-level chronic viremia, $CD4^+$ T cell depletion, and post-ART viral rebound using primary HIV isolates has facilitated the development of a potent HIV-specific CAR T cell therapy capable of reducing HIV replication and preventing HIV-induced $CD4^+$ T cell loss. Further, the in vivo characterization of Dual-CAR T cells convincingly reconciles the functional differences imparted by the CD28 and 4-1BB costimulatory domains, whereby expression of independent CARs accentuates antigen-driven T cell proliferation, survival, and effector function. Importantly, the profound in vivo expansion potential of Dual-CAR T cells, coupled with their susceptibility to HIV-infection, highlights the importance of engineering CD4-based CAR T cells (and likely also scFv-based CAR T cells), with sterilizing resistance to HIV infection that must be present in the vast majority of the infusion product in order to improve their in vivo antiviral activity. Collectively, the findings described herein provide extraordinary insight regarding the hurdles facing engineered T cell-based therapy for HIV cure, in a stringent preclinical animal model. Furthermore, in pursuit of overcoming these hurdles a novel Dual-CAR T cell product was created that is capable of mitigating HIV-induced disease, with broad utility for viral infections and malignancies.

Example 13

Figure 32:
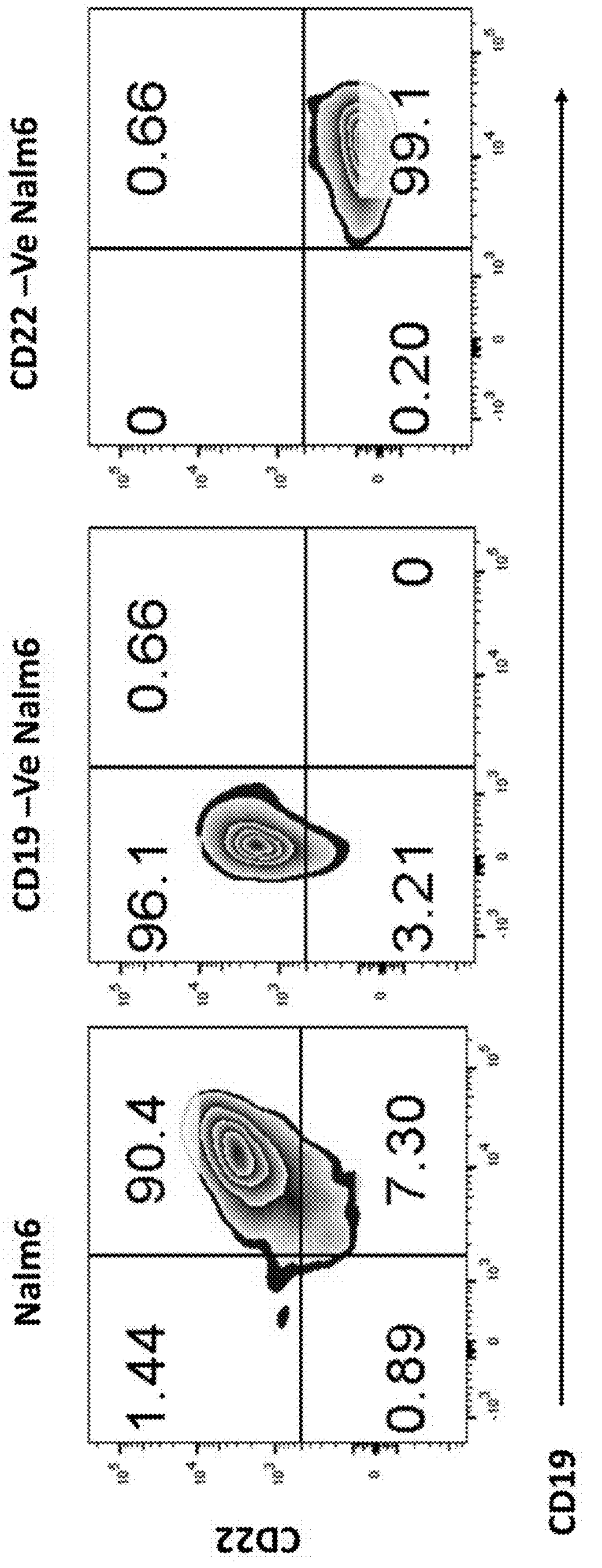
FIG. 32 illustrates CD19 and CD22 antigens are highly expressed on B-ALL.

FIG. 32 illustrates CD19 and CD22 antigens are highly expressed on B-ALL.

Figure 33A:
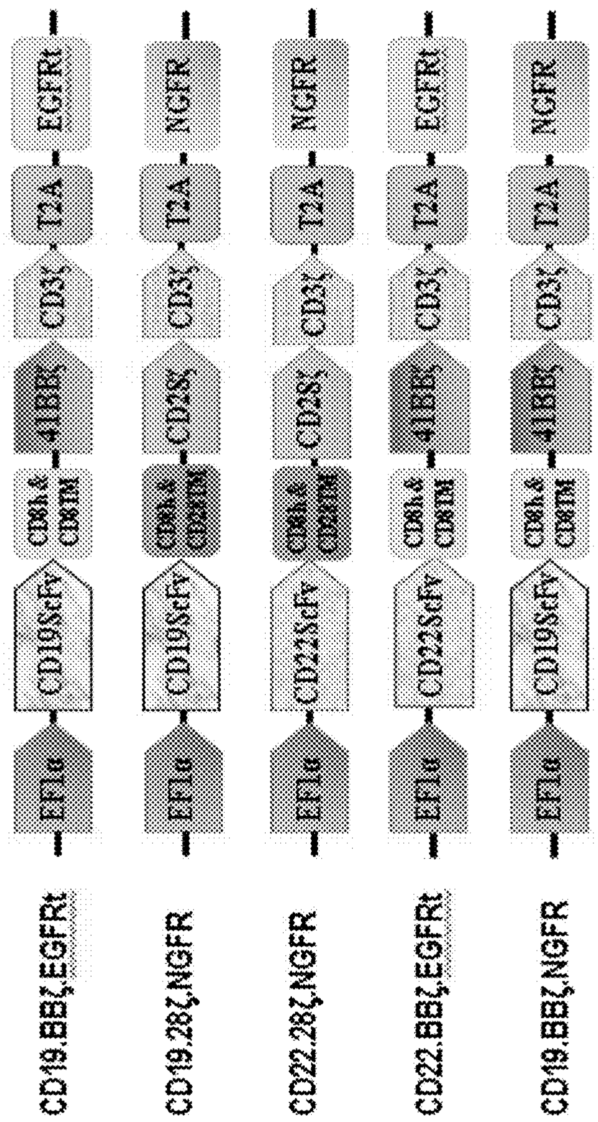
FIGS. 33A-33C illustrate CD19 and CD22 CAR structures and high yield of purified T cells expressing two independent CARs after two-step immunomagnetic selection process.
Figure 33B:
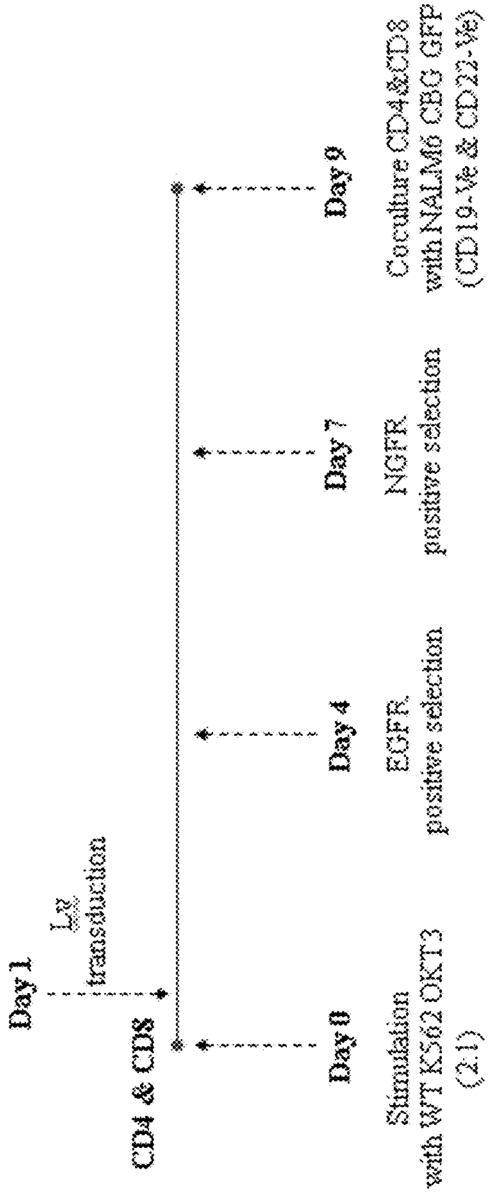
Figure 33C:
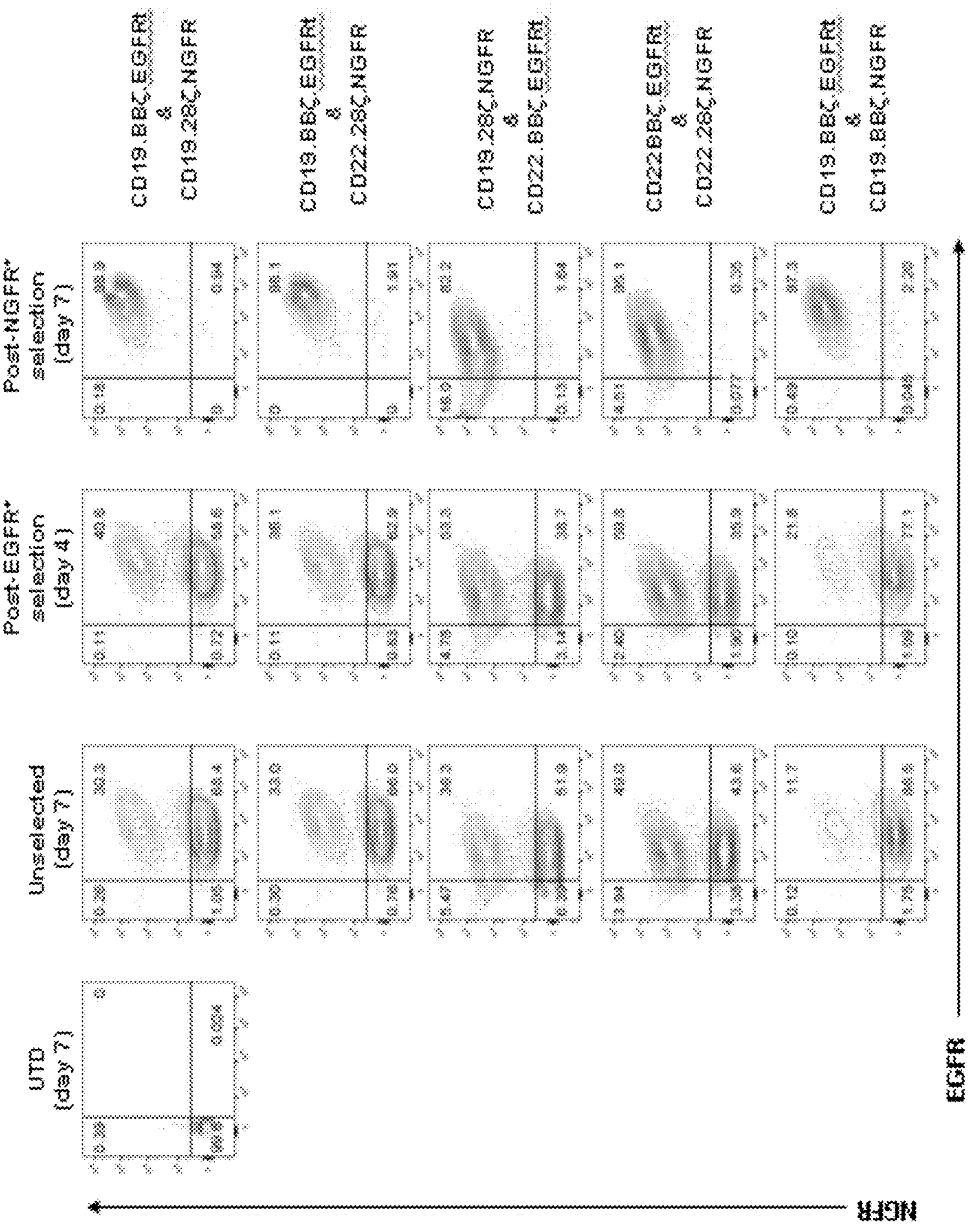

FIGS. 33A-33C illustrate CD19 and CD22 CAR structures and high yield of purified T cells expressing two independent CARs after two-step immunomagnetic selection process.

Figure 34A:
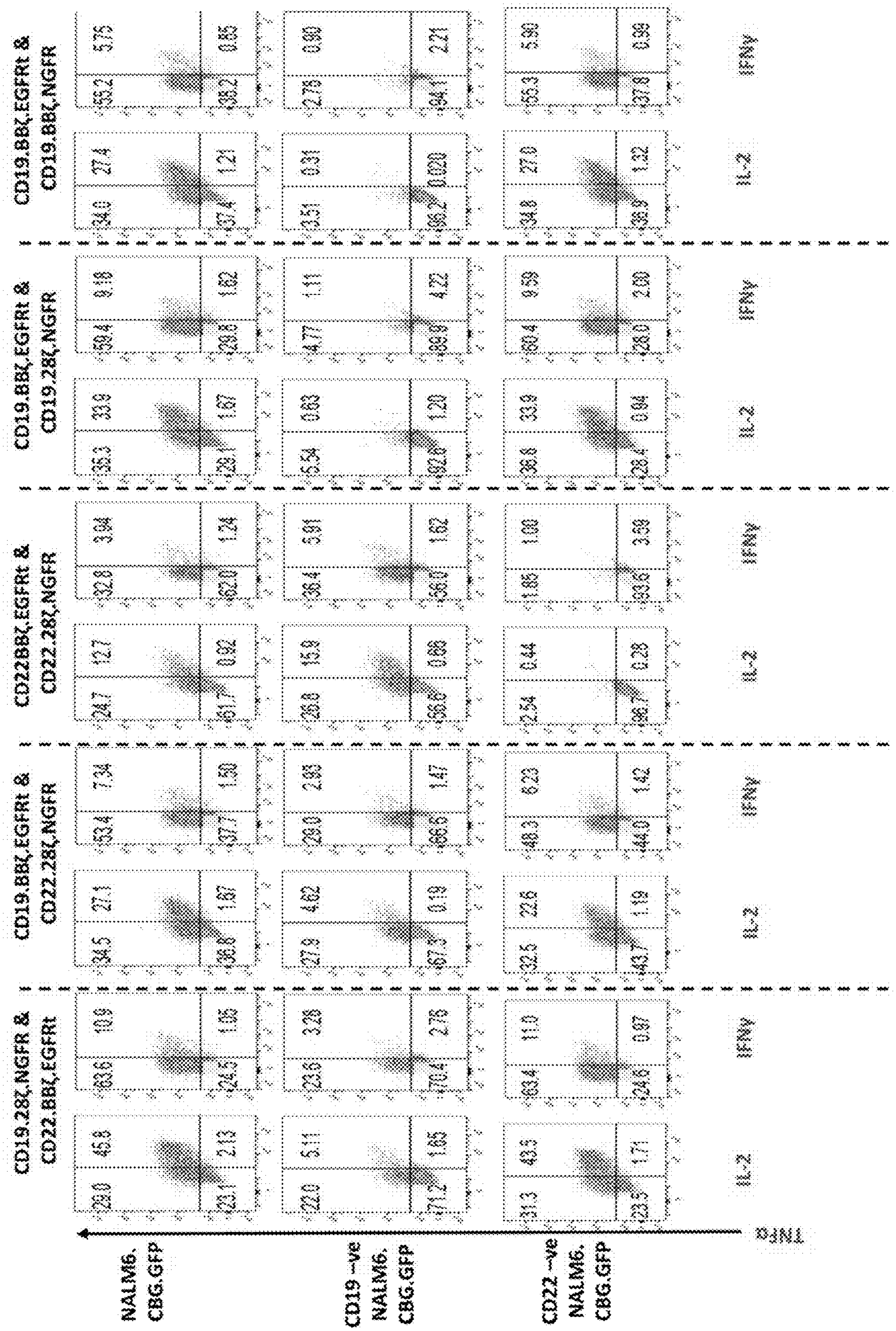
FIGS. 34A-34B illustrate anti-CD19/anti-CD22 transduced T cells exhibit cytokine production in co-culture with double positive targets as well as CD19 knock out targets.
Figure 34B:
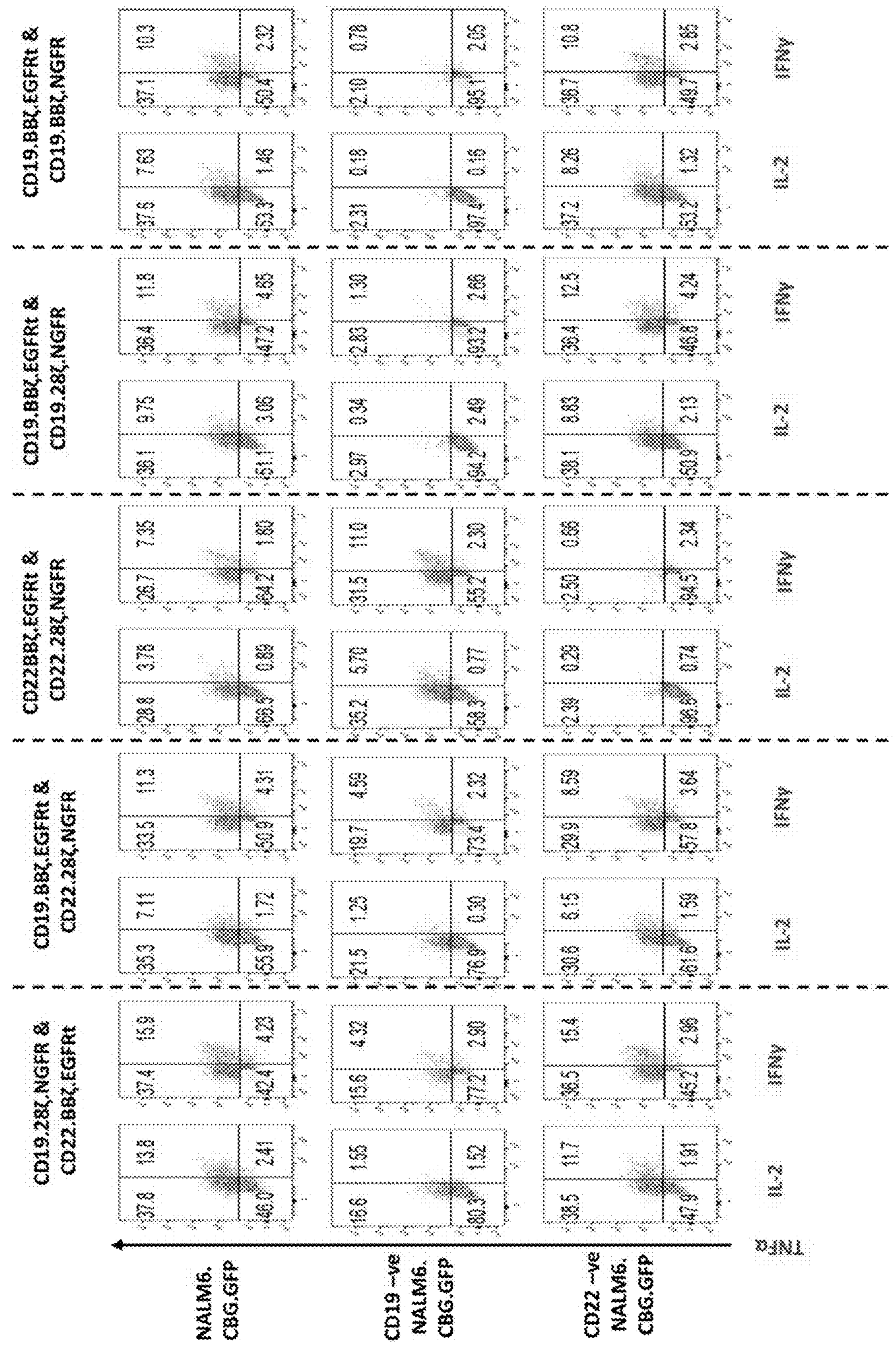
Figure 35A:
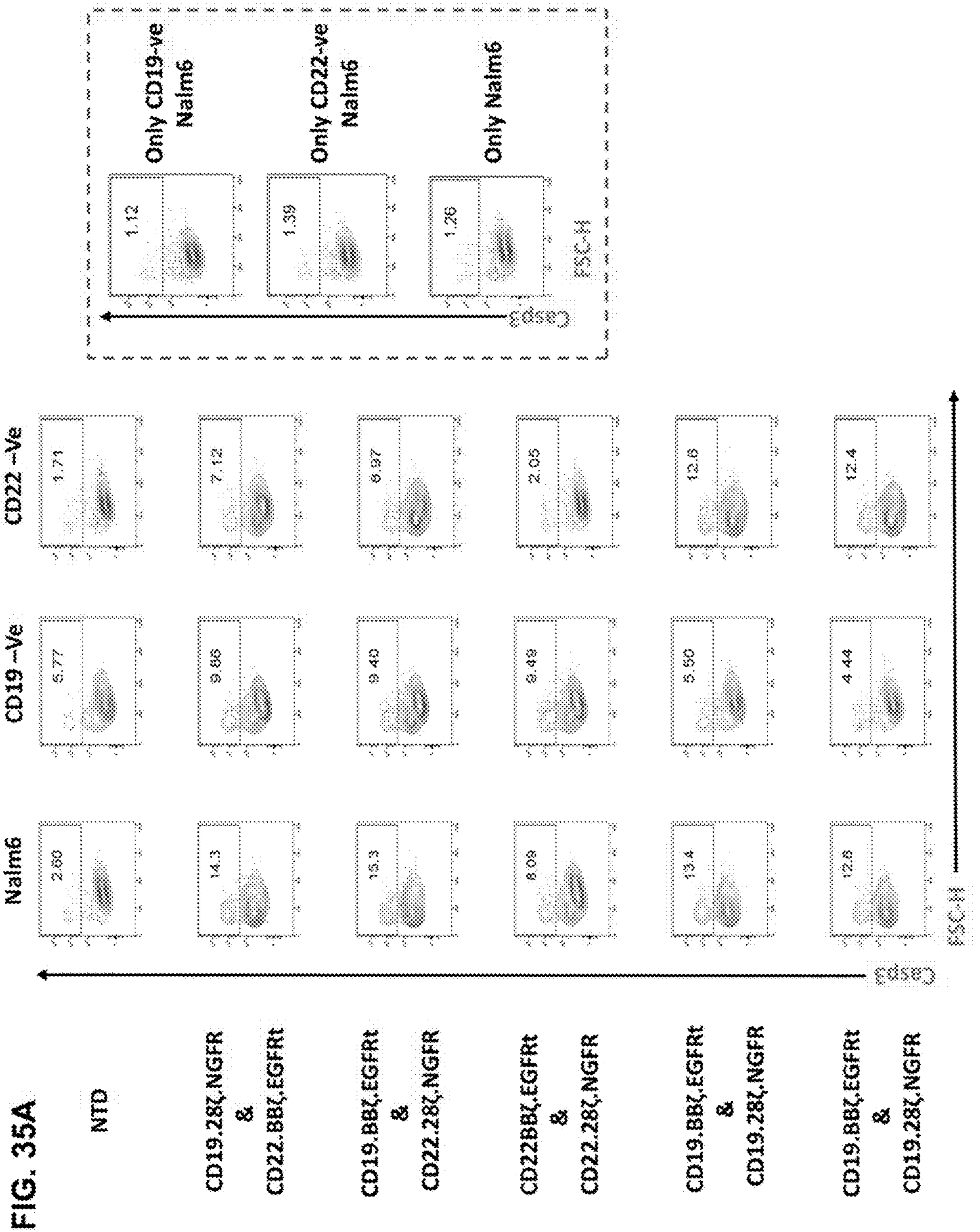
FIGS. 35A-35D illustrate anti-CD19/anti-CD22 transduced T cells kill double positive targets as well as CD19 knock out targets.
Figures 35B, 35C, 35D:
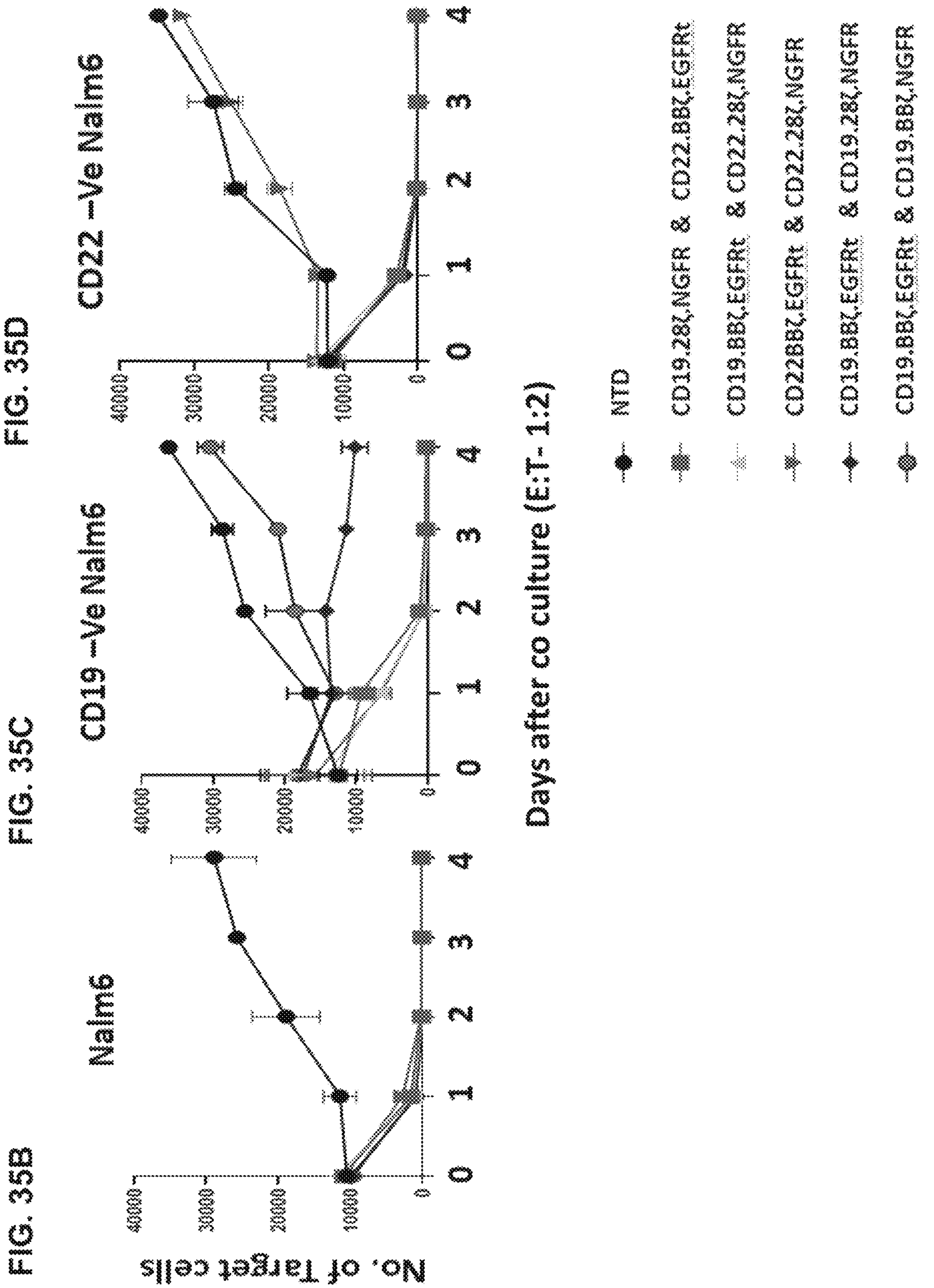

FIGS. 34A-34B illustrate anti-CD19/anti-CD22 transduced T cells exhibit cytokine production in co-culture with double positive targets as well as CD19 knock out targets.

FIGS. 35A-35D illustrate anti-CD19/anti-CD22 transduced T cells kill double positive targets as well as CD19 knock out targets.

Figure 36:
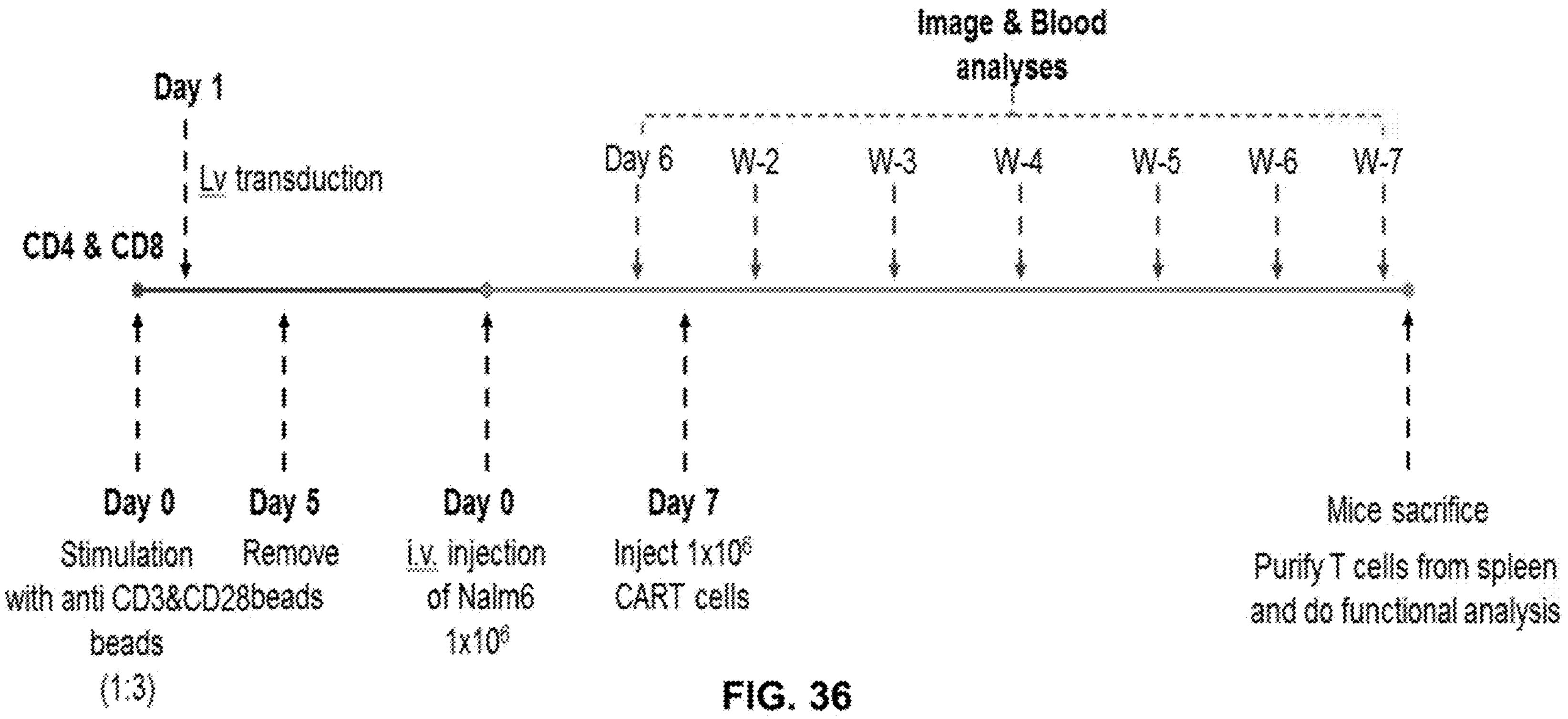
FIG. 36 illustrates anti-CD19/anti-CD22 transduced T cells demonstrate anti-leukemic activity in vivo against $CD19^+$ Ve as well as $CD19^-$Ve B-ALL.

FIG. 36 illustrates anti-CD19/anti-CD22 transduced T cells demonstrate anti-leukemic activity in vivo against CD19+Ve as well as CD19-Ve B-ALL.

Figure 37:
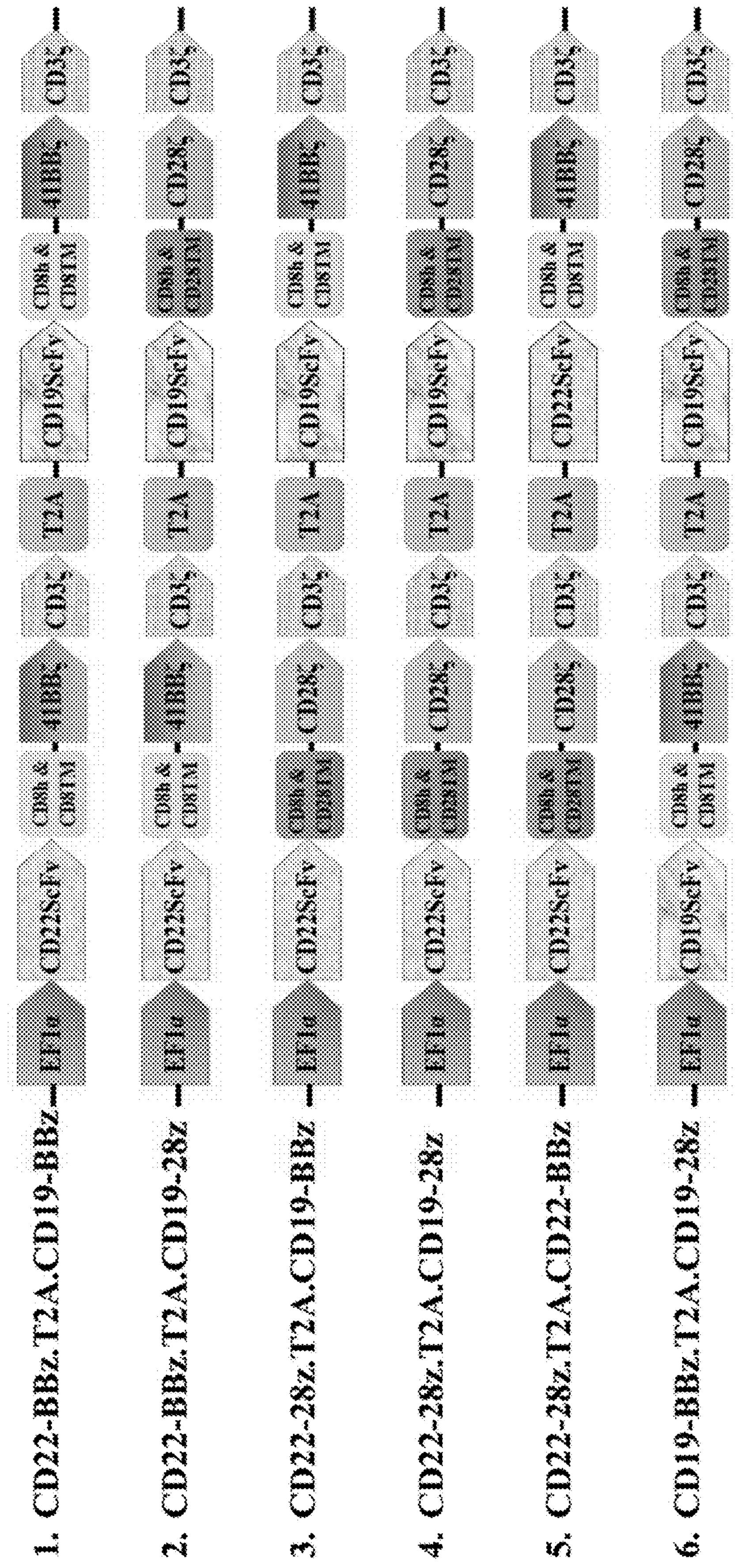
FIG. 37 is a schematic of Dual CD19T2ACD22 CARs structure and anti-CD19 and anti-CD22 CAR expression in T2A CAR transduced T cells.

FIG. 37 is a schematic of Dual CD19T2ACD22 CARs structure and anti CD19 and anti CD22 CAR expression in T2A CAR transduced T cells.

Figure 38:
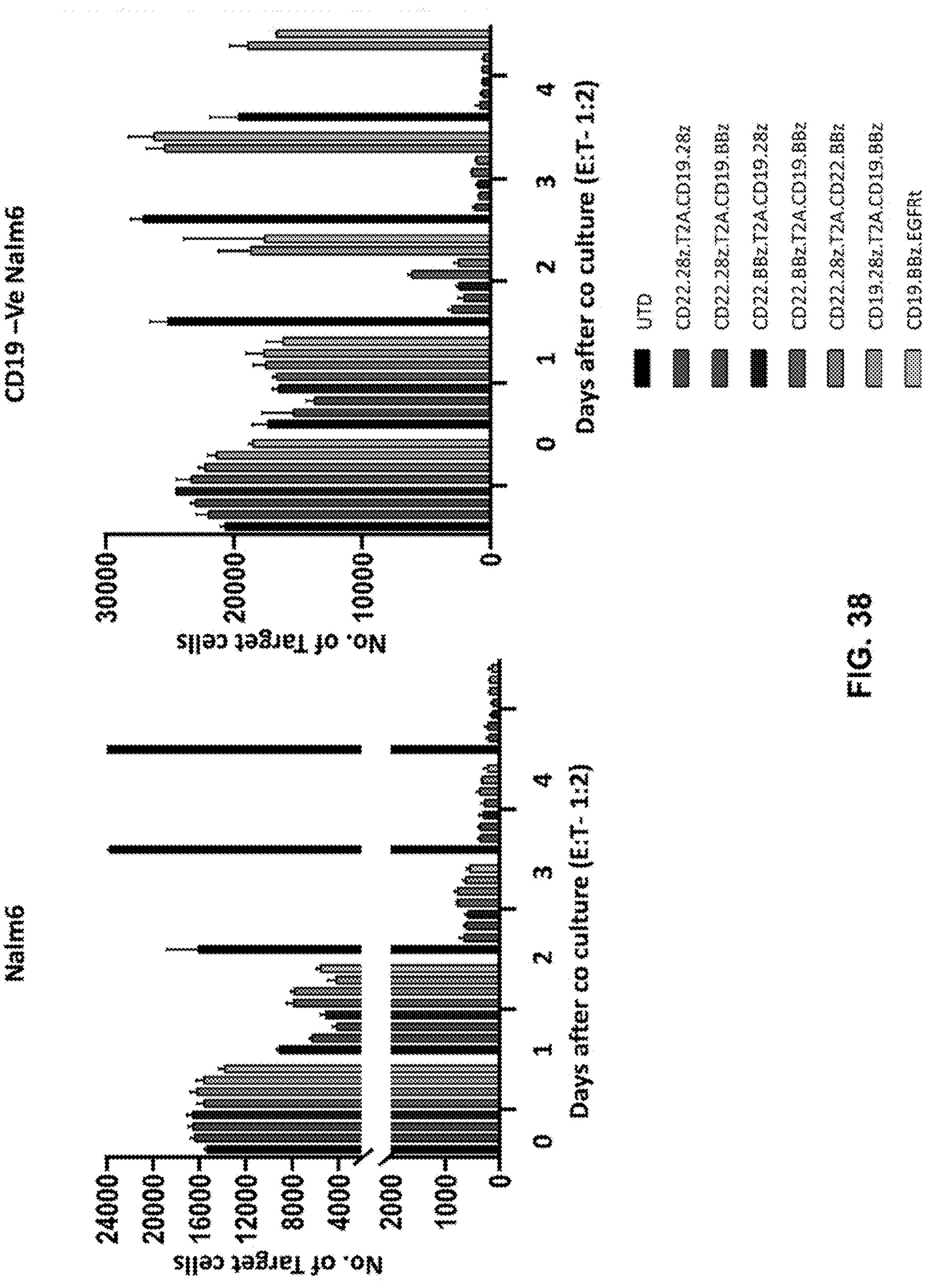
FIG. 38 illustrates Dual CD19T2ACD22 CAR T cells demonstrate anti-leukemic activity in vitro and in vivo against $CD19^+$ Ve as well as $CD19^-$Ve B-ALL.

FIG. 38 illustrates Dual CD19T2ACD22 CAR T cells demonstrate anti-leukemic activity in vitro and in vivo against CD19+Ve as well as CD19-Ve B-ALL.

Figure 39:
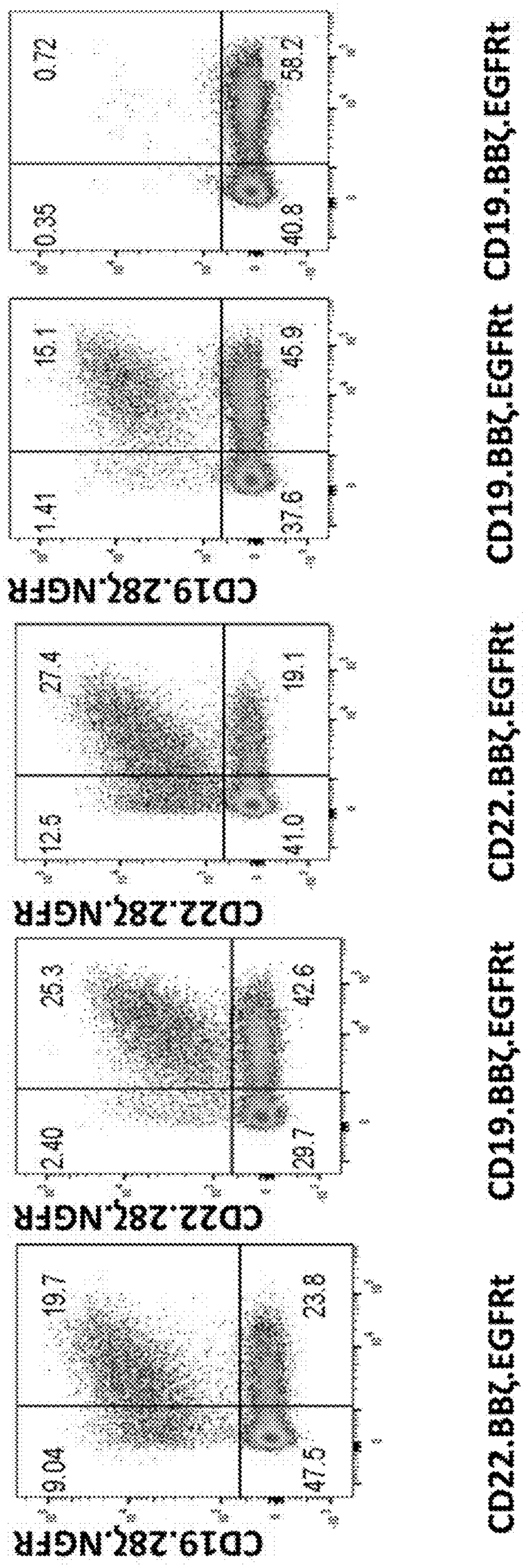
FIG. 39 illustrates anti-CD19 and anti-CD22 CAR expression in CD4 & CD8 T cells.

FIG. 39 illustrates anti-CD19 and anti-CD22 CAR expression in CD4 & CD8 T cells.

Figure 40A:
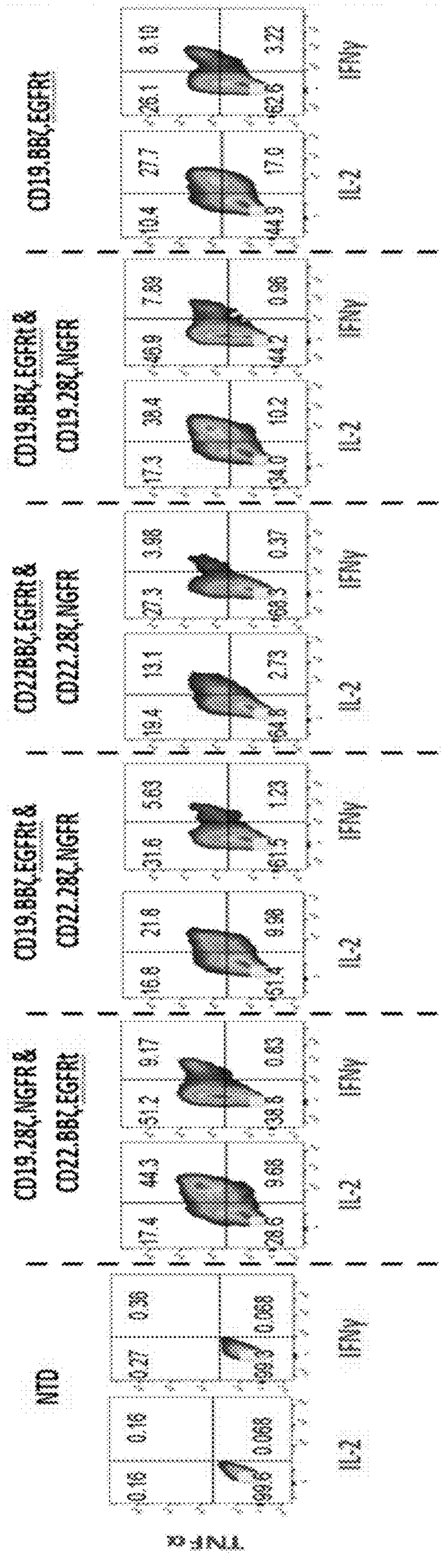
FIGS. 40A-40B illustrate dual anti-CD19 and anti-CD22 CAR T cells enhance cytokine response in CD4 and CD8 T cells after co culture with NALM6.
Figure 40B:
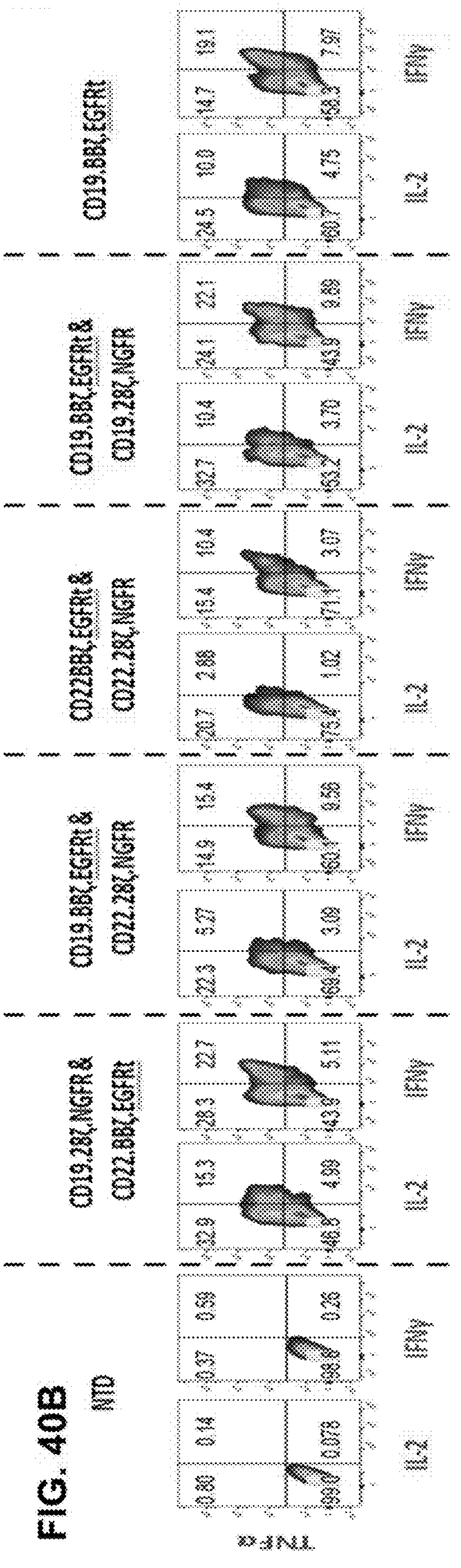

FIGS. 40A-40B illustrate dual anti-CD19 and anti-CD22 CAR T cells enhance cytokine response in CD4 and CD8 T cells after co culture with NALM6.

Figure 41A:
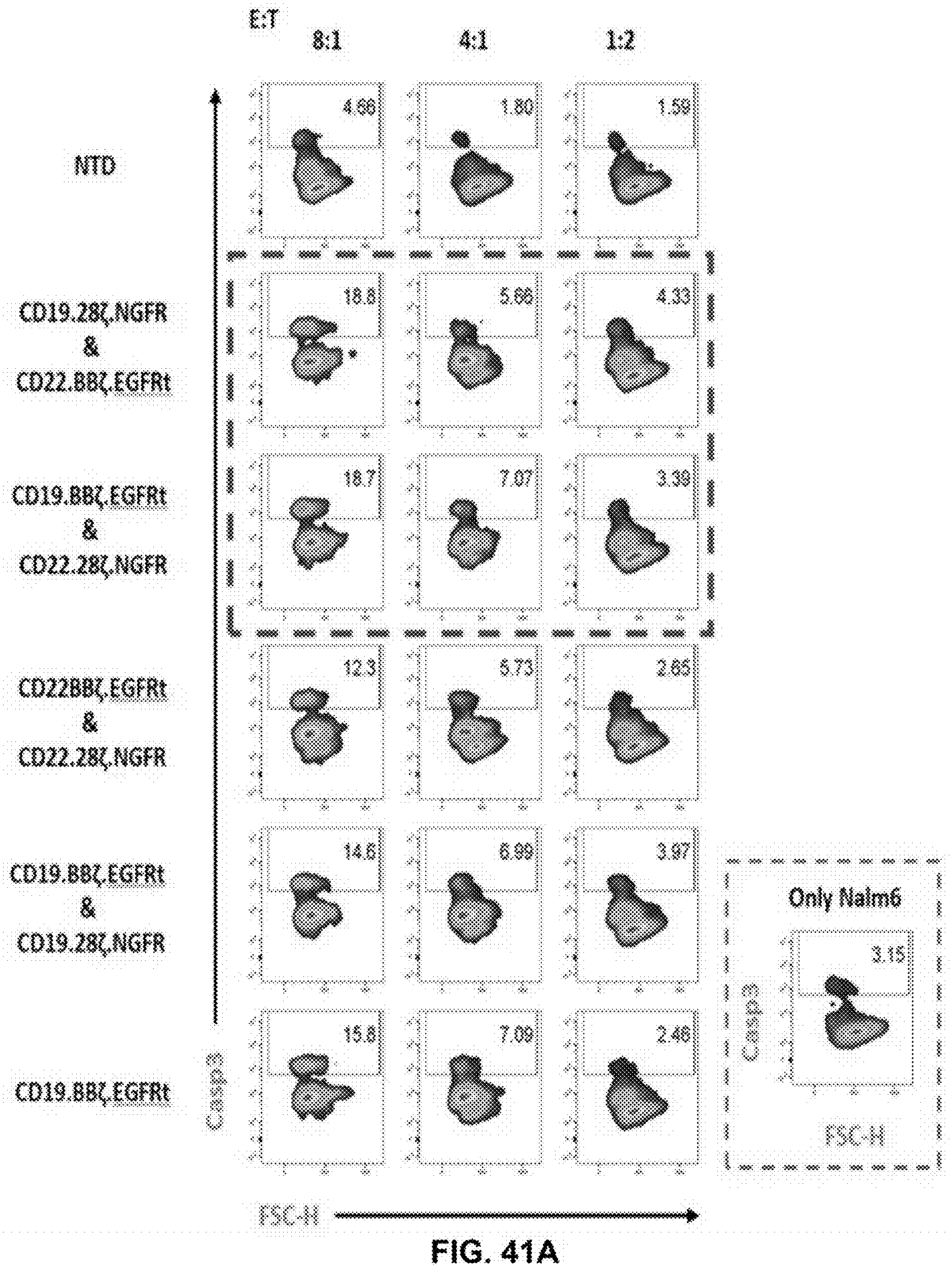
FIGS. 41A-41B illustrate Dual anti CD19 and anti CD22 CAR T cells demonstrate anti-leukemic activity in vitro against NALM6.
Figure 41B:
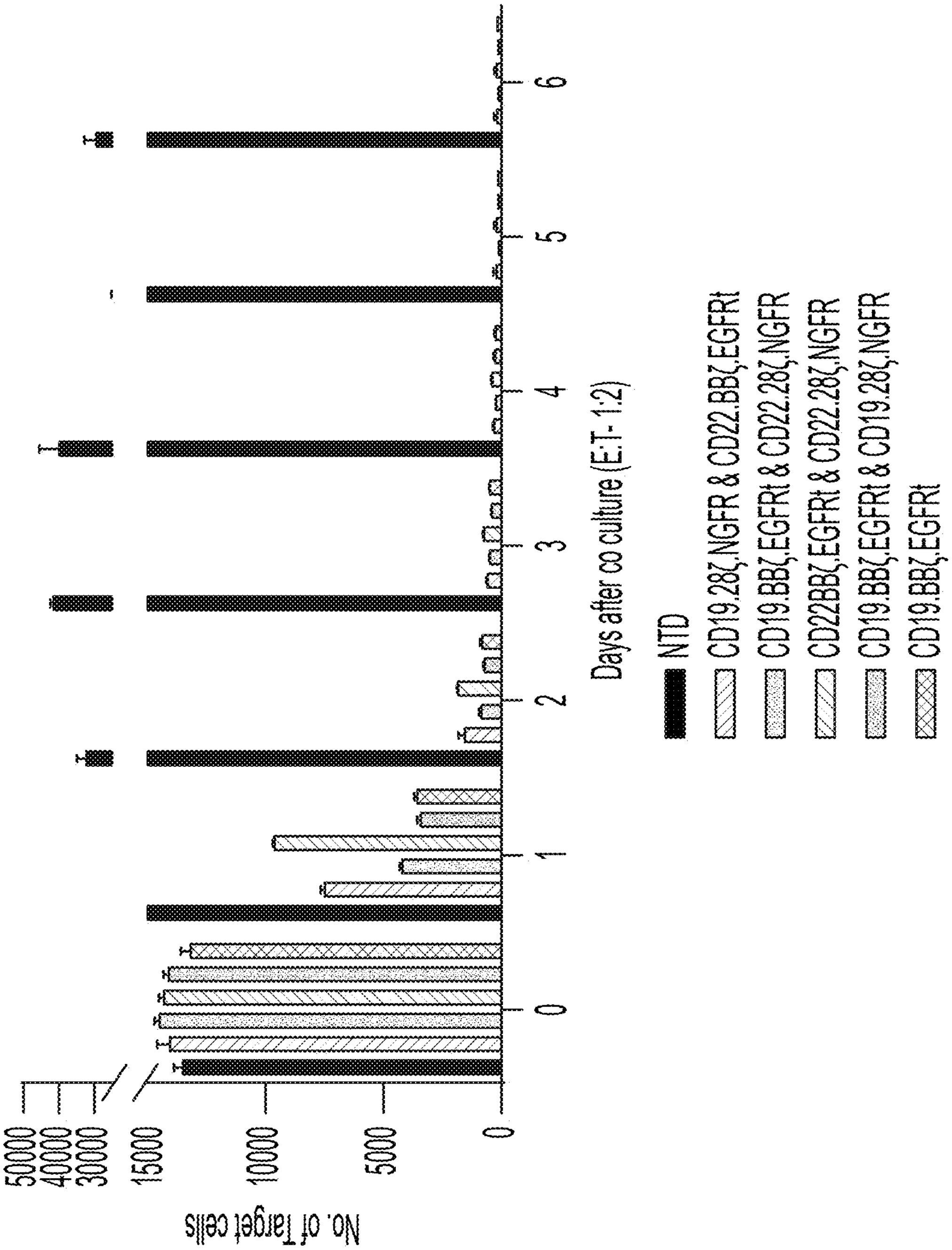

FIGS. 41A-41B illustrate Dual anti CD19 and anti CD22 CAR T cells demonstrate anti-leukemic activity in vitro against NALM6.

Figure 42:
FIG. 42 illustrates Dual CD19T2ACD22 CAR T cells enhance cytokine response in CD4 T cells after co culture with NALM6.

FIG. 42 illustrates Dual CD19T2ACD22 CAR T cells enhance cytokine response in CD4 T cells after co culture with NALM6.

Figure 43:
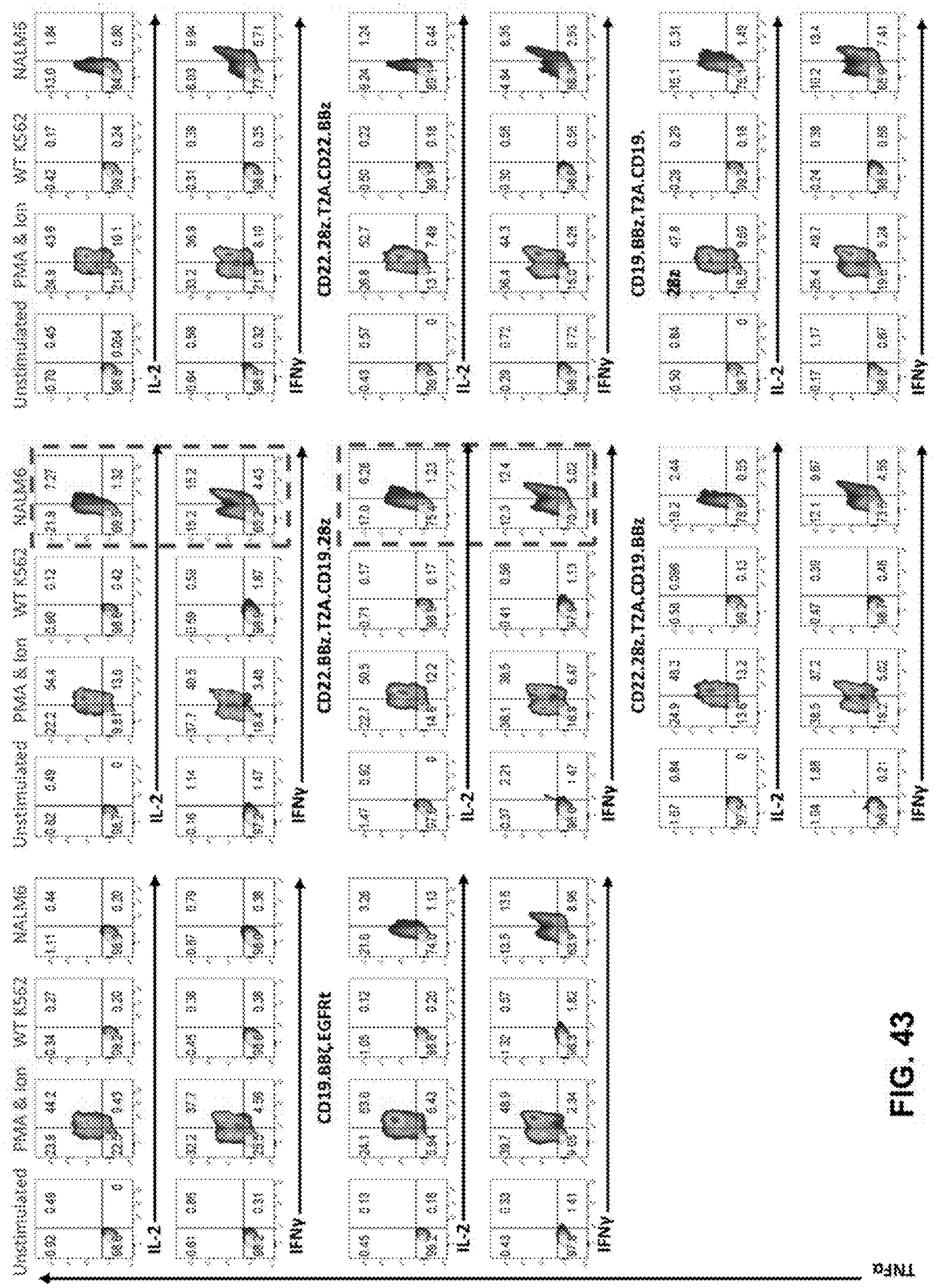
FIG. 43 illustrates Dual CD19T2ACD22 CAR T cells enhance cytokine response in CD8 T cells after co culture with NALM6.

FIG. 43 illustrates Dual CD19T2ACD22 CAR T cells enhance cytokine response in CD8 T cells after co culture with NALM6.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A nucleic acid comprising:

(a) a first polynucleotide sequence encoding a first chimeric antigen receptor comprising:

(i) a first target-specific binding domain, (ii) a first transmembrane domain, wherein the first transmembrane domain is a 4-1BB or a CD8α transmembrane domain, (iii) a first intracellular domain of a 4-1BB costimulatory molecule, and (iv) a CD3z intracellular signaling domain; and (b) a second polynucleotide sequence encoding a second chimeric antigen receptor comprising:

(i) a second target-specific binding domain, (ii) a second transmembrane domain, wherein the second transmembrane domain is a CD28 transmembrane domain, (iii) a second intracellular domain of a CD28 costimulatory molecule, and (iv) a CD3z intracellular signaling domain;

wherein the first target-specific binding domain of the first chimeric antigen receptor and the second target-specific binding domain of the second chimeric antigen receptor bind to the same target and are identical in amino acid sequence;

wherein the first polynucleotide and second polynucleotide are separated by a linker, wherein the linker comprises an internal ribosome entry site (IRES), a furin cleavage site, a self-cleaving peptide, or any combination thereof; and wherein expression of the first and second polynucleotide by a T cell confers greater proliferative capacity to the T cell compared to expression of only the first or second polynucleotide by the T cell.

2. The nucleic acid of claim 1, wherein the first transmembrane domain is a CD8α transmembrane domain.

3. The nucleic acid of claim 1, wherein the first chimeric antigen receptor and/or the second chimeric antigen receptor further comprises a hinge region.

4. The nucleic acid of claim 3, wherein the hinge region is selected from the group consisting of an Fc fragment of an antibody, a hinge region of an antibody, a CH2 region of an antibody, a CH3 region of an antibody, an artificial hinge domain, a hinge comprising an amino acid sequence of CD8, and any combination thereof.

5. The nucleic acid of claim 1, wherein the first and second target-specific binding domains bind a target selected from the group consisting of a tumor-associated antigen (TAA) and a viral antigen.

6. The nucleic acid of claim 5, wherein the first and second target-specific binding domains bind a TAA.

7. The nucleic acid of claim 6, wherein the TAA is expressed on a leukemia or lymphoma.

8. The nucleic acid of claim 7, wherein the TAA is CD19 or CD22.

9. The nucleic acid of claim 6, wherein the TAA is a solid tumor antigen.

10. A nucleic acid comprising:

(a) a first polynucleotide sequence encoding a first chimeric antigen receptor comprising the extracellular domain of a CD4 molecule, a CD8α transmembrane domain, a 4-1BB costimulatory domain, and a CD3z intracellular signaling domain; and (b) a second polynucleotide sequence encoding a second chimeric antigen receptor comprising the extracellular domain of a CD4 molecule, a CD28 transmembrane domain, a CD28 costimulatory domain, and a CD3z intracellular signaling domain;

wherein the first polynucleotide and second polynucleotide are separated by a linker, wherein the linker comprises an internal ribosome entry site (IRES), a furin cleavage site, a self-cleaving peptide, or any combination thereof.

11. The nucleic acid of claim 10, wherein the first polynucleotide comprises a first hinge region between the extracellular domain of a CD4 molecule and the CD8α transmembrane domain and the second polynucleotide comprises a second hinge region between the extracellular domain of a CD4 molecule and the CD28 transmembrane domain.

12. The nucleic acid of claim 11, wherein the first hinge region and second hinge region are from CD8α.

13. The nucleic acid of claim 10, wherein the extracellular domain of the CD4 molecule of the first chimeric antigen receptor and the second chimeric antigen receptor have the same amino acid sequence.

14. The nucleic acid of claim 10, wherein the linker comprises a furin cleavage site and a self-cleaving peptide.

15. The nucleic acid of claim 14, wherein the self-cleaving peptide is a 2A peptide.

16. The nucleic acid of claim 15, wherein the 2A peptide is selected from the group consisting of porcine teschovirus-1 2A (P2A), *Thosea asigna* virus 2A (T2A), equine rhinitis A virus 2A (E2A), and foot-and-mouth disease virus 2A (F2A).

17. The nucleic acid of claim 10, wherein the nucleic acid comprises from 5' to 3': the first polynucleotide sequence, the linker, and the second polynucleotide sequence.

18. The nucleic acid of claim 10, wherein the nucleic acid comprises from 5' to 3': the second polynucleotide sequence, the linker, and the first polynucleotide sequence.

19. An expression construct comprising the nucleic acid of claim 10.

20. The expression construct of claim 19, further comprising an EF-la promoter.

21. The expression construct of claim 19, further comprising a rev response element (RRE).

22. The expression construct of claim 19, further comprising a woodchuck hepatitis virus posttranscriptional regulatory element (WPRE).

23. The expression construct of claim 19, further comprising a cPPT sequence.

24. The expression construct of claim 19, wherein the expression construct is a viral vector selected from the group consisting of a retroviral vector, a lentiviral vector, an adenoviral vector, and an adeno-associated viral vector.

25. The expression construct of claim 19, wherein the expression construct is a lentiviral vector.

26. The expression construct of claim 25, wherein the lentiviral vector is a self-inactivating lentiviral vector.

* * * * *